US007598055B2

(12) United States Patent
Bobrowicz et al.

(10) Patent No.: US 7,598,055 B2
(45) Date of Patent: Oct. 6, 2009

(54) N-ACETYLGLUCOSAMINYLTRANSFERASE III EXPRESSION IN LOWER EUKARYOTES

(75) Inventors: Piotr Bobrowicz, Hanover, NH (US); Stephen R. Hamilton, Enfield, NH (US); Tillman U. Gerngross, Hanover, NH (US); Stefan Wildt, Lebanon, NH (US); Byung-Kwon Choi, Norwich, NH (US); Juergen H. Nett, Grantham, NH (US); Robert C. Davidson, Enfield, NH (US)

(73) Assignee: GlycoFi, Inc., Lebanon, NH (US)

( * ) Notice: Subject to any disclaimer, the term of this patent is extended or adjusted under 35 U.S.C. 154(b) by 343 days.

(21) Appl. No.: 10/680,963

(22) Filed: Oct. 7, 2003

(65) Prior Publication Data

US 2005/0208617 A1    Sep. 22, 2005

Related U.S. Application Data

(63) Continuation-in-part of application No. 10/371,877, filed on Feb. 20, 2003, now Pat. No. 7,449,308, which is a continuation-in-part of application No. 09/892,591, filed on Jun. 27, 2001, now Pat. No. 7,029,872, application No. 10/680,963, which is a continuation-in-part of application No. PCT/US02/41510, filed on Dec. 24, 2002.

(60) Provisional application No. 60/214,358, filed on Jun. 28, 2000, provisional application No. 60/215,638, filed on Jun. 30, 2000, provisional application No. 60/279,997, filed on Mar. 30, 2001, provisional application No. 60/344,169, filed on Dec. 27, 2001.

(51) Int. Cl.
C12P 21/06    (2006.01)
A61K 38/43    (2006.01)

(52) U.S. Cl. ..................... 435/69.1; 424/94.1
(58) Field of Classification Search ................. 435/69.1
See application file for complete search history.

(56) References Cited

U.S. PATENT DOCUMENTS

| 4,414,329 A | 11/1983 | Wegner |
| 4,617,274 A | 10/1986 | Wegner |
| 4,683,293 A | 7/1987 | Craig |
| 4,775,622 A | 10/1988 | Hitzeman et al. |
| 4,808,537 A | 2/1989 | Stroman et al. |
| 4,812,405 A | 3/1989 | Lair et al. |
| 4,818,700 A | 4/1989 | Cregg et al. |
| 4,837,148 A | 6/1989 | Cregg |
| 4,855,231 A | 8/1989 | Stroman et al. |
| 4,857,467 A | 8/1989 | Sreekrishna et al. |
| 4,879,231 A | 11/1989 | Stroman et al. |
| 4,882,279 A | 11/1989 | Cregg |
| 4,885,242 A | 12/1989 | Cregg |
| 4,925,796 A | 5/1990 | Bergh et al. |
| 4,929,555 A | 5/1990 | Cregg et al. |
| 4,935,349 A | 6/1990 | McKnight et al. |
| 5,002,876 A | 3/1991 | Sreekrishna et al. |
| 5,004,688 A | 4/1991 | Craig et al. |
| 5,032,516 A | 7/1991 | Cregg |
| 5,032,519 A | 7/1991 | Paulson et al. |
| 5,047,335 A | 9/1991 | Paulson et al. |
| 5,122,465 A | 6/1992 | Cregg et al. |
| 5,135,854 A | 8/1992 | MacKay et al. |
| 5,166,329 A | 11/1992 | Cregg |
| 5,324,663 A | 6/1994 | Lowe |
| 5,595,900 A | 1/1997 | Lowe |
| 5,602,003 A | 2/1997 | Pierse et al. |
| 5,707,828 A | 1/1998 | Sreekrishna et al. |
| 5,766,910 A | 6/1998 | Fukuda et al. |
| 5,834,251 A | 11/1998 | Maras et al. |
| 5,849,904 A | 12/1998 | Gerardy-Schahn et al. |
| 5,854,018 A | 12/1998 | Hitzemane et al. |
| 5,861,293 A | 1/1999 | Kojiri et al. |
| 5,910,570 A | 6/1999 | Elhammer et al. |
| 5,945,314 A | 8/1999 | Prieto et al. |

(Continued)

FOREIGN PATENT DOCUMENTS

| EP | 0 905 232 A1 | 3/1999 |
| EP | 1 054 062 A1 | 11/2000 |
| EP | 1 211 310 A | 6/2002 |
| EP | 1522590 | 4/2005 |
| EP | 1297172 | 11/2005 |
| JP | 8-336387 | 8/1996 |
| JP | 8-336387 | 12/1996 |

(Continued)

OTHER PUBLICATIONS

Chui et al. (Cell, 1997, vol. 90, pp. 157-167).*

(Continued)

*Primary Examiner*—Michael C. Wilson
(74) *Attorney, Agent, or Firm*—John David Reilly; Catherine D. Fitch

(57) ABSTRACT

The present invention relates to eukaryotic host cells having modified oligosaccharides which may be modified further by heterologous expression of a set of glycosyltransferases, sugar transporters and mannosidases to become host-strains for the production of mammalian, e.g., human therapeutic glycoproteins. The process provides an engineered host cell which can be used to express and target any desirable gene(s) involved in glycosylation. Host cells with modified lipid-linked oligosaccharides are created or selected. N-glycans made in the engineered host cells exhibit GnTIII activity, which produce bisected N-glycan structures and may be modified further by heterologous expression of one or more enzymes, e.g., glycosyltransferases, sugar transporters and mannosidases, to yield human-like glycoproteins. For the production of therapeutic proteins, this method may be adapted to engineer cell lines in which any desired glycosylation structure may be obtained.

22 Claims, 73 Drawing Sheets

U.S. PATENT DOCUMENTS

| | | | |
|---|---|---|---|
| 5,945,322 | A | 8/1999 | Gotschlich |
| 5,955,347 | A | 9/1999 | Lowe |
| 5,955,422 | A | 9/1999 | Lin |
| 5,962,294 | A | 10/1999 | Paulson et al. |
| 6,017,743 | A | 1/2000 | Tsuji et al. |
| 6,096,512 | A | 8/2000 | Elhammer et al. |
| 6,204,431 | B1 | 3/2001 | Prieto et al. |
| 6,300,113 | B1 | 10/2001 | Landry |
| 6,410,246 | B1 | 6/2002 | Zhu et al. |
| 6,602,684 | B1 | 8/2003 | Umaña |
| 7,029,872 | B2 | 4/2006 | Gerngross |
| 7,064,191 | B2 | 6/2006 | Shinkawa et al. |
| 7,214,775 | B2 | 5/2007 | Hanai et al. |
| 2003/0175884 | A1 | 9/2003 | Umana et al. |
| 2004/0018590 | A1 | 1/2004 | Gerngross et al. |
| 2004/0171826 | A1 | 9/2004 | Hamilton |
| 2004/0230042 | A1 | 11/2004 | Hamilton |
| 2005/0170452 | A1 | 8/2005 | Wildt et al. |
| 2005/0208617 | A1 | 9/2005 | Bobrowicz et al. |
| 2005/0260729 | A1 | 11/2005 | Hamilton |
| 2006/0024292 | A1 | 2/2006 | Gerngross et al. |
| 2006/0024304 | A1 | 2/2006 | Gerngross et al. |
| 2006/0029604 | A1 | 2/2006 | Gerngross et al. |
| 2006/0034828 | A1 | 2/2006 | Gerngross et al. |
| 2006/0034829 | A1 | 2/2006 | Gerngross et al. |
| 2006/0034830 | A1 | 2/2006 | Gerngross et al. |
| 2006/0040353 | A1 | 2/2006 | Davidson et al. |
| 2006/0078963 | A1 | 4/2006 | Gerngross |
| 2006/0148035 | A1 | 7/2006 | Gerngross |
| 2006/0160179 | A1 | 7/2006 | Bobrowicz et al. |
| 2006/0177898 | A1 | 8/2006 | Gerngross |
| 2006/0211085 | A1 | 9/2006 | Bobrowicz |
| 2006/0286637 | A1 | 12/2006 | Hamilton |
| 2007/0105127 | A1 | 5/2007 | Gerngross |

FOREIGN PATENT DOCUMENTS

| | | |
|---|---|---|
| WO | WO 96/21038 A | 7/1996 |
| WO | WO 98/05768 | 2/1998 |
| WO | WO 99/31224 | 6/1999 |
| WO | WO 99/54342 | 10/1999 |
| WO | WO 01/14522 | 3/2001 |
| WO | WO 01/14522 A1 | 3/2001 |
| WO | WO 01/25406 | 4/2001 |
| WO | WO 01/36432 | 5/2001 |
| WO | WO 01/60860 | 8/2001 |
| WO | WO 02/00856 | 1/2002 |
| WO | WO 02/00856 A2 | 1/2002 |
| WO | WO 02/00879 | 1/2002 |
| WO | WO 02/097060 | 12/2002 |
| WO | WO 03/011878 | 2/2003 |
| WO | WO 03/025148 | 3/2003 |
| WO | WO 03/031464 A | 4/2003 |
| WO | WO 03/056914 | 7/2003 |
| WO | WO 2004/003194 A | 1/2004 |
| WO | WO 2004/074458 | 9/2004 |
| WO | WO 2004/074461 | 9/2004 |
| WO | WO 2004/074497 | 9/2004 |
| WO | WO 2004/074498 | 9/2004 |
| WO | WO 2004/074499 | 9/2004 |
| WO | WO 2007/028144 | 3/2007 |

OTHER PUBLICATIONS

Strasser et al. (Biochem J. 2005, vol. 387, pp. 385-391).*

Abeijon et al., "Molecular Cloning of the Golgi apparatus uridine diphosphate-N-acetylglucosamine transporter from *Kluyveromyces lactis*," Proc. Natl. Acad. Sci. USA 93:5963-5968 (1996).

Adachi et al., "Mus Musculus Adult Male Testis cDNA, Riken full length enriched library, clone: 4931438M07 product: mannosidase 2, alpha 2, full insert sequence" XP002293645, Database accession No. AK029913 Abstract, Database EMBL, Dec. 21, 2002.

Alani et al., "A Method for Gene Disruption that Allows Repeated Use of URA3 Selection in the Construction of Multiply Disrupted Yeast Strains," Genetics 116, 541-545, Aug. 1987.

Altman et al., "Processing of Asparagine-linked Oligosaccharides in Insect Cells: Evidence for Alpha-Mannosidase II," *Glycoconj. J* 12(2):150-155 (1995).

Altman et al., "Insect cells as hosts for the expression of recombinant glycoproteins," *Glycoconj. J.* 16(2):109-123 (1999).

Andersen et al., "The Effect of Cell-Culture Conditions on the Oligosaccharide Structures of Secreted Glycoproteins," *Curr Opin Biotechnol*, 5(5):546-549, Oct. 1994.

Aoki et al., "Expression and activity of chimeric molecules between human UDP-galactose transporter and CMP-sialic acid transporter," *J. Biochem.* (Tokyo), 126(5):940-50, Nov. 1999.

Bardor et al., "Analysis of the N-glycosylation of recombinant glycoproteins produced in transgenic plants," *Trends in Plant Science* 4(9): 376-380 (1999).

Beaudet et al., "High-level expression of mouse Mdr3 P-glycoprotein in yeast Pichia pastoris and characterization of ATPase activity," *Methods Enzymol* 292: 397-413 (1998).

Berka et al., "The Filamentous Fungus Aspergillus-Niger Var Awamori as Host for the Expression and Secretion of Fungal and Non-Fungal Heterologous Proteins," *Abstr Papers Amer Chem Soc* 203: 121-BIOT (1992).

Berninsone et al., "The Golgi Guanosine Diphophatase is Required For Transport of GDP-Mannose Into the Lumen of *Saccharomyces cerevisiae* Golgi Vesicles," *J. Biol. Chem.*, 269(1):207-211, Jan. 1994.

Berninsone et al., "Regulation of yeast Golgi glycosylation. Guanosine diphosphatase functions as a homodimer in the membrane," *J. Biol. Chem* 270(24): 14564-14567 (1995).

Berninsone et al., "Functional Expression of the Murine Golgi CMP-Sialic Acid Transporter in *Saccharomyces cerevisiae*," *J. Biol. Chem.* 272(19):12616-12619, May 1997.

Bianchi et al., "Transformation of the yeast *Kluyveromyces lactis* by new vectors derived from the 1.6 µm circular plasmid pKD1," *Current Genetics*, 12:185-192, 1987.

Boehm et al., "Disruption of the KEX1 Gene in *Pichia pastoris* Allows Expression of Full-Length Murine and Human Endostatin," *Yeast*, 15:563-572 (1999).

Bonneaud et al., "A family of low and high copy replicative, integrative and single-stranded *S. cerevisiae/E. coli* shuttle vectors," *Yeast* 7(6): 609-615 (1991).

Bretthauer et al., "Glycosylation of Pichia pastoris-derived proteins," *Biotechnol Appl Biochem* 30(Pt 3): 193-200 (1999).

Bretthauer et al., "Genetic engineering of Pichia pastoris to humanize N-glycosylation of proteins," *Trends in Biochem*, 21(11): 459-462 (2003).

Brockhausen et al., "Control of glycoprotein synthesis. The use of oligosaccharide substrates and HPLC to study the sequential pathway for N-acetylglucosaminyltransferases I, II, III, IV, V and VI in the biosynthesis of highly branched N-glycans by hen oviduct membranes," Biochem. Cell Biol. 66:1134-1151 (1988).

Callewaert et al., "Use of HDEL-Tagged *Trichoderma reesei* Mannosyl Oligosaccharide 1,2∀-D-Mannosidase for N-glycan Engineering in *Pichia pastoris*," FEBS Letters, 503(2-3):173-8, 2001.

Cereghino et al., "Heterologous protein expression in the methylotrophic yeast *Pichia pastoris*," *FEMS Microbiology Reviews*, 24(1): 45-66 (2000).

Cereghino et al., "New selectable marker/auxotrophic host strain combinations for molecular genetic manipulation of *Pichia pastoris*," Gene, 263:159-169 (2001).

Chandrasekaran et al., "Purification and Properties of Alpha-D-Mannose:beta-1,2-N-acetylglucosaminyl-transferases and alpha-D-Mannosidases from Human Adenocarcinoma," *Cancer Res.*, 44(9):4059-68, Sep. 1984.

Chiba et al., "Production of Human Compatible High Mannose-type ($Man_5GlcNA_{c2}$) Sugar Chains in *Saccharomyces cerevisiae*," *J. Biol. Chem.*, 273(41):26298-26304, Oct. 1998.

Choi et al., "Use of combinatroial genetic libraries to humanize N-linked glycosylation in the yeast *Pichia pastoris*," *Proc. Natl. Acad. Sci.* USA 100(9):5022-5027, Apr. 2003.

Chui et al., "Genetic Remodeling of Protein Glycosylation in vivo Induces Autoimmune Disease," *Proc. Natl. Acad. Sci.*, USA 98:1142-1147, Jan. 2001.

Chui et al., "Alpha-mannosidase-II Deficiency Results in Dyserythropoiesis and Unveils and Alternate Pathway in Oligosaccharide Biosynthesis," *Cell*, Jul. 11, 1997; 90(1):157-67.

Daniel et al, "Mammalian Alpha-Mannosidases—Multiple Forms but a Common Purpose?", *Glycobiology*, 4, 551-566, Oct. 1994.

Davidson et al., "A PCR-Based Strategy to Generate Integrative Targeting Alleles With Large Regions of Homology," *Microbiology*, 148 (Pt 8):2607-15).

Dente, "Human alpha-1-acid glycoprotein genes," *Prog. Clin. Biol. Res* 300:85-98 (1989).

Duvet et al., "Cytosolic Deglycosylation Process of Newly Synthesized Glycoproteins Generates Oligomannosides Possessing One GlcNAc Residue at the Reducing End," *Biochem J.*, 335, 1998, 389-396.

Eades et al., "Characterization of the Class I alpha-Mannosidase Gene Family in the Filamentous Fungus Aspergillus Nidulans," *Gene*, Sep. 5, 2000; 255(1):25-34.

Eckhardt et al., "Molecular Cloning of the Hamster CMP-Sialic Acid Transporter," *Eur. J. Biochem.*, 248(1):187-192 (1997).

Foster et al., "Cloning and Sequence Analysis of GmII, a Drosophila Melanogaster Homologue of the cDNA Encoding Murine Golgi alpha-Mannosidase II," *Gene* 154 (1995) 183-186.

Gleeson, Paul A. "Targeting of Proteins to the Golgi Apparatus," *Histochem. Cell Biol.*, 109:517-532 (1998).

Gonzalez, Daniel S et al: "The Alpha-Mannosidases: Phylogeny and Adaptive Diversification" Molecular Biology and Evolution, vol. 17, No. 2, Feb. 2000, pp. 292-300, XP002293609 ISSN: 0737-4038.

Graham et al., "Compartmental Organization of Golgi-specific Protein Modification and Vacuolar Protein Sorting Events Defined in Yeast sec18 (*NSF*) Mutant," *J. Cell. Biol.*, 114(2): 207-218 (1991).

Grard et al., "Oligomannosides or Oligosaccharide-lipids as Potential Substrates for Rat Liver Cytosolic ∀-D-Mannosidase," *Biochem. J.*, 316: 787-792 (1996).

Guillen et al., "Mammalian Golgi apparatus UDP-*N*-acetylglucosamine transporter: Molecular Cloning by Phenotypic Correction of a Yeast Mutant," *Proc. Natl. Acad. Sci. USA*, 95(14):7888-7892 (1998).

Hamilton et al., "Production of Complex Human Glycoproteins in Yeast," *Science* 301:1244-1246 (2003).

Harkki et al., "A Novel Fungal Express System—Secretion of Active Calf Chymosin from the Filamentous Fungus Trichoderma-Reesei," *Bio-Tech* 7:596-603 (1989).

Harris B.R..: "Caenorhabditis Elegans Cosmid F58H1" XP002293610, Protein F58H1.1, Abstract, Databaase EMBL Jul. 13, 1996.

Ichishima et al., "Molecular and Enzymic Properties of Recombinant 1,2-∀- Mannosidase from *Aspergillus saitoi* Overexpressed in *Aspergillus oryzae* Cells," 1999; *Biochem. J.*, 339(Pt 3): 589-597.

Ishida et al., "Molecular Cloning and Functional Expression of the Human Golgi UDP-*N*-Acetylglucosamine Transporter," *J. Biochem.*, 126(1):68-77 (1999).

Jarvis et al., "Isolation and Characterization of a Class II alpha-mannosidase cDNA from Lepidopteran Insect Cells," *Glycobiology*, 1997; 7(1):113-127 (1997).

Jarvis et al., "Engineering N-glycosylation pathways in the baculovirus-insect cell system," *Curr Opin Biotechnol* 9(5): 528-33 (1998).

Kainuma et al., "Coexpression of α1,2 galactosyltransferase and UDP-galactose transporter efficiently galatosylates *N*- and *O*-glycan in *Saccharomyces cerevisiae*," *Glycobiology*, 9(2): 133-141 (1999).

Kalsner et al., "Insertion into *Aspergillus nidulans* of functional UDP-GlcNAc: α3-D-mannoside β-1,2-*N*-acetylglucosaminyltransferase I, the enzyme catalysing the first committed step from oligomannose to hybrid and complex N-glycans," *Glycoconj. J.*, 12(3):360-370 (1995).

Kawar et al., "Insect Cells Encode a Class II ∀-Mannosidase with Unique Properties," *J. Biol. Chem.*, 276(19):16335-16340 (2001).

Khatra et al., "Some kinetic properties of human milk galactosyltransferase," *Eur. J. Biochem.* 44:537-560 (1974).

Krezdorn et al., "Human β1,4 galactosyltransferase and α2,6 sialytransferase expressed in *Saccharomyces cerevisiae* are retained as active enzymes in the endoplasmic reticulum," *Eur. J. Biochem.*, 220(3): 809-17 (1994).

Lal et al., "Isolation and Expression of Murine and Rabbit cDNAs Encoding an α1,2-Mannosidase Involved in the Processing of Asparagine-Linked Oligosaccharides," *J. Biol. Chem.*, 1994. 269(13): 9872-9881.

Lal et al. "Substrate Specificities of Recombnant Murine Golgi α1,2-Mannosidase IA and IB and Comparison with Endoplasmic Reticulum and Golgi Processing α1,2-Mannosidases," *Glycobiology* 8(10):981-995, 1998.

Liao et al., "Cloning, Expression, Purification, and Characterization of the Human Broad Specificity Lysosomal Acid ∀-Mannosidase," *J Biol Chem* 271(45): 28348-28358.

Lehle and Tanner, "Membrane-Bound Mannosyl Transferase in Yeast Glycoprotein Biosynthesis," *Biochem. Biophys. Acta*, 350(1): 225-235, 1974.

Lu et al., "Cloning and Disruption of the b-Isopropylmalate Dehydrogenase Gene of *Pichia stipitis* with URA3 and Recovery of the Double Auxotroph," *Appl. Microbiol. Biotechnol.*, 49 (2): 141-146 (1998).

Lussier et al., "The *KTR* and *MNNI* mannosyltransferase families of *Saccharomyces cerevisiae*," *Biochimica et Biophysica Acta* 1426: 323-334 (1999).

Malissard et al., "Expression of functional soluble forms of human beta-1, 4-galactosyltransferase I, alpha-2-6-sialyltransferase, and alpha-1, 3-fucosyltransferase VI in the methylotrophic yeast Pichia pastoris," *Biochem Biophys Res Commun* 267(1): 169-173 (2000).

Maras et al., "In vitro conversion of the carbohydrate moiety of fungal glycoproteins to mammalian-type oligosaccharides," *Eur. J. Biochem.*, 249: 701-707 (1997).

Maras et al., "Filamentous fungi as production organisms for glycoproteins of bio-medical interest," *Glycoconjugate Journal*, 16:99-107 (1999).

Maras et al., "Molecular Cloning and Enzymatic Characterization of a *Trichoderma reeisi* 1,2-alpha-D-mannosidase," *J. Biotechnol.*, 77(2-3):255-263, 2000.

Martinet et al., "Modification of the protein glycosylation pathway in the methylotrophic yeast *Pichia pastoris*," *Biotechnology Letters* 20(12): 1171-1177 (1998).

Maruyama et al., "A 1,2-alpha-D-Mannosidase from a Bacillus sp.: Purification, Characterization, and Mode of Action," *Carbohydrate Res.* 251:89-98 (1994).

McClure "Modeling the growth, survival and death of microorganisims in foods: the UK food micromodel approach," *Int J. Food Microbiol.*, 23(3-4) 265-265 (1994).

McGarvey et al., "Expression of the rabies virus glycoprotein in transgenic tomatoes," *Bio-Technology* 13(13): 1484-1487 (1995).

Merkle et al., "Cloning, Expression, Purification, and Characterixation of the Murine Lysosomal Acid Alpha-Mannosidase," *Biochim Biophys Acta*, 1336(2): 132-46 (1997).

Miele et al., "Glycosylation Properties of the *Pichia pastoris*-Expressed Recombinant Kringle 2 Domain of Tissue-Type Plasminogen Activator," *Biotechnol. Appl. Biochem.*, 25:151-157 (1997).

Moens et al., "Glycoproteins in prokaryotes," *Arch. Microbiol.* 168(3): 169-175 (1997).

Moremen, "Golgi α-mannosidase II deficiency in vertebrate systems: implications for asparagine-linked oligosaccharide processing in mammals," *Biochimica Biophysica Acta*, 1573: 225-235 (2002).

Moremen et al., "Biosynthesis and Modification of Golgi Mannosidase II in HeLa and 3T3 Cells," *J. Biol. Chem.*, 260(11): 6654-6662 (1985).

Moremen et al., "Topology of Mannosidase II in Rat Liver Golgi Membranes and Release of the Catalytic Domain by Selective Proteolysis," *J. Biol. Chem.*, 261(23): 10945-10951 (1986).

Moremen, "Isolation of a Rat Liver Golgi Mannosidase II Clone by Mixed Oligonucleotide-Primed Amplication of cDNA," *Proc. Natl. Acad. Sci.*, USA Jul. 1989;86(14):5276-80.

Moremen et al., "Isolation, Characterization, and Expression of cDNAs Encoding Murine ∀-Mannosidase II, a Golgi Enzyme that Controls Conversion of High Mannose to Complex N-Glycans," *Journal of Cell Biology*, Dec. 1991; 115(6):1521-34.

Moremen et al., "Glycosidases of the Asparagine-Linked Oligosaccharide Processing Pathway," *Glycobiology* 4(2): 113-125 (1994).

Nakanishi-Shindo et al., "Structure of the N-Linked Oligosaccharides That Show the Complete Loss of α-1,6-Polymannose Outer Chain from *och1*, *och1 mnn1*, and *och1 mnn1 alg3* Mutants in *Saccharomyces cerevisiae*," *J. Biol. Chem.*, 268(35):26338-45 (1993).

Nakayama et al., "OCHI1 Encodes a Novel Membrane Bound Mannosyltransferase: Outer Chain Elongation of Asparagine-Linked Oligosaccharides," *Embo J.*, 11(7):2511-19, 1992.

Nakayama et al. "Substrate Specificity of ∀-1,6-Mannosylatransferase that Initiates N-Linked Mannose Outer Chain Elongation in *Saccharomyces cerevisiae*", *FEBS Lett.*, 412(3):547-50, 1997.

Narasimhan, "Control of glycoprotein synthesis. UDP-GlcNAc:glycopeptide beta 4-N-acetylglucosaminyltransferase III, an enzyme in hen oviduct which adds GlcNAc in beta 1-4 linkage to the beta-linked mannose of the trimannosyl core of N-glycosyl oligosaccharides," *J. Biol. Chem.* 257(17):10235-10242 (1982).

Nikawa et al., "Structural and functional conservation of human and yeast HCP1 genese which can suppress the growth defect of the *Saccharomyces cerevisiae ire15* mutant," *Gene* 171(1): 107-111 (1996).

Ogawa et al., "Structure and Transcriptional Regulation of Human alpha-Mannosidase IIX (alpha-mannosidase II isotype) Gene," *Eur. J. Biochem.*, 242(3): 446-453 (1996).

Oh-eda et al., "Overexpression of the Golgi-Localized Enzyme ∀-mannosidase IIx in Chinese Hamster ovary Cells Results in the Conversion of Hexamannosyl-N-acetylchitobiose to Tetramannosyl-N-acetylchitobiose in the N-glycan-processing Pathway," *Eur. J. Biochem.*, 268: 1280-1288 (2001).

Papac et al., "A high-throughput microscale method to release N-linked oligosaccharides from glycoproteins for matrix-assisted laser desorption/ionization time-of-flight mass spectrometric analysis," *Glycobiology* 8(5): 445-454 (1998).

Perez et al., "Transport of Sugar Nucleotides into the Lumen of Vesicles Derived from Rat Liver Rough Endoplasmic Reticulum and Golgi Apparatus," *Methods in Enzymology*, 138: 709-715 (1987).

Puglielli et al., "Reconstitution, Identification, and Purification of the Rat Liver Golgi Membrane GDP-fucose Transporter," *J. Biol. Chem.* 274(50): 35596-35600 (1999).

Rabouille et al., "The *Drosophila* GMII Gene Enlcodes Golgi α-mannosidase II," *J. Cell Sci.*, Oct. 1999;112(Pt 19): 3319-30.

Raju et al., "Analysis of glycoconjugates," *Anal Biochem*. 283(2): 123-124 (2000).

Ren et al., "Purification and Properties of a Golgi-Derived (alpha 1,2)-mannosidase-I from Baculovirus-infected Lepidopteran Insect Cells (IPLB-SF21AE) with Preferential Activity Toward Mannose6-N-Acetylglucosamine2," *Biochem.*, 34(8): 2489-2495.

Roberts, D.B.: "Drosophila Melanogaster GMII gene, exons 1-5" XP002293614, Database accession No. AJ132715, Abstract, Database EMBL.

Romero et al., "Ktr1P is an ∀-1,2-mannosyltransferase of *Saccharomyces cerevisiae*," *Biochem. J.*, 321 (Pt 2): 289-295 (1997).

Romero et al., "Mutation of Arg$^{273}$ to Leu Alters the Specificity of the Yeast N-Glycan Processing Class I ∀1,2-Mannosidase," *J. Biol. Chem*, 275(15):11071-11074 (2000).

Ruther et al., "c-fos expression interferes with thymus development in transgenic mice," *Cell* 53(6): 847-856 (1988).

Schachter et al., "The 'Yellow Brick Road' to Branched Complex N-glycans," *Glycobiology* 1(5): 453-461, 1991.

Sato et al., "Arabidopsis Thaliana DNA Chromosome 5, BAC clone F2G14 (Essa project)", XP002293613, Database accession No. AL391146, gene "F2G14_70" encoding "alpha-mannosidase-like protein" of protein_id="CAC01814.1" Abstract, Database EMBL Aug. 7, 2000.

Satou and SatoH: "Ciona Intestinalis cDNA, clone: cieg014e11, full insert sequence." XP002293611, Database accession No. AK116684, the whole document, Datatbase EMBL.

Schneikert et al., "Characterization of a Novem Mouse Recombinant Processing alpha-mannosidase," *Glycobiology*, 4(4):445-450 (1994).

Schwientek et al., "Golgi Localization in Yeast is Mediated by the Membrane Anchor Region in Rat Liver Sialyltransferase," *J. Biol. Chem.*, 270(10):5483-5489 (1995).

Segawa et al., "*Schizosaccharomyces pombe* UDP-galatose transporter: identification of its functional form through cDNA cloning and expression in mammalian cells," *FEBS Letters*, 451(3): 295-298 (1999).

Shinn et al: "Arabidopsis Thaliana AT5g14950/F2G14_70 mRNA, complete cds." XP002293612, Database accession No. AY052707, Abstract, Database EMBL.

Sikorski et al., "A system of shuttle vectors and yeast host strains designed for efficient manipulation of DNA in *Saccharomyces cerevisiae*," *Genetics* 122(1): 19-27 (1989).

Soderholm et al. "Vector for pop-in/pop-out Gene Replacement in *Pichia pastoris*," *Biotchniques*, 31 (2):306-10 (2001).

Sommers et al., "Transport of Sugar Nucleotides into Rat Liver Golgi," *J. Cell Biol.*, 91(2): A406-A406 (1981).

Sommers et al., "Transport of Sugar Nucleotides into Rat Liver Golgi. A New Golgi Marker Activity," *J Biolog Chem*, 257(18): 10811-10817 (1982).

Staub et al., "High-yield production of a human therapeutic protein in tobacco chloroplasts," *Nature Biotechnology* 18(3): 333-338 (2000).

Stix, "Supercharging Protein Manufacture," *Scientific Amer.*, Jan. 2004: 32-33.

Svetina et al., "Expression of Catalytic Subunit of Bovine Enterokinase in the Filamentous Fungus Aspergillus Niger," *J. Biotechnol.*, 76(2-3): 245-251 (200).

Swiss Prot P11655.

Swiss Prot P32906.

Swiss Prot P39107.

Swiss Prot P50108.

Swiss Prot P53008.

Takeuchi, "Trial for molecular breeding of yeast for the production of glycoprotein therapeutics," *Trends in Glycoscience and Glycotechnology* 9:S29-S35 (1997).

Umaña et al., "Engineered Glycoforms of an Antineuroblastoma IgG1 with Optimized Antibody-Dependent Cellular Cytotoxic Activity," *Nature Biotechnology*, 17(1):176-80 (1999).

Umana et al., "Tetracycline-regulated overexpression of glycosyltransferases in Chinese hamster ovary cells," *Biotechnol. Bioeng.* 65(5):542-549 (1999).

Ware et al., "Expression of Human Platelet Glycoprotein Ib-Alpha in Transgenic Mice," *Thrombosis and Haemostasis* 69(6): 1194-1194 (1993).

Weikert et al., "Engineering Chinese Hamster Ovary Cells to Maximize Sialic Acid Content of Recombinant Glycoproteins", *Nature Biotechnology*, 17(11): 1116-1121, Nov. 1999.

Werner et al., "Appropriate Mammalian Expression Systems for Biopharmaceuticals," *Arzneimittelforschung*, Aug. 1998;48(8):870-80.

Wiggins et al., "Activity of the yeast MNN1 alpha-1,3-mannosyltransferase requires a notif conserved in many other families of glycosyltransfereases," *Proc. Nat. Acad. Sci. USA* 95(14): 7945-7950 (1998).

Yamashita et al., "An α—Mannosidase purified from Aspergillus Saitoi is specific for α1,2 linkages," *Biochemical and Biophysical Research Communications* 96(3): 1335-1342.

Yang et al., "Glycosylation and proteolytic processing of 70 kDa C-terminal recombinant polypeptides of *Plasmodium falciparum* merozoite surface protein 1 expressed in mammalian cells," *Glycobiology*, 9(12): (1999) 1347-55.

Yang et al., "Effects of Ammonia on CHO Cell Growth, Erythropoietin Production, and Glycosylation", *Biotechnol Bioeng.*, 68(4): 370-80 (2000).

Yip et al., "Cloning and analysis of the *Saccharomyces cerevisiae* MNN9 and MNN1 genes required for complex glycosylation of secreted proteins," *Proc. Natl. Acad. Sci. USA*, 91(7): 2723-2727 (1994).

Yoko-o et al., "*Schizosaccharomyces pombe* Och1(+) Encodes Alpha-1,6-Mannosyltranferase that is involved in Outer Chain Elongation of N-Linked Oligosaccharides," *FEBS Lett.*, 489(1): 75-80 (2001).

Yoshida et al., "1-2-alpha-D- mannosidase from Penicillium citriunum: molecular and enzymic properties of two isoenzymes," Biochem. J. 290 (Pt2): 349-354 (1993).
Yoshida et al., "Expression and charaterization of rat UDP-N-acetylgluocosamine: α-3-D-mannoside β-1,2-N-acetylglucosaminyltransferase I in Saccharomyces cerevisiae," Glycobiology,9 (1): 53-58 (1999).
GenBank Accession No. AF005034.
Genbank Accession No. AF106080.
Genbank Accession No. AK116684.
Genbank Accession No. D55649.
Genbank Accession No. NM_073594.
Genbank Accession No. NM_121499.
Genbank Accession No. U31520.
Genbank Accession No. X77652.
Genbank Accession No. XM_218816.
Genbank Accession No. NM 002406.
Genbank Accession No. CAA98114.
Genbank Accession No. NM_088548 (Genbank AN 6678787).
Genbank Accession No. NM006715.
Genbank Accession No. X61172.
Genbank Accession No. NM_000528.
Abdel-Salam et al., "Expression of mouse anticreatine kinase (MAK33) monoclonal antibody in the yeast Hansenula polymorpha", Appl. Microbiol. Biotechnol., 56:157-164 (2001).
Abeijon et al., "Molecular Cloning of the Golgi apparatus uridine diphosphate-N-acetylglucosamine transporter from Kluyveromyces lactis" Proc. Natl. Acad. Sci. USA 93:5963-5968 (1996).
Alani et al., "A Method for Gene Disruption That Allows Repeated Use of URA3 Selection in the Construction of Multiply Disrupted Yeast Strains" Genetics 116:541-545 (1987).
Altschul et al., "Basic Local Aligmnent Search Tool", J. Mol. Biol. 215:403-410 (1990).
Altschul et al., "Gapped BLAST and PSI-BLAST: a new generation of protein database search programs", Nucleic Acids Res. 25:3389-3402 (1997).
Anderson et al., "The effect of sell-culture conditions on the oligosaccharide structures of secreted glycoproteins", Curr Opin Biotechnol. 5(5):546-49 (1994).
Aoki et al., "Expression and activity of chimeric molecules between human UDP-galactose transporter and CMP-sialic acid transporter", J. Biochem. (Tokyo), 126(5):940-50 (1999).
Beaudet et al., "High-level expression of mouse Mdr3 P-glycoprotein in yeast Pichia pastoris and characterization of ATPase activity", Methods Enzymol., 292:397-413 (1998).
Berka et al., "The Filamentous Fungus Aspergillus niger var. Awamori as Host for the Expression and Secretion of Fungal and Non-Fungal Heterologous Proteins", Abstr. Papers Amer. Chem. Soc. 203:121-BIOT (1992).
Berninsone et al., "Functional Expression of the Murine Golgi CMP-Sialic Acid Transporter in Saccharomyces cerevisiae", J. Biol. Chem. 272(19):12616-9 (1997).
Berninsone et al., "Regulation of Yeast Golgi Glycosylation", J. Biol. Chem. 270(24):14564-14567 (1995).
Berninsone et al., "The Golgi guanosine diphophatase is required for transport of GDP-mannose into the lumen of Saccharomyces cerevisiae Golgi vesicles", J. Biol. Chem., 269(1):207211 (1994).
Bianchi et al., "Transformation of the yeast Kluyveromyces lactis by new vectors derived from the 1.6 µm circular plasmid pKD1", Current Genetics, 12:185-192 (1987).
Boehm et al., "Disruption of the KEX1 Gene in Pichia pastoris Allows Expression of Full-Length Murine and Human Endostatin", Yeast, 15:563-572 (1999).
Boeke et al., "A positive selection for mutants lacking orotidine-5'-phosphate decarboxylase activity in yeast: 5-fluoro-orotic acid resistance", Mol. Gen. Genet. 197:345-346 (1984).
Bonneaud et al., "A family of low and high copy replicative, integrative and single-stranded S. cerevisiae/E. coli shuttle vectors", Yeast, 7:609-615 (1991).
Borreback et al., "Human momoclonal antibodies produced by primary in vitro immunization of peripheral blood lymphocytes", Proc. Natl. Acad. Sci. USA, 85:3995-3999 (1988).

Bretthauer et al., "Glycosylation of Pichia pastoris-derived proteins", Biotehcnology and Applied Biochemistry 30:193-200 (1999).
Buckel et al., "Cloning and nucleotide sequence of heavy- and light-chain cDNAs from a creatine-kinase-specific monoclonal antibody", Gene, 51:13-19 (1987).
Cadwell and Joyce, "Randomization of Genes by PCR Mutagenesis", PCR Methods Applic. 2:28-33 (1992).
Callewaert et al., "Use of HDEL-tagged Trichoderma reesei mannosyl oligosaccharide 1,2-α-D-mannosidase for N-glycan engineering in Pichia pastoris", FEBS Lett. 503(2-3):173-8 (2001).
Cereghino et al., "Heterologous protein expression in the methylotrophic yeast Pichia pastoris", FEMS Microbiology Reviews, 24(1):45-66 (2000).
Cereghino et al., "New selectable marker/auxotrophic host strain combinations for molecular genetic manipulation of Pichia pastoris", Gene, 263:159-169 (2001).
Chiba et al., "Production of Human Compatible High Mannose-type Sugar Chains in Saccharomyces cerevisiae", J. Biol. Chem., 273(41):26298-26304 (1998).
Choi et al., "Use of combinatroial genetic libraries to humanize N-linked glycosylation in the yeast Pichia pastoris", Proc. Natl. Acad. Sci. USA 100:5022-5027 (2003).
Davidson et al., "A PCR-based strategy to generate integrative targeting alleles with large regions of homology", Microbiol., 148(Pt8):2607-15 (2002).
Davies et al., "Expression of GnTIII in a Recombinant Anti-CD20 CHO Production Cell Line: Expression of Antibodies with Altered Glycoforms Leads to an Increase in ADCC Through Higher Affinity for FcγRIII", Biotechnol. Bioeng., 74(4):288-294 (2001).
Dennis et al., "Protein glycosylation in development and disease", Bioessays, 21(5):412-21 (1999).
Eades et al., "Characterization of the Class I α-mannosidase gene family in the filamentous fungus Aspergillus nidulans", Gene, 255(1):25-34 (2000).
Eckhardt et al., "Molecualr cloning of the hamster CMP-sialic acid transporter", Eur. J. Biochem., 248(1):187-192 (1997).
Gavel, et al., "Sequence differences between glycosylated and non-glycosylated Asn-X-Thr/Ser acceptor sites: implications for protein engineering", Protein Eng., 3:433-42 (1990).
Gleeson, Paul A. "Targeting of proteins to the Golgi apparatus", Histochem. Cell Biol., 109:517-532 (1998).
Goochee et al., "The Olgosaccharides of Glycoproteins: Bioprocess Factors Affecting Oligosaccharide Structure and Their Effect on Glycoprotein Properties", Biotechnology, 9(12):1347-55 (1999).
Graham et al., "Compartmental Organization of Golgi-specific Protein Modification and Vacuolar Protein Sorting Events Defined in Yeast sec18 (NSF) Mutant", J. Cell. Biol., 114(2):207-218 (1991).
Grasziano et al., "Construction and Characterization of a Humanized Anti-γ-lg Receptor Type I (FcγRI) Monoclonal Antibody", J. Immunol.,155(10):4996-5002 (1995).
Guillen et al., "Mammalian Golgi apparatus UDP-N-acetylglucosamine transporter: Molecular cloning by phenotypic correction of a yeast mutant", Proc. Natl. Acad. Sci. USA, 95(14):7888-7892 (1998).
Hamilton et al., "Production of Complex Human Glycoproteins in Yeast", Science, 301:1244-46 (2003).
Harkki et al., "A Novel Fungal Expression System: Secretion of Active Calf Chymosin From the Filamentous Fungus Trichoderma reesei", Biotechnical Laboratory, 7(6):596 (1989).
Hayes et al., "Carbohydrate Compositions of the Rabbit Plasminogen Isozymes", J. Arch. Biochem. Biophys., 171:651-655 (1975).
Hernandez et al., "Structure of the Phosphorylated N-Linked Oligosaccharides from the mnn9 and mnn10 Mutants of Saccharomyces cerevisiae", the Journal of Biological Chemistry, 264(23):13648-13659 (1989).
Huffaker et al., "Yeast mutants deficient in protein glycosylation", Proc. Natl. Acad. Sci. USA, 80(24):7466-70 (1983).
Ishida et al., "Molecular Cloning and Characterization of a Novel Isoform of the Human UDP-Galactose Transporter, and of Related Complementary DNAs Belonging to the Nucleotide-Sugar Transporter Gene Family", J. Biochem., (Tokyo) 120(6):1074-1078 (1996).

Ishida et al., "Molecular Cloning and Functional Expression of the Human Golgi UDP-*N*-Acetylglucosamine Transporter", *J. Biochem.*, 126(1):68-77 (1999).

Jarvis et al., "Engineering N-glycosylation pathways in the baculovirus-insect cell system", *Current Opinion in Biotechnology*, 9:528-533 (1998).

Jefferis, "Glycosylation of Human IgG Antibodies", *Biopharm.*, 14:19-26 (2001).

Kainuma, "Coexpression of α1,2 galactosyltransferase and UDP-galactose transporter efficiently galatosylates *N*- and *O*-glycan in *Saccharomyces cerevisiae*", *Glycobiology*, 9(2): 133-141 (1999).

Kalsner et al., "Insertion into *Aspergillus nidulans* of functional UDP-GlcNAc: α3-D-mannoside β-1,2-*N*-acetylglucosaminyl-transferase I, the enzyme catalysing the first committed step from oligomannose to hybrid and complex N-glycans" *Glycoconj. J.*, 12(3):360-370 (1995).

Khatra et al., "Some Kinetic Properties of Human-Milk Galactosyl Transferase", *Eur. J. Biochem.*, 44:537-560 (1974).

Krezdorn et al., "Human β1,4 galactosyltransferase and α2,6 sialytransferase expressed in *Saccharomyces cerevisiae* are retained as active enzymes in the endoplasmic reticulum", *Eur. J. Biochem.*, 220(3):809-17 (1994).

Lagerkvist et al., "Single, Antigen-Specific B Cells Used to Generate Fab Fragments Using CD40-Mediated Amplification or Direct PCR Cloning", *Biotechniques*, 18:862-869 (1995).

Lal et al., "Sustrate specificities of recombinant murine Golgi α1,2-mannosidases IA and IB and comparison with endoplasmic reticulum and Golgi processing α1,2-mannosidases", *Glycobiology*, 8(10)981-95 (1998).

Leung et al., "A Method for Random Mutagenesis of a Defined DNA Segment Using a Modified Polymerase Chain Reaction", *Technique*, 1:11-15 (1989).

Lu et al., "Cloning and disruption of the β-isopropylmalate dehydrogenase gene (LEU2) of Pichia stipitis with URA3 and recovery of the double auxotroph", *Appl. Microbiol. Biotechnol.* 49:141-146 (1998).

Madden et al., "Applications of Network BLAST Server", *Meth. Enzymol.*, 266:131-141 (1996).

Malissard et al., "Expression of Functional Soluble Forms of Human β-1,4-Galactosyltransferase I, α-2,6-Sialytransferase, and α-1,3-Fucosyltransferase VI in the Methylotrophic Yeast *Pichia pastoris*", *Biochemical and Biophysical Research Communications*, 267:169-173 (2000).

Maras et al., "In vitro conversion of the carbohydrate moiety of fungal glycoproteins to mammalian-type oligosaccharides", *Eur. J. Biochem.*, 249:701-707 (1997).

Martinet et al., "Modification of the protein glycosylation pathway in the methylotrophic yeast *Pichia pastoris*" *Biotechnology Letters*, 20:1171-1177 (1998).

Miele et al., "Glycosylation properties of the *Pichia pastoris*-expressed recombinant kringle 2 domain of tissue-type plasminogen activator", *Biotechnol. Appl. Biochem.*, 25:151-157 (1997).

Moens et al., "Glycoproteins in prokaryotes", *Arch Microbiol.* 168(3):169-175 (1997).

Morin-Ganet et al., "Morphogenesis and Dynamics of the Yeast Golgi Apparatus", *Traffic*, 1(1):56-68 (2000).

Nakanishi-Shindo et al., "Structure of the N-Linked Oligosaccharides That Show the Complete Loss of α-1,6-Polymannose Outer Chain from *och1*, *och1 mnn1*, and *och1 mnn1 alg3* Mutants in *Saccharomyces cerevisiae*" *J. Biol. Chem.*, 268(35):26338-45 (1993).

Nakayama et al., "*OCH1* encodes a novel membrane bound mannosyltransferase:outer chain elongation of asparagine-linked oligosaccharides" *EMBO J.*, 11(7):2511-19 (1992).

Nakayama et al., "Substrate specificity of α-1,6-mannosyltransferase that initiates *N*-linked mannose outer chain elogation in *Saccharomyces cerevisiae*", *FEBS Lett.*, 412(3):547-50 (1997).

Narasimhan et al., "Control of Glycoprotein Synthesis", *J. Biol. Chem.*, 257:10235:42 (1982).

Neiman et al., "*Saccharomyces cerevisiae* HOC1, a Supressor of pkc1, Encodes a Putative Glycosyltransferase", *Genetics*, 145(3):637-45 (1997).

Ogunjimi et al., "High-level secretory expression of immunologically active intact antibody from the yeast *Pichia pastoris*", *Biotechnology Letters*, 21:561-567 (1999).

Orlandi et al., "Clonning immunoglobulin variable domains for expression by the.polymerase chain reaction", *Proc. Natl. Acad. Sci. USA*, 86:3833 (1988).

Papac et al., "A high-throughput microscale method to release N-linked oligosaccharides from glycoproteins for matrix-assisted laser desportion/ionization time-of-flight mass spectrometric analysis", *A.J.S., Glycobiology*, 8:445-454 (1998).

Pearson, "Rapid and Sensitive Sequence Comparison with FASTP and FASTA", *Methods Enzymol.* 183:63-98 (1990).

Perez et al., "Transport of Sugar Nucleotides into the Lumen of Vesicles Derived from Rat Liver Rough Endoplasmic Reticulum and Golgi Apparatus", *Methods in Enzymology*, 138:709-715 (1987).

Puglielli et al., "Reconstitution, Identification, and Purification of the Rat Liver Golgi Membrane GDP-fucose Transporter", *J. Biol. Chem.* 274(50):35596-35600 (1999).

Raju et al., "Species-specific variation in glycosylation of IgG: evidence for the species-specific sialyation and branch-specific galactosylation and importance for engineering recombinant glycoprotein therapeutics", *Glycobiology*, 10(5):477-486 (2000).

Raschke et al., "Genetic Control of Yeast Mannan Structure", *J. Biol. Chem.* 248(13):4660-66 (1973).

Recinos et al., "Sequences of cDNAs encoding immunoglobulin heavy- and light-chain variable regions from two anti-dioxin monoclonal antibodies", *Gene*, 149:385-386 (1994).

Recinos et al., "Sequences of cDNAs encoding immunoglobulin heavy- and light-chain variable regions from two anti-dioxin monoclonal antibodies", *Gene*, 158:311-312 (1995).

Reidhaar-Olson et al., "Combinatorial Cassette Mutagenesis as a Probe of the Informational Content of Protein Sequences", *Science*, 241:53-57 (1988).

Romero et al., "Mutation of Arg273 to Leu Alters the Specificity of the Yeast *N*-Glycan Processing Class I α1,2-Mannosidase", *J. Biol. Chem.*, 275(15):11071-4 (2000).

Rothstein et al., "Targeting, Disruption, Replacement, and Allele Rescue: Integrative DNA Transformation in Yeast", *Methods in Enzymology*, 194:281 (1991).

Sambrook et al., "Hybridization of Radiolabeled Probes to Immobilized Nucleic Acids", *Molecular Cloning: A Laboratory Manual*, 2d ed., Cold Spring Harbor Laboratory Press, Cold Spring Harbor, N.Y. (1989), pp. 9.51.

Schwientek et al., "Golgi Localization in Yeast is Mediated by the Membrane Anchor Region in Rat Liver Sialyltransferase", *J.Biol. Chem.*, 270(10):5483-5489 (1995).

Segawa, "*Schizosaccharomyces pombe* UDP-galatose transporter: identification of its functional fill form through cDNA cloning and expression in mammalian cells", *FEBS Letters*, 451(3):295-298 (1999).

Sikorski et al., "A system of Shuttle Vectors and Yeast Host Strains Designed for Efficient Manipulation of DNA in *Saccharomyces cerevisiae*", *Genetics*, 122:19-27 (1989).

Soderholm et al., "Vector for Pop-In/Pop-Out Gene Replacement in *Pichia pastoris*", *Biotechniques*, 31(2):306-10 (2001).

Sommers et al., "Transport of Sugar Nucleotides into Rat Liver Golgi", *J. Cell Biol.*, 257(18):811-817 (1982).

Sommers et al., "Transport of Sugar Nucleotides into Rat Liver Golgi", *J. Cell Biol.*, 91(2):A406 (1981).

Stanley et al., "Complementation between Mutants of CHO Cells Resistant to a Variety of Plant Lectins", *Somatic Cell Genet* 3(4):391-405 (1977).

Svetina et al., "Expression of catalytic subunit of bovine enterokinase in the filamentous fungus *Aspergillus niger*", *J. Biotechnol.*, 76(2-3): 245-251 (2000).

Takeuchi, "Trial for Molecular Breeding of Yeast for the Production of Glycoprotein Therapeutics", *Trends in Glycoscience and Glycotechnology*, 9:S29-S35 (1997).

Terness et al., "Idiotypic Vaccine for Treatment of Human B-Cell Lymphoma", *Hum. Immunol.*, 56:17-27 (1997).

Tremblay et al., "Molecular cloning, chromosomal mapping and tissue-specific expression of a novel human α1,2-mannosidase gene involved in N-glycan maturation", *Glycobiology*, 8(6):585-595, (1998).

Tsuji-Hayashi et al., "A Potential Endogenous Ligand of Annexin IV in the Exocrine Pancreas", *The Journal of Biological Chemistry*, 277(49):47493-47499 (2002).

Umana et al., "Engineered glycoforms of an antineuroblastoma IgG1 with optimized antibody-dependent cellular cytotoxic activity", *Nat. Biotechnol.*, 17(2):176-80 (1999).

Umana et al., "Tetracycline-Regulated Overexpression of Glycosyltransferase in Chinese Hamster Ovary Cells", *Biotechnol. Bioeng.*, 65(5):542-9 (1999).

Weikert et al., "Engineering Chinese hamster ovary cells to maximize sialic acid content of recombinant glycoproteins", *Nature Biotechnology*, 17:1116-1121(1999).

Welschof et al., "Amino acid sequence based PCR primers for amplification of rearranged human heavy and light chain immunoglobulin variable region genes", *J. Immunol. Methods*, 179:203-214 (1995).

Werner et al., "Appropriate Mammalian Expression Systems for Biopharmaceuticals", *Arzneimittelforschung*, 48(8):870-80 (1998).

Yang et al., "Effects of Ammonia on CHO Cell Growth, Erythropoietin Production, and Glycosylation", *Biotech. Bioeng.*, 68:370-80 (2000).

Yip et al., "Cloning and analysis of the *Saccharomyces cerevisiae* MNN9 and MNN1 genes required for complex glycosylation of secreted proteins", *Proc. Natl. Acad. Sci. USA*, 91(7):2723-7 (1994).

Yoshida et al., "Expression and characterization of rat UDP-N-acetylglucosamine: α-3-D-mannoside β-1,2-N-acetylglucosaminyltransferase I in *Saccharomyces cerevisiae*", *Glycobiology*, 9(1):53-8 (1999).

Zhang and Madden, "PowerBLAST: A New Network BLAST Application for Interactive or Automated Sequence Analysis and Annotation", *Genome Res.* 7:649-656 (1997).

Li et al., Nature Biotech., vol. 24 (2006), pp. 210-215, "Optimization of humanized IgGs in glycoengineered *Pichia pastoris*".

Lifely et al., Glycobiology, vol. 5 (1995), pp. 813-822, "Glycosylation and biological activity of CAMPTAH-1H expressed in different cell lines . . . . "

Yamane-Ohnuki et al., Biotech. Bioengin., vol. 87 (2004), pp. 614-622, "Establishment of FUT8 knockout Chinese hamster ovary cells: An ideal host cell line for producing . . . . "

Tatara et al., J. of Biol. Chem., vol. 278 (2003), pp. 25289-25294, "Identification of catalytic residues of Ca2+-independent 1,2-alpha-D-mannosidase from *Aspergillus saitoi* . . . . "

EP 1297172 B1—Glycode Opposition Brief (English translation).

EP 1297172 B1—Novozyme Opposition Brief.

EP 1297172 B1—Patentee's Reply to the Notice of Opinion.

EP 1297172 B1—EPO Non-Binding Opinion.

Fujita et al., Biochem. & Biophys. Res. Comm., vol. 238 (1997), pp. 779-783, "Five crucial carboxyl residues of 1,2-alpha-mannosidase from *Aspergillus saitoi* (A. phoenicis), . . . . "

Schlegel et al., Database GSN Derwent No. ABV29386, XP002293375 (2002).

Voet et al., Biochemistry (1990), pp. 266-267, Section 10-3. Glycoproteins.

Fukuta et al., Glycobiology, vol. 10 (2000), pp. 421-430, Remodeling of sugar chain structures of human interferon-γ.

Minowa et al., J. Biol. Chem., vol. 273 (1998), pp. 11556-11562, "cDNA cloning and expression of bovine UDP-N-acetylglucosamine: . . . . "

Duman et al., Biotechnol. Appl. Biochem., vol. 28 (1998), pp. 39-45, "O-mannosylation of *Pichia pastoris* cellular and recombinant proteins".

Weng et al., Glycobiology, vol. 6 (1996), pp. 861-868, "Evaluation of the early procesing routes of N-linked oligosaccharides of glycoproteins through the characteization of Man8GlcNAc2 . . . . "

Merriam-Webster, definition of "domain".

Lee et al. Biotechnol. Prog., vol. 13 (1997), pp. 368-373, "Sequential δ-integration for the regulated insertion of cloned genes . . . . "

Zhu et al., Archives of Biochem. & Biophysics, vol. 352 (1998), pp. 1-8, "Structural studies of alpha-N-acetylgalactosaminidase: Effect of glycosylation . . . . "

Vervecken et al., Appl. Environ. Microbiol., vol. 70 (2004), pp. 2639-2646, "In vivo synthesis of mammalian-like, . . . ."

Spiro et al., J. Biol. Chem., vol. 272 (1997), pp. 29356-29363, "Molecular cloning and expression of rat liver endo-α-mannosidase . . . . "

Spiro, J. Biol. Chem., vol. 275 (2000), pp. 35657-35660, "Glucose residues as key determinants in the biosynthesis and quality control . . . . "

Tang et al., XP-002293372, WO2003025148-A2, Mar. 27, 2003, "New polynucleotides and secreted proteins, useful for treating myeloid or lymphoid cell disorders . . . . "

Tang et al., XP-002293373, WO2003025148-A2, Mar. 27, 2003, "New polynucleotides and secreted proteins, useful for treating myeloid or lymphoid cell disorders . . . . "

Swarnakar et al., XP-002293374, WO200297060-A2, Dec. 5, 2002, "Novel human carbohydrate associated polypeptide, useful in diagnosis, treatment and prevention . . . . "

Carninci et al., XP-002293371, AK030141, dated Dec. 5, 2002, "Mus musculus adult male testis cDNA . . . . "

Schlegel et al., XP-002293375, WO200160860-A2, Aug. 23, 2001, "Human prostate expression marker cDNA 29377".

\* cited by examiner

M. musculus alpha-1,2-mannosidase IA open reading frame. The transmembrane and catalytic domains are highlighted in bold respectively. The sequence of the primers used to generate the N-terminal truncations are highlighted by underlining and the start of each respective protein fragment indicated by an arrow.

```
  1  atgcccgtgggggggcctgtgtgccgctctcttcagtagcccctggggggggggctggggcggcagtggcctggcttggcgcggggaagggg
  1▸ M  P  V  G  G  L  L  P  L  F  S  S  P  G  G  G  L  G  S  G  L  G  G  L  G  G  R  K  G 97  tctggccccgctgccttccgcctcacggagaagttcgtgctgctgttcagcgccttcatcacgtgctttgggcaatc
 33▸ S  G  P  A  A  F  R  L  T  E  K  F  V  L  L  V  F  S  A  F  I  T  C  F  G  A  I 184  ttcttcctgcctgactcctccaagctcctcagcggggtcttgttcactccaaccctgcctcgcagccgccggaacacccaagcccggggctcg
 62▸ F  F  L  P  D  S  S  K  L  L  S  G  V  L  F  H  S  N  P  A  L  Q  P  P  A  E  H  K  P  G  L
         d65 primer 278  gggcgcgtgcgggatgccgccgagggagtccggcgccgggaagcgcctgggactggagctggggagctggggagctagccaact
 93▸ G  A  R  A  E  D  A  A  E  G  R  V  R  H  R  E  E  G  A  P  G  D  P  G  A  G  L  E  D  N  L  A
                                  d105 primer 374  ggatccgccgaaaaccacgagcggggcctctcaggaagccaagagacctgccagagatccaagagacattctgctggagaagg
125▸ R  I  R  E  N  H  E  R  A  L  R  E  A  K  E  T  L  Q  K  L  P  E  E  I  Q  R  D  I  L  L  E  K 470  aaaaggtggccagccaggtgcgtgacagctgcgtggacagctgttctgtttaggggcttgaccatcctccctccccgtcgggatagacccggagc
157▸ E  K  V  A  Q  D  L  R  D  K  D  L  F  R  G  L  P  K  V  D  F  L  P  P  V  G  V  E  N  R  E
                                                                                      d187 primer 566  ccgctgacgccaccatccgtgagaagagggcaaagatcaaagagatgatgacccatgcttggaataattataaacgctatgcgtggggc
189▸ P  A  D  A  T  I  R  E  K  R  A  K  I  K  E  M  M  T  H  A  W  N  N  Y  K  R  Y  A  W  G
```

FIG. 3

FIG. 3 CON'T

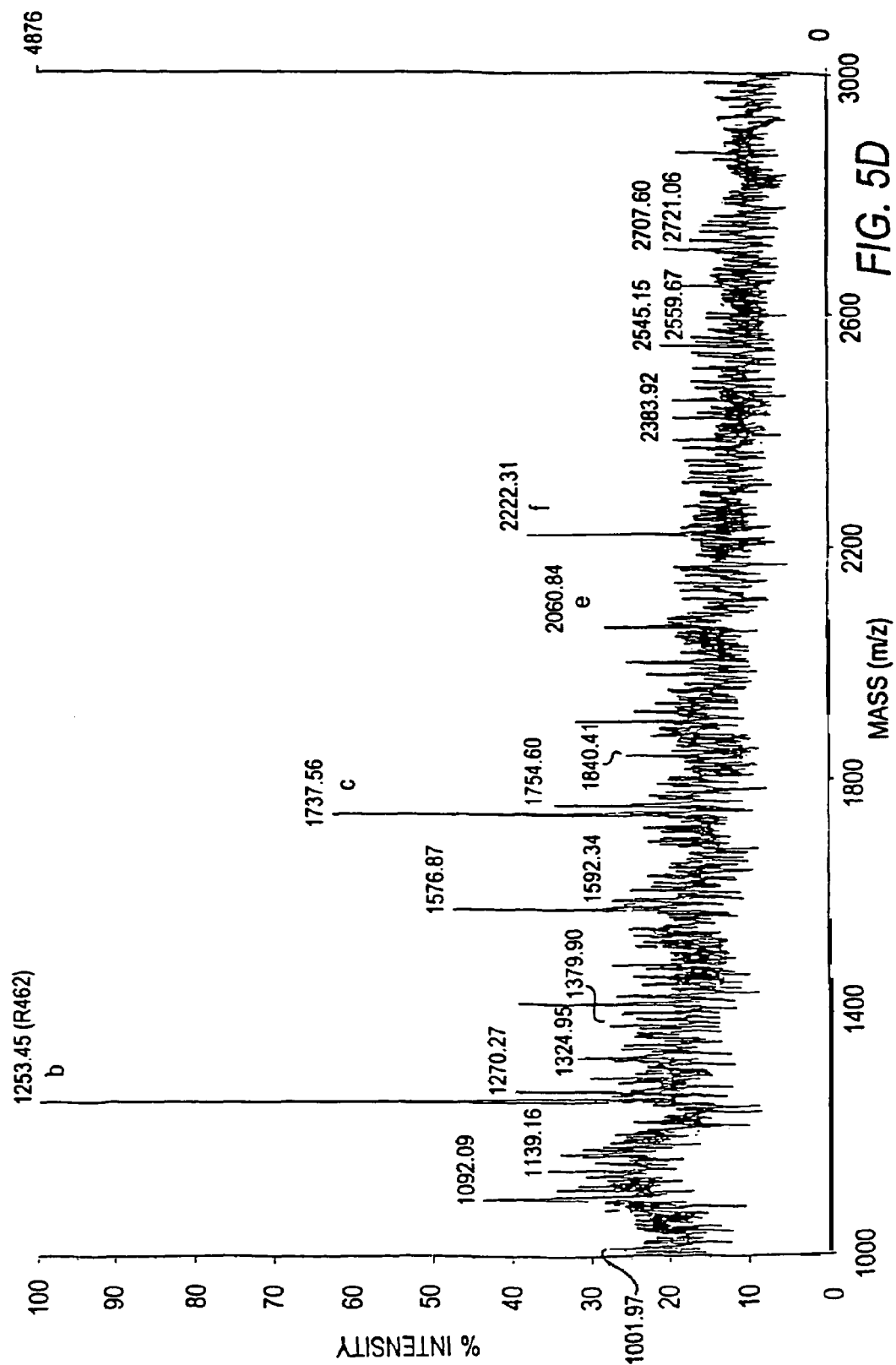

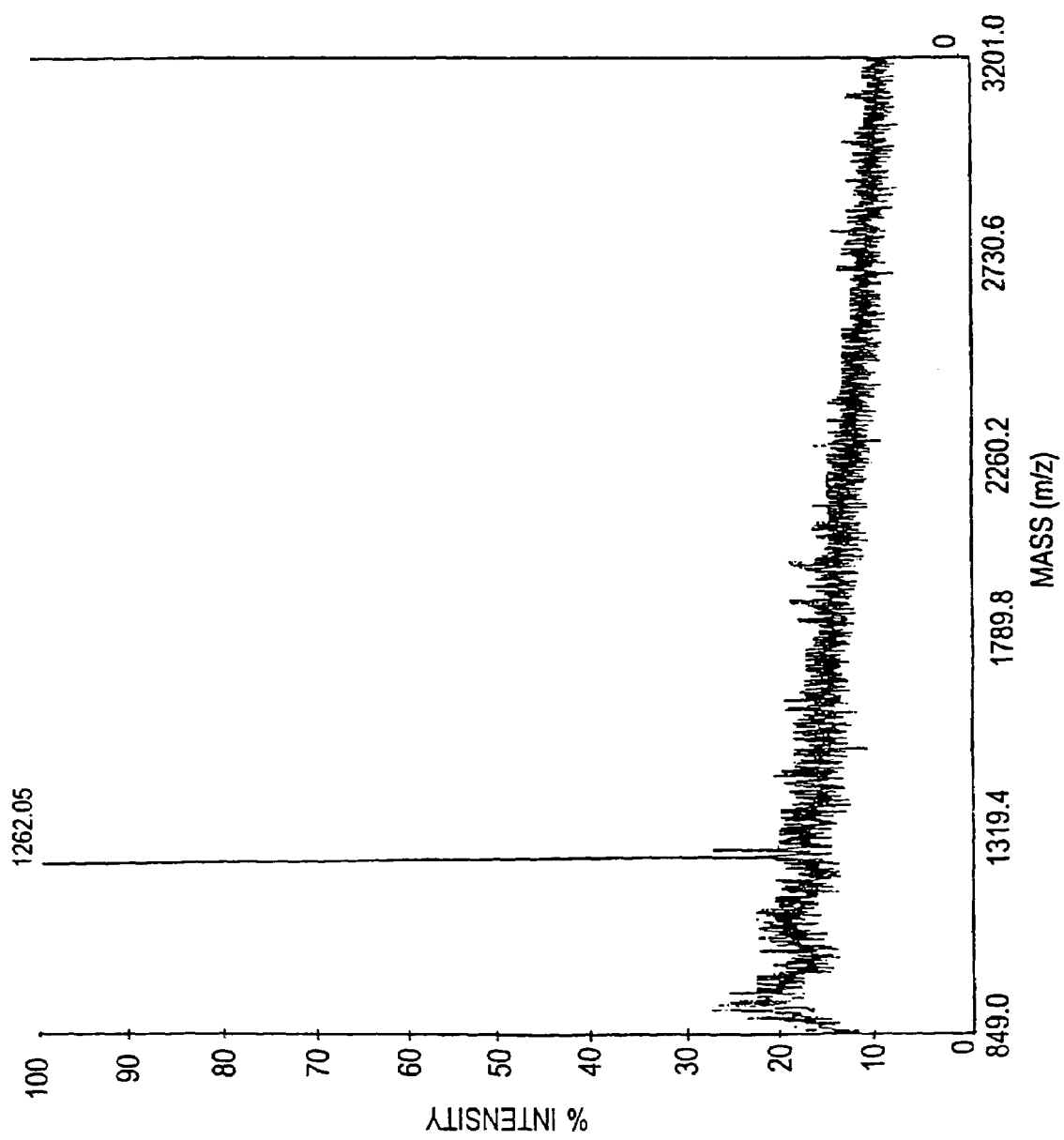

ALG3 Blast 05-22-01

```
Sequences producing significant alignments:                        (bits)  Value gi|586444|sp|P38179|ALG3_YEAST    DOLICHYL-P-MAN:MAN(5)GLCNAC(...797   0.0
gi|3024226|sp|Q92685|ALG3_HUMAN   DOLICHYL-P-MAN:MAN(5)GLCNAC...173   7e-43
gi|3024221|sp|Q24332|NT56_DROVI   LETHAL(2)NEIGHBOUR OF TID P...145   3e-34
gi|3024222|sp|Q27333|NT56_DROME   LETHAL(2)NEIGHBOUR OF TID P...121   3e-27
gi|10720153|sp|P82149|NT53_DROME  LETHAL(2)NEIGHBOUR OF TID ...121   5e-27
gi|1707982|sp|P40989|GLS2_YEAST   1,3-BETA-GLUCAN SYNTHASE CO... 32   2.8
gi|1346146|sp|P38631|GLS1_YEAST   1,3-BETA-GLUCAN SYNTHASE CO... 31   6.6
```

Alignments

Yeast

>gi|586444|sp|P38179|ALG3_YEAST DOLICHYL-P-
MAN:MAN(5)GLCNAC(2)-PP-DOLICHYL MANNOSYLTRANSFERASE
(DOL-P-MAN DEPENDENT ALPHA(1-3)-MANNOSYLTRANSFERASE)
(HM-1 KILLER TOXIN RESISTANCE PROTEIN)
Length = 458

Score = 797 bits (2059), Expect = 0.0
Identities = 422/458 (92%), Positives = 422/458 (92%)

```
Query: 1    MEGEQSPQGEKSLQRKQFVRPPLDLWQDLKDGVRYVIFDCRANLIVMPLLILFESMLCKI 60
            MEGEQSPQGEKSLQRKQFVRPPLDLWQDLKDGVRYVIFDCRANLIVMPLLILFESMLCKI
Sbjct: 1    MEGEQSPQGEKSLQRKQFVRPPLDLWQDLKDGVRYVIFDCRANLIVMPLLILFESMLCKI 60

Query: 61   IIKKVAYTEIDYKAYMEQIEMIQLDGMLDYSQVSGGTGPLVYPAGHVLIYKMMYWLTEGM 120
            IIKKVAYTEIDYKAYMEQIEMIQLDGMLDYSQVSGGTGPLVYPAGHVLIYKMMYWLTEGM
Sbjct: 61   IIKKVAYTEIDYKAYMEQIEMIQLDGMLDYSQVSGGTGPLVYPAGHVLIYKMMYWLTEGM 120

Query: 121  DHVERGQVFFRYLYLLTLALQMACYYLLHLPPWCVVLACLSKRLHSIYVLRLFNDCFTTL 180
            DHVERGQVFFRYLYLLTLALQMACYYLLHLPPWCVVLACLSKRLHSIYVLRLFNDCFTTL
Sbjct: 121  DHVERGQVFFRYLYLLTLALQMACYYLLHLPPWCVVLACLSKRLHSIYVLRLFNDCFTTL 180

Query: 181  FMVVTVLGAIVASRCHQRPKLKKSLALVISATYSMAVSIKMNALLYFPAMMISLFILNDA 240
            FMVVTVLGAIVASRCHQRPKLKKSLALVISATYSMAVSIKMNALLYFPAMMISLFILNDA
Sbjct: 181  FMVVTVLGAIVASRCHQRPKLKKSLALVISATYSMAVSIKMNALLYFPAMMISLFILNDA 240

Query: 241  NVILTLLDLVAMIAWQVAVAVPFLRSFPQQYLHCAFNFGRKFMYQWSINWQMMDEEAFND 300
            NVILTLLDLVAMIAWQVAVAVPFLRSFPQQYLHCAFNFGRKFMYQWSINWQMMDEEAFND
Sbjct: 241  NVILTLLDLVAMIAWQVAVAVPFLRSFPQQYLHCAFNFGRKFMYQWSINWQMMDEEAFND 300

Query: 301  KRFXXXXXXXXXXXXXXXFVTRYPRILPDLWSSLCHPLRKNAVLNANPAKTIPFVLIASN 360
            KRF             FVTRYPRILPDLWSSLCHPLRKNAVLNANPAKTIPFVLIASN
Sbjct: 301  KRFHLALLISHLIALTTLFVTRYPRILPDLWSSLCHPLRKNAVLNANPAKTIPFVLIASN 360

Query: 361  FIGVLFSRSLHYQFLSWYHWTLPILIFWSGMPFFVGPIWYVLHEWCWNSYPPNSQXXXXX 420
            FIGVLFSRSLHYQFLSWYHWTLPILIFWSGMPFFVGPIWYVLHEWCWNSYPPNSQ
Sbjct: 361  FIGVLFSRSLHYQFLSWYHWTLPILIFWSGMPFFVGPIWYVLHEWCWNSYPPNSQASTLL 420

Query: 421  XXXXXXXXXXXXXXXXSGSVALAKSHLRTTSSMEKKLN 458
                            SGSVALAKSHLRTTSSMEKKLN
Sbjct: 421  LALNTVLLLLLALTQLSGSVALAKSHLRTTSSMEKKLN 458
```

FIG. 16-1

Human

>gi|3024226|sp|Q92685|ALG3_HUMAN DOLICHYL-P-MAN:MAN(5)GLCNAC(2)-PP-DOLICHYL
MANNOSYLTRANSFERASE
        (DOL-P-MAN DEPENDENT ALPHA(1-3)-MANNOSYLTRANSFERASE)
        (NOT56-LIKE PROTEIN)
        Length = 438

Score = 173 bits (439), Expect = 7e-43
 Identities = 133/396 (33%), Positives = 195/396 (48%), Gaps = 28/396 (7%)

```
Query:  26  WQDLKDGVRYVIFDCRANLIVMPLLILFESMLCKIIIKKVAYTEIDYKAYMEQIEMIQLD  85
            WQ+      R ++ + R L+V  L L E  +   +I +VAYTEID+KAYM ++E +  ++
Sbjct:  29  WQER----RLLLREPRYTLLVAACLCLAEVGITFWVIHRVAYTEIDWKAYMAEVEGV-IN  83

Query:  86  GMLDYSQVSGGTGPLVYPAGHVLIYKMMYWLTEGMDHVERGQVFFRYLYLLTLALQMACY  145
            G  DY+Q+ G TGPLVYPAG V I+ +Y+ T     + Q F LYL TL L    Y
Sbjct:  84  GTYDYTQLQGDTGPLVYPAGFVYIFMGLYYATSRGTDIRMAQNIFAVLYLATLLLVFLIY  143

Query: 146  Y-LLHLPPWC-VVLACLSKRLHSIYVLRLFNDCFTTLFMVVTVLGAIVASRCHQRPKLKK  203
            +    +PP+    + C S R+HSI+VLRLFND    + + +L +      QR
Sbjct: 144  HQTCKVPPFVFFFMCCASYRVHSIFVLRLFNDP-----VAMVLLFLSINLLLAQRWGWG-  197

Query: 204  SLALVISATYSMAVSIKMNALLYFPAMMISLFILNDANVILTLLDLVAMIAWQVAVAVPF  263
                   +S+AVS+KMN LL+ P ++    L       L L + A + QV +  +PF
Sbjct: 198  ------CCFFSLAVSVKMNVLLFAPGLLFLLLTQFGFRGALPKLGICAGL--QVVLGLPF  249

Query: 264  LRSFPQQYLHCAFNFGRKFMYQWSINWQMMDEEAFNDKRFXXXXXXXXXXXXXXXXFVTRY  323
            L   P  YL +F+ GR+F++ W++NW+ + E F  + F                 + R+
Sbjct: 250  LLENPSGYLSRSFDLGRQFLFHWTVNWRFLPEALFLHRAFHLALLTAHLTLLLLFALCRW  309

Query: 324  PRILPDLWSSLCHPLRKNAVLNANPAKTIPFVLIASNFIGVLFSRSLHYQFLSWYHWTLP  383
            R    + S L  P ++           I    L SNFIG+ FSRSLHYQF  WY  TLP
Sbjct: 310  HRTGESILSLLRDPSKRKVPPQPLTPNQIVSTLFTSNFIGICFSRSLHYQFYVWYFHTLP  369

Query: 384  ILIF-----WSGMPFFVGPIWYVLHEWCWNSYPPNS  414
            +L++     W    +  +  +   E WN+YP  S
Sbjct: 370  YLLWAMPARWLTHLLRLLVLGLI--ELSWNTYPSTS  403
```

Drosophila Vi

>gi|3024221|sp|Q24332|NT56_DROVI LETHAL(2)NEIGHBOUR OF TID PROTEIN (NOT58)
        Length = 526

Score = 145 bits (366), Expect = 3e-34
 Identities = 103/273 (37%), Positives = 157/273 (56%), Gaps = 17/273 (6%)

```
Query:  33  VRYVIFDCRANLIVMPLLILFESMLCKIIIKKVAYTEIDYKAYMEQIEMIQLDGMLDYSQ  92
            ++Y+ F+  A   IV  L++L E+++    ++I++V YTEID+KAYM++ E   L+G  +YS
Sbjct:  34  IKYLAFEPAALPIVSVLIVLAEAVINVLVIQRVPYTEIDWKAYMQECEGF-LNGTTNYSL  92

Query:  93  VSGGTGPLVYPAGHVLIYKMMYWLTEGMDHVERGQVFFRYLYLLTLALQMACYYLLH-LP  151
            + G TGPLVYPA  V IY +Y+LT  +V  Q F +YLL + L + Y        +P
Sbjct:  93  LRGDTGPLVYPAAFVYIYSGLYYLTGQGTNVRLAQYIFACIYLLQMCLVLRLYTKSRKVP  152

Query: 152  PWCVVLACL-SKRLHSIYVLRLFNDCFTTLFMVVTVLGAIVASRCHQRPKLKKSLALVIS  210
            P+  +VL+    S R+HSIYVLRLFND      L   +L A +    QR L        S
Sbjct: 153  PYVLVLSAFTSYRIHSIYVLRLFNDPVAIL-----LLYAALNLFLDQRWTLG-------S  200

Query: 211  ATYSMAVSIKMNALLYFPAMMISLFILNDANVILTLLDLVAMIAWQVAVAVPFLRSFPQQ  270
                YS+AV +KMN + A + LF L   +  V+ TL+ L   Q+ +   PFLR+ P +
Sbjct: 201  ICYSLAVGVKMN--ILLFAPALLLFYLANLGVLRTLVQLTICAVLQLFIGAPFLRTHPME  258
```

FIG. 16-2

```
Query: 271 YLHCAFNFGRKFMYQWSINWQMMDEEAFNDKRF 303
            YL +F+ GR F ++W++N++ + +E F  + F
Sbjct: 259 YLRGSFDLGRIFEHKWTVNYRFLSKELFEQREF 291

Score =  53.3 bits (127), Expect = 1e-06
 Identities = 31/62 (50%), Positives = 41/62 (66%), Gaps = 6/62 (9%)

Query: 352 IPFVLIASNFIGVLFSRSLHYQFLSWYHWTLPILIFWSGMPFFVGPIWYVLH--EWCWNS 409
            +PF L  NFIGV +RSLHYQF WY +LP L+ WS P+ +G + +L  E+CWN+
Sbjct: 412 LPFFL--CNFIGVACARSLHYQFYIWYFHSLPYLV-WS-TPYSLGVRYLILGIIEYCWNT 467

Query: 410 YP 411
            YP
Sbjct: 468 YP 469
```

Drosophila melanogaster

```
>gi|3024222|sp|Q27333|NT56_DROME LETHAL(2)NEIGHBOUR OF TID PROTEIN (NOT56)
(NOT45)
          Length = 510

Score =  121 bits (305), Expect = 3e-27
 Identities = 96/272 (35%), Positives = 154/272 (56%), Gaps = 17/272 (6%)

Query: 34  RYVIFDCRANLIVMPLLILFESMLCKIIKKVAYTEIDYKAYMEQIEMIQLDGMLDYSQV 93
           +Y++ + A IV ++L E ++ ++I++V YTEID+ AYM++ E  L+G +YS +
Sbjct: 36  KYLLLEPAALPIVGLFVLLAELVINVVVIQRVPYTEIDWVAYMQECEGF-LNGTTNYSLL 94

Query: 94  SGGTGPLVYPAGHVLIYKMMYWLTEGMDHVERGQVFFRYLYLLTLALQMACYYLLH-LPP 152
             G TGPLVYPA V IY +Y++T  +V Q F +YLL LAL +  Y   +PP
Sbjct: 95  RGDTGPLVYPAAFVYIYSALYYVTSHGTNVRLAQYIFAGIYLLQLALVLRLYSKSRKVPP 154

Query: 153 WCVVLACL-SKRLHSIYVLRLFNDCFTTLFMVVTVLGAIVASRCHQRPKLKKSLALVISA 211
           + +VL+  S R+HSIYVLRLFND  + V +L A +  +R L         S
Sbjct: 155 YVLVLSAFTSYRIHSIYVLRLFNDP-----VAVLLLYAALNLFLDRRWTLG-------ST 202

Query: 212 TYSMAVSIKMNALLYFPAMMISLFILNDANVILTLLDLVAMIAWQVAVAVPFLRSFPQQY 271
            +S+AV +KMN +  A + LF L +  ++ T+L L   O+ + PFL + P +Y
Sbjct: 203 FFSLAVGVKMN--ILLFAPALLLFYLANLGLLRTILQLAVCGVIQLLLGAPFLLTHPVEY 260

Query: 272 LHCAFNFGRKFMYQWSINWQMMDEEAFNDKRF 303
           L  +F+ GR F ++W++N++ + + F ++ F
Sbjct: 261 LRGSFDLGRIFEHKWTVNYRFLSRDVFENRTF 292

Score = 49.4 bits (117), Expect = 2e-05
 Identities = 27/60 (45%), Positives = 35/60 (58%), Gaps = 2/60 (3%)

Query: 352 IPFVLIASNFIGVLFSRSLHYQFLSWYHWTLPILIFWSGMPFFVGPIWYVLHEWCWNSYP 411
           +PF L  N +GV SRSLHYQF WY +LP L + +  V +  L E+CWN+YP
Sbjct: 407 LPFFL--CNLVGVACSRSLHYQFYVWYFHSLPYLAWSTPYSLGVRCLILGLIEYCWNTYP 464
```

FIG. 16-3

```
Matrix: BLOSUM62
Gap Penalties: Existence: 11, Extension: 1
Number of Hits to DB: 28883317
Number of Sequences: 96469
Number of extensions: 1107545
Number of successful extensions: 2870
Number of sequences better than 10.0: 16
Number of HSP's better than 10.0 without gapping: 5
Number of HSP's successfully gapped in prelim test: 11
Number of HSP's that attempted gapping in prelim test: 2839
Number of HSP's gapped (non-prelim): 23 length of query: 458
length of database: 35,174,128
effective HSP length: 45
effective length of query: 413
effective length of database: 30,833,023
effective search space: 12734038499
effective search space used: 12734038499
T: 11
A: 40
X1: 15 ( 7.1 bits)
X2: 38 (14.6 bits)
X3: 64 (24.7 bits)
S1: 40 (21.8 bits)
S2: 67 (30.4 bits)
```

FIG.16-4

*S. cerevisiae ALG3*
ATGGAAGGTGAACAGTCTCCGCAAGGTGAAAAGTCTCTGCAAAGGAAGC
AATTTGTCAGACCTCCGCTGGATCTGTGGCAGGATCTCAAGGACGGTGTG
CGCTACGTGATCTTCGATTGTAGGGCCAATCTTATCGTTATGCCCCTTTTG
ATTTTGTTCGAAAGCATGCTGTGCAAGATTATCATTAAGAAGGTAGCTTAC
ACAGAGATCGATTACAAGGCGTACATGGAGCAGATCGAGATGATTCAGCT
CGATGGCATGCTGGACTACTCAGGTGAGTGGTGGAACGGGCCCGCTGG
TGTATCCAGCAGGCCACGTCTTGATCTACAAGATGATGTACTGGCTAACA
GAGGGAATGGACCACGTTGAGCGCGGGCAAGTGTTTTTCAGATACTTGTA
TCTCCTTACACTGGCGTTACAAATGGCGTGTTACTACCTTTTACATCTACC
ACCGTGGTGTGTGGTCTTGGCGTGCCTCTCTAAAAGATTGCACTCTATTTA
CGTGCTACGGTTATTCAATGATTGCTTCACTACTTTGTTTATGGTCGTCACG
GTTTTGGGGGCTATCGTGGCCAGCAGGTGCCATCAGCGCCCCAAATTAAA
GAAGTCCCTTGCGCTGGTGATCTCCGCAACATACAGTATGGCTGTGAGCA
TTAAGATGAATGCGCTGTTGTATTTCCCTGCAATGATGATTTCTCTATTCAT
CCTTAATGACGCGAACGTAATCCTTACTTTGTTGGATCTCGTTGCGATGAT
TGCATGGCAAGTCGCAGTTGCAGTGCCCTTCCTGCGCAGCTTTCCGCAACA
GTACCTGCATTGCGCTTTTAATTTCGGCAGGAAGTTTATGTACCAATGGAG
TATCAATTGGCAAATGATGGATGAAGAGGCTTTCAATGATAAGAGGTTCC
ACTTGGCCCTTTTAATCAGCCACCTGATAGCGCTCACCACACTGTTCGTCA
CAAGATACCCTCGCATCCTGCCCGATTTATGGTCTTCCCTGTGCCATCCGC
TGAGGAAAAATGCAGTGCTCAATGCCAATCCCGCCAAGACTATTCCATTC
GTTCTAATCGCATCCAACTTCATCGGCGTCCTATTTTCAAGGTCCCTCCAC
TACCAGTTTCTATCCTGGTATCACTGGACTTTGCCTATACTGATCTTTTGGT
CGGGAATGCCCTTCTTCGTTGGTCCCATTTGGTACGTCTTGCACGAGTGGT
GCTGGAATTCCTATCCACCAAACTCACAAGCAAGCACGCTATTGTTGGCA
TTGAATACTGTTCTGTTGCTTCTATTGGCCTTGACGCAGCTATCTGGTTCGG
TCGCCCTCGCCAAAAGCCATCTTCGTACCACCAGCTCTATGGAAAAAAG
CTCAACTGA

*S. cerevisiae* Alg3p
MEGEQSPQGEKSLQRKQFVRPPLDLWQDLKDGVRYVIFDCRANLIVMPLLIL
FESMLCKIIKKVAYTEIDYKAYMEQIEMIQLDGMLDYSQVSGGTGPLVYPAG
HVLIYKMMYWLTEGMDHVERGQVFFRYLYLLTLALQMACYYLLHLPPWCV
VLACLSKRLHSIYVLRLFNDCFTTLFMVVTVLGAIVASRCHQRPKLKKSLALV
ISATYSMAVSIKMNALLYFPAMMISLFILNDANVILTLLDLVAMIAWQVAVA
VPFLRSFPQQYLHCAFNFGRKFMYQWSINWQMMDEEAFNDKRFHLALLISHL
IALTTLFVTRYPRILPDLWSSLCHPLRKNAVLNANPAKTIPFVLIASNFIGVLFS
RSLHYQFLSWYHWTLPILIFWSGMPFFVGPIWYVLHEWCWNSYPPNSQASTL
LLALNTVLLLLLALTQLSGSVALAKSHLRTTSSMEKKLN

FIG. 17

*P. pastoris ALG3*
ATGCCTCCGATAGAGCCAGCTGAAAGGCCAAAGCTTACGCTGAAAAATGT
TATCGGTGATCTAGTGGCTCTTATTCAAAACGTTTTATTTAACCCAGATTTT
AGTGTCTTCGTTGCACCTCTTTTATGGTTAGCTGATTCCATTGTTATCAAGG
TGATCATTGGCACTGTTTCCTACACAGATATTGATTTTCTTCATATATGCA
ACAAATCTTTAAAATTCGACAAGGAGAATTAGATTATAGCAACATATTTG
GTGACACCGGTCCATTGGTTTACCCAGCCGGCCATGTTCATGCTTACTCAG
TACTTTCGTGGTACAGTGATGGTGGAGAAGACGTCAGTTTCGTTCAACAA
GCATTTGGTTGGTTATACCTAGGTTGCTTGTTACTATCCATCAGCTCCTACT
TTTTCTCTGGCTTAGGGAAAATACCTCCGGTTTATTTTGTTTGTTGGTAGC
GTCCAAGAGACTGCATTCAATATTTGTATTGAGACTCTTCAATGACTGTTT
AACAACATTTTTGATGTTGGCAACTATAATCATCCTTCAACAAGCAAGTAG
CTGGAGGAAAGATGGCACAACTATTCCATTATCTGTCCCTGATGCTGCAG
ATACGTACAGTTTAGCCATCTCTGTAAAGATGAATGCGCTGCTATACCTCC
CAGCATTCCTACTACTCATATATCTCATTTGTGACGAAAATTTGATTAAAG
CCTTGGCACCTGTTCTAGTTTTGATATTGGTGCAAGTAGGAGTCGGTTATT
CGTTCATTTTACCGTTGCACTATGATGATCAGGCAAATGAAATTCGTTCTG
CCTACTTTAGACAGGCTTTTGACTTTAGTCGCCAATTTCTTTATAAGTGGA
CGGTTAATTGGCGCTTTTGAGCCAAGAAACTTTCAACAATGTCCATTTTC
ACCAGCTCCTGTTTGCTCTCCATATTATTACGTTAGTCTTGTTCATCCTCAA
GTTCCTCTCTCCTAAAAACATTGGAAAACCGCTTGGTAGATTTGTGTTGGA
CATTTTCAAATTTTGGAAGCCAACCTTATCTCCAACCAATATTATCAACGA
CCCAGAAAGAAGCCCAGATTTTGTTTACACCGTCATGGCTACTACCAACTT
AATAGGGGTGCTTTTTGCAAGATCTTTACACTACCAGTTCCTAAGCTGGTA
TGCGTTCTCTTTGCCATATCTCCTTTACAAGGCTCGTCTGAACTTTATAGCA
TCTATTATTGTTTATGCCGCTCACGAGTATTGCTGGTTGGTTTTCCCAGCTA
CAGAACAAAGTTCCGCGTTGTTGGTATCTATCTTACTACTTATCCTGATTC
TCATTTTTACCAACGAACAGTTATTTCCTTCTCAATCGGTCCCTGCAGAAA
AAAAGAATACATAA

*P. pastoris Alg3p*
MPPIEPAERPKLTLKNVIGDLVALIQNVLFNPDFSVFVAPLLWLADSIVIKVIIG
TVSYTDIDFSSYMQQIFKIRQGELDYSNIFGDTGPLVYPAGHVHAYSVLSWYS
DGGEDVSFVQQAFGWLYLGCLLLSISSYFFSGLGKIPPVYFVLLVASKRLHSIF
VLRLFNDCLTTFLMLATIILQQASSWRKDGTTIPLSVPDAADTYSLAISVKMN
ALLYLPAFLLLIYLICDENLIKALAPVLVLILVQVGVGYSFILPLHYDDQANEIR
SAYFRQAFDFSRQFLYKWTVNWRFLSQETFNNVHFHQLLFALHIITLVLFILKF
LSPKNIGKPLGRFVLDIFKFWKPTLSPTNIINDPERSPDFVYTVMATTNLIGVLF
ARSLHYQFLSWYAFSLPYLLYKARLNFIASIIVYAAHEYCWLVFPATEQSSAL
LVSILLLILILIFTNEQLFPSQSVPAEKKNT

FIG. 18

*P. pastoris* ALG3 BLAST

```
Sequences producing significant alignments:                          (bits)  Value gi|586444|sp|P38179|ALG3_YEAST  Dolichyl-P-Man:Man(5)GlcNAc(...228   2e-58
gi|12802365|gb|AAK07848.1|AF309689_10  putative NOT-56 manno...212   8e-54
gi|984725|gb|AAA75352.1|  ORF 1                               206    4e-52
gi|7492702|pir||T39084  probable mannosyltransferase - fissi...176   8e-43
gi|16226531|gb|AAL16193.1|AF428424_1  At2g47760/F17A22.15 [A...164   2e-39
gi|25367230|pir||B84919  Not56-like protein [imported] - Ara...164   3e-39
gi|25814791|emb|CAB70171.2|  Hypothetical protein K09E4.2 [C...161   2e-38
gi|17535001|ref|NP_496950.1|  Putative plasma membrane membr...160   3e-38
gi|1654000|emb|CAA70220.1|  Not56-like protein [Homo sapiens...155   2e-36
gi|13279206|gb|AAH04313.1|AAH04313  Unknown (protein for IMA...154   2e-36
gi|22122365|ref|NP_666051.1|  hypothetical protein MGC36684  ...150  3e-35
gi|21292031|gb|EAA04176.1|  agCP3388 [Anopheles gambiae str....120   4e-26
gi|1780792|emb|CAA71167.1|  lethal(2)neighbour of tid [Droso...114   3e-24
```

Alignments

*S. cerevisiae*

```
Score =  228 bits (580), Expect = 2e-58
Identities = 154/429 (35%), Positives = 229/429 (53%), Gaps = 37/429 (8%)

Query:   9  RPKLTLKNVIGDLVALIQNVLFNPDFSVFVAPLLWLADSIVIKVIIGTVSYTDIDFSSYM  68
            RP L L   DL   ++ V+F+   ++ V PLL L +S++ K+II  V+YT+ID+ +YM
Sbjct:  20  RPPLDLWQ---DLKDGVRYVIFDCRANLIVMPLLILFESMLCKIIIKKVAYTEIDYKAYM  76

Query:  69  QQIFKIR-QGELDYSNIFGDTGPLVYPAGHVHAYSVLSWYSDGGEDVSFVQQAFGWLYLG 127
            +QI I+  G LDYS + G TGPLVYPAGHV  Y ++ W ++G + V Q F +LYL
Sbjct:  77  EQIEMIQLDGMLDYSQVSGGTGPLVYPAGHVLIYKMMYWLTEGMDHVERGQVFFRYLYLL 136

Query: 128  CLLLSISSYFFSGLGKIPPVYFVLLVASKRLHSIFVLRLFNDCLTTFLMLATI---IILQ 184
            L L ++ Y+   L  +PP  VL   SKRLHSI+VLRLFNDC TT M+ T+    I+
Sbjct: 137  TLALQMACYY---LLHLPPWCVVLACLSKRLHSIYVLRLFNDCFTTLFMVVTVLGAIVAS 193

Query: 185  QASSWRKDGTTIPLSVPDAADTYSLAISVKMNXXXXXXXXXXXXXXXXCDENLIKALAPXX 244
            +    K   L +  + TYS+A+S+KMN                    D N+I L
Sbjct: 194  RCHQRPKLKKSLALVI---SATYSMAVSIKMNALLYFPAMMISLFILNDANVILTLLDLV 250

Query: 245  XXXXXXXXXXYSFILPLHYDDQANEIRSAYFRQAFDFSRQFLYKWTVNWRFLSQETFNNV 304
                      F+          Y    AF+F R+F+Y+W++NW+ + ++E FN+
Sbjct: 251  AMIAWQVAVAVPFL--------RSFPQQYLHCAFNFGRKFMYQWSINWQMMDEEAFNDK  301

Query: 305  HFHQLLFALHIITL-VLFILKFLSPKNIGKPLGRFVLDIFKFWKPTLSPTNIIN-DPERS 362
             FH  L  H+I L  LF+ ++      R + D++   L   ++N +P ++
Sbjct: 302  RFHLALLISHLIALTTLFVTRY----------PRILPDLWSSLCHPLRKNAVLNANPAKT 351

Query: 363  PDFVYTVMATTNLIGVLFARSLHYQFLSWYAFSLPYLLYKARLNFIASIIVYAAHEYCWL 422
               F   V+  +N  IGVLF+RSLHYQFLSWY  +LP L++  +   F  I Y HE+CW
Sbjct: 352  IPF---VLIASNFIGVLFSRSLHYQFLSWYHWTLPILIFWSGMPFFVGPIWYVLHEWCWN 408

Query: 423  VFPATEQSS 431
            +P   Q+S
Sbjct: 409  SYPPNSQAS 417
```

FIG. 19-1

*Neurospora crassa*

Score = 212 bits (540), Expect = 8e-54
Identities = 140/400 (35%), Positives = 212/400 (53%), Gaps = 29/400 (7%)

```
Query:  35 SVFVAPLLWLADSIVIKVIIGTVSYTDIDFSSYMQQIFKIRQGELDYSNIFGDTGPLVYP 94
           S  + P L+L D+++   +II V YT+ID+++YM+Q+  +I  GE DY+ + G TGPLVYP
Sbjct:  33 SKLIPPALFLVDALLCGLIIWKVPYTEIDWAAYMEQVSQILSGERDYTKVRGGTGPLVYP 92

Query:  95 AGHVHAYSVLSWYSDGGEDVSFVQQAFGWLYLGCLLLSISSYFFSGLGKIPPVYFVLLVA 154
           A HV+ Y+ L  +D G ++  QQ F  LY+  L +  + Y+    K PP  F LL
Sbjct:  93 AAHVYIYTGLYHLTDEGRNILLAQQLFAGLYMVTLAVVMGCYW---QAKAPPYLFPLLTL 149

Query: 155 SKRLHSIFVLRLFNDCLTTFLMLATIIILQQASSWRKDGTTIPLSVPDAADTYSLAISVK 214
           SKRLHSIFVLR FNDC    + I  Q+  +W+              A  Y+L + VK
Sbjct: 150 SKRLHSIFVLRCFNDCFAVLFLWLAIFFFQR-RNWQA-----------GALLYTLGLGVK 197

Query: 215 MNXXXXXXXXXXXXXXXXCDENLIKALAPXXXXXXXXXXXXYSFILPLHYDDQANEIRSAY 274
           M        + +  L          F+  HY +                Y
Sbjct: 198 MTLLLSLPAVGIVLFLGSG-SFVTTLQLVATMGLVQILIGVPFL--AHYPTE-------Y 247

Query: 275 FRQAFDFSRQFLYKWTVNWRFLSQETFNNVHFHQLLFALHIITLVLFI-LKFLSPKNIGK 333
            +AF+  SRQF  +KWTVNWRF+  +E F  +  F   L ALH++  L  +FI +++  P    K
Sbjct: 248 LSRAFELSRQFFFKWTVNWRFVGEEIFLSKGFALTLLALHVLVLGIFITTRWIKPAR--K 305

Query: 334 PLGRFVLDIFKFWKPTLS-PTNIINDPERSPDFVYTVMATTNLIGVLFARSLHYQFLSWY 392
           L ++  +   KP L+ P +      +P ++ T + + N +G+LFARSLHYQF ++
Sbjct: 306 SLVQLISPVLLAGKPPLTVPEHRAAARDVTPRYIMTTILSANAVGLLFARSLHYQFYAYV 365

Query: 393 AFSLPYLLYKARLNFIASIIVYAAHEYCWLVFPATEQSSA 432
           A+S P+LL++A L+ +    +++A HE+ W VFP+T SSA
Sbjct: 366 AWSTPFLLWRAGLHPVLVYLLWAVHEWAWNVFPSTPASSA 405
```

*Schizosaccharomyces pombe*

Score = 176 bits (445), Expect = 8e-43
Identities = 132/390 (33%), Positives = 194/390 (49%), Gaps = 35/390 (8%)

```
Query:  42 LWLADSIVIKVIIGTVSYTDIDFSSYMQQIFKIRQGELDYSNIFGDTGPLVYPAGHVHAY 101
           L L +   + II V YT+ID+ +YM+Q+    GE DY ++ G TGPLVYP GHV Y
Sbjct:  30 LLLLEIPFVFAIISKVPYTEIDWIAYMEQVNSFLLGERDYKSLVGCTGPLVYPGGHVFLY 89

Query: 102 SVLSWYSDGGEDVSFVQQAFGWLYLGCLLLSISSYFFSGLGKIPPVYFVLLVASKRLHSI 161
           ++L + +DGG ++  Q F ++Y + +I Y F + + P +VLL+ SKRLHSI
Sbjct:  90 TLLYYLTDGGTNIVRAQYIFAFVYW--ITTAIVGYLFK-IVRAPFYIYVLLILSKRLHSI 146

Query: 162 FVLRLFNDCLTTFLMLATIIILQQASSWRKDGTTIPLSVPDAADTYSLAISVKMNXXXXX 221
           F+LRLFND   +L  I+   W +            A+  S+A SVKM+
Sbjct: 147 FILRLFNDGFNS-LFSSLFILSSCKKKWVR----------ASILLSVACSVKMSSLLYV 194

Query: 222 XXXXXXXXXXCDENLIKALAPXXXXXXXXXXXXYSFILPLHYDDQANEIRSAYFRQAFDF 281
                     L++ L P               +  +  +  +Y+ QAFDF
Sbjct: 195 PAYLVL--------LLQILGPKKTWMHIFVIIVQILFSIPF----LAYFWSYWTQAFDF 242

Query: 282 SRQFLYKWTVNWRFLSQETFNNVHFHQLLFALHIITLVLFILKFLSPKNIGKPLGRFVLD 341
            R F YKWTVNWRF+  +  F   F   +  LH+  LV F  K  +    P
Sbjct: 243 GRAFDYKWTVNWRFIPRSIFESTSFSTSILFLHVALLVAFTCKHWNKLSRATP------- 295

Query: 342 IFKFWKPTLSPTNIINDPERSPDFVYTVMATTNLIGVLFARSLHYQFLSWYAFSLPYLLY 401
            F       L+  +    +P+F+++T +AT+NLIG+L ARSLHYQF +W+A+  PYL Y
```

FIG. 19-2

```
Sbjct: 296  -FAMVNSMLTLKPLPKLQLATPNFIFTALATSNLIGILCARSLHYQFYAWFAWYSPYLCY 354

Query: 402  KARLNFIASIIVYAAHEYCWLVFPATEQSS 431
            +A      I  ++   EY W VFP+T+ SS
Sbjct: 355  QASFPAPIVIGLWMLQEYAWNVFPSTKLSS 384
Arabidopsis thaliana Score =  164 bits (415), Expect = 2e-39
 Identities = 131/391 (33%), Positives = 194/391 (49%), Gaps = 29/391 (7%)

Query:  42  LWLADSIVIKVIIGTVSYTDIDFSSYMQQIFKIRQGELDYSNIFGDTGPLVYPAGHVHAY 101
            L LAD+I++ +II V YT ID+ +YM Q+    GE DY N+ GDTGPLVYPAG ++ Y
Sbjct:  39  LILADAILVALIIAYVPYTKIDWDAYMSQVSGFLGGERDYGNLKGDTGPLVYPAGFLYVY  98

Query: 102  SVLSWYSDGGEDVSFVQQAFGWLYLGCLLLSISSYFFSGLGKIPPVYFVLLVASKRLHSI 161
            S +   + G +V  Q  FG LY+ L ++  Y  +   +P    LL  SKR+HSI
Sbjct:  99  SAVQNLTGG--EVYPAQILFGVLYIVNLGIVLIIYVKTDV--VPWWALSLLCLSKRIHSI 154

Query: 162  FVLRLFNDCLTTFLMLATIIILQQASSWRKDGTTIPLSVPDAADTYSLAISVKMNXXXXX 221
            FVLRLFNDC    L+ A++ +      +RK    + +           +S A+SVKMN
Sbjct: 155  FVLRLFNDCFAMTLLHASMALFL----YRKWHLGMLV--------FSGAVSVKMNVLLYA 202

Query: 222  XXXXXXXXXXCDENLIKALAPXXXXXXXXXXXXYSFILPLHYDDQANEIRSAYFRQAFDF 281
                       N+I  ++           F++            +Y    AFD
Sbjct: 203  PTLLLLLLKAM--NIIGVVSALAGAALAQILVGLPFLITYPV---------SYIANAFDL 251

Query: 282  SRQFLYKWTVNWRFLSQETFNNVHFHQLLFALHIITLVLFILKFLSPKNIGKPLGRFVLD 341
            R F++  W+VN+++F+ +  F + F  L H+  LV F   +  K+ G  +G
Sbjct: 252  GRVFIHFWSVNFKFVPERVFVSKEFAVCLLIAHLFLLVAFA-NYKWCKHEGGIIGFMRSR 310

Query: 342  IFKFWKP-TLSPTNIINDPERSPDFVYTVMATTNLIGVLFARSLHYQFLSWYAFSLPYLL 400
              F  P +LS +++    + +V T M  N IG++FARSLHYQF SWY +SLPYLL
Sbjct: 311  HFFLTLPSSLSFSDVSASRIITKEHVVTAMFVGNFIGIVFARSLHYQFYSWYFYSLPYLL 370

Query: 401  YKARLNFIASIIVYAAHEYCWLVFPATEQSS 431
            ++         +I++   E CW V+P+T SS
Sbjct: 371  WRTPFPTWLRLIMFLGIELCWNVYPSTPSSS 401
```

FIG. 19-3

*K. lactis* ALG3

TTTGTTTACAAGCTGATACCAACGAACATGAATACACCGGCAGGTTTACT
GAAGATTGGCAAAGCTAACCTTTTACATCCTTTTACCGATGCTGTATTCAG
TGCGATGAGAGTAAACGCAGAACAAATTGCATACATTTTACTTGTTACCA
ATTACATTGGAGTACTATTTGCTCGATCATTACACTACCAATTCCTATCTT
GGTACCATTGGACGTTACCAGTACTATTGAATTGGGCCAATGTTCCGTATC
CGCTATGTGTGCTATGGTACCTAACACATGAGTGGTGCTGGAACAGCTAT
CCGCCAAACGCTACTGCATCCACACTGCTACACGCGTGTAACACATACTG
TTATTGGCTGTATTCTTAAGAGGACCCGCAAACTCGAAAAGTGGTGATAA
CGAAACAACACACGAGAAAGCTGAG

*K. lactis* Alg3p

FVYKLIPTNMNTPAGLLKIGKANLLHPFTDAVFSAMRVNAEQIAYILLVTNYI
GVLFARSLHYQFLSWYHWTLPVLLNWANVPYPLCVLWYLTHEWCWNSYPP
NATASTLLHACNTYCYWLYSZEDPQTRKVVITKQHTRKL

FIG. 20

K. lactis ALG3 BLAST

```
                                                                  Score      E
Sequences producing significant alignments:                      (bits)   Value gi|586444|sp|P38179|ALG3_YEAST  Dolichyl-P-Man:Man(5)GlcNAc(...   125    1e-28
gi|984725|gb|AAA75352.1|  ORF 1                                    94    4e-19
gi|16226531|gb|AAL16193.1|AF428424_1  At2g47760/F17A22.15 [A...    72    1e-12
gi|25367230|pir||B84919  Not56-like protein [imported] - Ara...    72    1e-12
gi|21292031|gb|EAA04176.1|  agCP3388 [Anopheles gambiae str...     69    2e-11
gi|20892051|ref|XP_148657.1|  similar to Lethal(2)neighbour ...    65    2e-10
```

Alignments

*S. cerevisiae*

```
Score = 125 bits (314), Expect = 1e-28
Identities = 60/120 (50%), Positives = 83/120 (69%), Gaps = 1/120 (0%)
Frame = +3

Query: 66   ANLLHPFT-DAVFSAMRVNAEQIAYILLVTNYIGVLFARSLHYQFLSWYHWTLPVLLNWA 242
            ++L HP   +AV +A     A+ I ++L+ +N+IGVLF+RSLHYQFLSWYHWTLP+L+ W+
Sbjct: 332  SSLCHPLRKNAVLNANP--AKTIPFVLIASNFIGVLFSRSLHYQFLSWYHWTLPILIFWS 389

Query: 243  NVPYPLCVLWYLTHEWCWNSYPPNATASTLLHACNTYCYWLYS*EDPQTRKVVITKQHTR 422
            +P+ +  +WY+ HEWCWNSYPPN+ ASTLL A NT    L +    + V + K H R
Sbjct: 390  GMPFFVGPIWYVLHEWCWNSYPPNSQASTLLLALNTVLLLLLA-LTQLSGSVALAKSHLR 448
```

*A. thaliana*

```
Score = 72.0 bits (175), Expect = 1e-12
Identities = 42/107 (39%), Positives = 57/107 (53%), Gaps = 3/107 (2%)
Frame = +3

Query: 84   FTDAVFSAMRVNAEQIAYILLVTNYIGVLFARSLHYQFLSWYHWTLPVLLNWANVPYPLC 263
            F+D  S + +E +   + V N+IG++FARSLHYQF SWY ++LP LL       P  L
Sbjct: 322  FSDVSASRI-ITKEHVVTAMFVGNFIGIVFARSLHYQFYSWYFYSLPYLLWRTPFPTWLR 380

Query: 264  VLWYLTHEWCWNSYPPNATASTL---LHACNTYCYWLYS*EDPQTRK 395
            ++ +L  E CWN YP  ++S L   LH    WL   DP  K
Sbjct: 381  LIMFLGIELCWNVYPSTPSSSGLLLCLHLIILVGLWLAPSVDPYQLK 427
```

FIG. 21

>gi|6754685|ref|NM_010795.1| Mus musculus mannoside acetyl glucosaminyltransferase 3 (Mgat3), mRNA

```
ATGAAGATGAGACGCTACAAGCTCTTTCTCATGTTCTGTATGGCTGGCCTGTGCCTCATATCCTTCCTGC
ACTTCTTTAAGACCTTATCCTATGTCACCTTCCCGAGAGAACTGGCCTCCCTCAGCCCTAACCTCGTATC
CAGCTTCTTCTGGAACAATGCCCCTGTCACTCCCCAGGCCAGTCCGGAGCCGGGTGGCCCCGACCTATTG
CGGACACCCCTCTACTCCCACTCTCCCCTGCTCCAGCCACTGTCCCCGAGCAAGGCCACAGAGGAACTGC
ACCGGGTGGACTTCGTGTTGCCGGAGGACACCACGGAGTATTTTGTGCGCACCAAAGCTGGTGGTGTGTG
CTTCAAACCAGGTACCAGGATGCTGGAGAAACCTTCGCCAGGGCGGACAGAGGAGAAGCCCGAAGTGTCT
GAGGGCTCCTCAGCCCGGGGACCTGCTCGGAGGCCCATGAGGCACGTGTTGAGTACGCGGGAGCGCCTGG
GCAGCCGGGGCACTAGGCGCAAGTGGGTTGAGTGTGTGTGCCTGCCAGGCTGGCACGGGCCCAGTTGCGG
GGTGCCCACGGTGGTGCAGTATTCCAACCTGCCCACCAAGGAACGCCTGGTACCCAGGGAGGTACCGAGG
CGGGTTATCAACGCCATCAACATCAACCACGAGTTCGACCTGCTGGATGTGCGCTTCCATGAGCTGGGAG
ATGTTGTGGACGCCTTCGTGGTCTGTGAATCTAATTTCACCGCCTACGGGGAGCCTCGGCCGCTCAAGTT
CCGAGAGATGCTGACCAATGGCACCTTCGAGTACATCCGCCACAAGGTGCTCTATGTCTTCCTGGACCAT
TTCCCACCTGGTGGCCGTCAGGACGGCTGGATTGCGGATGACTACCTGCGCACCTTCCTCACCCAGGATG
GCGTCTCCCGCCTGCGCAACCTGCGGCCCGATGACGTCTTTATCATCGACGATGCGGACGAGATCCCTGC
GCGTGATGGTGTGCTGTTCCTCAAACTCTACGATGGCTGGACAGAGCCCTTCGCCTTCCACATGCGGAAG
TCCCTGTATGGTTTCTTCTGGAAGCAGCCGGGCACACTGGAGGTGGTGTCAGGCTGCACCATGGACATGC
TGCAGGCCGTGTATGGGCTGGATGGCATCCGCCTGCGCCGCCGCCAGTACTACACCATGCCCAACTTCCG
GCAGTATGAGAACCGCACCGGCCACATCCTAGTGCAGTGGTCTCTCGGCAGCCCCCTGCACTTCGCGGGC
TGGCATTGCTCCTGGTGCTTCACACCCGAGGGCATCTACTTTAAACTCGTGTCAGCCCAGAATGGCGACT
TCCCCCGCTGGGGTGACTATGAGGACAAGAGGGACCTCAATTACATCCGCAGCTTGATCCGCACTGGGGG
ATGGTTCGACGGAACGCAGCAGGAGTACCCTCCTGCGGACCCCAGTGAGCACATGTATGCTCCTAAATAC
CTGCTCAAGAACTATGACCAGTTCCGCTACTTGCTGGAAAATCCCTACGGGAGCCCAAGAGCACTGTAG
AGGGTGGGCGCCAGAACCAGGGCTCAGATGGAAGGCCATCTGCTGTCAGGGGCAAGTTGGATACAGTGGA
GGGCTAG
```

>gi|2117717|pir||JC4362 beta-1,4-mannosyl-glycoprotein 4-beta-N-acetylglucosaminyltransferase (EC 2.4.1.144) III - mouse
MRRYKLFLMFCMAGLCLISFLHFFKTLSYVTFPRELASLSPNLISSFFWNNAPVTPQASPEPGDPDLLRT
PLYSHSPLLQPLSPSKATEELHRVDFVLPEDTTEYFVRTKAGGVCFKPGTRMLEKPSPGRTEEKTEVSEG
SSARGPARRPMRHVLSSRERLGSRGTRRKWVECVCLPGWHGPSCGVPTVVQYSNLPTKERLVPREVPRRV
INAININHEFDLLDVRFHELGDVVDAFVVCDSNFTAYGEPRPLKFREMLTNGTFEYIRHKVLYVFLDHFP
PGGRQDGWIADDYLRTFLTQDGVSRLRNLRPDDVFIIDDADEIPARDGVLFLKLYDGWTEPFAFHMRKSL
YGFFWKQPGTLEVVSGCTMDMLQAVYGLDGIRLRRRQYYTMPNFRQYENRTGHILVQWSLGSPLHFAGWH
CSWCFTPEGIYFKLVSAQNGDFPRWGDYEDKRDLNYIRSLIRTGGWFDGTQQEYPPADPSEHMYAPKYLL
KNYDQFRYLLENPYREPKSTVEGGRQNQGSDGRSSAVRGKLDTAEG

FIG. 24

FIG. 25
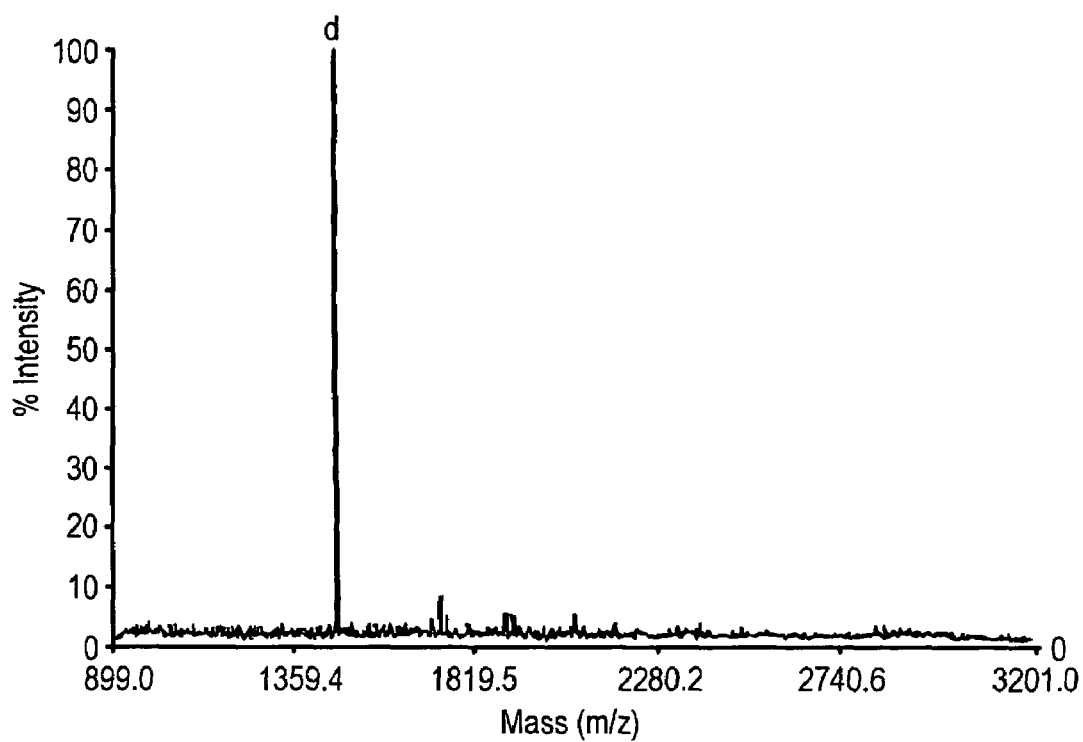
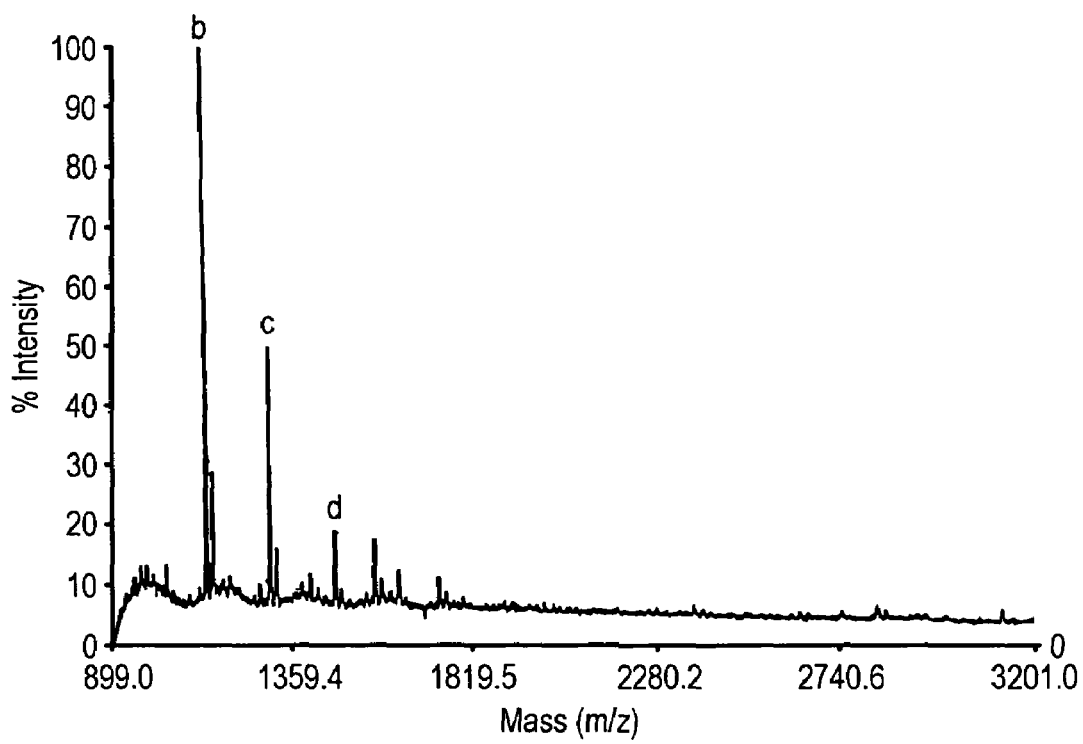

FIG. 26
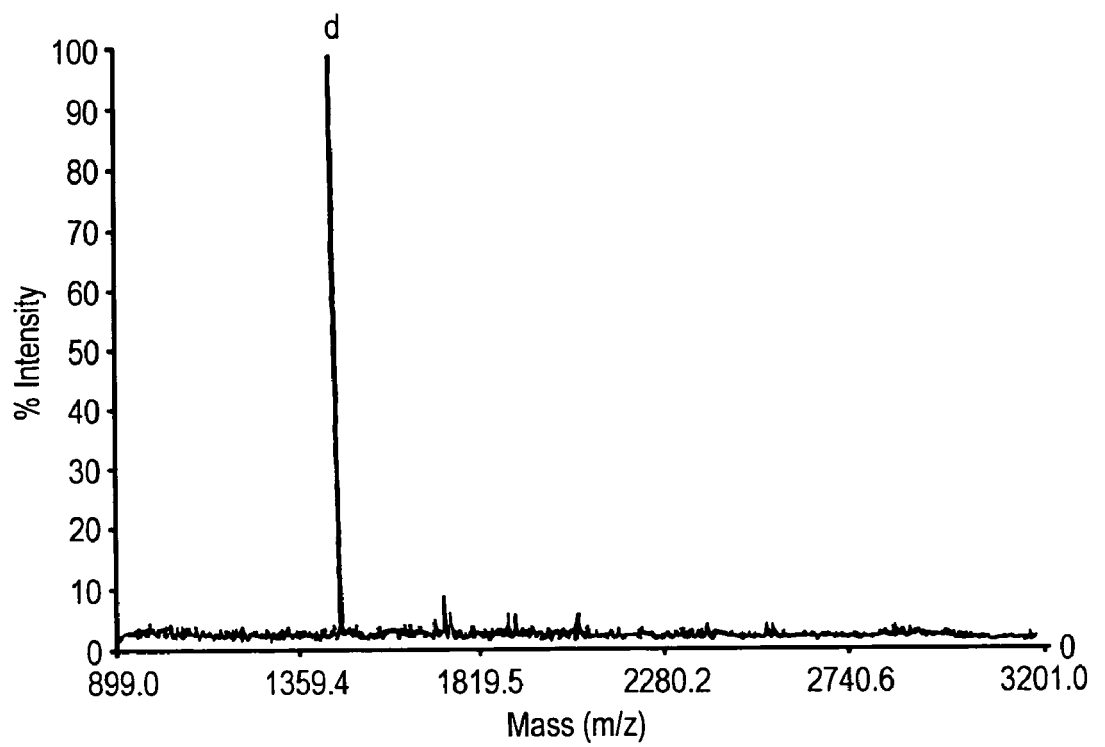
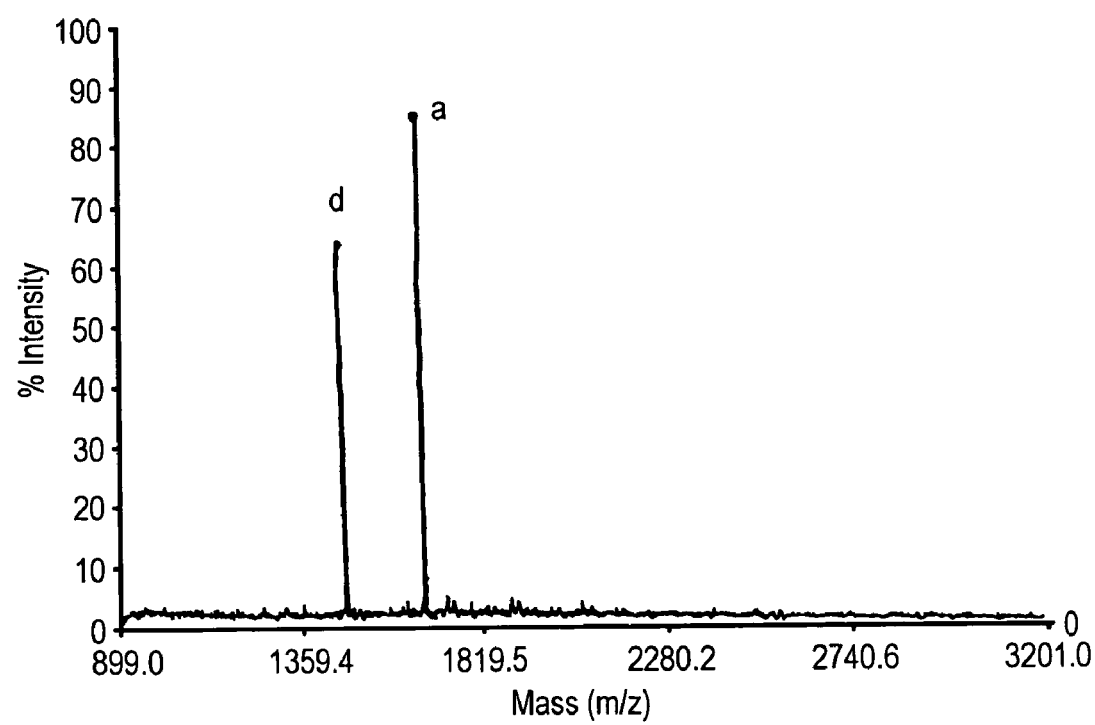

FIG. 27
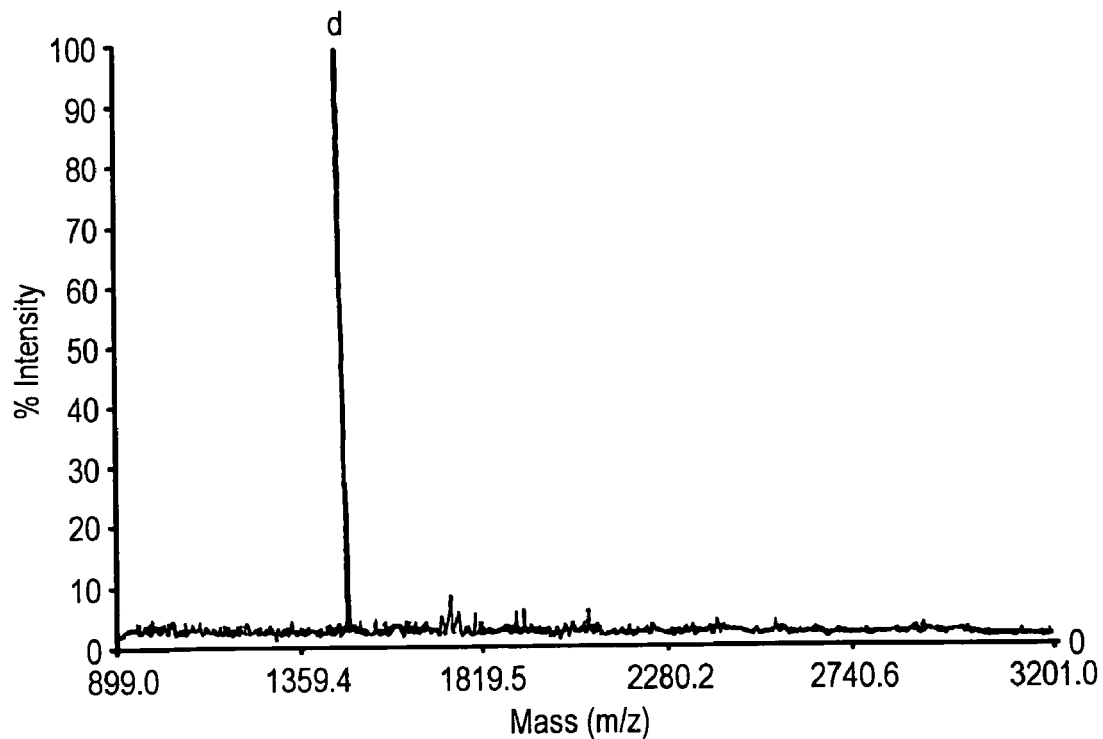
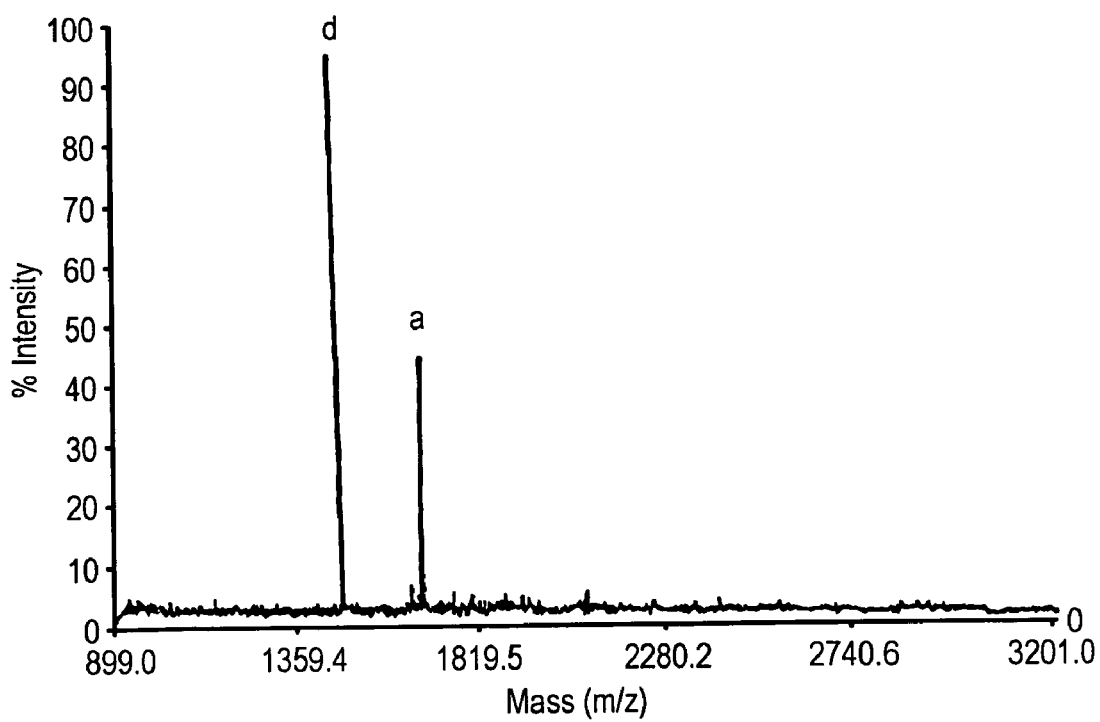

FIG. 28
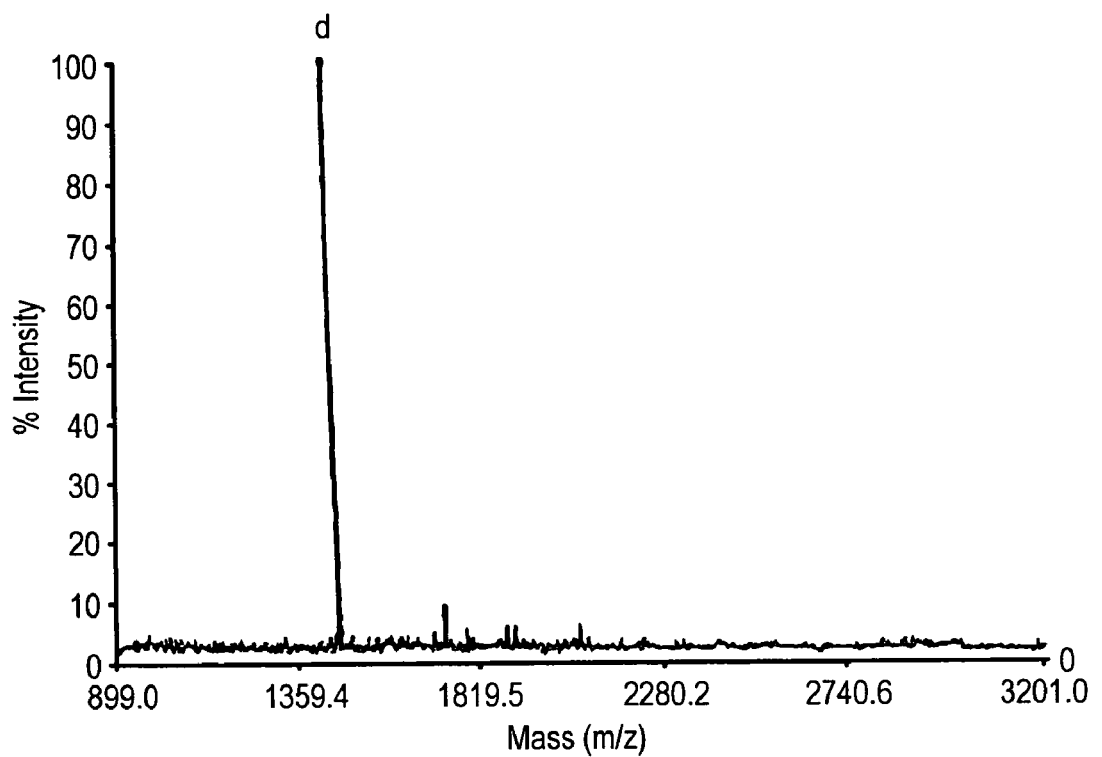
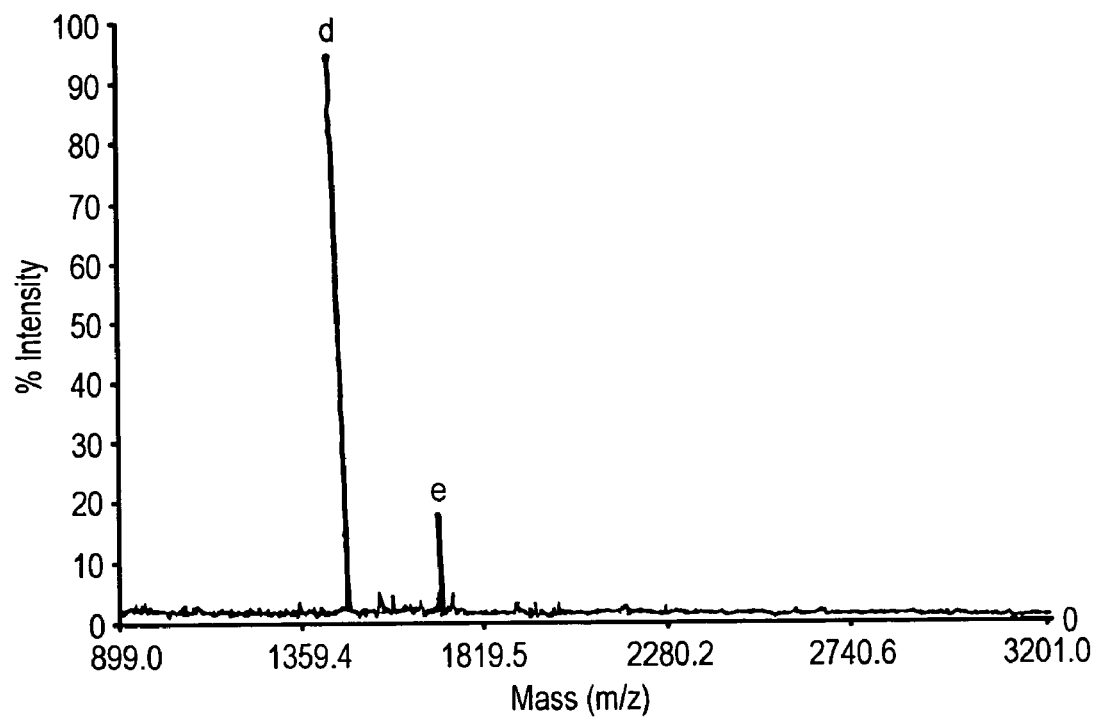

SEQUENCE LISTING

<160> NUMBER OF SEQ ID NOS: 101

<210> SEQ ID NO 1

<400> SEQUENCE: 1

000

<210> SEQ ID NO 2

<400> SEQUENCE: 2

000

<210> SEQ ID NO 3
<211> LENGTH: 21
<212> TYPE: DNA
<213> ORGANISM: artificial
<220> FEATURE:
<223> OTHER INFORMATION: Primer A for target gene in P. pastoris
      (1,6-mannosyltransferase)

<400> SEQUENCE: 3
atggcgaagg cagatggcag t                                            21

<210> SEQ ID NO 4
<211> LENGTH: 21
<212> TYPE: DNA
<213> ORGANISM: artificial
<220> FEATURE:
<223> OTHER INFORMATION: Primer B for target gene in P. pastoris
      (1,6-mannosyltransferase)

<400> SEQUENCE: 4
ttagtccttc caacttcctt c                                            21

<210> SEQ ID NO 5
<211> LENGTH: 26
<212> TYPE: DNA
<213> ORGANISM: artificial
<220> FEATURE:
<223> OTHER INFORMATION: Primer A for target gene in P. pastoris (1,2
      mannosyltransferases)
<220> FEATURE:
<221> NAME/KEY: misc_feature
<222> LOCATION: (9)..(9)
<223> OTHER INFORMATION: wherein "n" is equal to "a" or "t" or "g" or
      "c".
<220> FEATURE:
<221> NAME/KEY: misc_feature
<222> LOCATION: (12)..(12)
<223> OTHER INFORMATION: wherein "n" is equal to "a" or "t" or "g" or
      "c".
<220> FEATURE:
<221> NAME/KEY: misc_feature
<222> LOCATION: (18)..(18)
<223> OTHER INFORMATION: wherein "n" is equal to "a" or "t" or "g" or
      "c".

<400> SEQUENCE: 5
taytggmgng tngarcynga yathaa                                       26

<210> SEQ ID NO 6
<211> LENGTH: 20
<212> TYPE: DNA
<213> ORGANISM: artificial
<220> FEATURE:
<223> OTHER INFORMATION: Primer B for target gene in P. pastoris (1,2
      mannosyltransferases)
<220> FEATURE:
<221> NAME/KEY: misc_feature
<222> LOCATION: (6)..(6)
<223> OTHER INFORMATION: wherein "n" is equal to "a" or "t" or "g" or
      "c".
<220> FEATURE:
<221> NAME/KEY: misc_feature
<222> LOCATION: (12)..(12)
<223> OTHER INFORMATION: wherein "n" is equal to "a" or "t" or "g" or
      "c".

<400> SEQUENCE: 6
gcrtcncccc anckytcrta                                                    20

<210> SEQ ID NO 7

<400> SEQUENCE: 7

000

<210> SEQ ID NO 8

<400> SEQUENCE: 8

000

<210> SEQ ID NO 9
<211> LENGTH: 458
<212> TYPE: PRT
<213> ORGANISM: Saccharomyces cerevisiae

<400> SEQUENCE: 9

```
Met Glu Gly Glu Gln Ser Pro Gln Gly Glu Lys Ser Leu Gln Arg Lys
1               5                   10                  15

Gln Phe Val Arg Pro Pro Leu Asp Leu Trp Gln Asp Leu Lys Asp Gly
            20                  25                  30

Val Arg Tyr Val Ile Phe Asp Cys Arg Ala Asn Leu Ile Val Met Pro
        35                  40                  45

Leu Leu Ile Leu Phe Glu Ser Met Leu Cys Lys Ile Ile Lys Lys
    50                  55                  60

Val Ala Tyr Thr Glu Ile Asp Tyr Lys Ala Tyr Met Glu Gln Ile Glu
65                  70                  75                  80

Met Ile Gln Leu Asp Gly Met Leu Asp Tyr Ser Gln Val Ser Gly Gly
                85                  90                  95

Thr Gly Pro Leu Val Tyr Pro Ala Gly His Val Leu Ile Tyr Lys Met
            100                 105                 110

Met Tyr Trp Leu Thr Glu Gly Met Asp His Val Glu Arg Gly Gln Val
        115                 120                 125

Phe Phe Arg Tyr Leu Tyr Leu Leu Thr Leu Ala Leu Gln Met Ala Cys
    130                 135                 140

Tyr Tyr Leu Leu His Leu Pro Pro Trp Cys Val Val Leu Ala Cys Leu
145                 150                 155                 160

Ser Lys Arg Leu His Ser Ile Tyr Val Leu Arg Leu Phe Asn Asp Cys
                165                 170                 175

Phe Thr Thr Leu Phe Met Val Val Thr Val Leu Gly Ala Ile Val Ala
            180                 185                 190

Ser Arg Cys His Gln Arg Pro Lys Leu Lys Lys Ser Leu Ala Leu Val
        195                 200                 205

Ile Ser Ala Thr Tyr Ser Met Ala Val Ser Ile Lys Met Asn Ala Leu
    210                 215                 220

Leu Tyr Phe Pro Ala Met Met Ile Ser Leu Phe Ile Leu Asn Asp Ala
225                 230                 235                 240

Asn Val Ile Leu Thr Leu Leu Asp Leu Ala Met Ile Ala Trp Gln
                245                 250                 255

Val Ala Val Ala Val Pro Phe Leu Arg Ser Phe Pro Gln Gln Tyr Leu
            260                 265                 270

His Cys Ala Phe Asn Phe Gly Arg Lys Phe Met Tyr Gln Trp Ser Ile
```

```
               275                 280                 285
Asn Trp Gln Met Met Asp Glu Glu Ala Phe Asn Asp Lys Arg Phe His
        290                 295                 300

Leu Ala Leu Leu Ile Ser His Leu Ile Ala Leu Thr Thr Leu Phe Val
305                 310                 315                 320

Thr Arg Tyr Pro Arg Ile Leu Pro Asp Leu Trp Ser Ser Leu Cys His
                    325                 330                 335

Pro Leu Arg Lys Asn Ala Val Leu Asn Ala Asn Pro Ala Lys Thr Ile
                340                 345                 350

Pro Phe Val Leu Ile Ala Ser Asn Phe Ile Gly Val Leu Phe Ser Arg
            355                 360                 365

Ser Leu His Tyr Gln Phe Leu Ser Trp Tyr His Trp Thr Leu Pro Ile
        370                 375                 380

Leu Ile Phe Trp Ser Gly Met Pro Phe Phe Val Gly Pro Ile Trp Tyr
385                 390                 395                 400

Val Leu His Glu Trp Cys Trp Asn Ser Tyr Pro Pro Asn Ser Gln Ala
                    405                 410                 415

Ser Thr Leu Leu Leu Ala Leu Asn Thr Val Leu Leu Leu Leu Leu Ala
                420                 425                 430

Leu Thr Gln Leu Ser Gly Ser Val Ala Leu Ala Lys Ser His Leu Arg
            435                 440                 445

Thr Thr Ser Ser Met Glu Lys Lys Leu Asn
        450                 455

<210> SEQ ID NO 10
<211> LENGTH: 458
<212> TYPE: PRT
<213> ORGANISM: Saccharomyces cerevisiae

<400> SEQUENCE: 10

Met Glu Gly Glu Gln Ser Pro Gln Gly Glu Lys Ser Leu Gln Arg Lys
1               5                   10                  15

Gln Phe Val Arg Pro Pro Leu Asp Leu Trp Gln Asp Leu Lys Asp Gly
            20                  25                  30

Val Arg Tyr Val Ile Phe Asp Cys Arg Ala Asn Leu Ile Val Met Pro
        35                  40                  45

Leu Leu Ile Leu Phe Glu Ser Met Leu Cys Lys Ile Ile Lys Lys
    50                  55                  60

Val Ala Tyr Thr Glu Ile Asp Tyr Lys Ala Tyr Met Glu Gln Ile Glu
65                  70                  75                  80

Met Ile Gln Leu Asp Gly Met Leu Asp Tyr Ser Gln Val Ser Gly Gly
                85                  90                  95

Thr Gly Pro Leu Val Tyr Pro Ala Gly His Val Leu Ile Tyr Lys Met
            100                 105                 110

Met Tyr Trp Leu Thr Glu Gly Met Asp His Val Glu Arg Gly Gln Val
        115                 120                 125

Phe Phe Arg Tyr Leu Tyr Leu Leu Thr Leu Ala Leu Gln Met Ala Cys
    130                 135                 140

Tyr Tyr Leu Leu His Leu Pro Pro Trp Cys Val Val Leu Ala Cys Leu
145                 150                 155                 160

Ser Lys Arg Leu His Ser Ile Tyr Val Leu Arg Leu Phe Asn Asp Cys
                165                 170                 175

Phe Thr Thr Leu Phe Met Val Val Thr Val Leu Gly Ala Ile Val Ala
            180                 185                 190
```

```
Ser Arg Cys His Gln Arg Pro Lys Leu Lys Lys Ser Leu Ala Leu Val
            195                 200                 205

Ile Ser Ala Thr Tyr Ser Met Ala Val Ser Ile Lys Met Asn Ala Leu
        210                 215                 220

Leu Tyr Phe Pro Ala Met Met Ile Ser Leu Phe Ile Leu Asn Asp Ala
225                 230                 235                 240

Asn Val Ile Leu Thr Leu Leu Asp Leu Val Ala Met Ile Ala Trp Gln
                245                 250                 255

Val Ala Val Ala Val Pro Phe Leu Arg Ser Phe Pro Gln Gln Tyr Leu
            260                 265                 270

His Cys Ala Phe Asn Phe Gly Arg Lys Phe Met Tyr Gln Trp Ser Ile
        275                 280                 285

Asn Trp Gln Met Met Asp Glu Glu Ala Phe Asn Asp Lys Arg Phe His
    290                 295                 300

Leu Ala Leu Leu Ile Ser His Leu Ile Ala Leu Thr Thr Leu Phe Val
305                 310                 315                 320

Thr Arg Tyr Pro Arg Ile Leu Pro Asp Leu Trp Ser Leu Cys His
                325                 330                 335

Pro Leu Arg Lys Asn Ala Val Leu Asn Ala Asn Pro Ala Lys Thr Ile
            340                 345                 350

Pro Phe Val Leu Ile Ala Ser Asn Phe Ile Gly Val Leu Phe Ser Arg
        355                 360                 365

Ser Leu His Tyr Gln Phe Leu Ser Trp Tyr His Trp Thr Leu Pro Ile
    370                 375                 380

Leu Ile Phe Trp Ser Gly Met Pro Phe Phe Val Gly Pro Ile Trp Tyr
385                 390                 395                 400

Val Leu His Glu Trp Cys Trp Asn Ser Tyr Pro Pro Asn Ser Gln Ala
                405                 410                 415

Ser Thr Leu Leu Leu Ala Leu Asn Thr Val Leu Leu Leu Leu Leu Ala
            420                 425                 430

Leu Thr Gln Leu Ser Gly Ser Val Ala Leu Ala Lys Ser His Leu Arg
        435                 440                 445

Thr Thr Ser Ser Met Glu Lys Lys Leu Asn
    450                 455

<210> SEQ ID NO 11
<211> LENGTH: 389
<212> TYPE: PRT
<213> ORGANISM: Saccharomyces cerevisiae

<400> SEQUENCE: 11

Trp Gln Asp Leu Lys Asp Gly Val Arg Tyr Val Ile Phe Asp Cys Arg
1               5                   10                  15

Ala Asn Leu Ile Val Met Pro Leu Leu Ile Leu Phe Glu Ser Met Leu
            20                  25                  30

Cys Lys Ile Ile Ile Lys Lys Val Ala Tyr Thr Glu Ile Asp Tyr Lys
        35                  40                  45

Ala Tyr Met Glu Gln Ile Glu Met Ile Gln Leu Asp Gly Met Leu Asp
    50                  55                  60

Tyr Ser Gln Val Ser Gly Gly Thr Gly Pro Leu Val Tyr Pro Ala Gly
65                  70                  75                  80

His Val Leu Ile Tyr Lys Met Met Tyr Trp Leu Thr Glu Gly Met Asp
                85                  90                  95

His Val Glu Arg Gly Gln Val Phe Phe Arg Tyr Leu Tyr Leu Leu Thr
            100                 105                 110
```

```
Leu Ala Leu Gln Met Ala Cys Tyr Tyr Leu Leu His Leu Pro Pro Trp
            115                 120                 125

Cys Val Val Leu Ala Cys Leu Ser Lys Arg Leu His Ser Ile Tyr Val
        130                 135                 140

Leu Arg Leu Phe Asn Asp Cys Phe Thr Thr Leu Phe Met Val Val Thr
145                 150                 155                 160

Val Leu Gly Ala Ile Val Ala Ser Arg Cys His Gln Arg Pro Lys Leu
                165                 170                 175

Lys Lys Ser Leu Ala Leu Val Ile Ser Ala Thr Tyr Ser Met Ala Val
            180                 185                 190

Ser Ile Lys Met Asn Ala Leu Leu Tyr Phe Pro Ala Met Met Ile Ser
        195                 200                 205

Leu Phe Ile Leu Asn Asp Ala Asn Val Ile Leu Thr Leu Leu Asp Leu
    210                 215                 220

Val Ala Met Ile Ala Trp Gln Val Ala Val Ala Val Pro Phe Leu Arg
225                 230                 235                 240

Ser Phe Pro Gln Gln Tyr Leu His Cys Ala Phe Asn Phe Gly Arg Lys
                245                 250                 255

Phe Met Tyr Gln Trp Ser Ile Asn Trp Gln Met Met Asp Glu Glu Ala
            260                 265                 270

Phe Asn Asp Lys Arg Phe His Leu Ala Leu Leu Ile Ser His Leu Ile
        275                 280                 285

Ala Leu Thr Thr Leu Phe Val Thr Arg Tyr Pro Arg Ile Leu Pro Asp
    290                 295                 300

Leu Trp Ser Ser Leu Cys His Pro Leu Arg Lys Asn Ala Val Leu Asn
305                 310                 315                 320

Ala Asn Pro Ala Lys Thr Ile Pro Phe Val Leu Ile Ala Ser Asn Phe
                325                 330                 335

Ile Gly Val Leu Phe Ser Arg Ser Leu His Tyr Gln Phe Leu Ser Trp
            340                 345                 350

Tyr His Trp Thr Leu Pro Ile Leu Ile Phe Trp Ser Gly Met Pro Phe
        355                 360                 365

Phe Val Gly Pro Ile Trp Tyr Val Leu His Glu Trp Cys Trp Asn Ser
370                 375                 380

Tyr Pro Pro Asn Ser
385

<210> SEQ ID NO 12
<211> LENGTH: 375
<212> TYPE: PRT
<213> ORGANISM: Homo sapiens

<400> SEQUENCE: 12

Trp Gln Glu Arg Arg Leu Leu Arg Glu Pro Arg Tyr Thr Leu Leu
1               5                   10                  15

Val Ala Ala Cys Leu Cys Leu Ala Glu Val Gly Ile Thr Phe Trp Val
            20                  25                  30

Ile His Arg Val Ala Tyr Thr Glu Ile Asp Trp Lys Ala Tyr Met Ala
        35                  40                  45

Glu Val Glu Gly Val Ile Asn Gly Thr Tyr Tyr Thr Gln Leu Gln
    50                  55                  60

Gly Asp Thr Gly Pro Leu Val Tyr Pro Ala Gly Phe Val Tyr Ile Phe
65                  70                  75                  80

Met Gly Leu Tyr Tyr Ala Thr Ser Arg Gly Thr Asp Ile Arg Met Ala
```

```
                85                  90                  95
Gln Asn Ile Phe Ala Val Leu Tyr Leu Ala Thr Leu Leu Val Phe
            100                 105                 110

Leu Ile Tyr His Gln Thr Cys Lys Val Pro Pro Phe Val Phe Phe
            115                 120                 125

Met Cys Cys Ala Ser Tyr Arg Val His Ser Ile Phe Val Arg Leu
            130                 135                 140

Phe Asn Asp Pro Val Ala Met Val Leu Leu Phe Leu Ser Ile Asn Leu
145                 150                 155                 160

Leu Leu Ala Gln Arg Trp Gly Trp Gly Cys Cys Phe Phe Ser Leu Ala
                165                 170                 175

Val Ser Val Lys Met Asn Val Leu Leu Phe Ala Pro Gly Leu Leu Phe
            180                 185                 190

Leu Leu Leu Thr Gln Phe Gly Phe Arg Gly Ala Leu Pro Lys Leu Gly
            195                 200                 205

Ile Cys Ala Gly Leu Gln Val Val Leu Gly Leu Pro Phe Leu Leu Glu
            210                 215                 220

Asn Pro Ser Gly Tyr Leu Ser Arg Ser Phe Asp Leu Gly Arg Gln Phe
225                 230                 235                 240

Leu Phe His Trp Thr Val Asn Trp Arg Phe Leu Pro Glu Ala Leu Phe
                245                 250                 255

Leu His Arg Ala Phe His Leu Ala Leu Leu Thr Ala His Leu Thr Leu
                260                 265                 270

Leu Leu Leu Phe Ala Leu Cys Arg Trp His Arg Thr Gly Glu Ser Ile
            275                 280                 285

Leu Ser Leu Leu Arg Asp Pro Ser Lys Arg Lys Val Pro Pro Gln Pro
290                 295                 300

Leu Thr Pro Asn Gln Ile Val Ser Thr Leu Phe Thr Ser Asn Phe Ile
305                 310                 315                 320

Gly Ile Cys Phe Ser Arg Ser Leu His Tyr Gln Phe Tyr Val Trp Tyr
                325                 330                 335

Phe His Thr Leu Pro Tyr Leu Leu Trp Ala Met Pro Ala Arg Trp Leu
                340                 345                 350

Thr His Leu Leu Arg Leu Leu Val Leu Gly Leu Ile Glu Leu Ser Trp
                355                 360                 365

Asn Thr Tyr Pro Ser Thr Ser
                370                 375

<210> SEQ ID NO 13
<211> LENGTH: 271
<212> TYPE: PRT
<213> ORGANISM: Saccharomyces cerevisiae

<400> SEQUENCE: 13

Val Arg Tyr Val Ile Phe Asp Cys Arg Ala Asn Leu Ile Val Met Pro
1               5                   10                  15

Leu Leu Ile Leu Phe Glu Ser Met Leu Cys Lys Ile Ile Lys Lys
            20                  25                  30

Val Ala Tyr Thr Glu Ile Asp Tyr Lys Ala Tyr Met Glu Gln Ile Glu
            35                  40                  45

Met Ile Gln Leu Asp Gly Met Leu Asp Tyr Ser Gln Val Ser Gly Gly
            50                  55                  60

Thr Gly Pro Leu Val Tyr Pro Ala Gly His Val Leu Ile Tyr Lys Met
65                  70                  75                  80
```

```
Met Tyr Trp Leu Thr Glu Gly Met Asp His Val Glu Arg Gly Gln Val
                85                  90                  95

Phe Phe Arg Tyr Leu Tyr Leu Leu Thr Leu Ala Leu Gln Met Ala Cys
            100                 105                 110

Tyr Tyr Leu Leu His Leu Pro Pro Trp Cys Val Val Leu Ala Cys Leu
            115                 120                 125

Ser Lys Arg Leu His Ser Ile Tyr Val Leu Arg Leu Phe Asn Asp Cys
        130                 135                 140

Phe Thr Thr Leu Phe Met Val Val Thr Val Leu Gly Ala Ile Val Ala
145                 150                 155                 160

Ser Arg Cys His Gln Arg Pro Lys Leu Lys Ser Leu Ala Leu Val
                165                 170                 175

Ile Ser Ala Thr Tyr Ser Met Ala Val Ser Ile Lys Met Asn Ala Leu
                180                 185                 190

Leu Tyr Phe Pro Ala Met Met Ile Ser Leu Phe Ile Leu Asn Asp Ala
            195                 200                 205

Asn Val Ile Leu Thr Leu Leu Asp Leu Val Ala Met Ile Ala Trp Gln
        210                 215                 220

Val Ala Val Ala Val Pro Phe Leu Arg Ser Phe Pro Gln Gln Tyr Leu
225                 230                 235                 240

His Cys Ala Phe Asn Phe Gly Arg Lys Phe Met Tyr Gln Trp Ser Ile
                245                 250                 255

Asn Trp Gln Met Met Asp Glu Glu Ala Phe Asn Asp Lys Arg Phe
                260                 265                 270

<210> SEQ ID NO 14
<211> LENGTH: 258
<212> TYPE: PRT
<213> ORGANISM: Drosophila virilis

<400> SEQUENCE: 14

Ile Lys Tyr Leu Ala Phe Glu Pro Ala Ala Leu Pro Ile Val Ser Val
1               5                   10                  15

Leu Ile Val Leu Ala Glu Ala Val Ile Asn Val Leu Val Ile Gln Arg
            20                  25                  30

Val Pro Tyr Thr Glu Ile Asp Trp Lys Ala Tyr Met Gln Glu Cys Glu
        35                  40                  45

Gly Phe Leu Asn Gly Thr Thr Asn Tyr Ser Leu Leu Arg Gly Asp Thr
    50                  55                  60

Gly Pro Leu Val Tyr Pro Ala Ala Phe Val Tyr Ile Tyr Ser Gly Leu
65                  70                  75                  80

Tyr Tyr Leu Thr Gly Gln Gly Thr Asn Val Arg Leu Ala Gln Tyr Ile
                85                  90                  95

Phe Ala Cys Ile Tyr Leu Leu Gln Met Cys Leu Val Leu Arg Leu Tyr
            100                 105                 110

Thr Lys Ser Arg Lys Val Pro Pro Tyr Val Leu Val Leu Ser Ala Phe
        115                 120                 125

Thr Ser Tyr Arg Ile His Ser Ile Tyr Val Leu Arg Leu Phe Asn Asp
    130                 135                 140

Pro Val Ala Ile Leu Leu Leu Tyr Ala Ala Leu Asn Leu Phe Leu Asp
145                 150                 155                 160

Gln Arg Trp Thr Leu Gly Ser Ile Cys Tyr Ser Leu Ala Val Gly Val
                165                 170                 175

Lys Met Asn Ile Leu Leu Phe Ala Pro Ala Leu Leu Leu Phe Tyr Leu
                180                 185                 190
```

```
Ala Asn Leu Gly Val Leu Arg Thr Leu Val Gln Leu Thr Ile Cys Ala
            195                 200                 205

Val Leu Gln Leu Phe Ile Gly Ala Pro Phe Leu Arg Thr His Pro Met
        210                 215                 220

Glu Tyr Leu Arg Gly Ser Phe Asp Leu Gly Arg Ile Phe Glu His Lys
225                 230                 235                 240

Trp Thr Val Asn Tyr Arg Phe Leu Ser Lys Glu Leu Phe Glu Gln Arg
                245                 250                 255

Glu Phe

<210> SEQ ID NO 15
<211> LENGTH: 60
<212> TYPE: PRT
<213> ORGANISM: Saccharomyces cerevisiae

<400> SEQUENCE: 15

Ile Pro Phe Val Leu Ile Ala Ser Asn Phe Ile Gly Val Leu Phe Ser
1               5                   10                  15

Arg Ser Leu His Tyr Gln Phe Leu Ser Trp Tyr His Trp Thr Leu Pro
            20                  25                  30

Ile Leu Ile Phe Trp Ser Gly Met Pro Phe Phe Val Gly Pro Ile Trp
        35                  40                  45

Tyr Val Leu His Glu Trp Cys Trp Asn Ser Tyr Pro
    50                  55                  60

<210> SEQ ID NO 16
<211> LENGTH: 58
<212> TYPE: PRT
<213> ORGANISM: Drosophila virilis

<400> SEQUENCE: 16

Leu Pro Phe Phe Leu Cys Asn Phe Ile Gly Val Ala Cys Ala Arg Ser
1               5                   10                  15

Leu His Tyr Gln Phe Tyr Ile Trp Tyr Phe His Ser Leu Pro Tyr Leu
            20                  25                  30

Val Trp Ser Thr Pro Tyr Ser Leu Gly Val Arg Tyr Leu Ile Leu Gly
        35                  40                  45

Ile Ile Glu Tyr Cys Trp Asn Thr Tyr Pro
    50                  55

<210> SEQ ID NO 17
<211> LENGTH: 270
<212> TYPE: PRT
<213> ORGANISM: Saccharomyces cerevisiae

<400> SEQUENCE: 17

Arg Tyr Val Ile Phe Asp Cys Arg Ala Asn Leu Ile Val Met Pro Leu
1               5                   10                  15

Leu Ile Leu Phe Glu Ser Met Leu Cys Lys Ile Ile Lys Lys Val
            20                  25                  30

Ala Tyr Thr Glu Ile Asp Tyr Lys Ala Tyr Met Glu Gln Ile Glu Met
        35                  40                  45

Ile Gln Leu Asp Gly Met Leu Asp Tyr Ser Gln Val Ser Gly Gly Thr
    50                  55                  60

Gly Pro Leu Val Tyr Pro Ala Gly His Val Leu Ile Tyr Lys Met Met
65                  70                  75                  80

Tyr Trp Leu Thr Glu Gly Met Asp His Val Glu Arg Gly Gln Val Phe
```

```
                    85                  90                  95
Phe Arg Tyr Leu Tyr Leu Leu Thr Leu Ala Leu Gln Met Ala Cys Tyr
                100                 105                 110
Tyr Leu Leu His Leu Pro Pro Trp Cys Val Val Leu Ala Cys Leu Ser
                115                 120                 125
Lys Arg Leu His Ser Ile Tyr Val Leu Arg Leu Phe Asn Asp Cys Phe
            130                 135                 140
Thr Thr Leu Phe Met Val Val Thr Val Leu Gly Ala Ile Val Ala Ser
145                 150                 155                 160
Arg Cys His Gln Arg Pro Lys Leu Lys Lys Ser Leu Ala Leu Val Ile
                165                 170                 175
Ser Ala Thr Tyr Ser Met Ala Val Ser Ile Lys Met Asn Ala Leu Leu
                180                 185                 190
Tyr Phe Pro Ala Met Met Ile Ser Leu Phe Ile Leu Asn Asp Ala Asn
                195                 200                 205
Val Ile Leu Thr Leu Leu Asp Leu Val Ala Met Ile Ala Trp Gln Val
            210                 215                 220
Ala Val Ala Val Pro Phe Leu Arg Ser Phe Pro Gln Gln Tyr Leu His
225                 230                 235                 240
Cys Ala Phe Asn Phe Gly Arg Lys Phe Met Tyr Gln Trp Ser Ile Asn
                245                 250                 255
Trp Gln Met Met Asp Glu Glu Ala Phe Asn Asp Lys Arg Phe
                260                 265                 270

<210> SEQ ID NO 18
<211> LENGTH: 257
<212> TYPE: PRT
<213> ORGANISM: Drosophila melanogaster

<400> SEQUENCE: 18

Lys Tyr Leu Leu Leu Glu Pro Ala Ala Leu Pro Ile Val Gly Leu Phe
1               5                   10                  15
Val Leu Leu Ala Glu Leu Val Ile Asn Val Val Ile Gln Arg Val
                20                  25                  30
Pro Tyr Thr Glu Ile Asp Trp Val Ala Tyr Met Gln Glu Cys Glu Gly
            35                  40                  45
Phe Leu Asn Gly Thr Thr Asn Tyr Ser Leu Leu Arg Gly Asp Thr Gly
        50                  55                  60
Pro Leu Val Tyr Pro Ala Ala Phe Val Tyr Ile Tyr Ser Ala Leu Tyr
65                  70                  75                  80
Tyr Val Thr Ser His Gly Thr Asn Val Arg Leu Ala Gln Tyr Ile Phe
                85                  90                  95
Ala Gly Ile Tyr Leu Leu Gln Leu Ala Leu Val Leu Arg Leu Tyr Ser
                100                 105                 110
Lys Ser Arg Lys Val Pro Pro Tyr Val Leu Val Leu Ser Ala Phe Thr
                115                 120                 125
Ser Tyr Arg Ile His Ser Ile Tyr Val Leu Arg Leu Phe Asn Asp Pro
            130                 135                 140
Val Ala Val Leu Leu Leu Tyr Ala Ala Leu Asn Leu Phe Leu Asp Arg
145                 150                 155                 160
Arg Trp Thr Leu Gly Ser Thr Phe Phe Ser Leu Ala Val Gly Val Lys
                165                 170                 175
Met Asn Ile Leu Leu Phe Ala Pro Ala Leu Leu Phe Tyr Leu Ala
                180                 185                 190
```

```
Asn Leu Gly Leu Leu Arg Thr Ile Leu Gln Leu Ala Val Cys Gly Val
        195                 200                 205

Ile Gln Leu Leu Leu Gly Ala Pro Phe Leu Leu Thr His Pro Val Glu
    210                 215                 220

Tyr Leu Arg Gly Ser Phe Asp Leu Gly Arg Ile Phe Glu His Lys Trp
225                 230                 235                 240

Thr Val Asn Tyr Arg Phe Leu Ser Arg Asp Val Phe Glu Asn Arg Thr
                245                 250                 255

Phe

<210> SEQ ID NO 19
<211> LENGTH: 60
<212> TYPE: PRT
<213> ORGANISM: Saccharomyces cerevisiae

<400> SEQUENCE: 19

Ile Pro Phe Val Leu Ile Ala Ser Asn Phe Ile Gly Val Leu Phe Ser
1               5                   10                  15

Arg Ser Leu His Tyr Gln Phe Leu Ser Trp Tyr His Trp Thr Leu Pro
            20                  25                  30

Ile Leu Ile Phe Trp Ser Gly Met Pro Phe Phe Val Gly Pro Ile Trp
        35                  40                  45

Tyr Val Leu His Glu Trp Cys Trp Asn Ser Tyr Pro
    50                  55                  60

<210> SEQ ID NO 20
<211> LENGTH: 58
<212> TYPE: PRT
<213> ORGANISM: Drosophila melanogaster

<400> SEQUENCE: 20

Leu Pro Phe Phe Leu Cys Asn Leu Val Gly Val Ala Cys Ser Arg Ser
1               5                   10                  15

Leu His Tyr Gln Phe Tyr Val Trp Tyr Phe His Ser Leu Pro Tyr Leu
            20                  25                  30

Ala Trp Ser Thr Pro Tyr Ser Leu Gly Val Arg Cys Leu Ile Leu Gly
        35                  40                  45

Leu Ile Glu Tyr Cys Trp Asn Thr Tyr Pro
    50                  55

<210> SEQ ID NO 21
<211> LENGTH: 1377
<212> TYPE: DNA
<213> ORGANISM: Saccharomyces cerevisiae

<400> SEQUENCE: 21
atggaaggtg aacagtctcc gcaaggtgaa aagtctctgc aaaggaagca atttgtcaga      60
cctccgctgg atctgtggca ggatctcaag gacggtgtgc gctacgtgat cttcgattgt     120
agggccaatc ttatcgttat gccccttttg attttgttcg aaagcatgct gtgcaagatt     180
atcattaaga aggtagctta cacagagatc gattacaagg cgtacatgga gcagatcgag     240
atgattcagc tcgatggcat gctggactac tctcaggtga gtggtggaac gggcccgctg     300
gtgtatccag caggccacgt cttgatctac aagatgatga ctggctaac agagggaatg     360 gaccacgttg agcgcgggca agtgtttttc agatacttgt atctccttac actggcgtta     420
caaatggcgt gttactacct tttacatcta ccaccgtggt gtgtggtctt ggcgtgcctc     480
tctaaaagat tgcactctat ttacgtgcta cggttattca atgattgctt cactactttg     540
```

```
tttatggtcg tcacggtttt gggggctatc gtggccagca ggtgccatca gcgccccaaa    600
ttaaagaagt cccttgcgct ggtgatctcc gcaacataca gtatggctgt gagcattaag    660
atgaatgcgc tgttgtattt ccctgcaatg atgatttctc tattcatcct taatgacgcg    720
aacgtaatcc ttactttgtt ggatctcgtt gcgatgattg catggcaagt cgcagttgca    780
gtgcccttcc tgcgcagctt tccgcaacag tacctgcatt gcgcttttaa tttcggcagg    840
aagtttatgt accaatggag tatcaattgg caaatgatgg atgaagaggc tttcaatgat    900
aagaggttcc acttggccct tttaatcagc cacctgatag cgctcaccac actgttcgtc    960
acaagatacc ctcgcatcct gcccgattta tggtcttccc tgtgccatcc gctgaggaaa   1020
aatgcagtgc tcaatgccaa tcccgccaag actattccat cgttctaat cgcatccaac    1080
ttcatcggcg tcctattttc aaggtccctc cactaccagt ttctatcctg gtatcactgg   1140
actttgccta tactgatctt ttggtcggga atgcccttct tcgttggtcc catttggtac   1200
gtcttgcacg agtggtgctg gaattcctat ccaccaaact cacaagcaag cacgctattg   1260
ttggcattga atactgttct gttgcttcta ttggccttga cgcagctatc tggttcggtc   1320
gccctcgcca aaagccatct tcgtaccacc agctctatgg aaaaaaagct caactga      1377
```

<210> SEQ ID NO 22
<211> LENGTH: 458
<212> TYPE: PRT
<213> ORGANISM: Saccharomyces cerevisiae

<400> SEQUENCE: 22

```
Met Glu Gly Glu Gln Ser Pro Gln Gly Glu Lys Ser Leu Gln Arg Lys
1               5                   10                  15

Gln Phe Val Arg Pro Pro Leu Asp Leu Trp Gln Asp Leu Lys Asp Gly
            20                  25                  30

Val Arg Tyr Val Ile Phe Asp Cys Arg Ala Asn Leu Ile Val Met Pro
        35                  40                  45

Leu Leu Ile Leu Phe Glu Ser Met Leu Cys Lys Ile Ile Ile Lys Lys
    50                  55                  60

Val Ala Tyr Thr Glu Ile Asp Tyr Lys Ala Tyr Met Glu Gln Ile Glu
65                  70                  75                  80

Met Ile Gln Leu Asp Gly Met Leu Asp Tyr Ser Gln Val Ser Gly Gly
                85                  90                  95

Thr Gly Pro Leu Val Tyr Pro Ala Gly His Val Leu Ile Tyr Lys Met
            100                 105                 110

Met Tyr Trp Leu Thr Glu Gly Met Asp His Val Glu Arg Gly Gln Val
        115                 120                 125

Phe Phe Arg Tyr Leu Tyr Leu Leu Thr Leu Ala Leu Gln Met Ala Cys
    130                 135                 140

Tyr Tyr Leu Leu His Leu Pro Pro Trp Cys Val Val Leu Ala Cys Leu
145                 150                 155                 160

Ser Lys Arg Leu His Ser Ile Tyr Val Leu Arg Leu Phe Asn Asp Cys
                165                 170                 175

Phe Thr Thr Leu Phe Met Val Val Thr Val Leu Gly Ala Ile Val Ala
            180                 185                 190

Ser Arg Cys His Gln Arg Pro Lys Leu Lys Ser Leu Ala Leu Val
        195                 200                 205

Ile Ser Ala Thr Tyr Ser Met Ala Val Ser Ile Lys Met Asn Ala Leu
    210                 215                 220
```

```
Leu Tyr Phe Pro Ala Met Met Ile Ser Leu Phe Ile Leu Asn Asp Ala
225                 230                 235                 240

Asn Val Ile Leu Thr Leu Leu Asp Leu Val Ala Met Ile Ala Trp Gln
            245                 250                 255

Val Ala Val Ala Val Pro Phe Leu Arg Ser Phe Pro Gln Gln Tyr Leu
        260                 265                 270

His Cys Ala Phe Asn Phe Gly Arg Lys Phe Met Tyr Gln Trp Ser Ile
    275                 280                 285

Asn Trp Gln Met Met Asp Glu Glu Ala Phe Asn Asp Lys Arg Phe His
290                 295                 300

Leu Ala Leu Leu Ile Ser His Leu Ile Ala Leu Thr Thr Leu Phe Val
305                 310                 315                 320

Thr Arg Tyr Pro Arg Ile Leu Pro Asp Leu Trp Ser Ser Leu Cys His
                325                 330                 335

Pro Leu Arg Lys Asn Ala Val Leu Asn Ala Asn Pro Ala Lys Thr Ile
            340                 345                 350

Pro Phe Val Leu Ile Ala Ser Asn Phe Ile Gly Val Leu Phe Ser Arg
        355                 360                 365

Ser Leu His Tyr Gln Phe Leu Ser Trp Tyr His Trp Thr Leu Pro Ile
    370                 375                 380

Leu Ile Phe Trp Ser Gly Met Pro Phe Phe Val Gly Pro Ile Trp Tyr
385                 390                 395                 400

Val Leu His Glu Trp Cys Trp Asn Ser Tyr Pro Pro Asn Ser Gln Ala
                405                 410                 415

Ser Thr Leu Leu Leu Ala Leu Asn Thr Val Leu Leu Leu Leu Leu Ala
            420                 425                 430

Leu Thr Gln Leu Ser Gly Ser Val Ala Leu Ala Lys Ser His Leu Arg
        435                 440                 445

Thr Thr Ser Ser Met Glu Lys Lys Leu Asn
    450                 455

<210> SEQ ID NO 23
<211> LENGTH: 1395
<212> TYPE: DNA
<213> ORGANISM: Pichia pastoris

<400> SEQUENCE: 23
atgcctccga tagagccagc tgaaaggcca aagcttacgc tgaaaaatgt tatcggtgat      60
ctagtggctc ttattcaaaa cgttttattt aacccagatt ttagtgtctt cgttgcacct     120
cttttatggt tagctgattc cattgttatc aaggtgatca ttggcactgt tcctacaca      180 gatattgatt ttcttcata tatgcaacaa atctttaaaa ttcgacaagg agaattagat     240
tatagcaaca tatttggtga caccggtcca ttggtttacc cagccggcca tgttcatgct     300
tactcagtac tttcgtggta cagtgatggt ggagaagacg tcagtttcgt tcaacaagca     360
tttggttggt tatacctagg ttgcttgtta ctatccatca gctcctactt tttctctggc     420
ttagggaaaa tacctccggt ttattttgtt ttgttggtag cgtccaagag actgcattca     480
atatttgtat tgagactctt caatgactgt ttaacaacat ttttgatgtt ggcaactata     540
atcatccttc aacaagcaag tagctggagg aaagatggca aactattcc attatctgtc     600 cctgatgctg cagatacgta cagtttagcc atctctgtaa agatgaatgc gctgctatac     660
ctcccagcat tcctactact catatatctc atttgtgacg aaaatttgat taaagccttg     720
gcacctgttc tagtttttgat attggtgcaa gtaggagtcg gttattcgtt cattttaccg     780
```

-continued

```
ttgcactatg atgatcaggc aaatgaaatt cgttctgcct actttagaca ggcttttgac    840
tttagtcgcc aatttcttta taagtggacg gttaattggc gcttttgag ccaagaaact     900 ttcaacaatg tccattttca ccagctcctg tttgctctcc atattattac gttagtcttg    960
ttcatcctca agttcctctc tcctaaaaac attggaaaac cgcttggtag atttgtgttg   1020
gacattttca aattttggaa gccaacctta tctccaacca atattatcaa cgacccagaa   1080
agaagcccag attttgttta caccgtcatg gctactacca acttaatagg ggtgcttttt   1140
gcaagatctt tacactacca gttcctaagc tggtatgcgt tctctttgcc atatctcctt   1200
tacaaggctc gtctgaactt tatagcatct attattgttt atgccgctca cgagtattgc   1260
tggttggttt tcccagctac agaacaaagt tccgcgttgt tggtatctat cttactactt   1320
atcctgattc tcattttac caacgaacag ttatttcctt ctcaatcggt ccctgcagaa    1380
aaaaagaata cataa                                                     1395
```

<210> SEQ ID NO 24
<211> LENGTH: 464
<212> TYPE: PRT
<213> ORGANISM: Pichia pastoris

<400> SEQUENCE: 24

```
Met Pro Pro Ile Glu Pro Ala Glu Arg Pro Lys Leu Thr Leu Lys Asn
1               5                   10                  15

Val Ile Gly Asp Leu Val Ala Leu Ile Gln Asn Val Leu Phe Asn Pro
            20                  25                  30

Asp Phe Ser Val Phe Val Ala Pro Leu Leu Trp Leu Ala Asp Ser Ile
        35                  40                  45

Val Ile Lys Val Ile Ile Gly Thr Val Ser Tyr Thr Asp Ile Asp Phe
    50                  55                  60

Ser Ser Tyr Met Gln Gln Ile Phe Lys Ile Arg Gln Gly Glu Leu Asp
65                  70                  75                  80

Tyr Ser Asn Ile Phe Gly Asp Thr Gly Pro Leu Val Tyr Pro Ala Gly
                85                  90                  95

His Val His Ala Tyr Ser Val Leu Ser Trp Tyr Ser Asp Gly Gly Glu
            100                 105                 110

Asp Val Ser Phe Val Gln Gln Ala Phe Gly Trp Leu Tyr Leu Gly Cys
        115                 120                 125

Leu Leu Leu Ser Ile Ser Ser Tyr Phe Phe Ser Gly Leu Gly Lys Ile
    130                 135                 140

Pro Pro Val Tyr Phe Val Leu Leu Val Ala Ser Lys Arg Leu His Ser
145                 150                 155                 160

Ile Phe Val Leu Arg Leu Phe Asn Asp Cys Leu Thr Thr Phe Leu Met
                165                 170                 175

Leu Ala Thr Ile Ile Leu Gln Gln Ala Ser Ser Trp Arg Lys Asp
            180                 185                 190

Gly Thr Thr Ile Pro Leu Ser Val Pro Asp Ala Ala Asp Thr Tyr Ser
        195                 200                 205

Leu Ala Ile Ser Val Lys Met Asn Ala Leu Leu Tyr Leu Pro Ala Phe
    210                 215                 220

Leu Leu Leu Ile Tyr Leu Ile Cys Asp Glu Asn Leu Ile Lys Ala Leu
225                 230                 235                 240

Ala Pro Val Leu Val Leu Ile Leu Val Gln Val Gly Val Gly Tyr Ser
                245                 250                 255

Phe Ile Leu Pro Leu His Tyr Asp Asp Gln Ala Asn Glu Ile Arg Ser
```

```
                    260                 265                 270
Ala Tyr Phe Arg Gln Ala Phe Asp Phe Ser Arg Gln Phe Leu Tyr Lys
            275                 280                 285
Trp Thr Val Asn Trp Arg Phe Leu Ser Gln Glu Thr Phe Asn Asn Val
290                 295                 300
His Phe His Gln Leu Leu Phe Ala Leu His Ile Ile Thr Leu Val Leu
305                 310                 315                 320
Phe Ile Leu Lys Phe Leu Ser Pro Lys Asn Ile Gly Lys Pro Leu Gly
                325                 330                 335
Arg Phe Val Leu Asp Ile Phe Lys Phe Trp Lys Pro Thr Leu Ser Pro
            340                 345                 350
Thr Asn Ile Ile Asn Asp Pro Glu Arg Ser Pro Asp Phe Val Tyr Thr
355                 360                 365
Val Met Ala Thr Thr Asn Leu Ile Gly Val Leu Phe Ala Arg Ser Leu
        370                 375                 380
His Tyr Gln Phe Leu Ser Trp Tyr Ala Phe Ser Leu Pro Tyr Leu Leu
385                 390                 395                 400
Tyr Lys Ala Arg Leu Asn Phe Ile Ala Ser Ile Val Tyr Ala Ala
                405                 410                 415
His Glu Tyr Cys Trp Leu Val Phe Pro Ala Thr Glu Gln Ser Ser Ala
            420                 425                 430
Leu Leu Val Ser Ile Leu Leu Leu Ile Leu Ile Phe Thr Asn
            435                 440                 445
Glu Gln Leu Phe Pro Ser Gln Ser Val Pro Ala Glu Lys Lys Asn Thr
450                 455                 460

<210> SEQ ID NO 25
<211> LENGTH: 423
<212> TYPE: PRT
<213> ORGANISM: Pichia pastoris

<400> SEQUENCE: 25

Arg Pro Lys Leu Thr Leu Lys Asn Val Ile Gly Asp Leu Val Ala Leu
1               5                   10                  15
Ile Gln Asn Val Leu Phe Asn Pro Asp Phe Ser Val Phe Val Ala Pro
            20                  25                  30
Leu Leu Trp Leu Ala Asp Ser Ile Val Ile Lys Val Ile Gly Thr
        35                  40                  45
Val Ser Tyr Thr Asp Ile Asp Phe Ser Ser Tyr Met Gln Gln Ile Phe
50                  55                  60
Lys Ile Arg Gln Gly Glu Leu Asp Tyr Ser Asn Ile Phe Gly Asp Thr
65                  70                  75                  80
Gly Pro Leu Val Tyr Pro Ala Gly His Val His Ala Tyr Ser Val Leu
                85                  90                  95
Ser Trp Tyr Ser Asp Gly Gly Glu Asp Val Ser Phe Val Gln Gln Ala
            100                 105                 110
Phe Gly Trp Leu Tyr Leu Gly Cys Leu Leu Leu Ser Ile Ser Ser Tyr
        115                 120                 125
Phe Phe Ser Gly Leu Gly Lys Ile Pro Pro Val Tyr Phe Val Leu Leu
130                 135                 140
Val Ala Ser Lys Arg Leu His Ser Ile Phe Val Leu Arg Leu Phe Asn
145                 150                 155                 160
Asp Cys Leu Thr Thr Phe Leu Met Leu Ala Thr Ile Ile Ile Leu Gln
                165                 170                 175
```

```
Gln Ala Ser Ser Trp Arg Lys Asp Gly Thr Thr Ile Pro Leu Ser Val
            180                 185                 190

Pro Asp Ala Ala Asp Thr Tyr Ser Leu Ala Ile Ser Val Lys Met Asn
            195                 200                 205

Ala Leu Leu Tyr Leu Pro Ala Phe Leu Leu Ile Tyr Leu Ile Cys
    210                 215                 220

Asp Glu Asn Leu Ile Lys Ala Leu Ala Pro Val Leu Val Leu Ile Leu
225                 230                 235                 240

Val Gln Val Gly Val Gly Tyr Ser Phe Ile Leu Pro Leu His Tyr Asp
            245                 250                 255

Asp Gln Ala Asn Glu Ile Arg Ser Ala Tyr Phe Arg Gln Ala Phe Asp
            260                 265                 270

Phe Ser Arg Gln Phe Leu Tyr Lys Trp Thr Val Asn Trp Arg Phe Leu
            275                 280                 285

Ser Gln Glu Thr Phe Asn Asn Val His Phe His Gln Leu Leu Phe Ala
            290                 295                 300

Leu His Ile Ile Thr Leu Val Leu Phe Ile Leu Lys Phe Leu Ser Pro
305                 310                 315                 320

Lys Asn Ile Gly Lys Pro Leu Gly Arg Phe Val Leu Asp Ile Phe Lys
            325                 330                 335

Phe Trp Lys Pro Thr Leu Ser Pro Thr Asn Ile Ile Asn Asp Pro Glu
            340                 345                 350

Arg Ser Pro Asp Phe Val Tyr Thr Val Met Ala Thr Thr Asn Leu Ile
            355                 360                 365

Gly Val Leu Phe Ala Arg Ser Leu His Tyr Gln Phe Leu Ser Trp Tyr
            370                 375                 380

Ala Phe Ser Leu Pro Tyr Leu Leu Tyr Lys Ala Arg Leu Asn Phe Ile
385                 390                 395                 400

Ala Ser Ile Ile Val Tyr Ala Ala His Glu Tyr Cys Trp Leu Val Phe
            405                 410                 415

Pro Ala Thr Glu Gln Ser Ser
            420

<210> SEQ ID NO 26
<211> LENGTH: 398
<212> TYPE: PRT
<213> ORGANISM: Saccharomyces cerevisiae

<400> SEQUENCE: 26

Arg Pro Pro Leu Asp Leu Trp Gln Asp Leu Lys Asp Gly Val Arg Tyr
1               5                   10                  15

Val Ile Phe Asp Cys Arg Ala Asn Leu Ile Val Met Pro Leu Leu Ile
            20                  25                  30

Leu Phe Glu Ser Met Leu Cys Lys Ile Ile Lys Lys Val Ala Tyr
        35                  40                  45

Thr Glu Ile Asp Tyr Lys Ala Tyr Met Glu Gln Ile Glu Met Ile Gln
    50                  55                  60

Leu Asp Gly Met Leu Asp Tyr Ser Gln Val Ser Gly Thr Gly Pro
65                  70                  75                  80

Leu Val Tyr Pro Ala Gly His Val Leu Ile Tyr Lys Met Met Tyr Trp
            85                  90                  95

Leu Thr Glu Gly Met Asp His Val Glu Arg Gly Gln Val Phe Phe Arg
            100                 105                 110

Tyr Leu Tyr Leu Leu Thr Leu Ala Leu Gln Met Ala Cys Tyr Tyr Leu
            115                 120                 125
```

```
Leu His Leu Pro Pro Trp Cys Val Val Ala Cys Leu Ser Lys Arg
    130                 135                 140

Leu His Ser Ile Tyr Val Leu Arg Leu Phe Asn Asp Cys Phe Thr Thr
145                 150                 155                 160

Leu Phe Met Val Val Thr Val Leu Gly Ala Ile Val Ala Ser Arg Cys
                165                 170                 175

His Gln Arg Pro Lys Leu Lys Lys Ser Leu Ala Leu Val Ile Ser Ala
            180                 185                 190

Thr Tyr Ser Met Ala Val Ser Ile Lys Met Asn Ala Leu Leu Tyr Phe
        195                 200                 205

Pro Ala Met Met Ile Ser Leu Phe Ile Leu Asn Asp Ala Asn Val Ile
    210                 215                 220

Leu Thr Leu Leu Asp Leu Val Ala Met Ile Ala Trp Gln Val Ala Val
225                 230                 235                 240

Ala Val Pro Phe Leu Arg Ser Phe Pro Gln Gln Tyr Leu His Cys Ala
                245                 250                 255

Phe Asn Phe Gly Arg Lys Phe Met Tyr Gln Trp Ser Ile Asn Trp Gln
            260                 265                 270

Met Met Asp Glu Glu Ala Phe Asn Asp Lys Arg Phe His Leu Ala Leu
        275                 280                 285

Leu Ile Ser His Leu Ile Ala Leu Thr Thr Leu Phe Val Thr Arg Tyr
    290                 295                 300

Pro Arg Ile Leu Pro Asp Leu Trp Ser Ser Leu Cys His Pro Leu Arg
305                 310                 315                 320

Lys Asn Ala Val Leu Asn Ala Asn Pro Ala Lys Thr Ile Pro Phe Val
                325                 330                 335

Leu Ile Ala Ser Asn Phe Ile Gly Val Leu Phe Ser Arg Ser Leu His
            340                 345                 350

Tyr Gln Phe Leu Ser Trp Tyr His Trp Thr Leu Pro Ile Leu Ile Phe
        355                 360                 365

Trp Ser Gly Met Pro Phe Phe Val Gly Pro Ile Trp Tyr Val Leu His
    370                 375                 380

Glu Trp Cys Trp Asn Ser Tyr Pro Pro Asn Ser Gln Ala Ser
385                 390                 395

<210> SEQ ID NO 27
<211> LENGTH: 398
<212> TYPE: PRT
<213> ORGANISM: Pichia pastoris

<400> SEQUENCE: 27

Ser Val Phe Val Ala Pro Leu Leu Trp Leu Ala Asp Ser Ile Val Ile
1               5                   10                  15

Lys Val Ile Ile Gly Thr Val Ser Tyr Thr Asp Ile Asp Phe Ser Ser
            20                  25                  30

Tyr Met Gln Gln Ile Phe Lys Ile Arg Gln Gly Glu Leu Asp Tyr Ser
        35                  40                  45

Asn Ile Phe Gly Asp Thr Gly Pro Leu Val Tyr Pro Ala Gly His Val
    50                  55                  60

His Ala Tyr Ser Val Leu Ser Trp Tyr Ser Asp Gly Gly Glu Asp Val
65                  70                  75                  80

Ser Phe Val Gln Gln Ala Phe Gly Trp Leu Tyr Leu Gly Cys Leu Leu
                85                  90                  95

Leu Ser Ile Ser Ser Tyr Phe Phe Ser Gly Leu Gly Lys Ile Pro Pro
```

-continued

```
                100                 105                 110
Val Tyr Phe Val Leu Val Ala Ser Lys Arg Leu His Ser Ile Phe
            115                 120                 125
Val Leu Arg Leu Phe Asn Asp Cys Leu Thr Thr Phe Leu Met Leu Ala
130                 135                 140
Thr Ile Ile Ile Leu Gln Gln Ala Ser Ser Trp Arg Lys Asp Gly Thr
145                 150                 155                 160
Thr Ile Pro Leu Ser Val Pro Asp Ala Ala Asp Thr Tyr Ser Leu Ala
                165                 170                 175
Ile Ser Val Lys Met Asn Ala Leu Leu Tyr Leu Pro Ala Phe Leu Leu
            180                 185                 190
Leu Ile Tyr Leu Ile Cys Asp Glu Asn Leu Ile Lys Ala Leu Ala Pro
            195                 200                 205
Val Leu Val Leu Ile Leu Val Gln Val Gly Val Gly Tyr Ser Phe Ile
            210                 215                 220
Leu Pro Leu His Tyr Asp Asp Gln Ala Asn Glu Ile Arg Ser Ala Tyr
225                 230                 235                 240
Phe Arg Gln Ala Phe Asp Phe Ser Arg Gln Phe Leu Tyr Lys Trp Thr
                245                 250                 255
Val Asn Trp Arg Phe Leu Ser Gln Glu Thr Phe Asn Asn Val His Phe
            260                 265                 270
His Gln Leu Leu Phe Ala Leu His Ile Ile Thr Leu Val Leu Phe Ile
        275                 280                 285
Leu Lys Phe Leu Ser Pro Lys Asn Ile Gly Lys Pro Leu Gly Arg Phe
    290                 295                 300
Val Leu Asp Ile Phe Lys Phe Trp Lys Pro Thr Leu Ser Pro Thr Asn
305                 310                 315                 320
Ile Ile Asn Asp Pro Glu Arg Ser Pro Asp Phe Val Tyr Thr Val Met
                325                 330                 335
Ala Thr Thr Asn Leu Ile Gly Val Leu Phe Ala Arg Ser Leu His Tyr
            340                 345                 350
Gln Phe Leu Ser Trp Tyr Ala Phe Ser Leu Pro Tyr Leu Leu Tyr Lys
        355                 360                 365
Ala Arg Leu Asn Phe Ile Ala Ser Ile Ile Val Tyr Ala Ala His Glu
370                 375                 380
Tyr Cys Trp Leu Val Phe Pro Ala Thr Glu Gln Ser Ser Ala
385                 390                 395

<210> SEQ ID NO 28
<211> LENGTH: 373
<212> TYPE: PRT
<213> ORGANISM: Neurospora crassa

<400> SEQUENCE: 28

Ser Lys Leu Ile Pro Pro Ala Leu Phe Leu Val Asp Ala Leu Leu Cys
1               5                   10                  15
Gly Leu Ile Ile Trp Lys Val Pro Tyr Thr Glu Ile Asp Trp Ala Ala
            20                  25                  30
Tyr Met Glu Gln Val Ser Gln Ile Leu Ser Gly Glu Arg Asp Tyr Thr
        35                  40                  45
Lys Val Arg Gly Gly Thr Gly Pro Leu Val Tyr Pro Ala Ala His Val
    50                  55                  60
Tyr Ile Tyr Thr Gly Leu Tyr His Leu Thr Asp Glu Gly Arg Asn Ile
65                  70                  75                  80
```

-continued

```
Leu Leu Ala Gln Gln Leu Phe Ala Gly Leu Tyr Met Val Thr Leu Ala
             85                  90                  95

Val Val Met Gly Cys Tyr Trp Gln Ala Lys Ala Pro Pro Tyr Leu Phe
            100                 105                 110

Pro Leu Leu Thr Leu Ser Lys Arg Leu His Ser Ile Phe Val Leu Arg
            115                 120                 125

Cys Phe Asn Asp Cys Phe Ala Val Leu Phe Leu Trp Leu Ala Ile Phe
        130                 135                 140

Phe Phe Gln Arg Arg Asn Trp Gln Ala Gly Ala Leu Leu Tyr Thr Leu
145                 150                 155                 160

Gly Leu Gly Val Lys Met Thr Leu Leu Leu Ser Leu Pro Ala Val Gly
                165                 170                 175

Ile Val Leu Phe Leu Gly Ser Gly Ser Phe Val Thr Thr Leu Gln Leu
            180                 185                 190

Val Ala Thr Met Gly Leu Val Gln Ile Leu Ile Gly Val Pro Phe Leu
            195                 200                 205

Ala His Tyr Pro Thr Glu Tyr Leu Ser Arg Ala Phe Glu Leu Ser Arg
        210                 215                 220

Gln Phe Phe Lys Trp Thr Val Asn Trp Arg Phe Val Gly Glu Glu
225                 230                 235                 240

Ile Phe Leu Ser Lys Gly Phe Ala Leu Thr Leu Leu Ala Leu His Val
                245                 250                 255

Leu Val Leu Gly Ile Phe Ile Thr Thr Arg Trp Ile Lys Pro Ala Arg
            260                 265                 270

Lys Ser Leu Val Gln Leu Ile Ser Pro Val Leu Leu Ala Gly Lys Pro
        275                 280                 285

Pro Leu Thr Val Pro Glu His Arg Ala Ala Arg Asp Val Thr Pro
290                 295                 300

Arg Tyr Ile Met Thr Thr Ile Leu Ser Ala Asn Ala Val Gly Leu Leu
305                 310                 315                 320

Phe Ala Arg Ser Leu His Tyr Gln Phe Tyr Ala Tyr Val Ala Trp Ser
                325                 330                 335

Thr Pro Phe Leu Leu Trp Arg Ala Gly Leu His Pro Val Leu Val Tyr
            340                 345                 350

Leu Leu Trp Ala Val His Glu Trp Ala Trp Asn Val Phe Pro Ser Thr
        355                 360                 365

Pro Ala Ser Ser Ala
    370

<210> SEQ ID NO 29
<211> LENGTH: 390
<212> TYPE: PRT
<213> ORGANISM: Pichia pastoris

<400> SEQUENCE: 29

Leu Trp Leu Ala Asp Ser Ile Val Ile Lys Val Ile Gly Thr Val
1               5                  10                  15

Ser Tyr Thr Asp Ile Asp Phe Ser Ser Tyr Met Gln Gln Ile Phe Lys
            20                  25                  30

Ile Arg Gln Gly Glu Leu Asp Tyr Ser Asn Ile Phe Gly Asp Thr Gly
        35                  40                  45

Pro Leu Val Tyr Pro Ala Gly His Val His Ala Tyr Ser Val Leu Ser
    50                  55                  60

Trp Tyr Ser Asp Gly Gly Glu Asp Val Ser Phe Val Gln Gln Ala Phe
65                  70                  75                  80
```

```
Gly Trp Leu Tyr Leu Gly Cys Leu Leu Leu Ser Ile Ser Ser Tyr Phe
                85                  90                  95

Phe Ser Gly Leu Gly Lys Ile Pro Pro Val Tyr Phe Val Leu Leu Val
            100                 105                 110

Ala Ser Lys Arg Leu His Ser Ile Phe Val Leu Arg Leu Phe Asn Asp
            115                 120                 125

Cys Leu Thr Thr Phe Leu Met Leu Ala Thr Ile Ile Leu Gln Gln
130                 135                 140

Ala Ser Ser Trp Arg Lys Asp Gly Thr Thr Ile Pro Leu Ser Val Pro
145                 150                 155                 160

Asp Ala Ala Asp Thr Tyr Ser Leu Ala Ile Ser Val Lys Met Asn Ala
                165                 170                 175

Leu Leu Tyr Leu Pro Ala Phe Leu Leu Ile Tyr Leu Ile Cys Asp
                180                 185                 190

Glu Asn Leu Ile Lys Ala Leu Ala Pro Val Leu Val Leu Ile Leu Val
                195                 200                 205

Gln Val Gly Val Gly Tyr Ser Phe Ile Leu Pro Leu His Tyr Asp Asp
210                 215                 220

Gln Ala Asn Glu Ile Arg Ser Ala Tyr Phe Arg Gln Ala Phe Asp Phe
225                 230                 235                 240

Ser Arg Gln Phe Leu Tyr Lys Trp Thr Val Asn Trp Arg Phe Leu Ser
                245                 250                 255

Gln Glu Thr Phe Asn Asn Val His Phe His Gln Leu Leu Phe Ala Leu
                260                 265                 270

His Ile Ile Thr Leu Val Leu Phe Ile Leu Lys Phe Leu Ser Pro Lys
                275                 280                 285

Asn Ile Gly Lys Pro Leu Gly Arg Phe Val Leu Asp Ile Phe Lys Phe
                290                 295                 300

Trp Lys Pro Thr Leu Ser Pro Thr Asn Ile Ile Asn Asp Pro Glu Arg
305                 310                 315                 320

Ser Pro Asp Phe Val Tyr Thr Val Met Ala Thr Thr Asn Leu Ile Gly
                325                 330                 335

Val Leu Phe Ala Arg Ser Leu His Tyr Gln Phe Leu Ser Trp Tyr Ala
                340                 345                 350

Phe Ser Leu Pro Tyr Leu Leu Tyr Lys Ala Arg Leu Asn Phe Ile Ala
                355                 360                 365

Ser Ile Ile Val Tyr Ala Ala His Glu Tyr Cys Trp Leu Val Phe Pro
370                 375                 380

Ala Thr Glu Gln Ser Ser
385                 390

<210> SEQ ID NO 30
<211> LENGTH: 355
<212> TYPE: PRT
<213> ORGANISM: Schizosaccharomyces pombe

<400> SEQUENCE: 30

Leu Leu Leu Leu Glu Ile Pro Phe Val Phe Ala Ile Ile Ser Lys Val
1               5                   10                  15

Pro Tyr Thr Glu Ile Asp Trp Ile Ala Tyr Met Glu Gln Val Asn Ser
            20                  25                  30

Phe Leu Leu Gly Glu Arg Asp Tyr Lys Ser Leu Val Gly Cys Thr Gly
        35                  40                  45

Pro Leu Val Tyr Pro Gly Gly His Val Phe Leu Tyr Thr Leu Leu Tyr
```

```
                50                  55                  60
Tyr Leu Thr Asp Gly Gly Thr Asn Ile Val Arg Ala Gln Tyr Ile Phe
 65                  70                  75                  80

Ala Phe Val Tyr Trp Ile Thr Thr Ala Ile Val Gly Tyr Leu Phe Lys
                 85                  90                  95

Ile Val Arg Ala Pro Phe Tyr Ile Tyr Val Leu Leu Ile Leu Ser Lys
            100                 105                 110

Arg Leu His Ser Ile Phe Ile Leu Arg Leu Phe Asn Asp Gly Phe Asn
        115                 120                 125

Ser Leu Phe Ser Ser Leu Phe Ile Leu Ser Ser Cys Lys Lys Lys Trp
    130                 135                 140

Val Arg Ala Ser Ile Leu Leu Ser Val Ala Cys Ser Val Lys Met Ser
145                 150                 155                 160

Ser Leu Leu Tyr Val Pro Ala Tyr Leu Val Leu Leu Gln Ile Leu
                165                 170                 175

Gly Pro Lys Lys Thr Trp Met His Ile Phe Val Ile Ile Val Gln
            180                 185                 190

Ile Leu Phe Ser Ile Pro Phe Leu Ala Tyr Phe Trp Ser Tyr Trp Thr
        195                 200                 205

Gln Ala Phe Asp Phe Gly Arg Ala Phe Asp Tyr Lys Trp Thr Val Asn
    210                 215                 220

Trp Arg Phe Ile Pro Arg Ser Ile Phe Glu Ser Thr Ser Phe Ser Thr
225                 230                 235                 240

Ser Ile Leu Phe Leu His Val Ala Leu Leu Val Ala Phe Thr Cys Lys
                245                 250                 255

His Trp Asn Lys Leu Ser Arg Ala Thr Pro Phe Ala Met Val Asn Ser
            260                 265                 270

Met Leu Thr Leu Lys Pro Leu Pro Lys Leu Gln Leu Ala Thr Pro Asn
        275                 280                 285

Phe Ile Phe Thr Ala Leu Ala Thr Ser Asn Leu Ile Gly Ile Leu Cys
    290                 295                 300

Ala Arg Ser Leu His Tyr Gln Phe Tyr Ala Trp Phe Ala Trp Tyr Ser
305                 310                 315                 320

Pro Tyr Leu Cys Tyr Gln Ala Ser Phe Pro Ala Pro Ile Val Ile Gly
                325                 330                 335

Leu Trp Met Leu Gln Glu Tyr Ala Trp Asn Val Phe Pro Ser Thr Lys
            340                 345                 350

Leu Ser Ser
        355

<210> SEQ ID NO 31
<211> LENGTH: 390
<212> TYPE: PRT
<213> ORGANISM: Pichia pastoris

<400> SEQUENCE: 31

Leu Trp Leu Ala Asp Ser Ile Val Ile Lys Val Ile Ile Gly Thr Val
 1               5                  10                  15

Ser Tyr Thr Asp Ile Asp Phe Ser Ser Tyr Met Gln Gln Ile Phe Lys
                20                  25                  30

Ile Arg Gln Gly Glu Leu Asp Tyr Ser Asn Ile Phe Gly Asp Thr Gly
            35                  40                  45

Pro Leu Val Tyr Pro Ala Gly His Val His Ala Tyr Ser Val Leu Ser
        50                  55                  60
```

Trp Tyr Ser Asp Gly Gly Glu Asp Val Ser Phe Val Gln Gln Ala Phe
 65                  70                  75                  80

Gly Trp Leu Tyr Leu Gly Cys Leu Leu Leu Ser Ile Ser Ser Tyr Phe
                 85                  90                  95

Phe Ser Gly Leu Gly Lys Ile Pro Pro Val Tyr Phe Val Leu Leu Val
            100                 105                 110

Ala Ser Lys Arg Leu His Ser Ile Phe Val Leu Arg Leu Phe Asn Asp
        115                 120                 125

Cys Leu Thr Thr Phe Leu Met Leu Ala Thr Ile Ile Leu Gln Gln
    130                 135                 140

Ala Ser Ser Trp Arg Lys Asp Gly Thr Thr Ile Pro Leu Ser Val Pro
145                 150                 155                 160

Asp Ala Ala Asp Thr Tyr Ser Leu Ala Ile Ser Val Lys Met Asn Ala
                165                 170                 175

Leu Leu Tyr Leu Pro Ala Phe Leu Leu Leu Ile Tyr Leu Ile Cys Asp
            180                 185                 190

Glu Asn Leu Ile Lys Ala Leu Ala Pro Val Leu Val Leu Ile Leu Val
        195                 200                 205

Gln Val Gly Val Gly Tyr Ser Phe Ile Leu Pro Leu His Tyr Asp Asp
    210                 215                 220

Gln Ala Asn Glu Ile Arg Ser Ala Tyr Phe Arg Gln Ala Phe Asp Phe
225                 230                 235                 240

Ser Arg Gln Phe Leu Tyr Lys Trp Thr Val Asn Trp Arg Phe Leu Ser
                245                 250                 255

Gln Glu Thr Phe Asn Asn Val His Phe His Gln Leu Leu Phe Ala Leu
            260                 265                 270

His Ile Ile Thr Leu Val Leu Phe Ile Leu Lys Phe Leu Ser Pro Lys
        275                 280                 285

Asn Ile Gly Lys Pro Leu Gly Arg Phe Val Leu Asp Ile Phe Lys Phe
    290                 295                 300

Trp Lys Pro Thr Leu Ser Pro Thr Asn Ile Ile Asn Asp Pro Glu Arg
305                 310                 315                 320

Ser Pro Asp Phe Val Tyr Thr Val Met Ala Thr Thr Asn Leu Ile Gly
                325                 330                 335

Val Leu Phe Ala Arg Ser Leu His Tyr Gln Phe Leu Ser Trp Tyr Ala
            340                 345                 350

Phe Ser Leu Pro Tyr Leu Leu Tyr Lys Ala Arg Leu Asn Phe Ile Ala
        355                 360                 365

Ser Ile Ile Val Tyr Ala Ala His Glu Tyr Cys Trp Leu Val Phe Pro
    370                 375                 380

Ala Thr Glu Gln Ser Ser
385                 390

<210> SEQ ID NO 32
<211> LENGTH: 363
<212> TYPE: PRT
<213> ORGANISM: Arabidopsis thaliana

<400> SEQUENCE: 32

Leu Ile Leu Ala Asp Ala Ile Leu Val Ala Leu Ile Ile Ala Tyr Val
 1               5                  10                  15

Pro Tyr Thr Lys Ile Asp Trp Asp Ala Tyr Met Ser Gln Val Ser Gly
                20                  25                  30

Phe Leu Gly Gly Glu Arg Asp Tyr Gly Asn Leu Lys Gly Asp Thr Gly
            35                  40                  45

```
Pro Leu Val Tyr Pro Ala Gly Phe Leu Tyr Val Tyr Ser Ala Val Gln
    50                  55                  60

Asn Leu Thr Gly Gly Glu Val Tyr Pro Ala Gln Ile Leu Phe Gly Val
 65                  70                  75                  80

Leu Tyr Ile Val Asn Leu Gly Ile Val Leu Ile Ile Tyr Val Lys Thr
                 85                  90                  95

Asp Val Val Pro Trp Trp Ala Leu Ser Leu Leu Cys Leu Ser Lys Arg
            100                 105                 110

Ile His Ser Ile Phe Val Leu Arg Leu Phe Asn Asp Cys Phe Ala Met
        115                 120                 125

Thr Leu Leu His Ala Ser Met Ala Leu Phe Leu Tyr Arg Lys Trp His
    130                 135                 140

Leu Gly Met Leu Val Phe Ser Gly Ala Val Ser Val Lys Met Asn Val
145                 150                 155                 160

Leu Leu Tyr Ala Pro Thr Leu Leu Leu Leu Leu Lys Ala Met Asn
                165                 170                 175

Ile Ile Gly Val Val Ser Ala Leu Ala Gly Ala Ala Leu Ala Gln Ile
            180                 185                 190

Leu Val Gly Leu Pro Phe Leu Ile Thr Tyr Pro Val Ser Tyr Ile Ala
        195                 200                 205

Asn Ala Phe Asp Leu Gly Arg Val Phe Ile His Phe Trp Ser Val Asn
    210                 215                 220

Phe Lys Phe Val Pro Glu Arg Val Phe Ser Lys Glu Phe Ala Val
225                 230                 235                 240

Cys Leu Leu Ile Ala His Leu Phe Leu Leu Val Ala Phe Ala Asn Tyr
                245                 250                 255

Lys Trp Cys Lys His Glu Gly Gly Ile Ile Gly Phe Met Arg Ser Arg
            260                 265                 270

His Phe Phe Leu Thr Leu Pro Ser Ser Leu Ser Phe Ser Asp Val Ser
        275                 280                 285

Ala Ser Arg Ile Ile Thr Lys Glu His Val Val Thr Ala Met Phe Val
    290                 295                 300

Gly Asn Phe Ile Gly Ile Val Phe Ala Arg Ser Leu His Tyr Gln Phe
305                 310                 315                 320

Tyr Ser Trp Tyr Phe Tyr Ser Leu Pro Tyr Leu Leu Trp Arg Thr Pro
                325                 330                 335

Phe Pro Thr Trp Leu Arg Leu Ile Met Phe Leu Gly Ile Glu Leu Cys
            340                 345                 350

Trp Asn Val Tyr Pro Ser Thr Pro Ser Ser Ser
        355                 360
```

<210> SEQ ID NO 33
<211> LENGTH: 428
<212> TYPE: DNA
<213> ORGANISM: Kluyveromyces lactis

<400> SEQUENCE: 33

```
tttgtttaca agctgatacc aacgaacatg aatacaccgg caggtttact gaagattggc      60
aaagctaacc ttttacatcc ttttaccgat gctgtattca gtgcgatgag agtaaacgca     120
gaacaaattg catacatttt acttgttacc aattacattg gagtactatt tgctcgatca     180
ttacactacc aattcctatc ttggtaccat tggacgttac cagtactatt gaattgggcc     240
aatgttccgt atccgctatg tgtgctatgg tacctaacac atgagtggtg ctggaacagc     300
```

```
tatccgccaa acgctactgc atccacactg ctacacgcgt gtaacacata ctgttattgg    360
ctgtattctt aagaggaccc gcaaactcga aagtggtga taacgaaaca acacacgaga    420
aagctgag                                                             428
```

<210> SEQ ID NO 34
<211> LENGTH: 142
<212> TYPE: PRT
<213> ORGANISM: Kluyveromyces lactis

<400> SEQUENCE: 34

```
Phe Val Tyr Lys Leu Ile Pro Thr Asn Met Asn Thr Pro Ala Gly Leu
1               5                   10                  15

Leu Lys Ile Gly Lys Ala Asn Leu Leu His Pro Phe Thr Asp Ala Val
            20                  25                  30

Phe Ser Ala Met Arg Val Asn Ala Glu Gln Ile Ala Tyr Ile Leu Leu
        35                  40                  45

Val Thr Asn Tyr Ile Gly Val Leu Phe Ala Arg Ser Leu His Tyr Gln
    50                  55                  60

Phe Leu Ser Trp Tyr His Trp Thr Leu Pro Val Leu Leu Asn Trp Ala
65                  70                  75                  80

Asn Val Pro Tyr Pro Leu Cys Val Leu Trp Tyr Leu Thr His Glu Trp
                85                  90                  95

Cys Trp Asn Ser Tyr Pro Pro Asn Ala Thr Ala Ser Thr Leu Leu His
            100                 105                 110

Ala Cys Asn Thr Tyr Cys Tyr Trp Leu Tyr Ser Glx Glu Asp Pro Gln
        115                 120                 125

Thr Arg Lys Val Val Ile Thr Lys Gln His Thr Arg Lys Leu
    130                 135                 140
```

<210> SEQ ID NO 35
<211> LENGTH: 102
<212> TYPE: PRT
<213> ORGANISM: Kluyveromyces lactis

<400> SEQUENCE: 35

```
Ala Asn Leu Leu His Pro Phe Thr Asp Ala Val Phe Ser Ala Met Arg
1               5                   10                  15

Val Asn Ala Glu Gln Ile Ala Tyr Ile Leu Leu Val Thr Asn Tyr Ile
            20                  25                  30

Gly Val Leu Phe Ala Arg Ser Leu His Tyr Gln Phe Leu Ser Trp Tyr
        35                  40                  45

His Trp Thr Leu Pro Val Leu Leu Asn Trp Ala Asn Val Pro Tyr Pro
    50                  55                  60

Leu Cys Val Leu Trp Tyr Leu Thr His Glu Trp Cys Trp Asn Ser Tyr
65                  70                  75                  80

Pro Pro Asn Ala Thr Ala Ser Thr Leu Leu His Ala Cys Asn Thr Tyr
                85                  90                  95

Cys Tyr Trp Leu Tyr Ser
            100
```

<210> SEQ ID NO 36
<211> LENGTH: 16
<212> TYPE: PRT
<213> ORGANISM: Kluyveromyces lactis

<400> SEQUENCE: 36

```
Glu Asp Pro Gln Thr Arg Lys Val Val Ile Thr Lys Gln His Thr Arg
```

```
1               5                  10                 15

<210> SEQ ID NO 37
<211> LENGTH: 117
<212> TYPE: PRT
<213> ORGANISM: Saccharomyces cerevisiae

<400> SEQUENCE: 37

Ser Ser Leu Cys His Pro Leu Arg Lys Asn Ala Val Leu Asn Ala Asn
1               5                  10                 15

Pro Ala Lys Thr Ile Pro Phe Val Leu Ile Ala Ser Asn Phe Ile Gly
            20                 25                 30

Val Leu Phe Ser Arg Ser Leu His Tyr Gln Phe Leu Ser Trp Tyr His
        35                 40                 45

Trp Thr Leu Pro Ile Leu Ile Phe Trp Ser Gly Met Pro Phe Phe Val
    50                 55                 60

Gly Pro Ile Trp Tyr Val Leu His Glu Trp Cys Trp Asn Ser Tyr Pro
65                 70                 75                 80

Pro Asn Ser Gln Ala Ser Thr Leu Leu Ala Leu Asn Thr Val Leu
            85                 90                 95

Leu Leu Leu Leu Ala Leu Thr Gln Leu Ser Gly Ser Val Ala Leu Ala
        100                105                110

Lys Ser His Leu Arg
        115

<210> SEQ ID NO 38
<211> LENGTH: 96
<212> TYPE: PRT
<213> ORGANISM: Kluyveromyces lactis

<400> SEQUENCE: 38

Phe Thr Asp Ala Val Phe Ser Ala Met Arg Val Asn Ala Glu Gln Ile
1               5                  10                 15

Ala Tyr Ile Leu Leu Val Thr Asn Tyr Ile Gly Val Leu Phe Ala Arg
            20                 25                 30

Ser Leu His Tyr Gln Phe Leu Ser Trp Tyr His Trp Thr Leu Pro Val
        35                 40                 45

Leu Leu Asn Trp Ala Asn Val Pro Tyr Pro Leu Cys Val Leu Trp Tyr
    50                 55                 60

Leu Thr His Glu Trp Cys Trp Asn Ser Tyr Pro Pro Asn Ala Thr Ala
65                 70                 75                 80

Ser Thr Leu Leu His Ala Cys Asn Thr Tyr Cys Tyr Trp Leu Tyr Ser
            85                 90                 95

<210> SEQ ID NO 39
<211> LENGTH: 7
<212> TYPE: PRT
<213> ORGANISM: Kluyveromyces lactis

<400> SEQUENCE: 39

Glu Asp Pro Gln Thr Arg Lys
1               5

<210> SEQ ID NO 40
<211> LENGTH: 106
<212> TYPE: PRT
<213> ORGANISM: Arabidopsis thaliana

<400> SEQUENCE: 40
```

```
Phe Ser Asp Val Ser Ala Ser Arg Ile Ile Thr Lys Glu His Val Val
 1               5                  10                  15

Thr Ala Met Phe Val Gly Asn Phe Ile Gly Ile Val Phe Ala Arg Ser
             20                  25                  30

Leu His Tyr Gln Phe Tyr Ser Trp Tyr Phe Tyr Ser Leu Pro Tyr Leu
             35                  40                  45

Leu Trp Arg Thr Pro Phe Pro Thr Trp Leu Arg Leu Ile Met Phe Leu
 50                  55                  60

Gly Ile Glu Leu Cys Trp Asn Val Tyr Pro Ser Thr Pro Ser Ser Ser
 65                  70                  75                  80

Gly Leu Leu Leu Cys Leu His Leu Ile Ile Leu Val Gly Leu Trp Leu
                 85                  90                  95

Ala Pro Ser Val Asp Pro Tyr Gln Leu Lys
            100                 105
```

```
<210> SEQ ID NO 41
<211> LENGTH: 4
<212> TYPE: PRT
<213> ORGANISM: artificial
<220> FEATURE:
<223> OTHER INFORMATION: Signal tetrapeptide

<400> SEQUENCE: 41

His Asp Glu Leu
 1

<210> SEQ ID NO 42
<211> LENGTH: 4
<212> TYPE: PRT
<213> ORGANISM: artificial
<220> FEATURE:
<223> OTHER INFORMATION: Signal tetrapeptide

<400> SEQUENCE: 42

Lys Asp Glu Leu
 1

<210> SEQ ID NO 43

<400> SEQUENCE: 43

000

<210> SEQ ID NO 44

<400> SEQUENCE: 44

000

<210> SEQ ID NO 45
<211> LENGTH: 1617
<212> TYPE: DNA
<213> ORGANISM: Mus musculus

<400> SEQUENCE: 45
atgaagatga gacgctacaa gctctttctc atgttctgta tggctggcct gtgcctcata      60
tccttcctgc acttctttaa gaccttatcc tatgtcacct tcccgagaga actggcctcc     120
ctcagcccta acctcgtatc cagcttcttc tggaacaatg ccctgtcac tcccaggcc      180 agtccggagc cgggtggccc cgacctattg cggacacccc tctactccca ctctcccctg     240
ctccagccac tgtccccgag caaggccaca gaggaactgc accgggtgga cttcgtgttg     300
```

```
ccggaggaca ccacggagta ttttgtgcgc accaaagctg gtggtgtgtg cttcaaacca      360
ggtaccagga tgctggagaa accttcgcca gggcggacag aggagaagcc cgaagtgtct      420
gagggctcct cagcccgggg acctgctcgg aggcccatga ggcacgtgtt gagtacgcgg      480
gagcgcctgg gcagccgggg cactaggcgc aagtgggttg agtgtgtgtg cctgccaggc      540
tggcacgggc ccagttgcgg ggtgcccacg gtggtgcagt attccaacct gcccaccaag      600
gaacgcctgg tacccaggga ggtaccgagg cgggttatca cgccatcaa catcaaccac       660 gagttcgacc tgctggatgt gcgcttccat gagctgggag atgttgtgga cgccttcgtg      720
gtctgtgaat ctaatttcac cgcctacggg gagcctcggc cgctcaagtt ccgagagatg      780
ctgaccaatg gcaccttcga gtacatccgc cacaaggtgc tctatgtctt cctggaccat      840
ttcccacctg gtgccgtca ggacggctgg attgcggatg actacctgcg caccttcctc        900
acccaggatg gcgtctcccg cctgcgcaac ctgcggcccg atgacgtctt tatcatcgac      960
gatgcggacg agatccctgc gcgtgatggt gtgctgttcc tcaaactcta cgatggctgg     1020
acagagccct tcgccttcca catgcggaag tccctgtatg gtttcttctg gaagcagccg     1080
ggcacactgg aggtggtgtc aggctgcacc atggacatgc tgcaggccgt gtatgggctg     1140
gatggcatcc gcctgcgccg ccgccagtac tacaccatgc ccaacttccg gcagtatgag     1200
aaccgcaccg ccacatcct agtgcagtgg tctctcggca gccccctgca cttcgcgggc      1260
tggcattgct cctggtgctt cacacccgag ggcatctact ttaaactcgt gtcagcccag     1320
aatggcgact tccccgctg gggtgactat gaggacaaga gggacctcaa ttacatccgc      1380
agcttgatcc gcactggggg atggttcgac ggaacgcagc aggagtaccc tcctgcggac     1440
cccagtgagc acatgtatgc tcctaaatac ctgctcaaga actatgacca gttccgctac     1500
ttgctggaaa atccctaccg ggagcccaag agcactgtag agggtgggcg ccagaaccag     1560
ggctcagatg gaaggccatc tgctgtcagg ggcaagttgg atacagtgga gggctag       1617
```

<210> SEQ ID NO 46
<211> LENGTH: 536
<212> TYPE: PRT
<213> ORGANISM: Mus musculus

<400> SEQUENCE: 46

Met Arg Arg Tyr Lys Leu Phe Leu Met Phe Cys Met Ala Gly Leu Cys
1               5                   10                  15

Leu Ile Ser Phe Leu His Phe Pro Lys Thr Leu Ser Tyr Val Thr Phe
            20                  25                  30

Pro Arg Glu Leu Ala Ser Leu Ser Pro Asn Leu Ile Ser Ser Phe Phe
        35                  40                  45

Trp Asn Asn Ala Pro Val Thr Pro Gln Ala Ser Pro Glu Pro Gly Asp
    50                  55                  60

Pro Asp Leu Leu Arg Thr Pro Leu Tyr Ser His Ser Pro Leu Leu Gln
65                  70                  75                  80

Pro Leu Ser Pro Ser Lys Ala Thr Glu Glu Leu His Arg Val Asp Phe
                85                  90                  95

Val Leu Pro Glu Asp Thr Thr Glu Tyr Phe Val Arg Thr Lys Ala Gly
            100                 105                 110

Gly Val Cys Phe Lys Pro Gly Thr Arg Met Leu Glu Lys Pro Ser Pro
        115                 120                 125

Gly Arg Thr Glu Glu Lys Thr Glu Val Ser Glu Gly Ser Ser Ala Arg
    130                 135                 140

```
Gly Pro Ala Arg Arg Pro Met Arg His Val Leu Ser Ser Arg Glu Arg
145                 150                 155                 160

Leu Gly Ser Arg Gly Thr Arg Lys Trp Val Glu Cys Val Cys Leu
            165                 170                 175

Pro Gly Trp His Gly Pro Ser Cys Gly Val Pro Thr Val Val Gln Tyr
            180                 185                 190

Ser Asn Leu Pro Thr Lys Glu Arg Leu Val Pro Arg Glu Val Pro Arg
            195                 200                 205

Arg Val Ile Asn Ala Ile Asn Ile Asn His Glu Phe Asp Leu Leu Asp
            210                 215                 220

Val Arg Phe His Glu Leu Gly Asp Val Val Asp Ala Phe Val Val Cys
225                 230                 235                 240

Asp Ser Asn Phe Thr Ala Tyr Gly Glu Pro Arg Pro Leu Lys Phe Arg
            245                 250                 255

Glu Met Leu Thr Asn Gly Thr Phe Glu Tyr Ile Arg His Lys Val Leu
            260                 265                 270

Tyr Val Phe Leu Asp His Phe Pro Pro Gly Gly Arg Gln Asp Gly Trp
            275                 280                 285

Ile Ala Asp Asp Tyr Leu Arg Thr Phe Leu Thr Gln Asp Gly Val Ser
            290                 295                 300

Arg Leu Arg Asn Leu Arg Pro Asp Asp Val Phe Ile Ile Asp Asp Ala
305                 310                 315                 320

Asp Glu Ile Pro Ala Arg Asp Gly Val Leu Phe Leu Lys Leu Tyr Asp
            325                 330                 335

Gly Trp Thr Glu Pro Phe Ala Phe His Met Arg Lys Ser Leu Tyr Gly
            340                 345                 350

Phe Phe Trp Lys Gln Pro Gly Thr Leu Glu Val Val Ser Gly Cys Thr
            355                 360                 365

Met Asp Met Leu Gln Ala Val Tyr Gly Leu Asp Gly Ile Arg Leu Arg
            370                 375                 380

Arg Arg Gln Tyr Tyr Thr Met Pro Asn Phe Arg Gln Tyr Glu Asn Arg
385                 390                 395                 400

Thr Gly His Ile Leu Val Gln Trp Ser Leu Gly Ser Pro Leu His Phe
            405                 410                 415

Ala Gly Trp His Cys Ser Trp Cys Phe Thr Pro Glu Gly Ile Tyr Phe
            420                 425                 430

Lys Leu Val Ser Ala Gln Asn Gly Asp Phe Pro Arg Trp Gly Asp Tyr
            435                 440                 445

Glu Asp Lys Arg Asp Leu Asn Tyr Ile Arg Ser Leu Ile Arg Thr Gly
            450                 455                 460

Gly Trp Phe Asp Gly Thr Gln Gln Glu Tyr Pro Pro Ala Asp Pro Ser
465                 470                 475                 480

Glu His Met Tyr Ala Pro Lys Tyr Leu Leu Lys Asn Tyr Asp Gln Phe
            485                 490                 495

Arg Tyr Leu Leu Glu Asn Pro Tyr Arg Glu Pro Lys Ser Thr Val Glu
            500                 505                 510

Gly Gly Arg Gln Asn Gln Gly Ser Asp Gly Arg Ser Ser Ala Val Arg
            515                 520                 525

Gly Lys Leu Asp Thr Ala Glu Gly
            530                 535

<210> SEQ ID NO 47
<211> LENGTH: 21
<212> TYPE: DNA
```

```
<213> ORGANISM: artificial
<220> FEATURE:
<223> OTHER INFORMATION: cloning primer

<400> SEQUENCE: 47
actgccatct gccttcgcca t                                              21

<210> SEQ ID NO 48
<211> LENGTH: 22
<212> TYPE: DNA
<213> ORGANISM: artificial
<220> FEATURE:
<223> OTHER INFORMATION: cloning primer

<400> SEQUENCE: 48
gtaatacgac tcactatagg gc                                             22

<210> SEQ ID NO 49
<211> LENGTH: 20
<212> TYPE: DNA
<213> ORGANISM: artificial
<220> FEATURE:
<223> OTHER INFORMATION: cloning primer

<400> SEQUENCE: 49
aattaaccct cactaaaggg                                                20

<210> SEQ ID NO 50
<211> LENGTH: 1968
<212> TYPE: DNA
<213> ORGANISM: Mus musculus

<400> SEQUENCE: 50
atgcccgtgg ggggcctgtt gccgctcttc agtagccctg ggggcggcgg cctgggcagt      60
ggcctgggcg gggggcttgg cggcgggagg aagggggtctg gccccgctgc cttccgcctc    120
accgagaagt tcgtgctgct gctggtgttc agcgccttca tcacgctctg cttcggggca    180
atcttcttcc tgcctgactc ctccaagctg ctcagcgggg tcctgttcca ctccaaccct    240
gccttgcagc cgccggcgga gcacaagccc gggctcgggg cgcgtgcgga ggatgccgcc    300
gaggggagag tccggcaccg cgaggaaggc gcgcctgggg accctggagc tggactggaa    360
gacaacttag ccaggatccg cgaaaaccac gagcgggctc tcagggaagc caaggagacc    420
ctgcagaagc tgccggagga gatccaaaga gacattctgc tggagaagga aaaggtggcc    480
caggaccagc tgcgtgacaa ggatctgttt aggggcttgc ccaaggtgga cttcctgccc    540
cccgtcgggg tagagaaccg ggagcccgct gacgccacca tccgtgagaa gagggcaaag    600
atcaaagaga tgatgaccca tgcttggaat aattataaac gctatgcgtg gggcttgaac    660
gaactgaaac ctatatcaaa agaaggccat tcaagcagtt tgtttggcaa catcaaagga    720
gctacaatag tagatgccct ggatacccct ttcattatgg gcatgaagac tgaatttcaa    780
gaagctaaat cgtggattaa aaaatattta gattttaatg tgaatgctga agtttctgtt    840
tttgaagtca acatacgctt cgtcggtgga ctgctgtcag cctactattt gtccggagag    900
gagatatttc gaaagaaagc agtggaactt ggggtaaaat tgctacctgc atttcatact    960
ccctctggaa tacttgggc attgctgaat atgaaaagtg ggatcgggcg gaactggccc   1020
tgggcctctg gaggcagcag tatcctggcc gaatttggaa ctctgcattt agagtttatg   1080
cacttgtccc actatcagg agacccagtc tttgccgaaa aggttatgaa aattcgaaca   1140
gtgttgaaca aactggacaa accagaaggc ctttatccta actatctgaa ccccagtagt   1200
```

-continued

```
ggacagtggg gtcaacatca tgtgtcggtt ggaggacttg agacagcttt ttatgaatat    1260
ttgcttaagg cgtggttaat gtctgacaag acagatctcg aagccaagaa gatgtattt     1320 gatgctgttc aggccatcga gactcacttg atccgcaagt caagtggggg actaacgtac    1380
atcgcagagt ggaaggggg cctcctggaa cacaagatgg ccacctgac gtgctttgca     1440 ggaggcatgt ttgcacttgg ggcagatgga gctccggaag cccgggccca acactacctt    1500
gaactcggag ctgaaattgc ccgcacttgt catgaatctt ataatcgtac atatgtgaag    1560
ttgggaccgg aagcgtttcg atttgatggc ggtgtggaag ctattgccac gaggcaaaat    1620
gaaaagtatt acatcttacg gcccgaggtc atcgagacat acatgtacat gtggcgactg    1680
actcacgacc ccaagtacag gacctgggcc tgggaagccg tggaggctct agaaagtcac    1740
tgcagagtga acggaggcta tcaggctta cgggatgttt acattgcccg tgagagttat    1800
gacgatgtcc agcaaagttt cttcctggca gagacactga agtatttgta cttgatattt    1860
tccgatgatg accttcttcc actagaacac tggatcttca acaccgaggc tcatcctttc    1920
cctatactcc gtgaacagaa gaaggaaatt gatggcaaag agaaatga               1968
```

<210> SEQ ID NO 51
<211> LENGTH: 655
<212> TYPE: PRT
<213> ORGANISM: Mus musculus

<400> SEQUENCE: 51

```
Met Pro Val Gly Gly Leu Leu Pro Leu Phe Ser Ser Pro Gly Gly Gly
1               5                   10                  15

Gly Leu Gly Ser Gly Leu Gly Gly Leu Gly Gly Arg Lys Gly
            20                  25                  30

Ser Gly Pro Ala Ala Phe Arg Leu Thr Glu Lys Phe Val Leu Leu
        35                  40                  45

Val Phe Ser Ala Phe Ile Thr Leu Cys Phe Gly Ala Ile Phe Phe Leu
    50                  55                  60

Pro Asp Ser Ser Lys Leu Leu Ser Gly Val Leu Phe His Ser Asn Pro
65                  70                  75                  80

Ala Leu Gln Pro Pro Ala Glu His Lys Pro Gly Leu Gly Ala Arg Ala
                85                  90                  95

Glu Asp Ala Ala Glu Gly Arg Val Arg His Arg Glu Gly Ala Pro
            100                 105                 110

Gly Asp Pro Gly Ala Gly Leu Glu Asp Asn Leu Ala Arg Ile Arg Glu
        115                 120                 125

Asn His Glu Arg Ala Leu Arg Glu Ala Lys Glu Thr Leu Gln Lys Leu
    130                 135                 140

Pro Glu Glu Ile Gln Arg Asp Ile Leu Leu Glu Lys Glu Lys Val Ala
145                 150                 155                 160

Gln Asp Gln Leu Arg Asp Lys Asp Leu Phe Arg Gly Leu Pro Lys Val
                165                 170                 175

Asp Phe Leu Pro Pro Val Gly Val Glu Asn Arg Glu Pro Ala Asp Ala
            180                 185                 190

Thr Ile Arg Glu Lys Arg Ala Lys Ile Lys Glu Met Met Thr His Ala
        195                 200                 205

Trp Asn Asn Tyr Lys Arg Tyr Ala Trp Gly Leu Asn Glu Leu Lys Pro
    210                 215                 220

Ile Ser Lys Glu Gly His Ser Ser Leu Phe Gly Asn Ile Lys Gly
225                 230                 235                 240
```

-continued

Ala Thr Ile Val Asp Ala Leu Asp Thr Leu Phe Ile Met Gly Met Lys
            245                 250                 255

Thr Glu Phe Gln Glu Ala Lys Ser Trp Ile Lys Lys Tyr Leu Asp Phe
        260                 265                 270

Asn Val Asn Ala Glu Val Ser Val Phe Glu Val Asn Ile Arg Phe Val
    275                 280                 285

Gly Gly Leu Leu Ser Ala Tyr Tyr Leu Ser Gly Glu Ile Phe Arg
290                 295                 300

Lys Lys Ala Val Glu Leu Gly Val Lys Leu Leu Pro Ala Phe His Thr
305                 310                 315                 320

Pro Ser Gly Ile Pro Trp Ala Leu Leu Asn Met Lys Ser Gly Ile Gly
                325                 330                 335

Arg Asn Trp Pro Trp Ala Ser Gly Ser Ser Ile Leu Ala Glu Phe
            340                 345                 350

Gly Thr Leu His Leu Glu Phe Met His Leu Ser His Leu Ser Gly Asp
        355                 360                 365

Pro Val Phe Ala Glu Lys Val Met Lys Ile Arg Thr Val Leu Asn Lys
    370                 375                 380

Leu Asp Lys Pro Glu Gly Leu Tyr Pro Asn Tyr Leu Asn Pro Ser Ser
385                 390                 395                 400

Gly Gln Trp Gly Gln His His Val Ser Val Gly Gly Leu Gly Asp Ser
                405                 410                 415

Phe Tyr Glu Tyr Leu Leu Lys Ala Trp Leu Met Ser Asp Lys Thr Asp
            420                 425                 430

Leu Glu Ala Lys Lys Met Tyr Phe Asp Ala Val Gln Ala Ile Glu Thr
        435                 440                 445

His Leu Ile Arg Lys Ser Ser Gly Gly Leu Thr Tyr Ile Ala Glu Trp
    450                 455                 460

Lys Gly Gly Leu Leu Glu His Lys Met Gly His Leu Thr Cys Phe Ala
465                 470                 475                 480

Gly Gly Met Phe Ala Leu Gly Ala Asp Gly Ala Pro Glu Ala Arg Ala
                485                 490                 495

Gln His Tyr Leu Glu Leu Gly Ala Glu Ile Ala Arg Thr Cys His Glu
            500                 505                 510

Ser Tyr Asn Arg Thr Tyr Val Lys Leu Gly Pro Glu Ala Phe Arg Phe
        515                 520                 525

Asp Gly Gly Val Glu Ala Ile Ala Thr Arg Gln Asn Glu Lys Tyr Tyr
    530                 535                 540

Ile Leu Arg Pro Glu Val Ile Glu Thr Tyr Met Tyr Met Trp Arg Leu
545                 550                 555                 560

Thr His Asp Pro Lys Tyr Arg Thr Trp Ala Trp Glu Ala Val Glu Ala
                565                 570                 575

Leu Glu Ser His Cys Arg Val Asn Gly Gly Tyr Ser Gly Leu Arg Asp
            580                 585                 590

Val Tyr Ile Ala Arg Glu Ser Tyr Asp Asp Val Gln Gln Ser Phe Phe
        595                 600                 605

Leu Ala Glu Thr Leu Lys Tyr Leu Tyr Leu Ile Phe Ser Asp Asp Asp
    610                 615                 620

Leu Leu Pro Leu Glu His Trp Ile Phe Asn Thr Glu Ala His Pro Phe
625                 630                 635                 640

Pro Ile Leu Arg Glu Gln Lys Lys Glu Ile Asp Gly Lys Glu Lys
                645                 650                 655

<210> SEQ ID NO 52
<211> LENGTH: 36
<212> TYPE: DNA
<213> ORGANISM: artificial
<220> FEATURE:
<223> OTHER INFORMATION: cloning primer

<400> SEQUENCE: 52
atgcccgtgg ggggcctgtt gccgctcttc agtagc        36

<210> SEQ ID NO 53
<211> LENGTH: 40
<212> TYPE: DNA
<213> ORGANISM: artificial
<220> FEATURE:
<223> OTHER INFORMATION: cloning primer

<400> SEQUENCE: 53
tcatttctct tgccatcaa tttccttctt ctgttcacgg        40

<210> SEQ ID NO 54
<211> LENGTH: 44
<212> TYPE: DNA
<213> ORGANISM: artificial
<220> FEATURE:
<223> OTHER INFORMATION: cloning primer

<400> SEQUENCE: 54
ggcgcgccga ctcctccaag ctgctcagcg gggtcctgtt ccac        44

<210> SEQ ID NO 55
<211> LENGTH: 50
<212> TYPE: DNA
<213> ORGANISM: artificial
<220> FEATURE:
<223> OTHER INFORMATION: cloning primer

<400> SEQUENCE: 55
ccttaattaa tcatttctct tgccatcaa tttccttctt ctgttcacgg        50

<210> SEQ ID NO 56
<211> LENGTH: 51
<212> TYPE: DNA
<213> ORGANISM: artificial
<220> FEATURE:
<223> OTHER INFORMATION: cloning primer

<400> SEQUENCE: 56
ggcgagctcg gcctacccgg ccaaggctga gatcatttgt ccagcttcag a        51

<210> SEQ ID NO 57
<211> LENGTH: 55
<212> TYPE: DNA
<213> ORGANISM: artificial
<220> FEATURE:
<223> OTHER INFORMATION: cloning primer

<400> SEQUENCE: 57
gcccacgtcg acggatccgt ttaaacatcg attggagagg ctgacaccgc tacta        55

<210> SEQ ID NO 58
<211> LENGTH: 55
<212> TYPE: DNA
<213> ORGANISM: artificial
<220> FEATURE:
<223> OTHER INFORMATION: cloning primer

<400> SEQUENCE: 58
cgggatccac tagtatttaa atcatatgtg cgagtgtaca actcttccca catgg        55

<210> SEQ ID NO 59
<211> LENGTH: 55
<212> TYPE: DNA
<213> ORGANISM: artificial
<220> FEATURE:
<223> OTHER INFORMATION: cloning primer

<400> SEQUENCE: 59
ggacgcgtcg acggcctacc cggccgtacg aggaatttct cggatgactc ttttc        55

<210> SEQ ID NO 60
<211> LENGTH: 45
<212> TYPE: DNA
<213> ORGANISM: artificial
<220> FEATURE:
<223> OTHER INFORMATION: cloning primer

<400> SEQUENCE: 60
cgggatccct cgagagatct tttttgtaga aatgtcttgg tgcct                   45

<210> SEQ ID NO 61
<211> LENGTH: 63
<212> TYPE: DNA
<213> ORGANISM: artificial
<220> FEATURE:
<223> OTHER INFORMATION: cloning primer

<400> SEQUENCE: 61
ggacatgcat gcactagtgc ggccgccacg tgatagttgt tcaattgatt gaaataggga    60
caa                                                                 63

<210> SEQ ID NO 62
<211> LENGTH: 52
<212> TYPE: DNA
<213> ORGANISM: artificial
<220> FEATURE:
<223> OTHER INFORMATION: cloning primer

<400> SEQUENCE: 62
ccttgctagc ttaattaacc gcggcacgtc cgacggcggc ccacgggtcc ca            52

<210> SEQ ID NO 63
<211> LENGTH: 61
<212> TYPE: DNA
<213> ORGANISM: artificial
<220> FEATURE:
<223> OTHER INFORMATION: cloning primer

<400> SEQUENCE: 63
ggacatgcat gcggatccct taagagccgg cagcttgcaa attaaagcct tcgagcgtcc    60
c                                                                   61

<210> SEQ ID NO 64
<211> LENGTH: 61
<212> TYPE: DNA
<213> ORGANISM: artificial
<220> FEATURE:
<223> OTHER INFORMATION: cloning primer

<400> SEQUENCE: 64
gaaccacgtc gacggccatt gcggccaaaa ccttttttcc tattcaaaca caaggcattg    60

```
c                                                              61

<210> SEQ ID NO 65
<211> LENGTH: 43
<212> TYPE: DNA
<213> ORGANISM: artificial
<220> FEATURE:
<223> OTHER INFORMATION: cloning primer

<400> SEQUENCE: 65
ctccaatact agtcgaagat tatcttctac ggtgcctgga ctc                 43

<210> SEQ ID NO 66
<211> LENGTH: 53
<212> TYPE: DNA
<213> ORGANISM: artificial
<220> FEATURE:
<223> OTHER INFORMATION: cloning primer

<400> SEQUENCE: 66
tggaaggttt aaacaaagct agagtaaaat agatatagcg agattagaga atg      53

<210> SEQ ID NO 67
<211> LENGTH: 50
<212> TYPE: DNA
<213> ORGANISM: artificial
<220> FEATURE:
<223> OTHER INFORMATION: cloning primer

<400> SEQUENCE: 67
aagaattcgg ctggaaggcc ttgtaccttg atgtagttcc cgttttcatc          50

<210> SEQ ID NO 68
<211> LENGTH: 58
<212> TYPE: DNA
<213> ORGANISM: artificial
<220> FEATURE:
<223> OTHER INFORMATION: cloning primer

<400> SEQUENCE: 68
gcccaagccg gccttaaggg atctcctgat gactgactca ctgataataa aaatacgg  58

<210> SEQ ID NO 69
<211> LENGTH: 59
<212> TYPE: DNA
<213> ORGANISM: artificial
<220> FEATURE:
<223> OTHER INFORMATION: cloning primer

<400> SEQUENCE: 69
gggcgcgtat ttaaatacta gtggatctat cgaatctaaa tgtaagttaa aatctctaa  59

<210> SEQ ID NO 70
<211> LENGTH: 39
<212> TYPE: DNA
<213> ORGANISM: artificial
<220> FEATURE:
<223> OTHER INFORMATION: cloning primer

<400> SEQUENCE: 70
ggccgcctgc agatttaaat gaattcggcg cgccttaat                     39

<210> SEQ ID NO 71
<211> LENGTH: 34
<212> TYPE: DNA
```

```
<213> ORGANISM: artificial
<220> FEATURE:
<223> OTHER INFORMATION: cloning primer

<400> SEQUENCE: 71
taaggcgcgc cgaattcatt taaatctgca gggc                          34

<210> SEQ ID NO 72
<211> LENGTH: 29
<212> TYPE: DNA
<213> ORGANISM: artificial
<220> FEATURE:
<223> OTHER INFORMATION: cloning primer

<400> SEQUENCE: 72
tggcaggcgc gcctcagtca gcgctctcg                                29

<210> SEQ ID NO 73
<211> LENGTH: 29
<212> TYPE: DNA
<213> ORGANISM: artificial
<220> FEATURE:
<223> OTHER INFORMATION: cloning primer

<400> SEQUENCE: 73
aggttaatta agtgctaatt ccagctagg                                29

<210> SEQ ID NO 74
<211> LENGTH: 26
<212> TYPE: DNA
<213> ORGANISM: artificial
<220> FEATURE:
<223> OTHER INFORMATION: cloning primer

<400> SEQUENCE: 74
ccagaagaat tcaattytgy cartgg                                   26

<210> SEQ ID NO 75
<211> LENGTH: 25
<212> TYPE: DNA
<213> ORGANISM: artificial
<220> FEATURE:
<223> OTHER INFORMATION: cloning primer
<220> FEATURE:
<221> NAME/KEY: misc_feature
<222> LOCATION: (17)..(17)
<223> OTHER INFORMATION: wherein "n" is equal to "a" or "t" or "g" or
      "c".
<220> FEATURE:
<221> NAME/KEY: misc_feature
<222> LOCATION: (20)..(20)
<223> OTHER INFORMATION: wherein "n" is equal to "a" or "t" or "g" or
      "c".

<400> SEQUENCE: 75
cagtgaaaat acctggnccn gtcca                                    25

<210> SEQ ID NO 76
<211> LENGTH: 27
<212> TYPE: DNA
<213> ORGANISM: artificial
<220> FEATURE:
<223> OTHER INFORMATION: cloning primer

<400> SEQUENCE: 76
tgccatcttt taggtccagg cccgttc                                  27
```

```
<210> SEQ ID NO 77
<211> LENGTH: 27
<212> TYPE: DNA
<213> ORGANISM: artificial
<220> FEATURE:
<223> OTHER INFORMATION: cloning primer

<400> SEQUENCE: 77
gatcccacga cgcatcgtat ttctttc                                      27

<210> SEQ ID NO 78
<211> LENGTH: 35
<212> TYPE: DNA
<213> ORGANISM: artificial
<220> FEATURE:
<223> OTHER INFORMATION: cloning primer

<400> SEQUENCE: 78
ggtgttttgt tttctagatc tttgcaytay cartt                             35

<210> SEQ ID NO 79
<211> LENGTH: 36
<212> TYPE: DNA
<213> ORGANISM: artificial
<220> FEATURE:
<223> OTHER INFORMATION: cloning primer

<400> SEQUENCE: 79
agaatttggt gggtaagaat tccarcacca ytcrtg                            36

<210> SEQ ID NO 80
<211> LENGTH: 32
<212> TYPE: DNA
<213> ORGANISM: artificial
<220> FEATURE:
<223> OTHER INFORMATION: cloning primer

<400> SEQUENCE: 80
cctaagctgg tatgcgttct ctttgccata tc                                32

<210> SEQ ID NO 81
<211> LENGTH: 30
<212> TYPE: DNA
<213> ORGANISM: artificial
<220> FEATURE:
<223> OTHER INFORMATION: cloning primer

<400> SEQUENCE: 81
gcggcataaa caataataga tgctataaag                                   30

<210> SEQ ID NO 82
<211> LENGTH: 24
<212> TYPE: DNA
<213> ORGANISM: artificial
<220> FEATURE:
<223> OTHER INFORMATION: cloning primer

<400> SEQUENCE: 82
ccacatcatc cgtgctacat atag                                         24

<210> SEQ ID NO 83
<211> LENGTH: 44
<212> TYPE: DNA
<213> ORGANISM: artificial
<220> FEATURE:
<223> OTHER INFORMATION: cloning vector
```

-continued

```
<400> SEQUENCE: 83
acgaggcaag ctaaacagat ctcgaagtat cgagggttat ccag              44

<210> SEQ ID NO 84
<211> LENGTH: 44
<212> TYPE: DNA
<213> ORGANISM: artificial
<220> FEATURE:
<223> OTHER INFORMATION: cloning primer

<400> SEQUENCE: 84
ccatccagtg tcgaaaacga gccaatggtt catgtctata aatc              44

<210> SEQ ID NO 85
<211> LENGTH: 24
<212> TYPE: DNA
<213> ORGANISM: artificial
<220> FEATURE:
<223> OTHER INFORMATION: cloning primer

<400> SEQUENCE: 85
agcctcagcg ccaacaagcg atgg                                    24

<210> SEQ ID NO 86
<211> LENGTH: 44
<212> TYPE: DNA
<213> ORGANISM: artificial
<220> FEATURE:
<223> OTHER INFORMATION: cloning primer

<400> SEQUENCE: 86
ctggataacc ctcgatactt cgagatctgt ttagcttgcc tcgt              44

<210> SEQ ID NO 87
<211> LENGTH: 44
<212> TYPE: DNA
<213> ORGANISM: artificial
<220> FEATURE:
<223> OTHER INFORMATION: cloning primer

<400> SEQUENCE: 87
gatttataga catgaaccat tggctcgttt tcgacactgg atgg              44

<210> SEQ ID NO 88
<211> LENGTH: 20
<212> TYPE: DNA
<213> ORGANISM: artificial
<220> FEATURE:
<223> OTHER INFORMATION: cloning primer

<400> SEQUENCE: 88
atcctttacc gatgctgtat                                         20

<210> SEQ ID NO 89
<211> LENGTH: 27
<212> TYPE: DNA
<213> ORGANISM: artificial
<220> FEATURE:
<223> OTHER INFORMATION: cloning primer

<400> SEQUENCE: 89
ataacagtat gtgttacacg cgtgtag                                 27

<210> SEQ ID NO 90
<211> LENGTH: 25
```

```
<212> TYPE: DNA
<213> ORGANISM: Rattus norvegicus

<400> SEQUENCE: 90
ttcctcactg cagtcttcta taact                                              25

<210> SEQ ID NO 91
<211> LENGTH: 26
<212> TYPE: DNA
<213> ORGANISM: Rattus norvegicus

<400> SEQUENCE: 91
tggagaccat gaggttccgc atctac                                             26

<210> SEQ ID NO 92
<211> LENGTH: 35
<212> TYPE: DNA
<213> ORGANISM: Rattus norvegicus

<400> SEQUENCE: 92
ttggcgcgcc tccctagtgt accagttgaa ctttg                                   35

<210> SEQ ID NO 93
<211> LENGTH: 32
<212> TYPE: DNA
<213> ORGANISM: Rattus norvegicus

<400> SEQUENCE: 93
gattaattaa ctcactgcag tcttctataa ct                                      32

<210> SEQ ID NO 94
<211> LENGTH: 36
<212> TYPE: DNA
<213> ORGANISM: artificial
<220> FEATURE:
<223> OTHER INFORMATION: cloning primer

<400> SEQUENCE: 94
tcctggcgcg ccttcccgag agaactggcc tccctc                                  36

<210> SEQ ID NO 95
<211> LENGTH: 37
<212> TYPE: DNA
<213> ORGANISM: artificial
<220> FEATURE:
<223> OTHER INFORMATION: cloning primer

<400> SEQUENCE: 95
aattaattaa ccctagccct ccgctgtatc caacttg                                 37

<210> SEQ ID NO 96
<211> LENGTH: 39
<212> TYPE: DNA
<213> ORGANISM: Artificial
<220> FEATURE:
<223> OTHER INFORMATION: cloning primer

<400> SEQUENCE: 96
ggccgcctgc agatttaaat gaattcggcg cgccttaat                               39

<210> SEQ ID NO 97
<211> LENGTH: 34
<212> TYPE: DNA
<213> ORGANISM: Artificial
<220> FEATURE:
```

-continued

```
<223> OTHER INFORMATION: cloning primer

<400> SEQUENCE: 97
taaggcgcgc cgaattcatt taaatctgca gggc                              34

<210> SEQ ID NO 98
<211> LENGTH: 36
<212> TYPE: DNA
<213> ORGANISM: Artificial
<220> FEATURE:
<223> OTHER INFORMATION: cloning primer

<400> SEQUENCE: 98
tcctggcgcg ccttcccgag agaactggcc tccctc                            36

<210> SEQ ID NO 99
<211> LENGTH: 33
<212> TYPE: DNA
<213> ORGANISM: Artificial
<220> FEATURE:
<223> OTHER INFORMATION: cloning primer

<400> SEQUENCE: 99
ccgaggcgcg ccacagagga actgcaccgg gtg                               33

<210> SEQ ID NO 100
<211> LENGTH: 37
<212> TYPE: DNA
<213> ORGANISM: Artificial
<220> FEATURE:
<223> OTHER INFORMATION: cloning primer

<400> SEQUENCE: 100
accgaggcgc gccatcaacg ccatcaacat caaccac                           37

<210> SEQ ID NO 101
<211> LENGTH: 37
<212> TYPE: DNA
<213> ORGANISM: Artificial
<220> FEATURE:
<223> OTHER INFORMATION: cloning primer

<400> SEQUENCE: 101
aattaattaa ccctagccct ccgctgtatc caacttg                           37
```

N-ACETYLGLUCOSAMINYLTRANSFERASE III EXPRESSION IN LOWER EUKARYOTES

CROSS-REFERENCE TO RELATED APPLICATIONS

This application is a continuation-in-part of U.S. application Ser. No. 10/371,877, filed on Feb. 20, 2003, now issued U.S. Pat. No. 7,449,308, which is a continuation-in-part of U.S. application Ser. No. 09/892,591, filed Jun. 27, 2001, now issued U.S. Pat. No. 7,029,872, which claims the benefit under 35 U.S.C. §119(e) of U.S. Provisional Application No. 60/214,358, filed Jun. 28, 2000, U.S. Provisional Application No. 60/215,638, filed Jun. 30, 2000, and U.S. Provisional Application No. 60/279,997, filed Mar. 30, 2001, each of which is incorporated herein by reference in its entirety. This application is also a continuation-in-part of PCT/US02/41510, filed on Dec. 24, 2002, which claims the benefit of U.S. Provisional Application No. 60/344,169, filed on Dec. 27, 2001, each of which is incorporated herein by reference in its entirety.

FIELD OF THE INVENTION

The present invention is directed to methods and compositions by which non-human eukaryotic host cells, such as fungi or other eukaryotic cells, can be genetically modified to produce glycosylated proteins (glycoproteins) having patterns of glycosylation similar to those of glycoproteins produced by animal cells, especially human cells, which are useful as human or animal therapeutic agents.

BACKGROUND OF THE INVENTION

Glycosylation Pathways in Humans and Lower Eukaryotes

After DNA is transcribed and translated into a protein, further post-translational processing involves the attachment of sugar residues, a process known as glycosylation. Different organisms produce different glycosylation enzymes (glycosyltransferases and glycosidases), and have different substrates (nucleotide sugars) available, so that the glycosylation patterns as well as composition of the individual oligosaccharides, even of the same protein, will be different depending on the host system in which the particular protein is being expressed. Bacteria typically do not glycosylate proteins, and if so only in a very unspecific manner (Moens and Vanderleyden (1997) *Arch Microbiol.* 168(3):169-175). Lower eukaryotes such as filamentous fungi and yeast add primarily mannose and mannosylphosphate sugars. The resulting glycan is known as a "high-mannose" type glycan or a mannan. Plant cells and insect cells (such as Sf9 cells) glycosylate proteins in yet another way. By contrast, in higher eukaryotes such as humans, the nascent oligosaccharide side chain may be trimmed to remove several mannose residues and elongated with additional sugar residues that typically are not found in the N-glycans of lower eukaryotes. See, e.g., Bretthauer, et al. (1999) *Biotechnology and Applied Biochemistry* 30:193-200; Martinet, et al. (1998) *Biotechnology Letters* 20:1171-1177; Weikert, et al. (1999) *Nature Biotechnology*, 17:1116-1121; M. Malissard, et al. (2000) *Biochemical and Biophysical Research Communications* 267:169-173; Jarvis, et al., (1998) *Current Opinion in Biotechnology* 9:528-533; and Takeuchi (1997) *Trends in Glycoscience and Glycotechnology* 9:S29-S35.

Synthesis of a mammalian-type oligosaccharide structure begins with a set of sequential reactions in the course of which sugar residues are added and removed while the protein moves along the secretory pathway in the host organism. The enzymes which reside along the glycosylation pathway of the host organism or cell determine the resulting glycosylation patterns of secreted proteins. Thus, the resulting glycosylation pattern of proteins expressed in lower eukaryotic host cells differs substantially from the glycosylation pattern of proteins expressed in higher eukaryotes such as humans and other mammals (Bretthauer, 1999). The structure of a typical fungal N-glycan is shown in FIG. 1A.

The early steps of human glycosylation can be divided into at least two different phases: (i) lipid-linked $Glc_3Man_9GlcNAc_2$ oligosaccharides are assembled by a sequential set of reactions at the membrane of the endoplasmic reticulum (ER) (FIG. 13) and (ii) the transfer of this oligosaccharide from the lipid anchor dolichyl pyrophosphate onto de novo synthesized protein. The site of the specific transfer is defined by an asparagine (Asn) residue in the sequence Asn-Xaa-Ser/Thr where Xaa can be any amino acid except proline (Gavel and von Heijne (1990) *Protein Eng.* 3:433-42). Further processing by glucosidases and mannosidases occurs in the ER before the nascent glycoprotein is transferred to the early Golgi apparatus, where additional mannose residues are removed by Golgi specific alpha ($\alpha$)-1,2-mannosidases. Processing continues as the protein proceeds through the Golgi. In the medial Golgi, a number of modifying enzymes, including N-acetylglucosaminyl transferases (GnTI, GnTII, GnTIII, GnTIV and GnTV), mannosidase II and fucosyltransferases, add and remove specific sugar residues. Finally, in the trans-Golgi, galactosyltranferases (GalT) and sialyltransferases (ST) produce a glycoprotein structure that is released from the Golgi. It is this structure, characterized by bi-, tri- and tetra-antennary structures, containing galactose, fucose, N-acetylglucosamine and a high degree of terminal sialic acid, that gives glycoproteins their human characteristics. The structure of a typical human N-glycan is shown in FIG. 1B. See also FIGS. 14 and 15 for steps involved in mammalian-type N-glycan processing.

In nearly all eukaryotes, glycoproteins are derived from a common lipid-linked oligosaccharide precursor $Glc_3Man_9GlcNAc_2$-dolichol-pyrophosphate. Within the endoplasmic reticulum, synthesis and processing of dolichol pyrophosphate bound oligosaccharides are identical between all known eukaryotes. However, further processing of the core oligosaccharide by fungal cells, e.g., yeast, once it has been transferred to a peptide leaving the ER and entering the Golgi, differs significantly from humans as it moves along the secretory pathway and involves the addition of several mannose sugars.

In yeast, these steps are catalyzed by Golgi residing mannosyltransferases, like Och1p, Mnt1p and Mnn1p, which sequentially add mannose sugars to the core oligosaccharide. The resulting structure is undesirable for the production of human-like proteins and it is thus desirable to reduce or eliminate mannosyltransferase activity. Mutants of *S. cerevisiae*, deficient in mannosyltransferase activity (for example och1 or mnn9 mutants) have been shown to be non-lethal and display reduced mannose content in the oligosaccharide of yeast glycoproteins. Other oligosaccharide processing enzymes, such as mannosylphosphate transferase, may also have to be eliminated depending on the host's particular endogenous glycosylation pattern.

Sugar Nucleotide Precursors

The N-glycans of animal glycoproteins typically include galactose, fucose, and terminal sialic acid. These sugars are not found on glycoproteins produced in yeast and filamentous fungi. In humans, the full range of nucleotide sugar precursors (e.g., UDP-N-acetylglucosamine, UDP-N-acetylgalactosamine, CMP-N-acetylneuraminic acid, UDP-galactose, GDP-fucose, etc.) are synthesized in the cytosol and transported into the Golgi, where they are attached to the core oligosaccharide by glycosyltransferases. (Sommers and Hirschberg (1981) *J. Cell Biol.* 91(2):A406-A406; Sommers and Hirschberg (1982) *J. Biol. Chem.* 257(18):811-817; Perez and Hirschberg (1987) *Methods in Enzymology* 138:709-715).

Glycosyl transfer reactions typically yield a side product which is a nucleoside diphosphate or monophosphate. While monophosphates can be directly exported in exchange for nucleoside triphosphate sugars by an antiport mechanism, diphosphonucleosides (e.g., GDP) have to be cleaved by phosphatases (e.g. GDPase) to yield nucleoside monophosphates and inorganic phosphate prior to being exported. This reaction is important for efficient glycosylation; for example, GDPase from *Saccharomyces cerevisiae* (*S. cerevisiae*) has been found to be necessary for mannosylation. However that GDPase has 90% reduced activity toward UDP (Berninsone et al. (1994) *J. Biol. Chem.* 269(1):207-211). Lower eukaryotes typically lack UDP-specific diphosphatase activity in the Golgi since they do not utilize UDP-sugar precursors for Golgi-based glycoprotein synthesis. *Schizosaccharomyces pombe*, a yeast found to add galactose residues to cell wall polysaccharides (from UDP-galactose) has been found to have specific UDPase activity, indicating the potential requirement for such an enzyme (Berninsone et al. (1994) *J. Biol. Chem.* 269(1):207-211). UDP is known to be a potent inhibitor of glycosyltransferases and the removal of this glycosylation side product may be important to prevent glycosyltransferase inhibition in the lumen of the Golgi (Khatara et al. (1974) *Eur. J. Biochem.* 44:537-560). See Berninsone et al. (1995) *J. Biol. Chem.* 270(24):14564-14567; Beaudet et al. (1998) *Abc Transporters: Biochemical, Cellular, and Molecular Aspects* 292: 397-413.

Sequential Processing of N-Glycans by Compartmentalized Enzyme Activities

Sugar transferases and glycosidases (e.g., mannosidases) line the inner (luminal) surface of the ER and Golgi apparatus and thereby provide a "catalytic" surface that allows for the sequential processing of glycoproteins as they proceed through the ER and Golgi network. The multiple compartments of the cis, medial, and trans Golgi and the trans-Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases such that a specific carbohydrate structure may be synthesized. Much work has been dedicated to revealing the exact mechanism by which these enzymes are retained and anchored to their respective organelle. The evolving picture is complex but evidence suggests that stem region, membrane spanning region and cytoplasmic tail, individually or in concert, direct enzymes to the membrane of individual organelles and thereby localize the associated catalytic domain to that locus (see, e.g., Gleeson (1998) *Histochem. Cell Biol.* 109: 517-532).

In some cases, these specific interactions were found to function across species. For example, the membrane spanning domain of α2,6-ST from rats, an enzyme known to localize in the trans-Golgi of the animal, was shown to also localize a reporter gene (invertase) in the yeast Golgi (Schwientek et al. (1995) *J. Biol. Chem.* 270(10):5483-9). However, the very same membrane spanning domain as part of a full-length α2,6-ST was retained in the ER and not further transported to the Golgi of yeast (Krezdorn et al. (1994) *Eur. J. Biochem.* 220(3):809-17). A full length GalT from humans was not even synthesized in yeast, despite demonstrably high transcription levels. In contrast, the transmembrane region of the same human GalT fused to an invertase reporter was able to direct localization to the yeast Golgi, albeit it at low production levels. Schwientek and co-workers have shown that fusing 28 amino acids of a yeast mannosyltransferase (MNT1), a region containing a cytoplasmic tail, a transmembrane region and eight amino acids of the stem region, to the catalytic domain of human GalT are sufficient for Golgi localization of an active GalT. Other galactosyltransferases appear to rely on interactions with enzymes resident in particular organelles because, after removal of their transmembrane region, they are still able to localize properly.

Improper localization of a glycosylation enzyme may prevent proper functioning of the enzyme in the pathway. For example, *Aspergillus nidulans*, which has numerous α-1,2-mannosidases (Eades and Hintz (2000) *Gene* 255(1):25-34), does not add GlcNAc to $Man_5GlcNAc_2$ when transformed with the rabbit GnTI gene, despite a high overall level of GnTI activity (Kalsner et al. (1995) *Glycoconj. J.* 12(3):360-370). GnTI, although actively expressed, may be incorrectly localized such that the enzyme is not in contact with both of its substrates: UDP-GlcNAc and a productive $Man_5GlcNAc_2$ substrate (not all $Man_5GlcNAc_2$ structures are productive; see below). Alternatively, the host organism may not provide an adequate level of UDP-GlcNAc in the Golgi or the enzyme may be properly localized but nevertheless inactive in its new environment. In addition, $Man_5GlcNAc_2$ structures present in the host cell may differ in structure from $Man_5GlcNAc_2$ found in mammals. Maras and coworkers found that about one third of the N-glycans from cellobiohydrolase I (CBHI) obtained from *T. reesei* can be trimmed to $Man_5GlcNAc_2$ by *A. saitoi* 1,2 mannosidase in vitro. Fewer than 1% of those N-glycans, however, could serve as a productive substrate for GnTI. Maras et al. (1997) *Eur. J. Biochem.* 249:701-707. The mere presence of $Man_5GlcNAc_2$, therefore, does not assure that further in vivo processing of $Man_5GlcNAc_2$ can be achieved. It is formation of a productive, GnTI-reactive $Man_5GlcNAc_2$ structure that is required. Although $Man_5GlcNAc_2$ could be produced in the cell (about 27 mol %), only a small fraction could be converted to $Man_5GlcNAc_2$ (less than about 5%, see Chiba et al. WO 01/14522).

To date, there is no reliable way of predicting whether a particular heterologously expressed glycosyltransferase or mannosidase in a lower eukaryote will be (1), sufficiently translated (2), catalytically active or (3) located to the proper organelle within the secretory pathway. Because all three of these are necessary to affect glycosylation patterns in lower eukaryotes, a systematic scheme to achieve the desired catalytic function and proper retention of enzymes in the absence of predictive tools, which are currently not available, would be desirable.

Production of Therapeutic Glycoproteins

A significant number of proteins isolated from humans or animals are post-translationally modified, with glycosylation being one of the most significant modifications. An estimated 70% of all therapeutic proteins are glycosylated and thus currently rely on a production system (i.e., host cell) that is able to glycosylate in a manner similar to humans. Several studies have shown that glycosylation plays an important role in determining the (1) immunogenicity, (2) pharmacokinetic properties, (3) trafficking, and (4) efficacy of therapeutic proteins. It is thus not surprising that substantial efforts by the pharmaceutical industry have been directed at developing processes to obtain glycoproteins that are as "humanoid" or "human-like" as possible. To date, most glycoproteins are made in a mammalian host system. This may involve the genetic engineering of such mammalian cells to enhance the degree of sialylation (i.e., terminal addition of sialic acid) of proteins expressed by the cells, which is known to improve pharmacokinetic properties of such proteins. Alternatively, one may improve the degree of sialylation by in vitro addition of such sugars using known glycosyltransferases and their respective nucleotide sugars (e.g., 2,3-sialyltransferase and CMP-sialic acid).

While most higher eukaryotes carry out glycosylation reactions that are similar to those found in humans, recombinant human proteins expressed in the above mentioned host systems invariably differ from their "natural" human counterpart (Raju et al. (2000) *Glycobiology* 10(5): 477-486). Extensive development work has thus been directed at finding ways to improve the "human character" of proteins made in these expression systems. This includes the optimization of fermentation conditions and the genetic modification of protein expression hosts by introducing genes encoding enzymes involved in the formation of human-like glycoforms. Goochee et al. (1999) *Biotechnology* 9(12):1347-55; Andersen and Goochee (1994) *Curr Opin Biotechnol.* 5(5):546-49; Werner et al. (1998) *Arzneimittelforschung.* 48(8):870-80; Weikert et al. (1999) *Nat Biotechnol.* 17(11):1116-21; Yang and Butler (2000) *Biotech. Bioeng.* 68:370-80. Inherent problems associated with all mammalian expression systems have not been solved.

Glycoprotein Production Using Eukaryotic Microorganisms

Although the core oligosaccharide structure transferred to a protein in the endoplasmic reticulum is basically identical in mammals and lower eukaryotes, substantial differences have been found in the subsequent processing reactions which occur in the Golgi apparatus of fungi and mammals. In fact, even amongst different lower eukaryotes there exist a great variety of glycosylation structures. This has historically prevented the use of lower eukaryotes as hosts for the production of recombinant human glycoproteins despite otherwise notable advantages over mammalian expression systems.

Therapeutic glycoproteins produced in a microorganism host such as yeast utilizing the endogenous host glycosylation pathway differ structurally from those produced in mammalian cells and typically show greatly reduced therapeutic efficacy. Such glycoproteins are typically immunogenic in humans and show a reduced half-life (and thus bioactivity) in vivo after administration (Takeuchi (1997) *Trends in Glycoscience and Glycotechnology* 9:S29-S35). Specific receptors in humans and animals (i.e., macrophage mannose receptors) can recognize terminal mannose residues and promote the rapid clearance of the foreign glycoprotein from the bloodstream. Additional adverse effects may include changes in protein folding, solubility, susceptibility to proteases, trafficking, transport, compartmentalization, secretion, recognition by other proteins or factors, antigenicity, or allergenicity.

Yeast and filamentous fungi have both been successfully used for the production of recombinant proteins, both intracellular and secreted (Cereghino and Cregg (2000) *FEMS Microbiology Reviews* 24(1):45-66; Harkki et al. (1989) *Bio-Technology* 7(6):596; Berka et al. (1992) *Abstr. Papers Amer. Chem. Soc.* 203:121-BIOT; Svetina et al. (2000) *J. Biotechnol.* 76(2-3):245-251). Various yeasts, such as *K. lactis, Pichia pastoris, Pichia methanolica,* and *Hansenula polymorpha,* have played particularly important roles as eukaryotic expression systems because they are able to grow to high cell densities and secrete large quantities of recombinant protein. Likewise, filamentous fungi, such as *Aspergillus niger, Fusarium* sp, *Neurospora crassa* and others, have been used to efficiently produce glycoproteins at the industrial scale. However, as noted above, glycoproteins expressed in any of these eukaryotic microorganisms differ substantially in N-glycan structure from those in animals. This has prevented the use of yeast or filamentous fungi as hosts for the production of many therapeutic glycoproteins.

Although glycosylation in yeast and fungi is very different than in humans, some common elements are shared. The first step, the transfer of the core oligosaccharide structure to the nascent protein, is highly conserved in all eukaryotes including yeast, fungi, plants and humans (compare FIGS. 1A and 1B). Subsequent processing of the core oligosaccharide, however, differs significantly in yeast and involves the addition of several mannose sugars. This step is catalyzed by mannosyltransferases residing in the Golgi (e.g., OCH1, MNT1, MNN1, etc.), which sequentially add mannose sugars to the core oligosaccharide. The resulting structure is undesirable for the production of humanoid proteins and it is thus desirable to reduce or eliminate mannosyltransferase activity. Mutants of *S. cerevisiae* deficient in mannosyltransferase activity (e.g., och1 or mnn9 mutants) have shown to be non-lethal and display a reduced mannose content in the oligosaccharide of yeast glycoproteins. Other oligosaccharide processing enzymes, such as mannosylphosphate transferase, may also have to be eliminated depending on the host's particular endogenous glycosylation pattern. After reducing undesired endogenous glycosylation reactions, the formation of complex N-glycans has to be engineered into the host system. This requires the stable expression of several enzymes and sugar-nucleotide transporters. Moreover, one has to localize these enzymes so that a sequential processing of the maturing glycosylation structure is ensured.

Several efforts have been made to modify the glycosylation pathways of eukaryotic microorganisms to provide glycoproteins more suitable for use as mammalian therapeutic agents. For example, several glycosyltransferases have been separately cloned and expressed in *S. cerevisiae* (GalT, GnTI), *Aspergillus nidulans* (GnTI) and other fungi (Yoshida et al. (1999) *Glycobiology* 9(1):53-8, Kalsner et al. (1995) *Glycoconj. J* 12(3):360-370). However, N-glycans resembling those made in human cells were not obtained.

Yeasts produce a variety of mannosyltransferases (e.g., 1,3-mannosyltransferases such as MNN1 in *S. cerevisiae*; Graham and Emr (1991) *J. Cell. Biol.* 114(2):207-218), 1,2-mannosyltransferases (e.g., KTR/KRE family from *S. cerevisiae*), 1,6-mannosyltransferases (e.g., OCH1 from *S. cerevisiae*), mannosylphosphate transferases and their regulators (e.g., MNN4 and MNN6 from *S. cerevisiae*) and additional enzymes that are involved in endogenous glycosylation reactions. Many of these genes have been deleted individually giving rise to viable organisms having altered glycosylation profiles. Examples are shown in Table 1.

TABLE 1

Examples of yeast strains having altered mannosylation

| Strain | N-glycan (wild type) | Mutation | N-glycan (mutant) | Reference |
|---|---|---|---|---|
| S. pombe | $Man_{>9}GlcNAc_2$ | OCH1 | $Man_8GlcNAc_2$ | Yoko-o et al. (2001) FEBS Lett. 489(1): 75-80 |
| S. cerevisiae | $Man_{>9}GlcNAc_2$ | OCH1/MNN1 | $Man_8GlcNAc_2$ | Nakanishi-Shindo et al. (1993) J. Biol. Chem. 268(35): 26338-26345 |
| S. cerevisiae | $Man_{>9}GlcNAc_2$ | OCH1/MNN1/MNN4 | $Man_8GlcNAc_2$ | Chiba et al. (1998) J. Biol. Chem. 273, 26298-26304 |
| P. pastoris | Hyperglycosylated | OCH1 (complete deletion) | Not hyperglycosylated | Welfide, Japanese Application Publication No. 8-336387 |
| P. pastoris | $Man_{>8}GlcNAc_2$ | OCH1 (disruption) | $Man_{>8}GlcNAc_2$ | Contreras et al. WO 02/00856 A2 |

Japanese Patent Application Publication No. 8-336387 discloses the deletion of an OCH1 homolog in *Pichia pastoris*. In *S. cerevisiae*, OCH1 encodes a 1,6-mannosyltransferase, which adds a mannose to the glycan structure $Man_8GlcNAc_2$ to yield $Man_9GlcNAc_2$. The $Man_9GlcNAc_2$ structure, which contains three 1,6 mannose residues, is then a substrate for further 1,2-, 1,6-, and 1,3-mannosyltransferases in vivo, leading to the hypermannosylated glycoproteins that are characteristic for *S. cerevisiae* and which typically may have 30-40 mannose residues per N-glycan. Because the Och1p initiates the transfer of 1,6 mannose to the $Man_8GlcNAc_2$ core, it is often referred to as the "initiating 1,6 mannosyltransferase" to distinguish it from other 1,6 mannosyltransferases acting later in the Golgi. In an och1 mnn1 mnn4 mutant strain of *S. cerevisiae*, proteins glycosylated with $Man_8GlcNAc_2$ accumulate and hypermannosylation does not occur. However, $Man_8GlcNAc_2$ is not a substrate for mammalian glycosyltransferases, such as human UDP-GlcNAc transferase I, and accordingly, the use of that mutant strain, in itself, is not useful for producing mammalian-like proteins, i.e., those with complex or hybrid glycosylation patterns.

One can trim $Man_8GlcNAc_2$ structures to a $Man_5GlcNAc_2$ isomer in *S. cerevisiae* (although high efficiency trimming greater than 50% in vivo has yet to be demonstrated) by engineering a fungal mannosidase from *A. saitoi* into the endoplasmic reticulum (ER). The shortcomings of this approach are two-fold: (1) it is not clear whether the $Man_5GlcNAc_2$ structures formed are in fact formed in vivo (rather than having been secreted and further modified by mannosidases outside the cell); and (2) it is not clear whether any $Man_5GlcNAc_2$ structures formed, if in fact formed in vivo, are the correct isoform to be a productive substrate for subsequent N-glycan modification by GlcNAc transferase I (Maras et al. (1997) *Eur. J Biochem.* 249:701-707).

With the objective of providing a more human-like glycoprotein derived from a fungal host, U.S. Pat. No. 5,834,251 discloses a method for producing a hybrid glycoprotein derived from *Trichoderma reseei*. A hybrid N-glycan has only mannose residues on the Manα1-6 arm of the core mannose structure and one or two complex antennae on the Manα1-3 arm. While this structure has utility, the method has the disadvantage that numerous enzymatic steps must be performed in vitro, which is costly and time-consuming. Isolated enzymes are expensive to prepare and need costly substrates (e.g., UDP-GlcNAc). The method also does not allow for the production of complex glycans on a desired protein.

Intracellular Mannosidase Activity Involved in N-Glycan Trimming

Alpha-1,2-mannosidase activity is required for the trimming of $Man_8GlcNAc_2$ to form $Man_5GlcNAc_2$, which is a major intermediate for complex N-glycan formation in mammals. Previous work has shown that truncated murine, fungal and human α-1,2-mannosidase can be expressed in the methylotropic yeast *P. pastoris* and display $Man_8GlcNAc_2$ to $Man_5GlcNAc_2$ trimming activity (Lal et al. (1998) *Glycobiology* 8(10):981-95; Tremblay et al. (1998) *Glycobiology* 8(6):585-95, Callewaert et al. (2001) *FEBS Lett.* 503(2-3): 173-8). However, to date, no reports exist that show the high level in vivo trimming of $Man_8GlcNAc_2$ to $Man_5GlcNAc_2$ on a secreted glycoprotein from *P. pastoris*.

Moreover, the mere presence of an α-1,2-mannosidase in the cell does not, by itself, ensure proper intracellular trimming of $Man_8GlcNAc_2$ to $Man_5GlcNAc_2$. (See, e.g., Contreras et al. WO 02/00856 A2, in which an HDEL tagged mannosidase of *T. reesei* is localized primarily in the ER and co-expressed with an influenza haemagglutinin (HA) reporter protein on which virtually no $Man_5GlcNAc_2$ could be detected. See also Chiba et al. (1998) *J. Biol. Chem.* 273(41): 26298-26304, in which a chimeric α-1,2-mannosidase/ Och1p transmembrane domain fusion localized in the ER, early Golgi and cytosol of *S. cerevisiae*, had no mannosidase trimming activity). Accordingly, mere localization of a mannosidase in the ER or Golgi is insufficient to ensure activity of the respective enzyme in that targeted organelle. (See also, Martinet et al. (1998) *Biotech. Letters* 20(12): 1171-1177, showing that α-1,2-mannosidase from *T. reesei*, while localizing intracellularly, increased rather than decreased the extent of mannosylation). To date, there is no report that demonstrates the intracellular localization of an active heterologous α-1,2-mannosidase in either yeast or fungi using a transmembrane localization sequence.

While it is useful to engineer strains that are able to produce $Man_5GlcNAc_2$ as the primary N-glycan structure, any attempt to further modify these high mannose precursor structures to more closely resemble human glycans requires additional in vivo or in vitro steps. Methods to further humanize glycans from fungal and yeast sources in vitro are described in U.S. Pat. No. 5,834,251 (supra). If $Man_5GlcNAc_2$ is to be further humanized in vivo, one has to ensure that the generated $Man_5GlcNAc_2$ structures are, in fact, generated intracellularly and not the product of mannosidase activity in the medium. Complex N-glycan formation in yeast or fungi will require high levels of $Man_5GlcNAc_2$ to be generated within the cell because only intracellular $Man_5GlcNAc_2$ glycans can be further processed to hybrid and complex N-glycans in vivo. In addition, one has to demonstrate that the majority of $Man_5GlcNAc_2$ structures generated are in fact a substrate for GnTI and thus allow the formation of hybrid and complex N-glycans.

Accordingly, the need exists for methods to produce glycoproteins characterized by a high intracellular $Man_5GlcNAc_2$ content which can be further processed into human-like glycoprotein structures in non-human eukaryotic host cells, and particularly in yeast and filamentous fungi.

N-Acetylglucosaminyltransferases

N-Acetylglucosaminyltransferases ("GnTs") belong to another class of glycosylation enzymes that modify N-linked oligosaccharides in the secretory pathway. Such glycosyltransferases catalyze the transfer of a monosaccharide from specific sugar nucleotide donors onto particular hydroxyl position of a monosaccharide in a growing glycan chain in one of two possible anomeric linkages (either α or β). Dennis et al. (1999) *Bioessays* 21(5):412-21. Specific GnTs add N-acetylglucosamine ("GlcNAc") onto the Manα1,6 arm or the Manα1,3 arm of an N-glycan substrate (e.g., $Man_5GlcNAc_2$ ("mannose-5 core") and $Man_3GlcNAc_2$ (an "inner core structure")). The reaction product (e.g., $GlcNAcMan_5GlcNAc_2$ or $GlcNAc_2Man_3GlcNAc_2$) can then be modified into bi-, tri-, and tetra-antennary N-linked oligosaccharide structures.

N-Acetylglucosaminyltransferase III ("GnTIII") is an enzyme that catalyzes the addition of a GlcNAc, on the middle mannose of the trimannose core (Manα1,6 (Manα1,3) Man β1,4-GlcNAc β1,4-GlcNAc β1,4-Asn) of an N-linked oligosaccharide. The addition by GnTIII of a bisecting GlcNAc to an acceptor substrate (e.g. trimannose core) yields a so-called bisected N-glycan. For example, the addition by GnTIII of a bisecting GlcNAc to the $GlcNAcMan_3GlcNAc_2$ structure may yield a bisected N-glycan, $GlcNAc_2Man_3GlcNAc_2$. Similarly, the addition by GnTIII of a bisecting GlcNAc to a $GlcNAc_2Man_3GlcNAc_2$ structure yields another bisected N-glycan, $GlcNAc_3Man_3GlcNAc_2$. This latter structure has been implicated in greater antibody-dependent cellular cytotoxicity (ADCC). Umana et al. (1999) *Nat. Biotechnol.* 17(2): 176-80. Other bisected N-glycans can be formed by the action of GnTIII. For example, $GlcNAcMan_4GlcNAc_2$ can be converted to bisected $GlcNAc_2Man_4GlcNAc_2$, $Man_5GlcNAc_2$ can be converted to bisected $GlcNAcMan_5GlcNAc_2$, and $GlcNAcMan_5GlcNAc_2$ can be converted to bisected $GlcNAc_2Man_5GlcNAc_2$. See, e.g., Narasimhan (1982) *J. Biol. Chem.* 257:10235-42. Thus far, GnTIII activity has only been shown in mammalian cells.

Re-engineering glycoforms of immunoglobulins expressed by mammalian cells is a tedious and cumbersome task. Especially in the case of GnTIII, where over-expression of this enzyme has been implicated in growth inhibition, methods involving regulated (inducible) gene expression had to be employed to produce immunoglobulins with bisected N-glycans. Umana et al. (1999) *Biotechnol Bioeng.* 65(5): 542-9; Umana et al. (1999) *Nat. Biotechnol.* 17(2):176-80; Umana et al WO 03/011878; U.S. Pat. No. 6,602,684. Such a growth-inhibition effect complicates the ability to coexpress the target protein and GnTIII and may impose an upper limit on GnTIII overexpression. U.S. Pat. No. 6,602,684. Careful optimization of the expression levels of GnTIII may be necessary. Id. What is needed, therefore, is a protein production system utilizing the inherent capability of robust product titers such as those produced in lower eukaryotic host cells (e.g., yeast and filamentous fungi), which is capable of producing bisected N-glycans on proteins, especially therapeutic proteins, expressed in these cells. As described above, however, development of the lower eukaryotic host cells used in such a protein production system requires that the endogenous glycosylation pathways of the host cells be further modified.

SUMMARY OF THE INVENTION

Host cells and cell lines having genetically modified glycosylation pathways that allow them to carry out a sequence of enzymatic reactions which mimic the processing of glycoproteins in mammals, especially in humans, have been developed. Recombinant proteins expressed in these engineered hosts yield glycoproteins more similar, if not substantially identical, to their mammalian, e.g., human counterparts. Host cells of the invention, e.g., lower eukaryotic microorganisms and other non-human, eukaryotic host cells grown in culture, are modified to produce N-glycans, such as bisected N-glycans, or other structures produced along human glycosylation pathways. This result is achieved using a combination of engineering and/or selection of strains that do not, for example, express enzymes that create the undesirable structures characteristic of the fungal glycoproteins and that do, for example, express heterologous enzymes capable of producing a "human-like" glycoprotein.

The present invention thus provides a glycoprotein production method using (1) a lower eukaryotic host such as a unicellular or filamentous fungus, or (2) any non-human eukaryotic organism that has a different glycosylation pattern from humans, to modify the glycosylation composition and structures of the proteins made in a host organism ("host cell") so that they resemble more closely carbohydrate structures found in mammalian, e.g., human proteins. The process allows one to obtain an engineered host cell which can be used to express and target any desirable gene(s), e.g., one involved in glycosylation, by methods that are well-established in the scientific literature and generally known to the artisan in the field of protein expression. Host cells with modified oligosaccharides are created or selected. For the production of therapeutic proteins, this method may be adapted to engineer cell lines in which any desired glycosylation structure may be obtained.

Accordingly, in one embodiment, the invention provides methods for making a human-like glycoprotein in a lower eukaryotic host cell by introduction into the cell of an N-acetylglucosaminyltransferase III activity. In a preferred embodiment, the N-acetylglucosaminyltransferase III activity is expressed in the cell, and in an even more preferred embodiment, this expression results in the production of N-glycans comprising $GlcNAc_3Man_3GlcNAc_2$, $GlcNAc_2Man_3GlcNAc_2$, or $GlcNAc_2Man_5GlcNAc_2$ bisected structures. In another preferred embodiment, the N-acetylglucosaminyltransferase III activity is substantially intracellular. In another preferred embodiment of the invention, the glycoprotein including the N-glycans with bisected structures is isolated from the lower eukaryotic host cell. In an even more preferred embodiment, the glycoprotein produced in the host cell is a therapeutic protein.

In another aspect, the invention provides a lower eukaryotic host cell that includes both an N-acetylglucosaminyltransferase III activity and an N-acetylglucosaminyltransferase II activity. In a preferred embodiment, the host cell including the N-acetylglucosaminyltransferase III activity produces N-glycans comprising GlcNAcMan$_3$GlcNAc$_2$ structures that are capable of reacting with this activity. In a more preferred embodiment, the activity produces a bisected glycan. The lower eukaryotic host cell of some embodiments of the invention may thus include an N-glycan with a bisected glycan. In a preferred embodiment, the N-glycan includes greater than 10 mole % of the bisected glycan. In some embodiments, the host cell includes an N-glycan that comprises GlcNAc$_3$Man$_3$GlcNAc$_2$, GlcNAc$_2$Man$_3$GlcNAc$_2$, or GlcNAc$_2$Man$_5$GlcNAc$_2$ bisected structures. In a preferred embodiment, the host cell includes a Man$_5$GlcNAc$_2$ core structure or a Man$_3$GlcNAc$_2$ core structure that is modified by a bisecting GlcNAc. In an even more preferred embodiment, the cell produces greater than 10 mole % of the modified structure.

In another embodiment of the invention, the lower eukaryotic host cell contains an N-acetylglucosaminyltransferase I activity in addition to the N-acetylglucosaminyltransferase III activity. In a preferred embodiment, the activities are substantially intracellular. In another preferred embodiment, the cell produces N-glycans comprising GlcNAcMan$_3$GlcNAc$_2$ that are capable of reacting with the GnTIII activity. In an even more preferred embodiment, the GnTIII activity of the cell produces a bisected glycan.

In another embodiment, the lower eukaryotic host cell of the invention contains both an N-acetylglucosaminyltransferase III activity and a mannosidase II activity. In a preferred embodiment, the host cell further contains an N-acetylglucosaminyltransferase I activity. In another preferred embodiment, the host cell further contains an N-acetylglucosaminyltransferase II activity. In another preferred embodiment, the host cell further contains both an N-acetylglucosaminyltransferase I activity and an N-acetylglucosaminyltransferase II activity.

In another embodiment, the host cell of the invention is deficient in an OCH1 mannosyltransferase activity. Such a cell may, for example, be deficient in a Dol-P-Man:Man5GlcNAc2-PP-Dol mannosyltransferase activity. In yet another embodiment, the host cell of the invention may further comprise an α-1,2-mannosidase I activity. In another embodiment, the host cell may further comprise a UDP-GlcNAc transporter.

The present invention also provides glycoproteins that are made by the processes of the invention. In one embodiment, the glycoprotein includes a bisecting GlcNAc on a Man$_5$GlcNAc$_2$ or a Man$_3$GlcNAc$_2$ core structure and is produced in a lower eukaryotic host cell. In another embodiment, the glycoprotein includes a bisecting GlcNAc attached to a Man$_5$GlcNAc$_2$, Man$_4$GlcNAc$_2$, Man$_3$GlcNAc$_2$, GlcNAcMan$_3$GlcNAc$_2$, GlcNAcMan$_5$GlcNAc$_2$, or a GlcNAc$_2$Man$_3$GlcNAc$_2$ core structure and is produced in a lower eukaryotic host cell. In a preferred embodiment, greater than 10 mole % of the core structures of the glycoprotein of the invention are modified by the bisecting GlcNAc.

In another aspect, the invention provides pharmaceutical compositions that contain the human-like glycoproteins produced in a lower eukaryotic host cell. Also provided according to the invention are vectors encoding proteins having N-acetylglucosaminyltransferase III activity and containing attached targeting peptide sequences. In a preferred embodiment, the proteins encoded by the vectors are localized in a lower eukaryotic host cell such that they produce N-glycans having bisected structures.

BRIEF DESCRIPTION OF THE DRAWINGS

FIG. 2A diagrams the insertion of a targeting peptide fragment into pCR2.1-TOPO (Invitrogen, Carlsbad, Calif.). FIG. 2B shows the generated targeting peptide sub-library having restriction sites NotI-AscI. FIG. 2C diagrams the insertion of a catalytic domain region into pJN347, a modified pUC19 vector. FIG. 2D shows the generated catalytic domain sub-library having restriction sites NotI, AscI and PacI. FIG. 2E depicts one particular fusion construct generated from the targeting peptide sub-library and the catalytic domain sub-library.

FIG. 3 illustrates the *M. musculus* α-1,2-mannosidase IA open reading frame nucleic acid sequence (SEQ ID NO:50) and encoded polypeptide sequence (SEQ ID NO:51). The sequences of the PCR primers used to generate N-terminal truncations are underlined.

FIG. 5A depicts the standard Man$_5$GlcNAc$_2$ [a] glycan (Glyko, Novato, Calif.) and Man$_5$GlcNAc$_2$+Na$^+$[b]. FIG. 5B shows PNGase-released glycans from K3 wild type. The N-glycans shown are as follows: Man$_9$GlcNAc$_2$ [d]; Man$_{10}$GlcNAc$_2$ [e]; Man$_{11}$GlcNAc$_2$ [f]; Man$_{12}$GlcNAc$_2$ [g]. FIG. 5C depicts the och1 deletion resulting in the production of Man$_8$GlcNAc$_2$ [c] as the predominant N-glycan. FIGS. 5D and 5E show the production of Man$_5$GlcNAc$_2$ [b] after in vivo trimming of Man$_8$GlcNAc$_2$ with a chimeric α-1,2-mannosidase. The predominant N-glycan is indicated by a peak with a mass (m/z) of 1253 consistent with its identification as Man$_5$GlcNAc$_2$ [b].

FIG. 6A shows the standard Man$_5$GlcNAc$_2$ [a] and Man$_5$GlcNAc$_2$+Na$^+$ [b] as the standard (Glyko, Novato, Calif.). FIG. 6B shows PNGase-released glycans from IFN-β wildtype. FIG. 6C depicts the och1 knock-out producing Man$_8$GlcNAc$_2$ [c]; Man$_9$GlcNAc$_2$ [d]; Man$_{10}$GlcNAc$_2$ [e]; Man$_{11}$GlcNAc$_2$ [f]; Man$_{12}$GlcNAc$_2$ [g]; and no production of Man$_5$GlcNAc$_2$ [b]. FIG. 6D shows relatively small amount of Man$_5$GlcNAc$_2$ [b] among other intermediate N-glycans Man$_8$GlcNAc$_2$ [c] to Man$_{12}$GlcNAc$_2$ [g]. FIG. 6E shows a significant amount of Man$_5$GlcNAc$_2$ [b] relative to the other glycans Man$_8$GlcNAc$_2$ [c] and Man$_9$GlcNAc$_2$ [d] produced by pGC5 (*Saccharomyces* MNS1(m)/mouse mannosidase IB Δ99). FIG. 6F shows predominant production of Man$_5$GlcNAc$_2$ [b] on the secreted glycoprotein IFN-β by pFB8 (*Saccharomyces* SEC12(m)/mouse mannosidase IA Δ187). The N-glycan is indicated by a peak with a mass (m/z) of 1254 consistent with its identification as Man$_5$GlcNAc$_2$ [b].

FIG. 10A depicts a *P. pastoris* strain (YSH-3) with a human GnTI but without the UDP-GlcNAc transporter resulting in some production of GlcNAcMan$_5$GlcNAc$_2$ [b] but a predominant production of Man$_5$GlcNAc$_2$ [a]. FIG. 10B depicts the addition of UDP-GlcNAc transporter from *K. lactis* in a strain (PBP-3) with the human GnTI, which resulted in the predominant production of GlcNAcMan$_5$GlcNAc$_2$ [b]. The single prominent peak of mass (m/z) at 1457 is consistent with its identification as GlcNAcMan$_5$GlcNAc$_2$ [b] as shown in FIG. 10B.

FIG. 12A shows the N-glycans released from wild-type cells, which includes high-mannose type N-glycans. FIG. 12B shows the N-glycans released from och1 mnn1 deleted cells, revealing a distinct peak of mass (m/z) at 1908 consistent with its identification as Man$_9$GlcNAc$_2$ [d]. FIG. 12C shows the N-glycans released from och1 mnn1 deleted cells after in vitro α-1,2-mannosidase digest corresponding to a peak consistent with Man$_5$GlcNAc$_2$.

FIG. 16 shows *S. cerevisiae* Alg3 Sequence Comparisons (Blast) (SEQ ID NOs:9-20, respectively, in order of appearance)

FIG. 17 shows *S. cerevisiae* ALG3 (SEQ ID NO:21) and Alg3p (SEQ ID NO:22) Sequences FIG. 18 shows *P. pastoris* ALG3 (SEQ ID NO:23) and Alg3p (SEQ ID NO:24) Sequences FIG. 19 shows *P. pastoris* ALG3 Sequence Comparisons (Blast) (SEQ ID NO:25-32, respectively, in order of appearance)

FIG. 20 shows *K. lactis* ALG3 (SEQ ID NO:33) and Alg3p (SEQ ID NO:34) Sequences FIG. 21 shows *K. lactis* ALG3 Sequence Comparisons (Blast) (SEQ ID NOs:35-40, respectively, in order of appearance)

FIG. 24 shows *M. musculis* GnTIII Nucleic Acid (SEQ ID NO:45) And Amino Acid (SEQ ID NO:46) Sequences FIG. 25 (top) is a MALDI-TOF-MS analysis of N-glycans isolated from a kringle 3 glycoprotein produced in a *P. pastoris* YSH-1 displaying a predominant peak at 1461 m/z corresponding to the the mass of GlcNAcMan$_5$GlcNAc$_2$ [d]; FIG. 25 (bottom) shows a MALDI-TOF-MS analysis of N-glycans isolated from a kringle 3 glycoprotein produced in a *P. pastoris* YSH-1 transformed with *D. melanogaster* mannosidase IIΔ74/*S. cerevisiae* MNN2(s) showing a predominant peak at 1140 m/z corresponding to the mass of GlcNAcMan$_3$GlcNAc$_2$ [b] and other peaks corresponding to GlcNAcMan$_4$GlcNAc$_2$ [c] at 1303 m/z and GlcNAcMan$_5$GlcNAc$_2$ [d] at 1465 m/z. This strain was designated YSH-37.

FIG. 26 (top) is the MALDI-TOF-MS analysis of N-glycans isolated from a kringle 3 glycoprotein produced in *P. pastoris* YSH-1 as shown in FIG. 25 (top); FIG. 26 (bottom) is a MALDI-TOF-MS analysis of N-glycans isolated from a kringle 3 glycoprotein expressed in *P. pastoris* YSH-1 cells transformed with a pVA53 construct (*S. cerevisiae* MNN2(s)/mGnTIII). The peak at 1463 m/z corresponds the mass of GlcNAcMan$_5$GlcNAc$_2$ [d] and the peak at 1666 m/z corresponds to the mass of GlcNAc$_2$Man$_5$GlcNAc$_2$ [a].

FIG. 27 (top) is the MALDI-TOF-MS analysis of N-glycans isolated from a kringle 3 glycoprotein produced in *P. pastoris* YSH-1 as shown in FIG. 25 (top); FIG. 27 (bottom) is a MALDI-TOF-MS analysis of N-glycans isolated from a kringle 3 glycoprotein expressed in *P. pastoris* YSH-1 cells transformed with a pVA55 construct (*S. cerevisiae* MNN2(s)/mGnTIII). The peak at 1463 m/z corresponds to the mass of GlcNAcMan$_5$GlcNAc$_2$ [d] and the peak at 1667 m/z corresponds to the mass of GlcNAc$_2$Man$_5$GlcNAc$_2$ [a].

FIG. 28 (top) is the MALDI-TOF-MS analysis of N-glycans isolated from a kringle 3 glycoprotein produced in *P. pastoris* YSH-1 as shown in FIG. 25 (top); FIG. 28 (bottom) is a MALDI-TOF-MS analysis of N-glycans isolated from a kringle 3 glycoprotein expressed in *P. pastoris* YSH-1 cells transformed with a pVB51 construct (*K. lactis* GNT1(s)/mGnTIII). The predominant peak at 1463 m/z corresponds to the mass of GlcNAcMan$_5$GlcNAc$_2$ [d] and a second peak at 1726 m/z [e], which does not correpond to the mass of GlcNAc$_2$Man$_5$GlcNAc$_2$ is observed.

DETAILED DESCRIPTION OF THE INVENTION

Figure 1A:
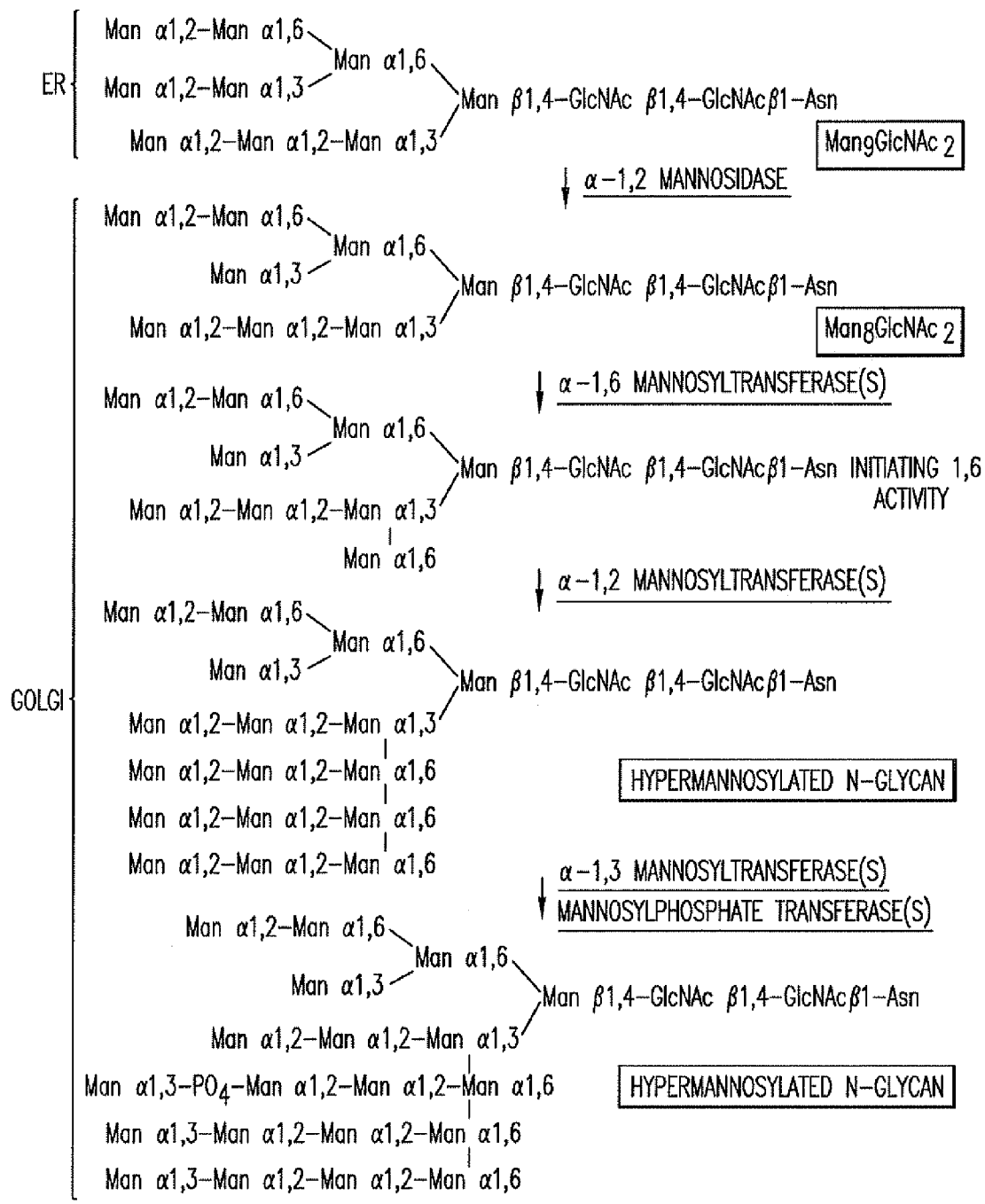
FIG. 1A is a schematic diagram of a typical fungal N-glycosylation pathway.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); *Introduction to Glycobiology*, Maureen E. Taylor, Kurt Drickamer, Oxford Univ. Press (2003); Worthington Enzyme Manual, Worthington Biochemical Corp. Freehold, N.J.; *Handbook of Biochemistry: Section A Proteins*, Vol I 1976 CRC Press; *Handbook of Biochemistry: Section A Proteins*, Vol II 1976 CRC Press; *Essentials of Glycobiology*, Cold Spring Harbor Laboratory Press (1999). The nomenclatures used in connection with, and the laboratory procedures and techniques of, molecular and cellular biology, protein biochemistry, enzymology and medicinal and pharmaceutical chemistry described herein are those well known and commonly used in the art.

All publications, patents and other references mentioned herein are incorporated by reference.

The following terms, unless otherwise indicated, shall be understood to have the following meanings:

As used herein, the term "N-glycan" refers to an N-linked oligosaccharide, e.g., one that is attached by an asparagine-N-acetylglucosamine linkage to an asparagine residue of a polypeptide. N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). The term "trimannose core" used with respect to the N-glycan also refers to the structure $Man_3GlcNAc_2$ ("$Man_3$"). The term "pentamannose core" or "Mannose-5 core" or "$Man_5$" used with respect to the N-glycan refers to the structure $Man_5GlcNAc_2$. N-glycans differ with respect to the number of branches (antennae) comprising peripheral sugars (e.g., GlcNAc, fucose, and sialic acid) that are attached to the $Man_3$ core structure. N-glycans are classified according to their branched constituents (e.g., high mannose, complex or hybrid).

A "high mannose" type N-glycan has five or more mannose residues. A "complex" type N-glycan typically has at least one GlcNAc attached to the 1,3 mannose arm and at least one GlcNAc attached to the 1,6 mannose arm of the trimannose core. Complex N-glycans may also have galactose ("Gal") residues that are optionally modified with sialic acid or derivatives ("NeuAc", where "Neu" refers to neuraminic acid and "Ac" refers to acetyl). A complex N-glycan typically has at least one branch that terminates in an oligosaccharide such as, for example: NeuNAc-; NeuAcα2-6GalNAcα1-; NeuAcα2-3Galβ1-3GalNAcα1-; NeuAcα2-3/6Galβ1-4GlcNAcβ1-; GlcNAcα1-4Galβ1-(mucins only); Fucα1-2Galβ1-(blood group H). Sulfate esters can occur on galactose, GalNAc, and GlcNAc residues, and phosphate esters can occur on mannose residues. NeuAc (Neu: neuraminic acid; Ac: acetyl) can be O-acetylated or replaced by NeuGl (N-glycolylneuraminic acid). Complex N-glycans may also have intrachain substitutions comprising "bisecting" GlcNAc and core fucose ("Fuc"). A "hybrid" N-glycan has at least one GlcNAc on the terminal of the 1,3 mannose arm of the trimannose core and zero or more mannoses on the 1,6 mannose arm of the trimannose core.

The term "predominant" or "predominantly" used with respect to the production of N-glycans refers to a structure which represents the major peak detected by matrix assisted laser desorption ionization time of flight mass spectrometry (MALDI-TOF) analysis.

Abbreviations used herein are of common usage in the art, see, e.g., abbreviations of sugars, above. Other common abbreviations include "PNGase", which refers to peptide N-glycosidase F (EC 3.2.2.18); "GlcNAc Tr" or "GnT," which refers to N-acetylglucosaminyl Transferase enzymes; "NANA" refers to N-acetylneuraminic acid.

As used herein, a "humanized glycoprotein" or a "human-like glycoprotein" refers alternatively to a protein having attached thereto N-glycans having fewer than four mannose residues, and synthetic glycoprotein intermediates (which are also useful and can be manipulated further in vitro or in vivo) having at least five mannose residues. Preferably, glycoproteins produced according to the invention contain at least 30 mole %, preferably at least 40 mole % and more preferably 50, 60, 70, 80, 90, or even 100 mole % of the $Man_5GlcNAc_2$ intermediate, at least transiently. This may be achieved, e.g., by engineering a host cell of the invention to express a "better", i.e., a more efficient glycosylation enzyme. For example, a mannosidase is selected such that it will have optimal activity under the conditions present at the site in the host cell where proteins are glycosylated and is introduced into the host cell preferably by targeting the enzyme to a host cell organelle where activity is desired.

The term "enzyme", when used herein in connection with altering host cell glycosylation, refers to a molecule having at least one enzymatic activity, and includes full-length enzymes, catalytically active fragments, chimerics, complexes, and the like. A "catalytically active fragment" of an enzyme refers to a polypeptide having a detectable level of functional (enzymatic) activity. Enzyme activity is "substantially intracellular" when less than 10% of the enzyme activity is measurable outside the cell compared to that measurable from lysed cells.

A lower eukaryotic host cell, when used herein in connection with glycosylation profiles, refers to any eukaryotic cell which ordinarily produces high mannose containing N-glycans, and thus is meant to include some animal or plant cells and most typical lower eukaryotic cells, including uni- and multicellular fungal and algal cells.

As used herein, the term "secretion pathway" refers to the assembly line of various glycosylation enzymes to which a lipid-linked oligosaccharide precursor and an N-glycan substrate are sequentially exposed, following the molecular flow of a nascent polypeptide chain from the cytoplasm to the endoplasmic reticulum (ER) and the compartments of the Golgi apparatus. Enzymes are said to be localized along this pathway. An enzyme X that acts on a lipid-linked glycan or an N-glycan before enzyme Y is said to be or to act "upstream" to enzyme Y; similarly, enzyme Y is or acts "downstream" from enzyme X.

The term "targeting peptide" as used herein refers to nucleotide or amino acid sequences encoding a cellular targeting signal peptide which mediates the localization. (or retention) of an associated sequence to sub-cellular locations, e.g., organelles.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA. A nucleic acid molecule of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson (1990) *Methods Enzymol.* 183:63-98, incorporated herein by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled artisan that hybridization at 65° C. will occur at different rates depending on a number of factors including the length and percent identity of the sequences which are hybridizing.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung et al. (1989) *Technique* 1:11-15 and Caldwell and Joyce (1992) *PCR Methods Applic.* 2:28-33); and "oligonucleotide-directed mutagenesis" (a process which enables the generation of site-specific mutations in any cloned DNA segment of interest. See, e.g., Reidhaar-Olson et al. (1988) *Science* 241:53-57).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a nucleic acid such as a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" as used herein encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art. As thus defined, "isolated" does not necessarily require that the protein, polypeptide, peptide or oligopeptide so described has been physically removed from its native environment.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well-known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art. See Ausubel et al., *Current Protocols in Molecular Biology*, Greene Publishing Associates (1992, and Supplements to 2002), hereby incorporated by reference.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N- trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson (1990) *Methods Enzymol.* 183:63-98).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing a inhibitory molecule sequence to a database containing a large number of sequences from different organisms is the computer program BLAST (Altschul et al. (1990) *J. Mol. Biol.* 215:403-410; Gish and States (1993) *Nature Genet.* 3:266-272; Madden et al. (1996) *Meth. Enzymol.* 266:131-141; Altschul et al. (1997) *Nucleic Acids Res.* 25:3389-3402; Zhang and Madden (1997) *Genome Res.* 7:649-656), especially blastp or tblastn (Altschul et al., 1997). Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (see Pearson (1990) *Methods Enzymol.* 183:63-98). For example, percent sequence identity between amino acid sequences can be determined using FASTA with its default parameters (a word size of 2 and the PAM250 scoring matrix), as provided in GCG Version 6.1, herein incorporated by reference.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in-frame with a nucleic acid sequence encoding a different protein or peptide and then expressing the fusion protein. Alternatively, a fusion protein can be produced chemically by crosslinking the polypeptide or a fragment thereof to another protein.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Methods for Producing Human-Like Glycoproteins in Lower Eukaryotic Host Cells

The invention provides methods for producing a glycoprotein having human-like glycosylation in a non-human eukaryotic host cell. As described in more detail below, a eukaryotic host cell that does not naturally express, or which is engineered not to express, one or more enzymes involved in production of high mannose structures is selected as a starting host cell. Such a selected host cell is engineered to express one or more enzymes or other factors required to produce human-like glycoproteins. A desired host strain can be engineered one enzyme or more than one enzyme at a time. In addition, a nucleic acid molecule encoding one or more enzymes or activities may be used to engineer a host strain of the invention. Preferably, a library of nucleic acid molecules encoding potentially useful enzymes (e.g., chimeric enzymes comprising a catalytically active enzyme fragment ligated in-frame to a heterologous subcellular targeting sequence) is created (e.g., by ligation of sub-libraries comprising enzymatic fragments and subcellular targeting sequences), and a strain having one or more enzymes with optimal activities or producing the most "human-like" glycoproteins may be selected by transforming target host cells with one or more members of the library.

In particular, the methods described herein enable one to obtain, in vivo, $Man_5GlcNAc_2$ structures in high yield, at least transiently, for the purpose of further modifying it to yield complex N-glycans. A successful scheme to obtain suitable $Man_5GlcNAc_2$ structures in appropriate yields in a host cell, such as a lower eukaryotic organism, generally involves two parallel approaches: (1) reducing high mannose structures made by endogenous mannosyltransferase activities, if any, and (2) removing 1,2-α-mannose by mannosidases to yield high levels of suitable $Man_5GlcNAc_2$ structures which may be further reacted inside the host cell to form complex, human-like glycoforms.

Accordingly, a first step involves the selection or creation of a eukaryotic host cell, e.g., a lower eukaryote, capable of producing a specific precursor structure of $Man_5GlcNAc_2$ that is able to accept in vivo GlcNAc by the action of a GlcNAc transferase I ("GnTI"). In one embodiment, the method involves making or using a non-human eukaryotic host cell depleted in a 1,6 mannosyltransferase activity with respect to the N-glycan on a glycoprotein. Preferably, the host cell is depleted in an initiating 1,6 mannosyltransferase activity (see below). Such a host cell will lack one or more enzymes involved in the production of high mannose structures which are undesirable for producing human-like glycoproteins.

One or more enzyme activities are then introduced into such a host cell to produce N-glycans within the host cell characterized by having at least 30 mol % of the $Man_5GlcNAc_2$ ("$Man_5$") carbohydrate structures. $Man_5GlcNAc_2$ structures are necessary for complex N-glycan formation: $Man_5GlcNAc_2$ must be formed in vivo in a high yield (e.g., in excess of 30%), at least transiently, as subsequent mammalian- and human-like glycosylation reactions require $Man_5GlcNAc_2$ or a derivative thereof.

This step also requires the formation of a particular isomeric structure of $Man_5GlcNAc_2$ within the cell at a high yield. While $Man_5GlcNAc_2$ structures are necessary for complex N-glycan formation, their presence is by no means sufficient. That is because $Man_5GlcNAc_2$ may occur in different isomeric forms, which may or may not serve as a substrate for GlcNAc transferase I. As most glycosylation reactions are not complete, a particular glycosylated protein generally contains a range of different carbohydrate structures (i.e., glycoforms) on its surface. Thus, the mere presence of trace amounts (i.e., less than 5%) of a particular structure like $Man_5GlcNAc_2$ is of little practical relevance for producing mammalian- or human-like glycoproteins. It is the formation of a GlcNAc transferase I-accepting $Man_5GlcNAc_2$ intermediate (FIG. 1B) in high yield (i.e., above 30%), which is required. The formation of this intermediate is necessary to enable subsequent in vivo synthesis of complex N-glycans on glycosylated proteins of interest (target proteins).

Accordingly, some or all of the $Man_5GlcNAc_2$ produced by the selected host cell must be a productive substrate for enzyme activities along a mammalian glycosylation pathway, e.g., can serve as a substrate for a GlcNAc transferase I activity in vivo, thereby forming the human-like N-glycan intermediate $GlcNAcMan_5GlcNAc_2$ in the host cell. In a preferred embodiment, at least 10%, more preferably at least 30% and most preferably 50% or more of the $Man_5GlcNAc_2$ intermediate produced in the host cell of the invention is a productive substrate for GnTI in vivo. It is understood that if, for example, $GlcNAcMan_5GlcNAc_2$ is produced at 10% and $Man_5GlcNAc_2$ is produced at 25% on a target protein, that the total amount of transiently produced $Man_5GlcNAc_2$ is 35% because $GlcNAcMan_5GlcNAc_2$ is a product of $Man_5GlcNAc_2$.

One of ordinary skill in the art can select host cells from nature, e.g., existing fungi or other lower eukaryotes that produce significant levels of $Man_5GlcNAc_2$ in vivo. As yet, however, no lower eukaryote has been shown to provide such structures in vivo in excess of 1.8% of the total N-glycans (see e.g. Maras et al. (1997) Eur. J. Biochem. 249:701-707). Alternatively, such host cells may be genetically engineered to produce the $Man_5GlcNAc_2$ structure in vivo. Methods such as those described in U.S. Pat. No. 5,595,900 may be used to identify the absence or presence of particular glycosyltransferases, mannosidases and sugar nucleotide transporters in a target host cell or organism of interest.

Inactivation of Undesirable Host Cell Glycosylation Enzymes

The methods of the invention are directed to making host cells which produce glycoproteins having altered, and preferably human-like, N-glycan structures. In a preferred embodiment, the methods are directed to making host cells in which oligosaccharide precursors are enriched in $Man_5GlcNAc_2$. Preferably, a eukaryotic host cell is used that does not express one or more enzymes involved in the production of high mannose structures. Such a host cell may be found in nature or may be engineered, e.g., starting with or derived from one of many such mutants already described in yeasts. Thus, depending on the selected host cell, one or a number of genes that encode enzymes known to be characteristic of non-human glycosylation reactions will have to be deleted. Such genes and their corresponding proteins have been extensively characterized in a number of lower eukaryotes (e.g., S. cerevisiae, T. reesei, A. nidulans, etc.), thereby providing a list of known glycosyltransferases in lower eukaryotes, their activities and their respective genetic sequence. These genes are likely to be selected from the group of mannosyltransferases, e.g. 1,3 mannosyltransferases (e.g. MNN1 in *S. cerevisiae*) (Graham, 1991), 1,2 mannosyltransferases (e.g. KTR/KRE family from *S. cerevisiae*), 1,6 mannosyltransferases (OCH1 from *S. cerevisiae*), mannosylphosphate transferases and their regulators (MNN4 and MNN6 from *S. cerevisiae*) and additional enzymes that are involved in aberrant, i.e., non-human, glycosylation reactions. Many of these genes have in fact been deleted individually giving rise to viable phenotypes with altered glycosylation profiles. Examples are shown in Table 1.

Figure 35:
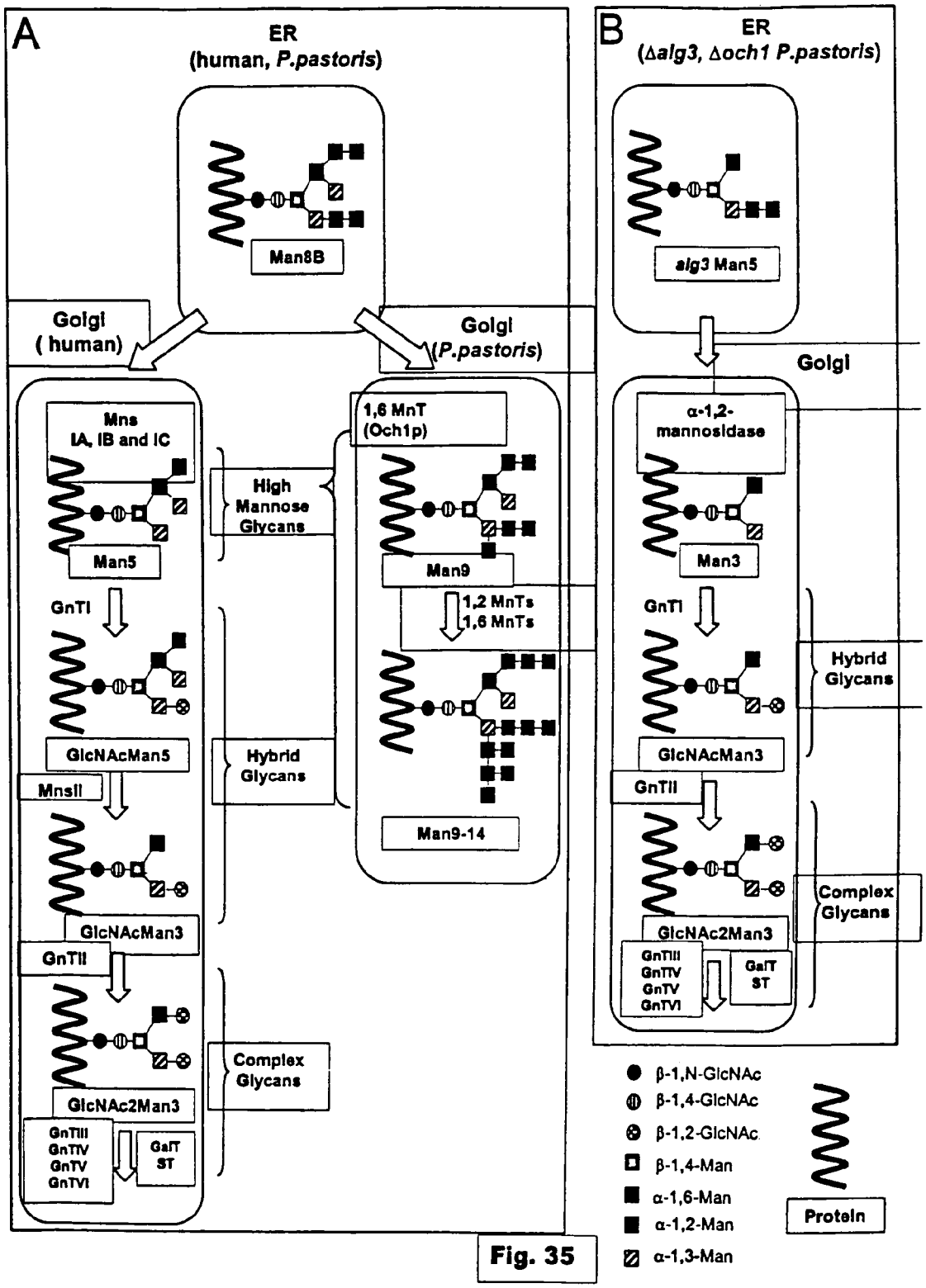
FIG. 35 is a schematic diagram comparing the normal glycosylation pathways in humans and *P. pastoris* (Panel A) with an engineered humanized N-glycosylation pathway in lower eukaryotes (Panel B). The engineered pathway represents the construction of *P. pastoris* strain PBP6-5, which after modification with GnTIII becomes *P. pastoris* strain PBP38.

Preferred lower eukaryotic host cells of the invention, as described herein to exemplify the required manipulation steps, are hypermannosylation-minus (och1) mutants of *Pichia pastoris* or *K. lactis*. Like other lower eukaryotes, *P. pastoris* processes Man$_9$GlcNAc$_2$ structures in the ER with an α-1,2-mannosidase to yield Man$_8$GlcNAc$_2$ (FIG. 1A). Through the action of several mannosyltransferases, this structure is then converted to hypermannosylated structures (Man$_{>9}$GlcNAc$_2$), also known as mannans (FIG. 35A). In addition, it has been found that *P. pastoris* is able to add non-terminal phosphate groups, through the action of mannosylphosphate transferases, to the carbohydrate structure. This differs from the reactions performed in mammalian cells, which involve the removal rather than addition of mannose sugars (FIG. 35A). It is of particular importance to eliminate the ability of the eukaryotic host cell, e.g., fungus, to hypermannosylate an existing Man$_8$GlcNAc$_2$ structure. This can be achieved by either selecting for a host cell that does not hypermannosylate or by genetically engineering such a cell.

Genes that are involved in the hypermannosylation process have been identified, e.g., in *Pichia pastoris*, and by creating mutations in these genes, one can reduce the production of "undesirable" glycoforms. Such genes can be identified by homology to existing mannosyltransferases or their regulators (e.g., OCH1, MNN4, MNN6, MNN1) found in other lower eukaryotes such as *C. albicans, Pichia angusta* or *S. cerevisiae* or by mutagenizing the host strain and selecting for a glycosylation phenotype with reduced mannosylation. Based on homologies amongst known mannosyltransferases and mannosylphosphate transferases, one may either design PCR primers (examples of which are shown in Table 2), or use genes or gene fragments encoding such enzymes as probes to identify homologs in DNA libraries of the target or a related organism. Alternatively, one may identify a functional homolog having mannosyltransferase activity by its ability to complement particular glycosylation phenotypes in related organisms.

TABLE 2

PCR Primers

| PCR primer A | PCR primer B | Target Gene(s) in *P. pastoris* | Homologs |
|---|---|---|---|
| ATGGCGAAGGCA GATGGCAGT (SEQ ID NO:3) | TTAGTCCTTCCAA CTTCCTTC (SEQ ID NO:4) | 1,6- mannosyl- transferase | OCH1 *S. cerevisiae*, *Pichia albicans* |
| TAYTGGMGNGTN GARCYNGAYATH AA (SEQ ID NO:5) | GCRTCNCCCCANC KYTCRTA (SEQ ID NO:6) | 1,2 mannosyl- transferases | KTR/KRE family, *S. cerevisiae* |

Legend:
M = A or C,
R = A or G,
W = A or T,
S = C or G,
Y = C or T,
K = G or T,
V = A or C or G,
H = A or C or T,
D = A or G or T,
B = C or G or T,
N = G or A or T or C.

To obtain the gene or genes encoding 1,6-mannosyltransferase activity in *P. pastoris*, for example, one would carry out the following steps: OCH1 mutants of *S. cerevisiae* are temperature sensitive and are slow growers at elevated temperatures. One can thus identify functional homologs of OCH1 in *P. pastoris* by complementing an OCH1 mutant of *S. cerevisiae* with a *P. pastoris* DNA or cDNA library. Mutants of *S. cerevisiae* are available, e.g., from Stanford University, and are commercially available from ResGen, Invitrogen Corp. (Carlsbad, Calif.). Mutants that display a normal growth phenotype at elevated temperature, after having been transformed with a *P. pastoris* DNA library, are likely to carry an OCH1 homolog of *P. pastoris*. Such a library can be created by partially digesting chromosomal DNA of *P. pastoris* with a suitable restriction enzyme and, after inactivating the restriction enzyme, ligating the digested DNA into a suitable vector, which has been digested with a compatible restriction enzyme.

Suitable vectors include, e.g., pRS314, a low copy (CEN6/ARS4) plasmid based on pBluescript containing the Trp1 marker (Sikorski and Hieter (1989) *Genetics* 122:19-27) and pFL44S, a high copy (2μ) plasmid based on a modified pUC19 containing the URA3 marker (Bonneaud et al. (1991) *Yeast* 7:609-615). Such vectors are commonly used by academic researchers and similar vectors are available from a number of different vendors (e.g., Invitrogen (Carlsbad, Calif.); Pharmacia (Piscataway, N.J.); New England Biolabs (Beverly, Mass.)). Further examples include pYES/GS, 2μ origin of replication based yeast expression plasmid from Invitrogen, or Yep24 cloning vehicle from New England Biolabs.

After ligation of the chromosomal DNA and the vector, one may transform the DNA library into a strain of S. cerevisiae with a specific mutation and select for the correction of the corresponding phenotype. After sub-cloning and sequencing the DNA fragment that is able to restore the wild-type phenotype, one may use this fragment to eliminate the activity of the gene product encoded by OCH1 in P. pastoris using in vivo mutagenesis and/or recombination techniques well-known to those skilled in the art.

Alternatively, if the entire genomic sequence of a particular host cell, e.g., fungus, of interest is known, one may identify such genes simply by searching publicly available DNA databases, which are available from several sources, such as NCBI, Swissprot. For example, by searching a given genomic sequence or database with sequences from a known 1,6 mannosyltransferase gene (e.g., OCH1 from S. cerevisiae), one can identify genes of high homology in such a host cell genome which may (but do not necessarily) encode proteins that have 1,6-mannosyltransferase activity. Nucleic acid sequence homology alone is not enough to prove, however, that one has identified and isolated a homolog encoding an enzyme having the same activity. To date, for example, no data exist to show that an OCH1 deletion in P. pastoris eliminates the crucial initiating 1,6-mannosyltransferase activity (Martinet et al. (1998) Biotech. Letters 20(12):1171-1177; Contreras et al. WO 02/00856 A2). Thus, no data prove that the P. pastoris OCH1 gene homolog actually encodes that function. That demonstration is provided for the first time herein.

Homologs to several S. cerevisiae mannosyltransferases have been identified in P. pastoris using these approaches. Homologous genes often have similar functions to genes involved in the mannosylation of proteins in S. cerevisiae and thus their deletion may be used to manipulate the glycosylation pattern in P. pastoris or, by analogy, in any other host cell, e.g., fungus, plant, insect or animal cells, with similar glycosylation pathways.

The creation of gene knock-outs, once a given target gene sequence has been determined, is a well-established technique in the art and can be carried out by one of ordinary skill in the art (see, e.g., Rothstein (1991) Methods in Enzymology 194:281). The choice of a host organism may be influenced by the availability of good transformation and gene disruption techniques.

If several mannosyltransferases are to be knocked out, the method developed by Alani and Kleckner (1987) Genetics 116:541-545, for example, enables the repeated use of a selectable marker, e.g., the URA3 marker in yeast, to sequentially eliminate all undesirable endogenous mannosyltransferase activity. This technique has been refined by others but basically involves the use of two repeated DNA sequences, flanking a counter selectable marker. For example: URA3 may be used as a marker to ensure the selection of a transformants that have integrated a construct. By flanking the URA3 marker with direct repeats one may first select for transformants that have integrated the construct and have thus disrupted the target gene. After isolation of the transformants, and their characterization, one may counter select in a second round for those that are resistant to 5-fluoroorotic acid (5-FOA). Colonies that are able to survive on plates containing 5-FOA have lost the URA3 marker again through a cross-over event involving the repeats mentioned earlier. This approach thus allows for the repeated use of the same marker and facilitates the disruption of multiple genes without requiring additional markers. Similar techniques for sequential elimination of genes adapted for use in another eukaryotic host cells with other selectable and counter-selectable markers may also be used.

Eliminating specific mannosyltransferases, such as 1,6 mannosyltransferase (OCH1) or mannosylphosphate transferases (MNN6, or genes complementing lbd mutants) or regulators (MNN4) in P. pastoris enables one to create engineered strains of this organism which synthesize primarily Man$_8$GlcNAc$_2$ and which can be used to further modify the glycosylation pattern to resemble more complex glycoform structures, e.g., those produced in mammalian, e.g., human cells. A preferred embodiment of this method utilizes DNA sequences encoding biochemical glycosylation activities to eliminate similar or identical biochemical functions in P. pastoris to modify the glycosylation structure of glycoproteins produced in the genetically altered P. pastoris strain.

Methods used to engineer the glycosylation pathway in yeasts as exemplified herein can be used in filamentous fungi to produce a preferred substrate for subsequent modification. Strategies for modifying glycosylation pathways in A. niger and other filamentous fungi, for example, can be developed using protocols analogous to those described herein for engineering strains to produce human-like glycoproteins in yeast. Undesired gene activities involved in 1,2 mannosyltransferase activity, e.g., KTR/KRE homologs, are modified or eliminated. A filamentous fungus, such as Aspergillus, is a preferred host because it lacks the 1,6 mannosyltransferase activity and as such, one would not expect a hypermannosylating gene activity, e.g. OCH1, in this host. By contrast, other desired activities (e.g., α-1,2-mannosidase, UDP-GlcNAc transporter, glycosyltransferase (GnT), galactosyltransferase (GalT) and sialyltransferase (ST)) involved in glycosylation are introduced into the host using the targeting methods of the invention.

Engineering or Selecting Hosts Having Diminished Initiating α-1,6 Mannosyltransferase Activity In a preferred embodiment, the method of the invention involves making or using a host cell which is diminished or depleted in the activity of an initiating α-1,6-mannosyltransferase, i.e., an initiation specific enzyme that initiates outer chain mannosylation on the α-1,3 arm of the Man$_3$GlcNAc$_2$ core structure. In S. cerevisiae, this enzyme is encoded by the OCH1 gene. Disruption of the OCH1 gene in S. cerevisiae results in a phenotype in which N-linked sugars completely lack the poly-mannose outer chain. Previous approaches for obtaining mammalian-type glycosylation in fungal strains have required inactivation of OCH1 (see, e.g., Chiba et al. (1998) J. Biol. Chem. 273:26298-304). Disruption of the initiating α-1,6-mannosyltransferase activity in a host cell of the invention may be optional, however (depending on the selected host cell), as the Och1p enzyme requires an intact Man$_8$GlcNAc$_2$ for efficient mannose outer chain initiation. Thus, host cells selected or produced according to this invention which accumulate oligosaccharides having seven or fewer mannose residues may produce hypoglycosylated N-glycans that will likely be poor substrates for Och1p (see, e.g., Nakayama et al. (1997) FEBS Lett. 412(3):547-50).

Figure 12:
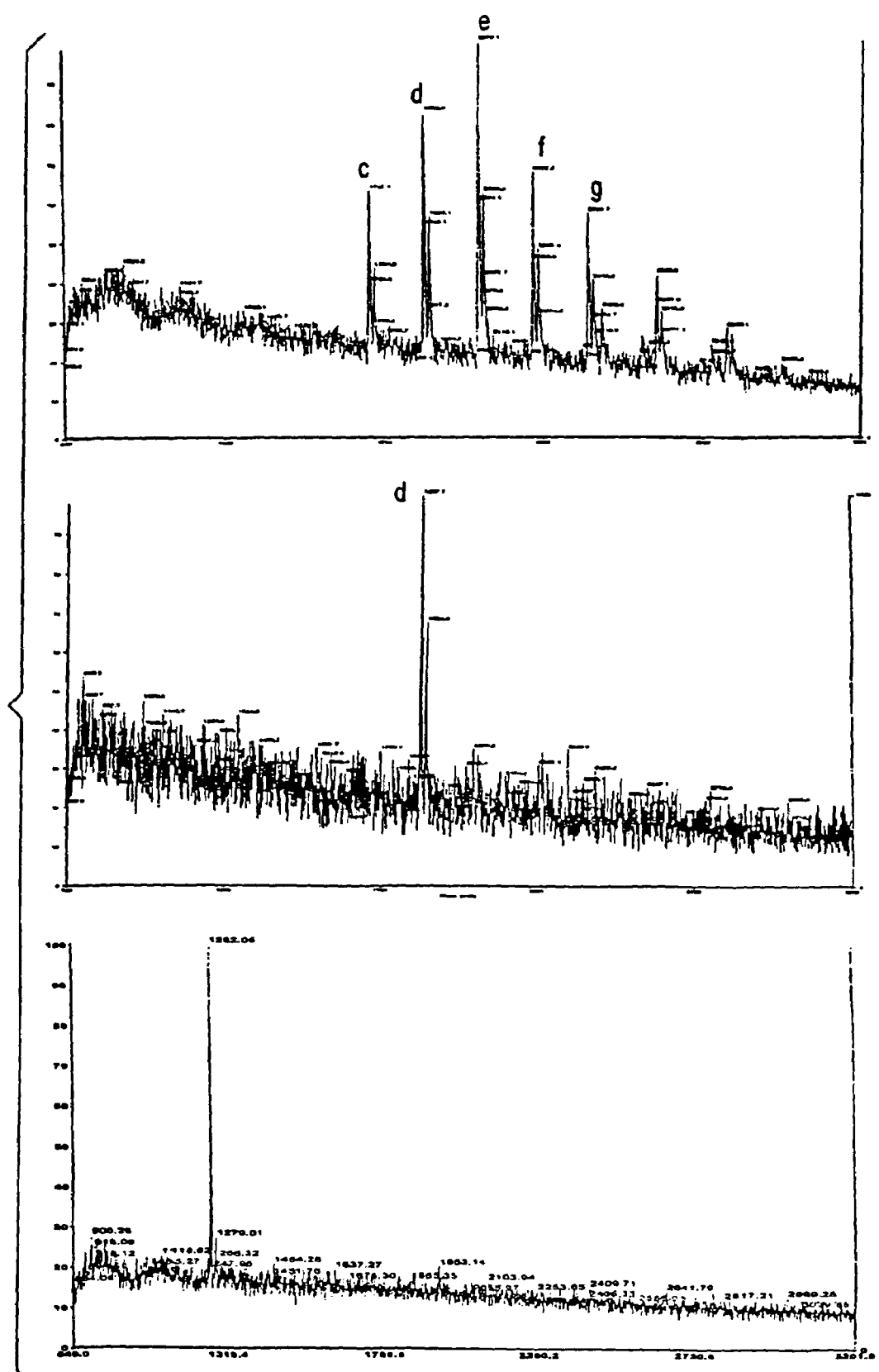
FIGS. 12A-12C show MALDI-TOF analysis of N-glycans released from a cell free extract of *K. lactis*.

The OCH1 gene was cloned from P. pastoris (Example 1) and K. lactis (Example 9), as described. Using gene-specific primers, a construct was made from each clone to delete the OCH1 gene from the genome of P. pastoris and K. lactis (Examples 1 and 9, respectively). Host cells depleted in initiating α-1,6-mannosyltransferase activity and engineered to produce N-glycans having a Man$_5$GlcNAc$_2$ carbohydrate structure were thereby obtained (see, e.g., FIGS. 5, 6, and 12; Examples 4 and 9).

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *K. lactis* OCH1 gene, and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided. Also provided are vectors, including expression vectors, which comprise the above nucleic acid molecules of the invention, as described further herein. Similarly, host cells transformed with the nucleic acid molecules or vectors of the invention are provided.

The invention further provides methods of making or using a non-human eukaryotic host cell diminished or depleted in an alg gene activity (i.e., alg activities, including equivalent enzymatic activities in non-fungal host cells) and introducing into the host cell at least one glycosidase activity. In a preferred embodiment, the glycosidase activity is introduced by causing expression of one or more mannosidase activities within the host cell, for example, by activation of a mannosidase activity, or by expression from a nucleic acid molecule of a mannosidase activity, in the host cell.

Figure 13:
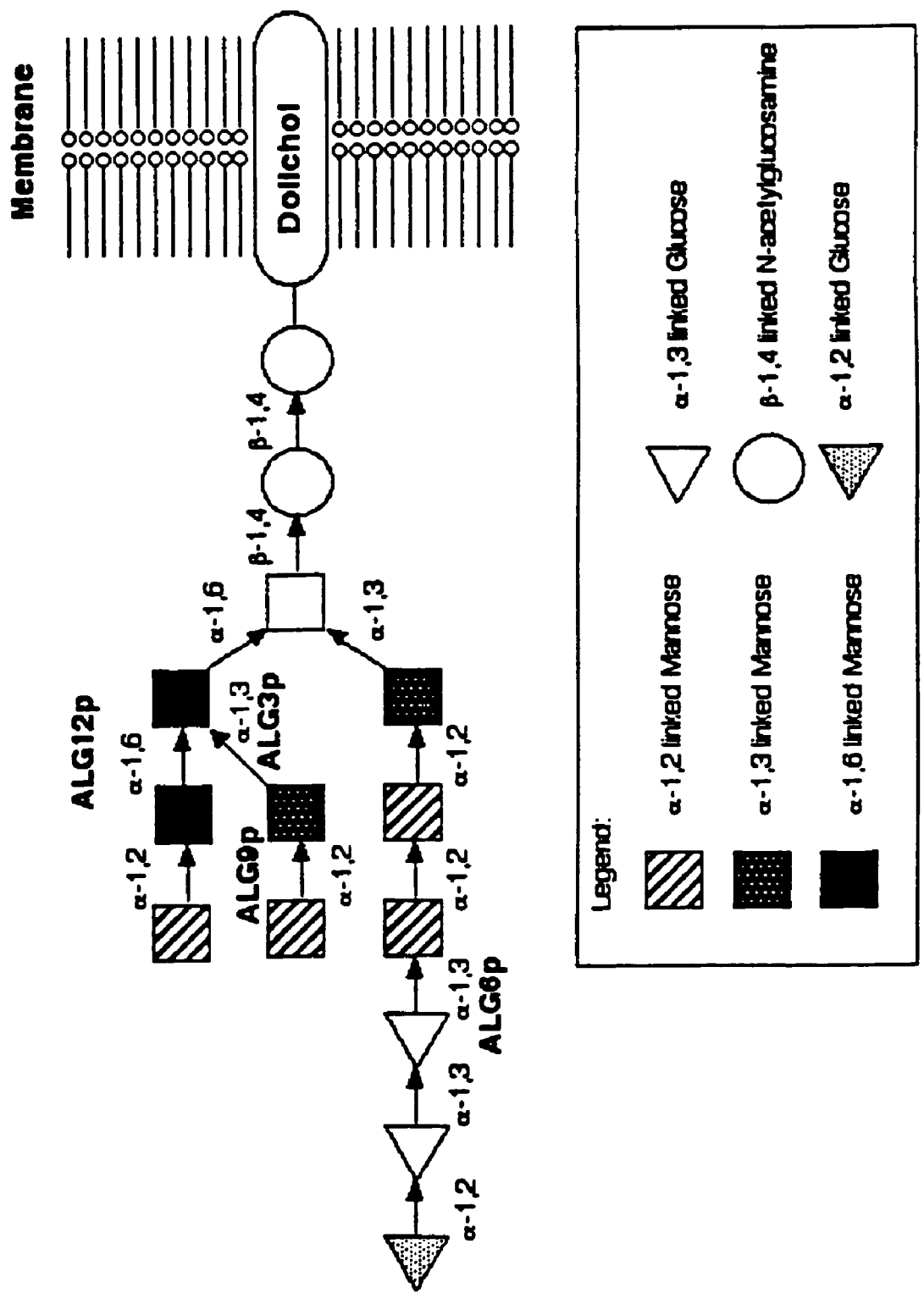
FIG. 13 is a schematic of the structure of the dolichyl pyrophosphate-linked oligosaccharide.

In another embodiment, the method involves making or using a host cell diminished or depleted in the activity of one or more enzymes that transfer a sugar residue to the 1,6 arm of lipid-linked oligosaccharide precursors (FIG. 13). A host cell of the invention is selected for or is engineered by introducing a mutation in one or more of the genes encoding an enzyme that transfers a sugar residue (e.g., mannosylates) the 1,6 arm of a lipid-linked oligosaccharide precursor. The sugar residue is more preferably mannose, is preferably a glucose, GlcNAc, galactose, sialic acid, fucose or GlcNAc phosphate residue. In a preferred embodiment, the activity of one or more enzymes that mannosylate the 1,6 arm of lipid-linked oligosaccharide precursors is diminished or depleted. The method may further comprise the step of introducing into the host cell at least one glycosidase activity (see below).

In yet another embodiment, the invention provides a method for producing a human-like glycoprotein in a non-human host, wherein the glycoprotein comprises an N-glycan having at least two GlcNAcs attached to a trimannose core structure.

Figure 14:
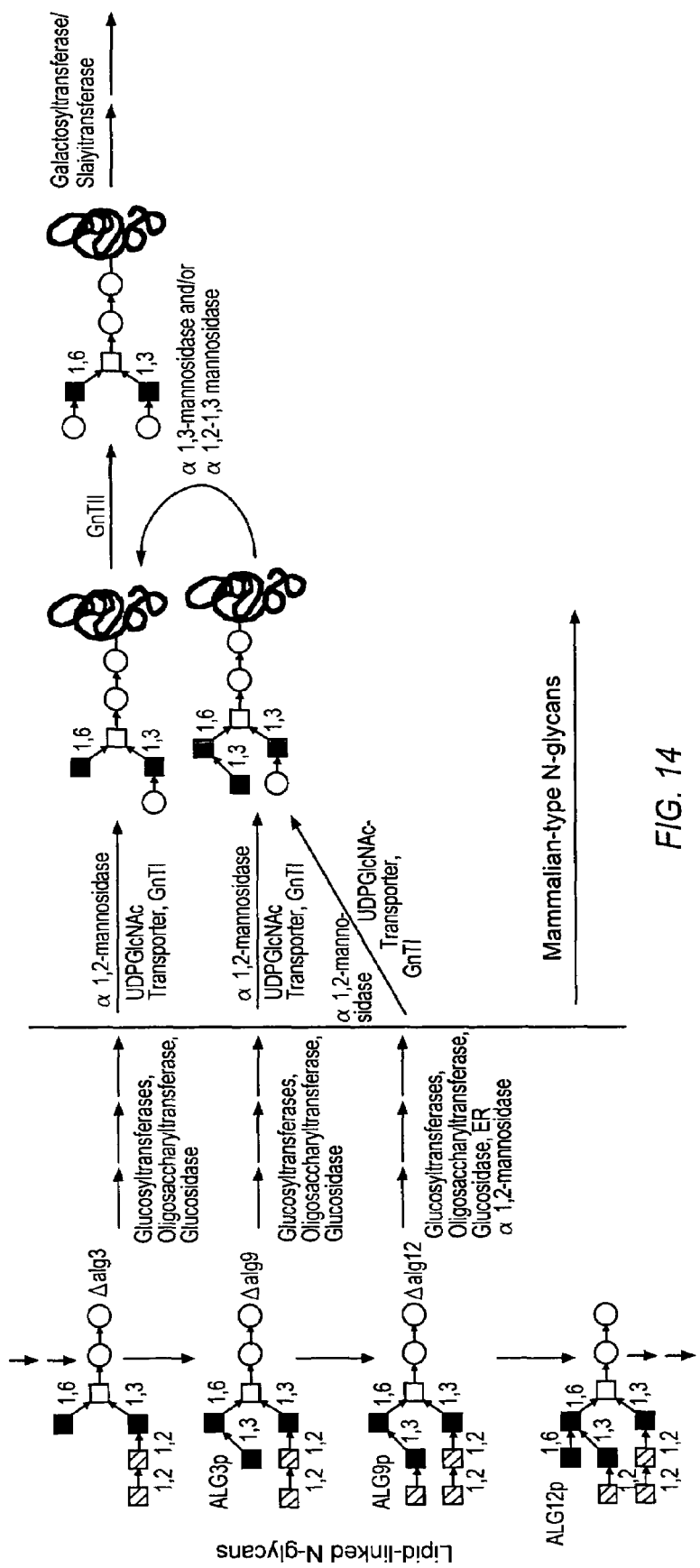
FIG. 14 is a schematic of the generation of GlcNAc$_2$Man$_3$GlcNAc$_2$ N-glycans from fungal host cells which are deficient in alg3, alg9, or alg12 activities.
Figure 15:
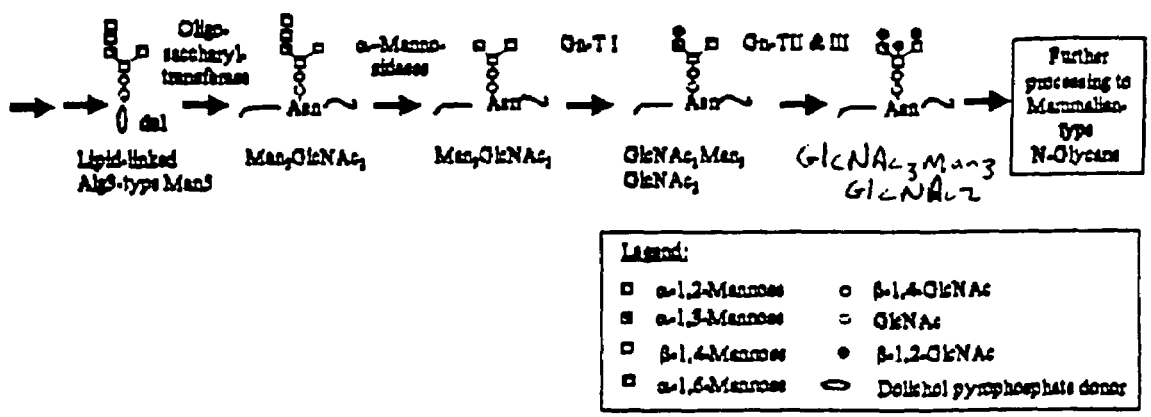
FIG. 15 is a schematic of processing reactions required to produce mammalian-type oligosaccharide structures in a fungal host cell with an alg3, och1 genotype.

In each above embodiment, the method is directed to making a host cell in which the lipid-linked oligosaccharide precursors are enriched in $Man_X GlcNAc_2$ structures, where X is 3, 4 or 5 (FIG. 14). These structures are transferred in the ER of the host cell onto nascent polypeptide chains by an oligosaccharyl-transferase and may then be processed by treatment with glycosidases (e.g., α-mannosidases) and glycosyltransferases (e.g., GnTI) to produce N-glycans having $GlcNAcMan_X GlcNAc_2$ core structures, wherein X is 3, 4 or 5, and is preferably 3 (FIGS. 14 and 15). As shown in FIG. 14, N-glycans having a $GlcNAcMan_X GlcNAc_2$ core structure where X is greater than 3 may be converted to $GlcNAcMan_3 GlcNAc_2$, e.g., by treatment with an α-1,3 and/or α-1,2-1,3 mannosidase activity, where applicable.

Additional processing of $GlcNAcMan_3 GlcNAc_2$ by treatment with glycosyltransferases (e.g., GnTII) produces $GlcNAc_2 Man_3 GlcNAc_2$ core structures which may then be modified, as desired, e.g., by ex vivo treatment or by heterologous expression in the host cell of a set of glycosylation enzymes, including glycosyltransferases, sugar transporters and mannosidases (see below), to become human-like N-glycans. Preferred human-like glycoproteins which may be produced according to the invention include those which comprise N-glycans having seven or fewer, or three or fewer, mannose residues; comprise one or more sugars selected from the group consisting of galactose, GlcNAc, sialic acid, and fucose; and comprise at least one oligosaccharide branch comprising the structure NeuNAc-Gal-GlcNAc-Man.

In one embodiment, the host cell has diminished or depleted Dol-P-Man:$Man_5 GlcNAc_2$-PP-Dol Mannosyltransferase activity, which is an activity involved in the first mannosylation step from $Man_5 GlcNAc_2$-PP-Dol to $Man_6 GlcNAc_2$-PP-Dol at the luminal side of the ER (e.g., ALG3 FIG. 13; FIG. 14). In *S. cerevisiae*, this enzyme is encoded by the ALG3 gene. As described above, *S. cerevisiae* cells harboring a leaky alg3-1 mutation accumulate $Man_5 GlcNAc_2$-PP-Dol and cells having a deletion in alg3 appear to transfer $Man_5 GlcNAc_2$ structures onto nascent polypeptide chains within the ER. Accordingly, in this embodiment, host cells will accumulate N-glycans enriched in $Man_5 GlcNAc_2$ structures which can then be converted to $GlcNAc_2 Man_3 GlcNAc_2$ by treatment with glycosidases (e.g., with α-1,2 mannosidase, α-1,3 mannosidase, or α-1,2-1,3 mannosidase activities) and glycosyltransferase activities (e.g., GnTI, GnTII) (FIG. 14; FIG. 35B).

As described in Example 10, degenerate primers were designed based on an alignment of Alg3 protein sequences from *S. cerevisiae*, *D. melanogaster* and humans (*H. sapiens*) (FIGS. 16 and 17), and were used to amplify a product from *P. pastoris* genomic DNA. The resulting PCR product was used as a probe to identify and isolate a *P. pastoris* genomic clone comprising an open reading frame (ORF) that encodes a protein having 35% overall sequence identity and 53% sequence similarity to the *S. cerevisiae* ALG3 gene (FIGS. 18 and 19). This *P. pastoris* gene is referred to herein as "PpALG3". The ALG3 gene was similarly identified and isolated from *K. lactis* (Example 10; FIGS. 20 and 21).

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *P. pastoris* ALG3 gene (FIG. 18) and the *K. lactis* ALG3 gene (FIG. 20), and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided (*P. pastoris* and *K. lactis* ALG3 gene products are shown in FIGS. 18 and 20). In addition, also provided are vectors, including expression vectors, which comprise a nucleic acid molecule of the invention, as described further herein.

Using gene-specific primers, a construct was made to delete the PpALG3 gene from the genome of *P. pastoris* (Example 10). This strain was used to generate a host cell depleted in Dol-P-Man:$Man_5 GlcNAc_2$-PP-Dol Mannosyltransferase activity and produce lipid-linked $Man_5 GlcNAc_2$-PP-Dol precursors which are transferred onto nascent polypeptide chains to produce N-glycans having a $Man_5 GlcNAc_2$ carbohydrate structure.

As described in Example 11, such a host cell may be engineered by expression of appropriate mannosidases to produce N-glycans having the desired $Man_3 GlcNAc_2$ core carbohydrate structure. Expression of GnTs in the host cell (e.g., by targeting a nucleic acid molecule or a library of nucleic acid molecules as described below) enables the modified host cell to produce N-glycans having one or two GlcNAc structures attached to each of the Man3 core structure (i.e., GlcNAc$_1$Man$_3$GlcNAc$_2$, GlcNAc$_2$Man$_3$GlcNAc$_2$, or GlcNAc$_3$Man$_3$GlcNAc$_2$; see FIG. 15). These structures may be processed further using the methods of the invention to produce human-like N-glycans on proteins which enter the secretion pathway of the host cell.

In a preferred embodiment, the method of the invention involves making or using a host cell which is both (a) diminished or depleted in the activity of an alg gene or in one or more activities that mannosylate N-glycans on the α-1,6 arm of the Man$_3$GlcNAc$_2$ ("Man3") core carbohydrate structure; and (b) diminished or depleted in the activity of an initiating α-1,6-mannosyltransferase, i.e., an initiation specific enzyme that initiates outer chain mannosylation (on the α-1,3 arm of the Man3 core structure). In *S. cerevisiae*, this enzyme is encoded by the OCH1 gene. Disruption of the och1 gene in *S. cerevisiae* results in a phenotype in which N-linked sugars completely lack the poly-mannose outer chain. Previous approaches for obtaining mammalian-type glycosylation in fungal strains have required inactivation of OCH1 (see, e.g., Chiba et al. (1998) *J. Biol. Chem.* 273:26298-304). Disruption of the initiating α-1,6-mannosyltransferase activity in a host cell of the invention is optional, however (depending on the selected host cell), as the Och1p enzyme requires an intact Man$_8$GlcNAc for efficient mannose outer chain initiation. Thus, the host cells selected or produced according to this invention, which accumulate lipid-linked oligosaccharides having seven or fewer mannose residues will, after transfer, produce hypoglycosylated N-glycans that will likely be poor substrates for Och1p (see, e.g., Nakayama et al. (1997) *FEBS Lett.* 412(3):547-50).

Engineering or Selecting Hosts Having N-Acetylglucosaminyltransferase III Activity The invention additionally provides a method for producing a human-like glycoprotein in a lower eukaryotic host cell by expressing an N-acetylglucosaminyltransferase III activity (including a full-length enzyme, homologs, variants, derivatives, and catalytically active fragments thereof). In one embodiment, a host cell (e.g., *P. pastoris*) is engineered to produce more human-like N-glycans, e.g., by activation of an N-acetylglucosaminyltransferase III activity or by expression from a nucleic acid molecule of an N-acetylglucosaminyltransferase III activity. Using well-known techniques in the art, gene-specific primers are designed to complement the homologous regions of a GnTIII gene, preferably a mammalian GnTIII gene (e.g., mouse GnTIII) (FIG. 24), sequences for which are readily available in the art (e.g., Genbank Accession No. L39373) and are PCR amplified.

In one embodiment, the invention provides a method for producing a human-like glycoprotein in a lower eukaryote (e.g., *P. pastoris*), wherein the glycoprotein comprises an N-glycan exhibiting a bisecting GlcNAc on a trimannose or trimannosyl (Man$_3$GlcNAc$_2$) core structure. In this embodiment, GlcNAcMan$_3$GlcNAc$_2$ (which may be produced by reacting a trimannose core with N-acetylglucosaminyltransferase I ("GnTI") activity, but which is typically produced by trimming of GlcNAcMan$_5$GlcNAc$_2$ by an α-1,3/α-1,6-mannosidase activity, such as Mannosidase II (Hamilton et al. (2003) *Science* 301:1244-46)) is reacted with an N-acetylglucosaminyltransferase III activity to produce a bisected GlcNAc$_2$Man$_3$GlcNAc$_2$. Accordingly, the invention provides GnTIII activity, which transfers β-1,4 GlcNAc onto substrates that are capable of accepting the bisecting GlcNAc in lower eukaryotes.

Figure 38:
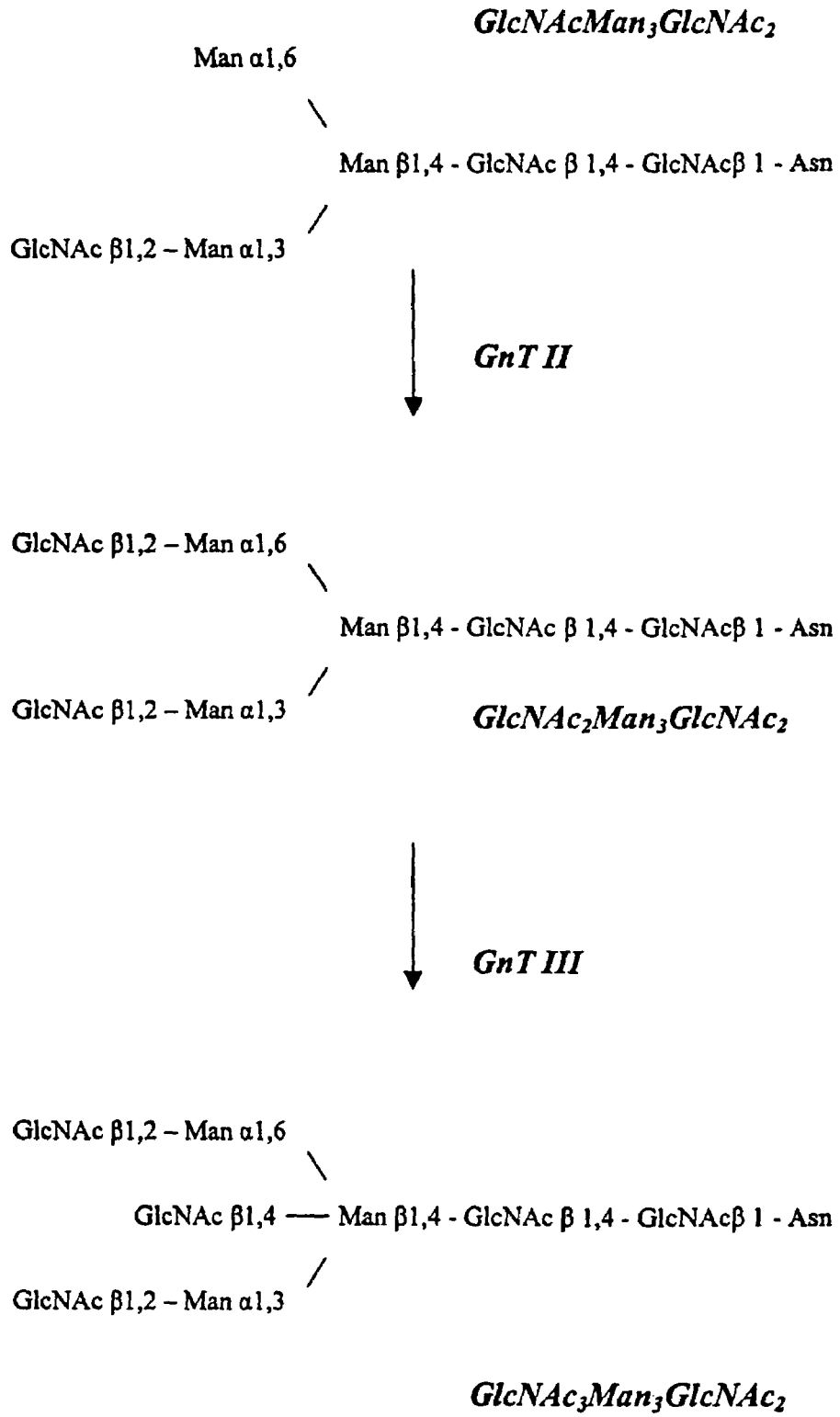
FIG. 38 is a structural representation of the transfer of a GlcNAc to the oligosaccharide intermediate, $GlcNAcMan_3GlcNAc_2$, produced on glycoproteins in a lower eukaryotic host cell, as catalyzed by GnTII, and the subsequent transfer of a GlcNAc to the product of that reaction, $GlcNAc_2Man_3GlcNAc_2$, as catalyzed by GnTIII.

In another embodiment, the invention provides a method for producing a human-like glycoprotein in a lower eukaryote (e.g., *P. pastoris*), wherein the glycoprotein comprises an N-glycan exhibiting a bisecting GlcNAc on a trimannose or trimannosyl (Man$_3$GlcNAc$_2$) core structure having at least two GlcNAcs attached to the trimannose core. In this embodiment, Man$_3$GlcNAc$_2$ is reacted with a GnTI activity and then with an N-acetylglucosaminyltransferase II ("GnTII") activity and a GnTIII activity (in either order) to produce a bisected GlcNAc$_3$Man$_3$GlcNAc$_2$ (FIG. 38). It should be appreciated that the bisected trimannosyl core structure of this embodiment may also contain an additional mannosyl group in place of a GlcNAc residue. For example, GlcNAcMan$_4$GlcNAc$_2$ may be reacted with a GnTIII activity to produce a bisected GlcNAc$_2$Man$_4$GlcNAc$_2$.

The invention also provides a method for producing a more human-like glycoprotein in a lower eukaryote (e.g. *P. pastoris*), wherein the glycoprotein produced comprises an N-glycan having at least two GlcNAcs attached to a pentamannose core structure (Man$_5$GlcNAc$_2$) and which exhibits a bisected N-glycan. Accordingly, in this embodiment, a pentamannose core structure (Man$_5$GlcNAc$_2$) is reacted with GnTIII activity to produce a bisected GlcNAcMan$_5$GlcNAc$_2$ and GlcNAc$_2$Man$_5$GlcNAc$_2$ structure.

Figure 37:
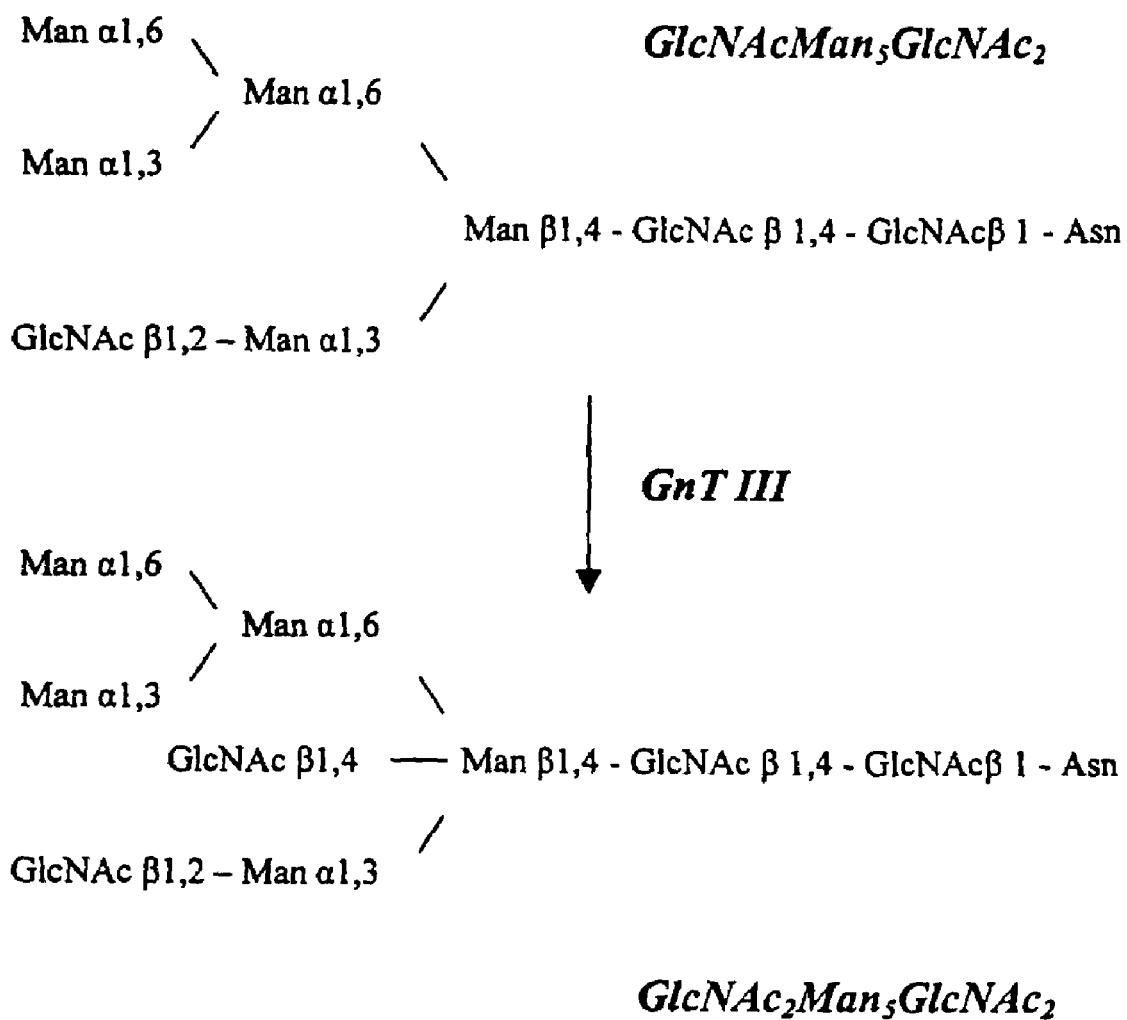
FIG. 37 is a structural representation of the transfer of a GlcNAc to the oligosaccharide intermediate, $GlcNAcMan_5GlcNAc_2$, produced on glycoproteins in a lower eukaryotic host cell, as catalyzed by GnTIII.

In an alternative embodiment, a pentamannose core structure produced via the mutation of och1 and alg3 genes is reacted with α1,2-mannosidase, GnTI, GnTII and GnTIII activities and UDP-GlcNAc to produce a bisected GlcNAc$_3$Man$_3$GlcNAc$_2$ glycan (FIG. 35B). In another embodiment, a pentamannose core structure is reacted with GnTI and GnTIII activities (in either order or in combination) to produce a bisected GlcNAc$_2$Man$_5$GlcNAc$_2$ structure (FIG. 37).

In a more preferred embodiment, using the combinatorial DNA library method of the invention, as described below, a pVA53 construct comprising the *S. cerevisiae* MNN2(s) leader (GenBank Accession No. NP_009571) fused to a catalytically active GnTIII domain from mouse (GnTIII Δ32) is expressed in a *P. pastoris* strain YSH-1 (Example 13) thereby producing N-glycans having a bisected GlcNAc$_2$Man$_5$GlcNAc$_2$ structure (Example 20). FIG. 26 (bottom) displays the MALDI-TOF spectrum of N-glycans released from a kringle 3 protein expressed in the above-mentioned strain, which is designated PBP26 (FIG. 36), exhibiting a predominant peak at 1666 m/z [a], which corresponds to bisected GlcNAc$_2$Man$_5$GlcNAc$_2$. (For comparison, FIG. 26 (top) displays the MALDI-TOF spectrum of N-glycans released from a kringle 3 protein expressed in strain YSH-1 lacking the pVA53 construct. The predominant peak at 1461 m/z [d] corresponds to the unmodified glycan: GlcNAcMan$_5$GlcNAc$_2$.) Accordingly, in one embodiment, a host of the present invention is characterized by its ability to produce, at least transiently, N-glycans which exhibit at least 50 mole % of a GlcNAc$_2$Man$_5$GlcNAc$_2$ or at least 50 mole % of a GlcNAc$_2$Man$_3$GlcNAc$_2$ structure having a bisecting GlcNAc. The mole percent of the glycans is in reference to percent of total neutral glycans as detected by MALDI-TOF. It is understood that if, for example, GlcNAc$_2$Man$_3$GlcNAc$_2$ having a bisecting GlcNAc is produced at 20% and GlcNAc$_3$Man$_3$GlcNAc$_2$ is produced at 25% on a target protein, the total amount of transiently produced GlcNAc$_2$Man$_3$GlcNAc$_2$ having a bisecting GlcNAc is 45%, because GlcNAc$_3$Man$_3$GlcNAc$_2$ is a product of a GlcNAc$_2$Man$_3$GlcNAc$_2$ having a bisecting GlcNAc further reacted with GnTII.

Similarly, in another embodiment, a pVA55 construct comprising the *S. cerevisiae* MNN2(l) leader (GenBank Accession No. NP_009571) fused to a catalytically active GnTIII domain from mouse (GnTIII Δ32) is expressed in a *P. pastoris* strain (YSH-1) thereby producing N-glycans GlcNAcMan$_5$GlcNAc$_2$ and bisected N-glycans GlcNAc$_2$Man$_5$GlcNAc$_2$ structure. As shown in FIG. 27 (bottom), these structures correspond to peaks at 1463 m/z and 1667 m/z, respectively. (For comparison, FIG. 27 (top) displays the MALDI-TOF spectrum of N-glycans released from a kringle 3 protein expressed in strain YSH-1 lacking the pVA53 construct. The predominant peak corresponds to unmodified GlcNAcMan$_5$GlcNAc$_2$ at 1461 m/z [d].) Accordingly, in another embodiment, a host of the present invention is characterized by its ability to produce, at least transiently, N-glycans which exhibit at least 20 mole % of a GlcNAc$_2$Man$_5$GlcNAc$_2$ or at least 20 mole % of a GlcNAc$_2$Man$_3$GlcNAc$_2$ structure having a bisecting GlcNAc.

Figure 29:
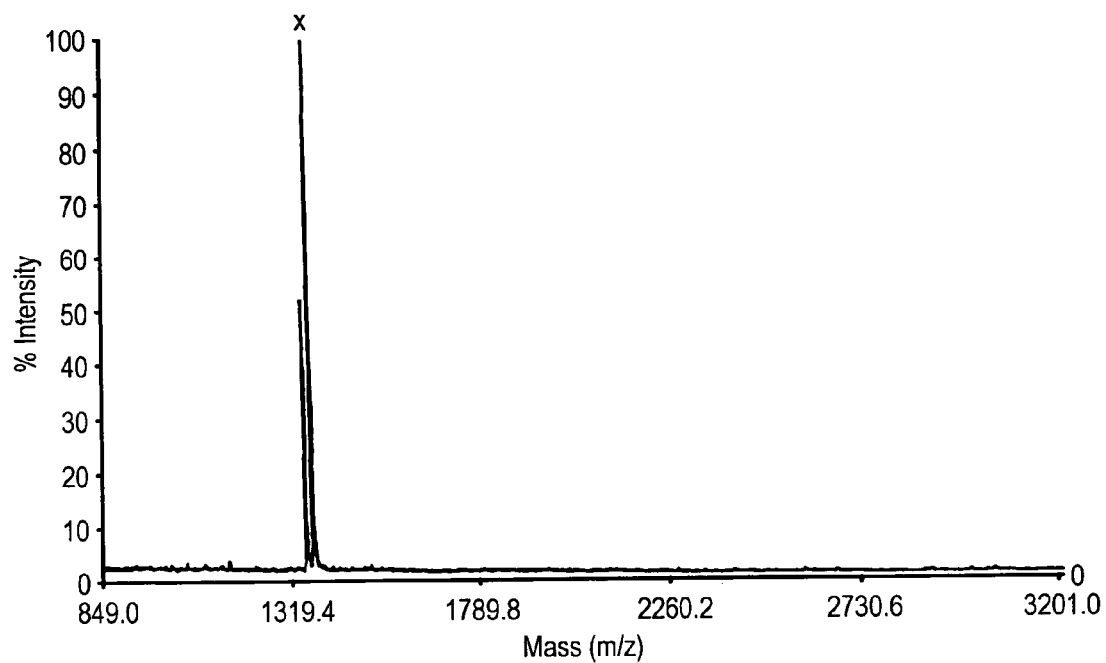
FIG. 29 is a MALDI-TOF-MS analysis of N-glycans isolated from a kringle 3 glycoprotein expressed in *P. pastoris* YSH-44 cells. The predominant peak at 1356 m/z corresponds to the mass of GlcNAc$_2$Man$_3$GlcNAc$_2$ [x].
Figure 30:
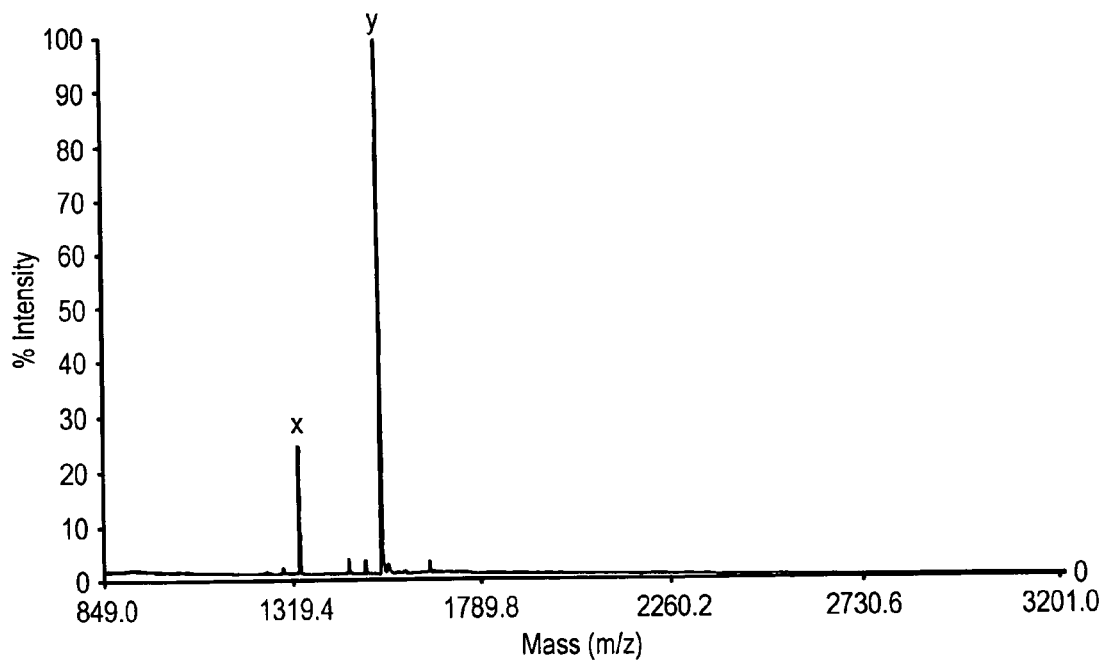
FIG. 30 is a MALDI-TOF-MS analysis of N-glycans isolated from a kringle 3 glycoprotein expressed in *P. pastoris* YSH-44 cells transformed with a pVA53 construct (*S. cerevisiae MNN2(s)/mGnTIII). The peak at 1340 m/z corresponds to the mass of $GlcNAc_2Man_3GlcNAc_2$ [x] and the peak at 1542 m/z corresponds to the mass of $GlcNAc_3Man_3GlcNAc_2$ [y].
Figure 31:
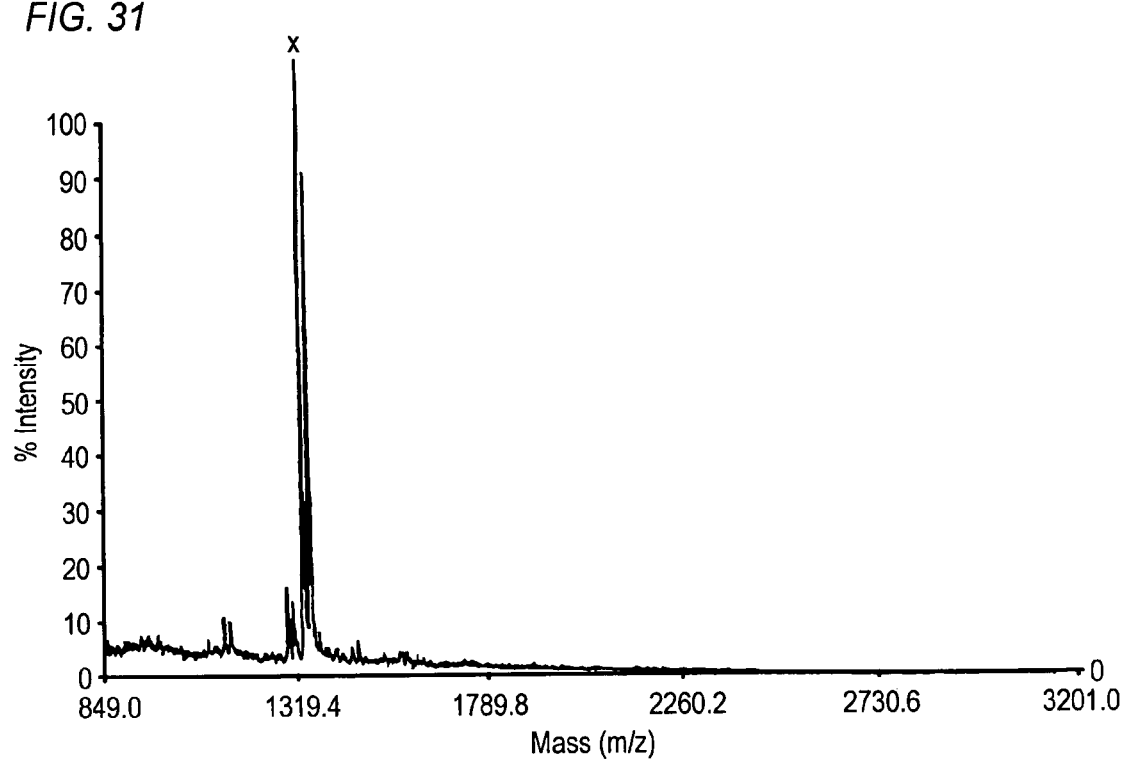
FIG. 31 is a MALDI-TOF-MS analysis of N-glycans isolated from a kringle 3 glycoprotein expressed in *P. pastoris* PBP6-5 cells. The predominant peak at 1340 m/z corresponds to the mass of $GlcNAc_2Man_3GlcNAc_2$ [x].

In an even more preferred embodiment, a pVA53 construct comprising the *S. cerevisiae* MNN2(s) leader (GenBank Accession No. NP_009571) fused to a catalytically active GnTIII domain from mouse (GnTIII Δ32) is expressed in a *P. pastoris* strain YSH-44 (Example 15) thereby producing N-glycans having a bisected GlcNAc$_3$Man$_3$GlcNAc$_2$ structure (Example 20). FIG. 30 displays the MALDI-TOF spectrum of N-glycans released from a kringle 3 protein expressed in the above-mentioned strain designated as YSH-57, exhibiting a predominant peak at 1542 m/z [y], which corresponds to the bisected glycan GlcNAc$_3$Man$_3$GlcNAc$_2$. (For comparison, FIG. 29 displays the MALDI-TOF spectrum of N-glycans released from a kringle 3 protein expressed in strain YSH-44 lacking the pVA53 construct. The predominant peak at 1356 m/z [x] in FIG. 29 corresponds to the unmodified glycan: GlcNAc$_2$Man$_3$GlcNAc$_2$.) Accordingly, in one embodiment, a host of the present invention is characterized by its ability to produce, at least transiently, N-glycans which exhibit at least 80 mole % of a GlcNAc$_3$Man$_3$GlcNAc$_2$ structure having a bisecting GlcNAc. The mole percent of the glycans is in reference to percent of total neutral glycans as detected by MALDI-TOF.

Figure 32:
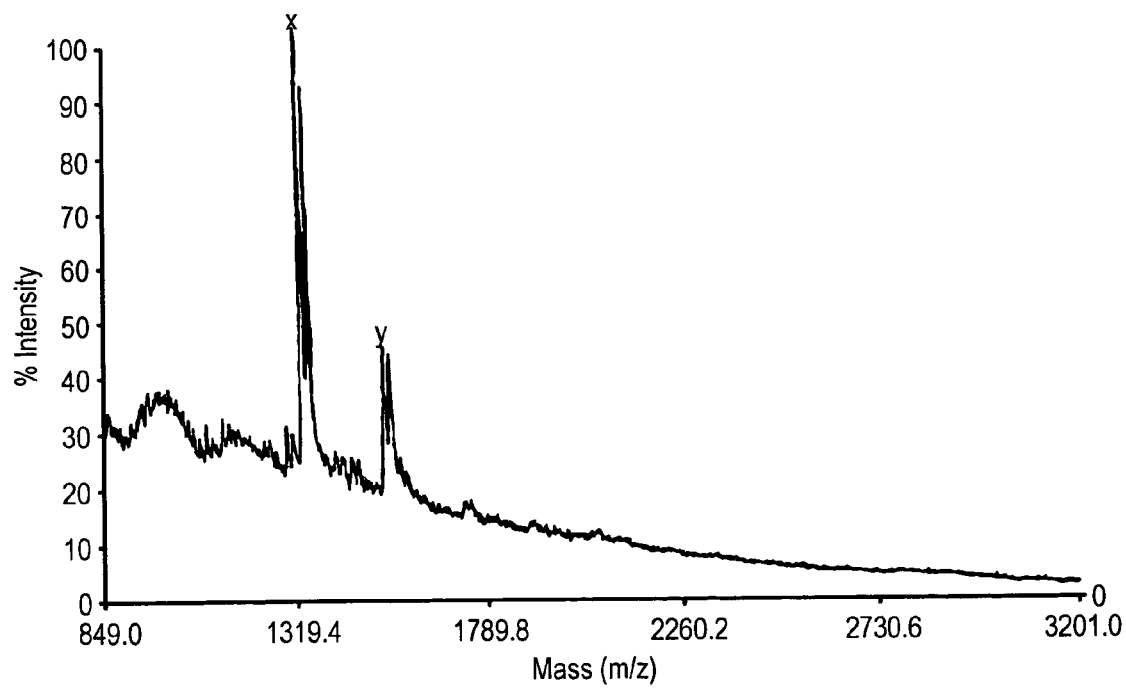
FIG. 32 is a MALDI-TOF-MS analysis of N-glycans isolated from a kringle 3 glycoprotein expressed in *P. pastoris* PBP6-5 cells transformed with a pVA53 construct (*S. cerevisiae* MNN2(s)/mGnTIII). The peak at 1340 m/z corresponds to the mass of $GlcNAc_2Man_3GlcNAc_2$ [x] and the peak at 1543 m/z corresponds to the mass of $GlcNAc_3Man_3GlcNAc_2$ [y].

Alternatively, in another embodiment, a pVA53 construct comprising the *S. cerevisiae* MNN2(s) leader (GenBank Accession No. NP_009571) fused to a catalytically active GnTIII domain from mouse (GnTIII Δ32) is expressed in a *P. pastoris* strain (PBP6-5) (Example 11) thereby producing N-glycans having a GlcNAc$_2$Man$_3$GlcNAc$_2$ and a bisected GlcNAc$_3$Man$_3$GlcNAc$_2$ structure. As shown in FIG. 32, these structures correspond to peaks at 1340 m/z and 1543 m/z, respectively. Accordingly, in another embodiment, a host of the present invention is characterized by its ability to produce, at least transiently, N-glycans which exhibit at least 20 mole % of a GlcNAc$_3$Man$_3$GlcNAc$_2$ structure having a bisecting GlcNAc in an alg3 mutant host cell.

The invention provides methods for producing a human-like glycoprotein in a lower eukaryote, wherein the glycoprotein comprises a Man$_5$GlcNAc$_2$ core structure or a Man$_3$GlcNAc$_2$ core structure, and wherein the core structure is further modified by two or more GlcNAcs. In some embodiments of the invention, 10% or more of the core structures are modified by the two or more GlcNAcs. In other preferred embodiments, 20%, 30%, 40%, 50%, 60%, 70%, 80% or even more of the core structures are so modified. In a highly preferred embodiment, one of the GlcNAcs is a bisecting GlcNAc.

In another aspect of the invention, a combinatorial nucleic acid library which encodes at least one GnTIII catalytic domain is used to express a GnTIII activity in a lower eukaryotic host cell (Example 18). Preferably, a library of the invention comprises a sublibrary of leader sequences fused in frame to a single nucleic acid molecule or a sublibrary of nucleic acid molecules comprising GnTIII sequences, one or more of which encode a catalytic domain having GnTIII activity in the host cell. Alternatively, a single nucleic acid molecule or a sublibrary of nucleic acid molecules comprising leader sequences is fused in frame to a sublibrary of nucleic acid molecules comprising GnTIII sequences, one or more of which encode a catalytic domain having GnTIII activity in the host cell. (See below.) Expression of these and other such combinatorial libraries is performed in a host cell which expresses a target glycoprotein whose N-glycan structures are analyzed to determine whether and how much GnTIII is expressed. A wide range of catalytically active GnTIII enzymes may be produced in a host cell using the methods and libraries of the invention. It is this aspect of the invention that allows a skilled artisan to create and delinate between GnTIII enzymes having little or no activity and those enzymes that are actively expressed and which produce predominant levels of a desired bisected oligosaccharide intermediate such as GlcNAc$_2$Man$_5$GlcNAc$_2$, GlcNAc$_3$Man$_3$GlcNAc$_2$ or GlcNAc$_2$Man$_3$GlcNAc$_2$ in the host cells.

As described further below, the proper targeting of an enzyme responsible for a given step in the glycosylation pathway to the appropriate subcellular location and the sufficiency of the enzyme's activity at the particular pH of that subcellular location are important factors in the production of glycoproteins having N-glycans with the desired structures. The use of combinatorial libraries of fusion proteins to generate diverse populations of enzyme chimeras and the screening of these libraries in transformed cells provides a powerful method to identify host strains with the activity of interest in the appropriate location. In preferred embodiments of the invention, the enzyme activity is located such that an N-glycan-containing glycoprotein expressed in the cell is capable of reacting with the activity during the secretion process.

Not all combinations of leader/catalytic domains produce desired enzyme activities however. A wide variety of leader/catalytic domain combinations is created, only a few of which may be useful in producing the presently desired intermediates. The present invention, nevertheless, encompasses even those combinations that do not presently exhibit a desired enzymatic activity in the exemplified host cell. FIG. 28 (bottom) shows a pVB51 construct comprising the *K. lactis* GNT(s) leader (GenBank Accession No. AF106080) fused to a catalytically active GnTIII domain from mouse (GnTIII Δ32) expressed in a *P. pastoris* strain YSH-1, which does not readily exhibit GnTIII activity. (For comparison, FIG. 28 (top) displays the MALDI-TOF spectrum of N-glycans released from a kringle 3 protein expressed in strain YSH-1 lacking the pVA53 construct. The predominant peak corresponds to unmodified GlcNAcMan$_5$GlcNAc$_2$ at 1461 m/z.) The predominant peak in FIG. 28 (bottom) at 1463 m/z, which correlates to the mass of GlcNAcMan$_5$GlcNAc$_2$, is observed. A second peak at 1726 m/z, which does not correlate to the mass of GlcNAc$_2$Man$_5$GlcNAc$_2$ is also observed. It is contemplated that these and other such combinations may be useful, with or without slight modifications using techniques well known in the art, when they are expressed, e.g., in other host cells including those which have been modified to produce human-like glycoforms.

The use of combinatorial libraries to generate diverse populations of enzyme chimeras and the screening of these libraries in transformed cells further allows strains to be identified in which the enzyme activity is substantially intracellular. Example 6, below, provides an example of assay conditions useful for measuring extracellular α-1,2-mannosidase activity. Examples 22 and 23 also provide examples of assays for glycosyltransferase activity (GnTIII) in the medium. See also Table 9, below, and Choi et al. (20033 *Proc. Natl. Acad. Sci. U.S.A.* 100(9):5022-27. For purposes of the invention, an enzyme activity is substantially intracellular when less than 10% of the enzyme activity is measurable in the extracellular medium.

As described in Examples 11, 12, 13, 14, 15, and 19-21, a host cell may be engineered by the expression of appropriate glycosyltransferases (e.g., N-acetylglucosaminyltransferase) to produce N-glycans having the desired carbohydrate structures (e.g., $GlcNAc_2Man_3GlcNAc_2$, $GlcNAc_3Man_3GlcNAc_2$). Expression of GnTs in the host cell (e.g., by targeting a nucleic acid molecule or a library of nucleic acid molecules as described below and in Choi et al. (2003) *Proc. Natl. Acad. Sci. USA.* 100(9):5022-27 and WO 02/00879) enables the modified host cell to produce N-glycans having the bisecting GlcNAc on the middle mannose. These structures may be processed further using the methods of the invention to produce human-like N-glycans on proteins which enter the secretion pathway of the host cell.

In a more preferred embodiment, co-expression of appropriate UDP-sugar-transporter(s) and transferase(s) will cap the terminal $\alpha$-1,6 and $\alpha$-1,3 residues as well as the middle mannose with GlcNAc, resulting in the precursor for mammalian-type complex (e.g. $GlcNAc_3Man_3GlcNAc_2$) and hybrid N-glycosylation. These peptide-bound N-linked oligosaccharide chains then serve as a precursor for further modification to a mammalian-type oligosaccharide structure. Subsequent expression of galactosyl-tranferases and genetically engineering the capacity to transfer sialylic acid to the termini (see FIG. 1B) will produce a mammalian-type (e.g., human-like) N-glycan structure.

Host Cells of the Invention

A preferred host cell of the invention is a lower eukaryotic cell, e.g., yeast, a unicellular and multicellular or filamentous fungus. However, a wide variety of host cells are envisioned as being useful in the methods of the invention. Plant cells or insect cells, for instance, may be engineered to express a human-like glycoprotein according to the invention. Likewise, a variety of non-human, mammalian host cells may be altered to express more human-like or otherwise altered glycoproteins using the methods of the invention. As one of skill in the art will appreciate, any eukaryotic host cell (including a human cell) may be used in conjunction with a library of the invention to express one or more chimeric proteins which is targeted to a subcellular location, e.g., organelle, in the host cell where the activity of the protein is modified, and preferably is enhanced. Such a protein is preferably—but need not necessarily be—an enzyme involved in protein glycosylation, as exemplified herein. It is envisioned that any protein coding sequence may be targeted and selected for modified activity in a eukaryotic host cell using the methods described herein.

Figure 1B:
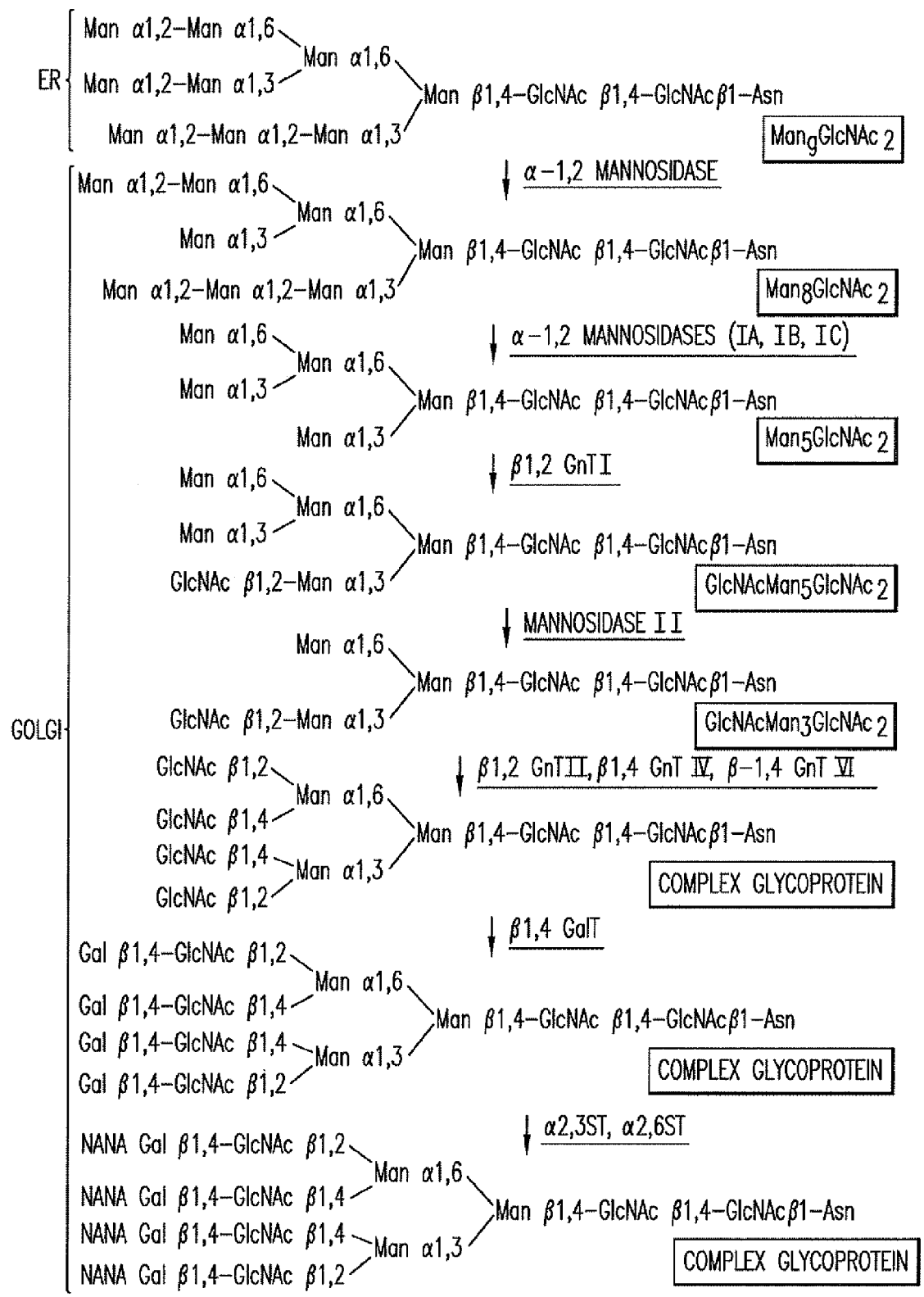
FIG. 1B is a schematic diagram of a typical human N-glycosylation pathway.

Lower eukaryotes that are able to produce glycoproteins having the attached N-glycan $Man_5GlcNAc_2$ are particularly useful because (a) lacking a high degree of mannosylation (e.g., greater than 8 mannoses per N-glycan, or especially 30-40 mannoses), they show reduced immunogenicity in humans; and (b) the N-glycan is a substrate for further glycosylation reactions to form an even more human-like glycoform, e.g., by the action of GlcNAc transferase I (FIG. 1B; $\beta$1,2 GnTI) to form $GlcNAcMan_5GlcNAc_2$. A yield is obtained of greater than 30 mole %, more preferably a yield of 50, 60, 70, 80, 90, or even 100 mole %, glycoproteins with N-glycans having a $Man_5GlcNAc_2$ structure. In a preferred embodiment, more than 50% of the $Man_5GlcNAc_2$ structure is shown to be a substrate for a GnTI activity and can serve as such a substrate in vivo.

Preferred lower eukaryotes of the invention include but are not limited to: *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reseei, Chrysosporium lucknowense, Fusarium* sp. *Fusarium gramineum, Fusarium venenatum,* and *Neurospora crassa.*

In each above embodiment, the method is directed to making a host cell in which the oligosaccharide precursors are enriched in $Man_5GlcNAc_2$. These structures are desirable because they may then be processed by treatment in vitro, for example, using the method of Maras and Contreras, U.S. Pat. No. 5,834,251. In a preferred embodiment, however, precursors enriched in $Man_5GlcNAc_2$ are processed by at least one further glycosylation reaction in vivo—with glycosidases (e.g., $\alpha$-mannosidases) and glycosyltransferases (e.g., GnTI)—to produce human-like N-glycans. Oligosaccharide precursors enriched in $Man_5GlcNAc_2$, for example, are preferably processed to those having $GlcNAcMan_xGlcNAc_2$ core structures, wherein X is 3, 4 or 5, and is preferably 3. N-glycans having a $GlcNAcMan_xGlcNAc_2$ core structure where X is greater than 3 may be converted to $GlcNAcMan_3GlcNAc_2$, e.g., by treatment with an $\alpha$-1,3 and/or $\alpha$-1,6 mannosidase activity, where applicable. Additional processing of $GlcNAcMan_3GlcNAc_2$ by treatment with glycosyltransferases (e.g., GnTII) produces $GlcNAc_2Man_3GlcNAc_2$ core structures which may then be modified, as desired, e.g., by ex vivo treatment or by heterologous expression in the host cell of additional glycosylation enzymes, including glycosyltransferases, sugar transporters and mannosidases (see below), to become human-like N-glycans.

Preferred human-like glycoproteins which may be produced according to the invention include those which comprise N-glycans having seven or fewer, or three or fewer, mannose residues; and which comprise one or more sugars selected from the group consisting of galactose, GlcNAc, sialic acid, and fucose.

Another preferred non-human host cell of the invention is a lower eukaryotic cell, e.g., a unicellular or filamentous fungus, which is diminished or depleted in the activity of one or more alg gene activities (including an enzymatic activity which is a homolog or equivalent to an alg activity). Another preferred host cell of the invention is diminished or depleted in the activity of one or more enzymes (other than alg activities) that mannosylate the $\alpha$-1,6 arm of a lipid-linked oligosaccharide structure.

While lower eukaryotic host cells are preferred, a wide variety of host cells having the aforementioned properties are envisioned as being useful in the methods of the invention. Plant cells, for instance, may be engineered to express a human-like glycoprotein according to the invention. Likewise, a variety of non-human, mammalian host cells may be altered to express more human-like glycoproteins using the methods of the invention. An appropriate host cell can be engineered, or one of the many such mutants already described in yeasts may be used. A preferred host cell of the invention, as exemplified herein, is a hypermannosylation-minus (OCH1) mutant in *Pichia pastoris* which has further been modified to delete the alg3 gene.

The invention additionally provides lower eukaryotic host cells capable of producing glycoproteins having bisected N-glycans, such as bisected $GlcNAcMan_5GlcNAc_2$, $GlcNAc_2Man_5GlcNAc_2$, $GlcNAc_2Man_3GlcNAc_2$, and, preferably, $GlcNAc_3Man_3GlcNAc_2$. In a preferred embodiment of the invention, the host cells comprise a GnTIII activity. In a more preferred embodiment, the host cells further comprise one or more activities selected from: GnTI, GnTII, GnTIV, and GnTV. Preferred host cells express GnTI, GnTII, and GnTIII. Other preferred host cells additionally express GnTIV and/or GnTV. Even more preferably, the one or more GnT activities of the host cells are substantially intracellular.

Thus, in preferred embodiments of the invention, host cells comprising the one or more GnT activities produce N-glycans comprising structures, including but not limited to $GlcNAcMan_3GlcNAc_2$, $GlcNAcMan_4GlcNAc_2$, or $GlcNAcMan_5GlcNAc_2$, that are capable of reacting with a GnTIII enzyme activity to produce corresponding bisected N-glycans. The enzyme activities thereby convert glycoproteins containing these N-glycans into forms with new and more desirable properties. Because GnTIII is currently understood to inhibit additional GnT activity in mammalian cells, the skilled artisan should appreciate that sequential glycosylation reaction may or may not be of importance. The present invention contemplates, however, the addition of GnTI and GnTIII in either order or together. It should also be understood that other enzyme activities within the cell, such as, e.g., one or more desired mannosidase activities (e.g., α 1,2 mannosidase, Mannosidase I, Mannosidase II), may act in concert with the GnT activities to generate yet other human-like glycoproteins of interest (see FIG. 1B).

In a preferred embodiment, a mannosidase II or a catalytically active fragment thereof is introduced into the host cell to trim the α1,3 and α1,6 mannose containing arms of a bisected pentamannose core structure such as $GlcNAc_2Man_5GlcNAc_2$. The resulting glycans (e.g., bisected $GlcNAc_2Man_4GlcNAc_2$ and $GlcNAc_2Man_3GlcNAc_2$) are preferred substrates for subsequent human-like N-glycan modification.

In another embodiment of the invention, the host cells comprise a $Man_5GlcNAc_2$ core structure or a $Man_3GlcNAc_2$ core structure modified by two or more GlcNAcs. It should be understood that either core structure may include further modifications in addition to the modification by GlcNAc. Preferably, 10% or more of the core structures are modified by GlcNAcs. Most preferably, 20%, 30%, 40%, 50%, 60%, 70%, 80% or even more of the core structures contain the GlcNAc modification.

Formation of Complex N-Glycans

Formation of complex N-glycan synthesis is a sequential process by which specific sugar residues are removed and attached to the core oligosaccharide structure. In higher eukaryotes, this is achieved by having the substrate sequentially exposed to various processing enzymes. These enzymes carry out specific reactions depending on their particular location within the entire processing cascade. This "assembly line" consists of ER, early, medial and late Golgi, and the trans Golgi network all with their specific processing environment. To re-create the processing of human glycoproteins in the Golgi and ER of lower eukaryotes, numerous enzymes (e.g., glycosyltransferases, glycosidases, phosphatases and transporters) have to be expressed and specifically targeted to these organelles, and preferably, in a location so that they function most efficiently in relation to their environment as well as to other enzymes in the pathway.

Because one goal of the methods described herein is to achieve a robust protein production strain that is able to perform well in an industrial fermentation process, the integration of multiple genes into the host cell chromosome involves careful planning. As described above, one or more genes which encode enzymes known to be characteristic of non-human glycosylation reactions are preferably deleted. The engineered cell strain is transformed with a range of different genes encoding desired activities, and these genes are transformed in a stable fashion, thereby ensuring that the desired activity is maintained throughout the fermentation process.

Any combination of the following enzyme activities may be engineered singly or multiply into the host using methods of the invention: sialyltransferases, mannosidases, fucosyltransferases, galactosyltransferases, GlcNAc transferases, ER and Golgi specific transporters (e.g. syn- and antiport transporters for UDP-galactose and other precursors), other enzymes involved in the processing of oligosaccharides, and enzymes involved in the synthesis of activated oligosaccharide precursors such as UDP-galactose and CMP-N-acetylneuraminic acid. Preferably, enzyme activities are introduced on one or more nucleic acid molecules (see also below). Nucleic acid molecules may be introduced singly or multiply, e.g., in the context of a nucleic acid library such as a combinatorial library of the invention. It is to be understood, however, that single or multiple enzymatic activities may be introduced into a host cell in any fashion, including but not limited to protein delivery methods and/or by use of one or more nucleic acid molecules without necessarily using a nucleic acid library or combinatorial library of the invention.

Expression of Glycosyltransferases to Produce Complex N-Glycans:

With DNA sequence information, the skilled artisan can clone DNA molecules encoding GnT activities (e.g., Example 3, 8, 11, 15, and 18). Using standard techniques well-known to those of skill in the art, nucleic acid molecules encoding GnTI, II, III, IV or V (or encoding catalytically active fragments thereof) may be inserted into appropriate expression vectors under the transcriptional control of promoters and other expression control sequences capable of driving transcription in a selected host cell of the invention, e.g., a fungal host such as *Pichia* sp., *Kluyveromyces* sp. and *Aspergillus* sp., as described herein, such that one or more of these mammalian GnT enzymes may be actively expressed in a host cell of choice for production of a human-like complex glycoprotein (e.g., Examples 8, 20, and 21).

Several individual glycosyltransferases have been cloned and expressed in *S. cerevisiae* (GalT, GnTI), *Aspergillus nidulans* (GnTI) and other fungi, without however demonstrating the desired outcome of "humanization" on the glycosylation pattern of the organisms (Yoshida et al. (1999) *Glycobiology* 9(1):53-8; Kalsner et al. (1995) *Glycoconj. J* 12(3):360-370). It was speculated that the carbohydrate structure required to accept sugars by the action of such glycosyltransferases was not present in sufficient amounts, which most likely contributed to the lack of complex N-glycan formation.

A preferred method of the invention provides the functional expression of a GnT, such as GnTI, GnTII, and GnTIII, in the early, medial or late Golgi apparatus, as well as ensuring a sufficient supply of UDP-GlcNAc (e.g., by expression of a UDP-GlcNAc transporter; see Examples below).

Methods for Providing Sugar Nucleotide Precursors to the Golgi Apparatus:

For a glycosyltransferase to function satisfactorily in the Golgi, the enzyme requires a sufficient concentration of an appropriate nucleotide sugar, which is the high-energy donor of the sugar moiety added to a nascent glycoprotein. In humans, the full range of nucleotide sugar precursors (e.g., UDP-N-acetylglucosamine, UDP-N-acetylgalactosamine, CMP-N-acetylneuraminic acid, UDP-galactose, etc.) are generally synthesized in the cytosol and transported into the Golgi, where they are attached to the core oligosaccharide by glycosyltransferases.

To replicate this process in non-human host cells, such as lower eukaryotes, sugar nucleoside specific transporters have to be expressed in the Golgi to ensure adequate levels of nucleoside sugar precursors (Sommers and Hirschberg (1981) *J. Cell Biol.* 91(2):A406-A406; Sommers and Hirschberg (1982) *J. Biol. Chem.* 257(18):811-817; Perez and Hirschberg (1987) *Methods in Enzymology* 138:709-715). Nucleotide sugars may be provided to the appropriate compartments, e.g., by expressing in the host microorganism an exogenous gene encoding a sugar nucleotide transporter. The choice of transporter enzyme is influenced by the nature of the exogenous glycosyltransferase being used. For example, a GlcNAc transferase may require a UDP-GlcNAc transporter, a fucosyltransferase may require a GDP-fucose transporter, a galactosyltransferase may require a UDP-galactose transporter, and a sialyltransferase may require a CMP-sialic acid transporter.

The added transporter protein conveys a nucleotide sugar from the cytosol into the Golgi apparatus, where the nucleotide sugar may be reacted by the glycosyltransferase, e.g., to elongate an N-glycan. The reaction liberates a nucleoside diphosphate or monophosphate, e.g., UDP, GDP, or CMP. Nucleoside monophosphates can be directly exported from the Golgi in exchange for nucleoside triphosphate sugars by an antiport mechanism. Accumulation of a nucleoside diphosphate, however, inhibits the further activity of a glycosyltransferase. As this reaction appears to be important for efficient glycosylation, it is frequently desirable to provide an expressed copy of a gene encoding a nucleotide diphosphatase. The diphosphatase (specific for UDP or GDP as appropriate) hydrolyzes the diphosphonucleoside to yield a nucleoside monophosphate and inorganic phosphate.

Suitable transporter enzymes, which are typically of mammalian origin, are described below. Such enzymes may be engineered into a selected host cell using the methods of the invention.

In another example, $\alpha$2,3- or $\alpha$2,6-sialyltransferase caps galactose residues with sialic acid in the trans-Golgi and TGN of humans leading to a mature form of the glycoprotein (FIG. 1B). To reengineer this processing step into a metabolically engineered yeast or fungus will require (1) $\alpha$2,3- or $\alpha$2,6-sialyltransferase activity and (2) a sufficient supply of CMP-N-acetyl neuraminic acid, in the late Golgi of yeast. To obtain sufficient a 2,3-sialyltransferase activity in the late Golgi, for example, the catalytic domain of a known sialyltransferase (e.g. from humans) has to be directed to the late Golgi in fungi (see above). Likewise, transporters have to be engineered to allow the transport of CMP-N-acetyl neuraminic acid into the late Golgi. There is currently no indication that fungi synthesize or can even transport sufficient amounts of CMP-N-acetyl neuraminic acid into the Golgi. Consequently, to ensure the adequate supply of substrate for the corresponding glycosyltransferases, one has to metabolically engineer the production of CMP-sialic acid into the fungus.

UDP-N-Acetylglucosamine

The cDNA of human UDP-N-acetylglucosamine transporter, which was recognized through a homology search in the expressed sequence tags database (dbEST), has been cloned (Ishida (1999) *J. Biochem.* 126(1):68-77). The mammalian Golgi membrane transporter for UDP-N-acetylglucosamine was cloned by phenotypic correction with cDNA from canine kidney cells (MDCK) of a recently characterized *Kluyveromyces lactis* mutant deficient in Golgi transport of the above nucleotide sugar (Guillen et al. (1998) *Proc. Natl. Acad. Sci. USA* 95(14):7888-7892). Results demonstrate that the mammalian Golgi UDP-GlcNAc transporter gene has all of the necessary information for the protein to be expressed and targeted functionally to the Golgi apparatus of yeast and that two proteins with very different amino acid sequences may transport the same solute within the same Golgi membrane (Guillen et al. (1998) *Proc. Natl. Acad. Sci. USA* 95(14):7888-7892).

Accordingly, one may incorporate the expression of a UDP-GlcNAc transporter in a host cell by means of a nucleic acid construct which may contain, for example: (1) a region by which the transformed construct is maintained in the cell (e.g., origin of replication or a region that mediates chromosomal integration), (2) a marker gene that allows for the selection of cells that have been transformed, including counterselectable and recyclable markers such as ura3 or T-urf13 (Soderholm et al. (2001) *Biotechniques* 31(2):306-10) or other well characterized selection-markers (e.g., his4, bla, Sh ble etc.), (3) a gene or fragment thereof encoding a functional UDP-GlcNAc transporter (e.g., from *K. lactis*, (Abeijon, (1996) *Proc. Natl. Acad. Sci. USA*. 93:5963-5968), or from *H. sapiens* (Ishida et al. (1996) *J. Biochem.* (Tokyo) 120(6): 1074-8), and (4) a promoter activating the expression of the above mentioned localization/catalytic domain fusion construct library.

GDP-Fucose

The rat liver Golgi membrane GDP-fucose transporter has been identified and purified by Puglielli and Hirschberg (1999) *J. Biol. Chem.* 274(50):35596-35600. The corresponding gene has not been identified, however, N-terminal sequencing can be used for the design of oligonucleotide probes specific for the corresponding gene. These oligonucleotides can be used as probes to clone the gene encoding for GDP-fucose transporter.

UDP-Galactose

Two heterologous genes, gma12(+) encoding alpha 1,2-galactosyltransferase (alpha 1,2 GalT) from *Schizosaccharomyces pombe* and (hUGT2) encoding human UDP-galactose (UDP-Gal) transporter, have been functionally expressed in *S. cerevisiae* to examine the intracellular conditions required for galactosylation. Correlation between protein galactosylation and UDP-galactose transport activity indicated that an exogenous supply of UDP-Gal transporter, rather than alpha 1,2 GalT played a key role for efficient galactosylation in *S. cerevisiae* (Kainuma (1999) *Glycobiology* 9(2):133-141). Likewise, an UDP-galactose transporter from *S. pombe* was cloned (Segawa (1999) *FEBS Letters* 451 (3):295-298).

CMP-N-Acetylneuraminic Acid (CMP-Sialic Acid)

Human CMP-sialic acid transporter (hCST) has been cloned and expressed in Lec 8 CHO cells (Aoki et al. (1999) *J. Biochem.* (Tokyo) 126(5):940-50; Eckhardt et al. (1997) *Eur. J Biochem.* 248(1):187-92). The functional expression of the murine CMP-sialic acid transporter was achieved in *Saccharomyces cerevisiae* (Berninsone et al. (1997) *J. Biol. Chem.* 272(19):12616-9). Sialic acid has been found in some fungi, however it is not clear whether the chosen host system will be able to supply sufficient levels of CMP-Sialic acid. Sialic acid can be either supplied in the medium or alternatively fungal pathways involved in sialic acid synthesis can also be integrated into the host genome.

Expression of Diphosphatases:

When sugars are transferred onto a glycoprotein, either a nucleoside diphosphate or monophosphate is released from the sugar nucleotide precursors. While monophosphates can be directly exported in exchange for nucleoside triphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction appears to be important for efficient glycosylation, as GDPase from S. cerevisiae has been found to be necessary for mannosylation. However, the enzyme only has 10% of the activity towards UDP (Berninsone et al. (1994) J. Biol. Chem. 269(1):207-211). Lower eukaryotes often do not have UDP-specific diphosphatase activity in the Golgi as they do not utilize UDP-sugar precursors for glycoprotein synthesis in the Golgi. Schizosaccharomyces pombe, a yeast which adds galactose residues to cell wall polysaccharides (from UDP-galactose), was found to have specific UDPase activity, further suggesting the requirement for such an enzyme (Berninsone et al. (1994) J. Biol. Chem. 269(1):207-211). UDP is known to be a potent inhibitor of glycosyltransferases and the removal of this glycosylation side product is important to prevent glycosyltransferase inhibition in the lumen of the Golgi (Khatara et al. (1974) Eur. J. Biochem. 44:537-560).

Methods for Altering N-Glycans in a Host by Expressing a Targeted Enzymatic Activity from a Nucleic Acid Molecule The present invention further provides a method for producing a human-like glycoprotein in a non-human host cell comprising the step of introducing into the cell one or more nucleic acid molecules which encode an enzyme or enzymes for production of the $Man_5GlcNAc_2$ carbohydrate structure. In one preferred embodiment, a nucleic acid molecule encoding one or more mannosidase activities involved in the production of $Man_5GlcNAc_2$ from $Man_8GlcNAc_2$ or $Man_9GlcNAc_2$ is introduced into the host. The invention additionally relates to methods for making altered glycoproteins in a host cell comprising the step of introducing into the host cell a nucleic acid molecule which encodes one or more glycosylation enzymes or activities. Preferred enzyme activities are selected from the group consisting of UDP-GlcNAc transferase, UDP-galactosyltransferase, GDP-fucosyltransferase, CMP-sialyltransferase, UDP-GlcNAc transporter, UDP-galactose transporter, GDP-fucose transporter, CMP-sialic acid transporter, and nucleotide diphosphatases. In a particularly preferred embodiment, the host is selected or engineered to express two or more enzymatic activities in which the product of one activity increases substrate levels of another activity, e.g., a glycosyltransferase and a corresponding sugar transporter, e.g., GnTI and UDP-GlcNAc transporter activities. In another preferred embodiment, the host is selected or engineered to expresses an activity to remove products which may inhibit subsequent glycosylation reactions, e.g. a UDP- or GDP-specific diphosphatase activity.

Preferred methods of the invention involve expressing one or more enzymatic activities from a nucleic acid molecule in a host cell and comprise the step of targeting at least one enzymatic activity to a desired subcellular location (e.g., an organelle) by forming a fusion protein comprising a catalytic domain of the enzyme and a cellular targeting signal peptide, e.g., a heterologous signal peptide which is not normally ligated to or associated with the catalytic domain. The fusion protein is encoded by at least one genetic construct ("fusion construct") comprising a nucleic acid fragment encoding a cellular targeting signal peptide ligated in the same translational reading frame ("in-frame") to a nucleic acid fragment encoding an enzyme (e.g., glycosylation enzyme), or catalytically active fragment thereof.

The targeting signal peptide component of the fusion construct or protein is preferably derived from a member of the group consisting of: membrane-bound proteins of the ER or Golgi, retrieval signals, Type II membrane proteins, Type I membrane proteins, membrane spanning nucleotide sugar transporters, mannosidases, sialyltransferases, glucosidases, mannosyltransferases and phosphomannosyltransferases.

The catalytic domain component of the fusion construct or protein is preferably derived from a glycosidase, mannosidase or a glycosyltransferase activity derived from a member of the group consisting of GnTI, GnTII, GnTIII, GnTIV, GnTV, GnTVI, GalT, Fucosyltransferase and Sialyltransferase. The catalytic domain preferably has a pH optimum within 1.4 pH units of the average pH optimum of other representative enzymes in the organelle in which the enzyme is localized, or has optimal activity at a pH between 5.1 and 8.0. In a preferred embodiment, the catalytic domain encodes a mannosidase selected from the group consisting of C. elegans mannosidase IA, C. elegans mannosidase IB, D. melanogaster mannosidase IA, H. sapiens mannosidase IB, P. citrinum mannosidase I, mouse mannosidase IA, mouse mannosidase IB, A. nidulans mannosidase IA, A. nidulans mannosidase IB, A. nidulans mannosidase IC, mouse mannosidase II, C. elegans mannosidase II, H. sapiens mannosidase II, mannosidase IIx, and mannosidase III.

Selecting a Glycosylation Enzyme: pH Optima and Subcellular Localization

In one embodiment of the invention, a human-like glycoprotein is made efficiently in a non-human eukaryotic host cell by introducing into a subcellular compartment of the cell a glycosylation enzyme selected to have a pH optimum similar to the pH optima of other enzymes in the targeted subcellular compartment. For example, most enzymes that are active in the ER and Golgi apparatus of S. cerevisiae have pH optima that are between about 6.5 and 7.5 (see Table 3). Because the glycosylation of proteins is a highly evolved and efficient process, the internal pH of the ER and the Golgi is likely also in the range of about 6-8. All previous approaches to reduce mannosylation by the action of recombinant mannosidases in fungal hosts, however, have introduced enzymes that have a pH optimum of around pH 5.0 (Martinet et al. (1998) Biotech. Letters 20(12): 1171-1177, and Chiba et al. (1998) J. Biol. Chem. 273(41): 26298-26304). At pH 7.0, the in vitro determined activity of those mannosidases is reduced to less than 10%, which is likely insufficient activity at their point of use, namely, the ER and early Golgi, for the efficient in vivo production of $Man_5GlcNAc_2$ on N-glycans.

Accordingly, a preferred embodiment of this invention targets a selected glycosylation enzyme (or catalytic domain thereof), e.g., an α-mannosidase, to a subcellular location in the host cell (e.g., an organelle) where the pH optimum of the enzyme or domain is within 1.4 pH units of the average pH optimum of other representative marker enzymes localized in the same organelle(s). The pH optimum of the enzyme to be targeted to a specific organelle should be matched with the pH optimum of other enzymes found in the same organelle to maximize the activity per unit enzyme obtained. Table 3 summarizes the activity of mannosidases from various sources and their respective pH optima. Table 4 summarizes their typical subcellular locations.

TABLE 3

Mannosidases and their pH optimum.

| Source | Enzyme | pH optimum | Reference |
|---|---|---|---|
| *Aspergillus saitoi* | α-1,2-mannosidase | 5.0 | Ichishima et al. (1999) Biochem. J. 339(Pt 3): 589-597 |
| *Trichoderma reesei* | α-1,2-mannosidase | 5.0 | Maras et al. (2000) J. Biotechnol. 77(2-3): 255-263 |
| *Penicillium citrinum* | α-D-1,2-mannosidase | 5.0 | Yoshida et al. (1993) Biochem. J. 290(Pt 2): 349-354 |
| *C. elegans* | α-1,2-mannosidase | 5.5 | see FIG. 11 |
| *Aspergillus nidulans* | α-1,2-mannosidase | 6.0 | Eades and Hintz (2000) Gene 255(1): 25-34 |
| *Homo sapiens* IA(Golgi) | α-1,2-mannosidase | 6.0 | |
| *Homo sapiens* IB (Golgi) | α-1,2-mannosidase | 6.0 | |
| *Lepidopteran* insect cells | Type I α-1,2-Man$_6$-mannosidase | 6.0 | Ren et al. (1995) Biochem. 34(8): 2489-2495 |
| *Homo sapiens* | α-D-mannosidase | 6.0 | Chandrasekaran et al. (1984) Cancer Res. 44(9): 4059-68 |
| *Xanthomonas manihotis* | α-1,2,3-mannosidase | 6.0 | U.S. Pat. No. 6,300,113 |
| Mouse IB (Golgi) | α-1,2-mannosidase | 6.5 | Schneikert and Herscovics (1994) Glycobiology. 4(4): 445-50 |
| *Bacillus* sp. (secreted) | α-D-1,2-mannosidase | 7.0 | Maruyama et al. (1994) Carbohydrate Res. 251: 89-98 |

In a preferred embodiment, a particular enzyme or catalytic domain is targeted to a subcellular location in the host cell by means of a chimeric fusion construct encoding a protein comprising a cellular targeting signal peptide not normally associated with the enzymatic domain. Preferably, an enzyme or domain is targeted to the ER, the early, medial or late Golgi, or the trans Golgi apparatus of the host cell.

In a more preferred embodiment, the targeted glycosylation enzyme is a mannosidase, glycosyltransferase or a glycosidase. In an especially preferred embodiment, mannosidase activity is targeted to the ER or cis Golgi, where the early reactions of glycosylation occur. While this method is useful for producing a human-like glycoprotein in a non-human host cell, it will be appreciated that the method is also useful more generally for modifying carbohydrate profiles of a glycoprotein in any eukaryotic host cell, including human host cells.

Targeting sequences which mediate retention of proteins in certain organelles of the host cell secretory pathway are well-known and described in the scientific literature and public databases, as discussed in more detail below with respect to libraries for selection of targeting sequences and targeted enzymes. Such subcellular targeting sequences may be used alone or in combination to target a selected glycosylation enzyme (or catalytic domain thereof) to a particular subcellular location in a host cell, i.e., especially to one where the enzyme will have enhanced or optimal activity based on pH optima or the presence of other stimulatory factors.

When one attempts to trim high mannose structures to yield Man$_5$GlcNAc$_2$ in the ER or the Golgi apparatus of a host cell such as *S. cerevisiae*, for example, one may choose any enzyme or combination of enzymes that (1) has a sufficiently close pH optimum (i.e., between pH 5.2 and pH 7.8), and (2) is known to generate, alone or in concert, the specific isomeric Man$_5$GlcNAc$_2$ structure required to accept subsequent addition of GlcNAc by GnTI. Any enzyme or combination of enzymes that is shown to generate a structure that can be converted to GlcNAcMan$_5$GlcNAc$_2$ by GnTI in vitro would constitute an appropriate choice. This knowledge may be obtained from the scientific literature or experimentally. For example, one may determine whether a potential mannosidase can convert Man$_8$GlcNAc$_2$-2AB (2-aminobenzamide) to Man$_5$GlcNAc$_2$-AB and then verify that the obtained Man$_5$GlcNAc$_2$-2AB structure can serve a substrate for GnTI and UDP-GlcNAc to give GlcNAcMan$_5$GlcNAc$_2$ in vitro. Mannosidase IA from a human or murine source, for example, would be an appropriate choice (see, e.g., Example 4). Examples described herein utilize 2-aminobenzamide labeled N-linked oligomannose followed by HPLC analysis to make this determination.

TABLE 4

Cellular location and pH optima of various glycosylation-related enzymes of *S. cerevisiae*.

| Gene | Activity | Location | pH optimum | Reference(s) |
|---|---|---|---|---|
| KTR1 | α-1,2 mannosyltransferase | Golgi | 7.0 | Romero et al. (1997) Biochem. J. 321(Pt 2): 289-295 |
| MNS1 | α-1,2-mannosidase | ER | 6.5 | Lipari et al. (1994) Glycobiology. Oct; 4(5): 697-702 |
| CWH41 | glucosidase I | ER | 6.8 | |
| — | mannosyltransferase | Golgi | 7-8 | Lehele and Tanner (1974) Biochim. Biophys. Acta 350(1): 225-235 |
| KRE2 | α-1,2 mannosyltransferase | Golgi | 6.5-9.0 | Romero et al. (1997) Biochem. J. 321(Pt 2): 289-295 |

Accordingly, a glycosylation enzyme such as an α-1,2-mannosidase enzyme used according to the invention has an optimal activity at a pH of between 5.1 and 8.0. In a preferred embodiment, the enzyme has an optimal activity at a pH of between 5.5 and 7.5. The *C. elegans* mannosidase enzyme, for example, works well in the methods of the invention and has an apparent pH optimum of about 5.5). Preferred mannosidases include those listed in Table 3 having appropriate pH optima, e.g. *Aspergillus nidulans, Homo sapiens* IA (Golgi), *Homo sapiens* IB (Golgi), *Lepidopteran* insect cells (IPLB-SF21AE), *Homo sapiens*, mouse IB (Golgi), *Xanthomonas manihotis, Drosophila melanogaster* and *C. elegans*.

Figure 11:
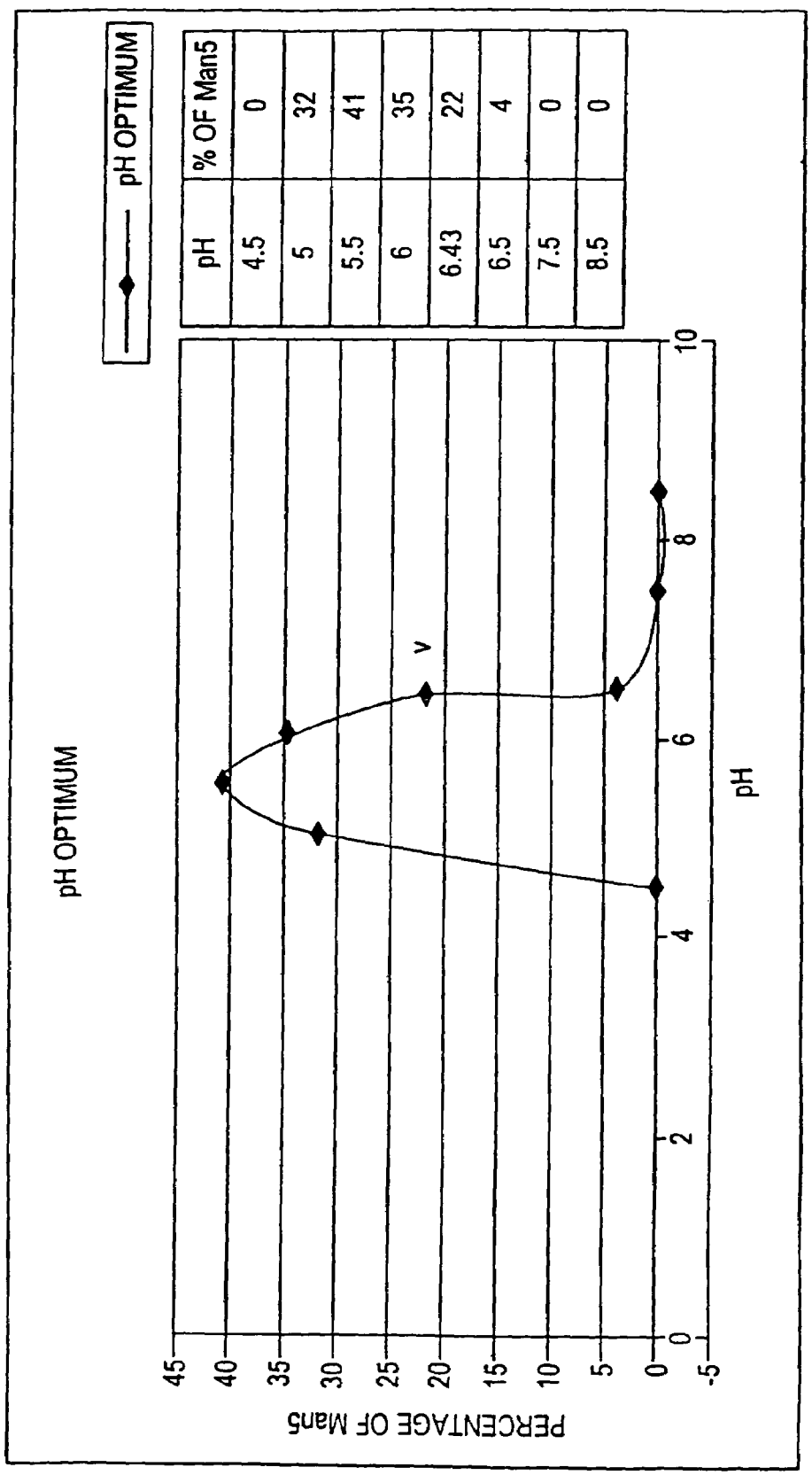
FIG. 11 shows a pH optimum of a heterologous mannosidase enzyme encoded by pBB27-2 (*Saccharomyces* MNN10(s)/*C. elegans* mannosidase IB Δ31) expressed in *P. pastoris*.

An experiment which illustrates the pH optimum for an α-1,2-mannosidase enzyme is described in Example 7. A chimeric fusion protein BB27-2 (*Saccharomyces* MNN10(s)/ *C. elegans* mannosidase IB Δ31), which leaks into the medium was subjected to various pH ranges to determine the optimal activity of the enzyme. The results of the experiment show that the α-1,2-mannosidase has an optimal pH of about 5.5 for its function (FIG. 11).

In a preferred embodiment, a single cloned mannosidase gene is expressed in the host organism. However, in some cases it may be desirable to express several different mannosidase genes, or several copies of one particular gene, in order to achieve adequate production of $Man_5GlcNAc_2$. In cases where multiple genes are used, the encoded mannosidases preferably all have pH optima within the preferred range of about 5.1 to about 8.0, or especially between about 5.5 and about 7.5. Preferred mannosidase activities include α-1,2-mannosidases derived from mouse, human, Lepidoptera, *Aspergillus nidulans*, or *Bacillus* sp., *C. elegans, D. melanogaster, P. citrinum, X. laevis* or *A. nidulans*.

In Vivo Alteration of Host Cell Glycosylation Using a Combinatorial DNA Library

Certain methods of the invention are preferably (but need not necessarily be) carried out using one or more nucleic acid libraries. An exemplary feature of a combinatorial nucleic acid library of the invention is that it comprises sequences encoding cellular targeting signal peptides and sequences encoding proteins to be targeted (e.g., enzymes or catalytic domains thereof, including but not limited to those which mediate glycosylation).

In one embodiment, a combinatorial nucleic acid library comprises: (a) at least two nucleic acid sequences encoding different cellular targeting signal peptides; and (b) at least one nucleic acid sequence encoding a polypeptide to be targeted. In another embodiment, a combinatorial nucleic acid library comprises: (a) at least one nucleic acid sequence encoding a cellular targeting signal peptide; and (b) at least two nucleic acid sequences encoding a polypeptide to be targeted into a host cell. As described further below, a nucleic acid sequence derived from (a) and a nucleic acid sequence derived from (b) are ligated to produce one or more fusion constructs encoding a cellular targeting signal peptide functionally linked to a polypeptide domain of interest. One example of a functional linkage is when the cellular targeting signal peptide is ligated to the polypeptide domain of interest in the same translational reading frame ("in-frame").

In a preferred embodiment, a combinatorial DNA library expresses one or more fusion proteins comprising cellular targeting signal peptides ligated in-frame to catalytic enzyme domains. The encoded fusion protein preferably comprises a catalytic domain of an enzyme involved in mammalian- or human-like modification of N-glycans. In a more preferred embodiment, the catalytic domain is derived from an enzyme selected from the group consisting of mannosidases, glycosyltransferases and other glycosidases which is ligated in-frame to one or more targeting signal peptides. The enzyme domain may be exogenous and/or endogenous to the host cell. A particularly preferred signal peptide is one normally associated with a protein that undergoes ER to Golgi transport.

The combinatorial DNA library of the present invention may be used for producing and localizing in vivo enzymes involved in mammalian- or human-like N-glycan modification. The fusion constructs of the combinatorial DNA library are engineered so that the encoded enzymes are localized in the ER, Golgi or the trans-Golgi network of the host cell where they are involved in producing particular N-glycans on a glycoprotein of interest. Localization of N-glycan modifying enzymes of the present invention is achieved through an anchoring mechanism or through protein-protein interaction where the localization peptide constructed from the combinatorial DNA library localizes to a desired organelle of the secretory pathway such as the ER, Golgi or the trans Golgi network.

An example of a useful N-glycan, which is produced efficiently and in sufficient quantities for further modification by human-like (complex) glycosylation reactions is $Man_5GlcNAc_2$. A sufficient amount of $Man_5GlcNAc_2$ is needed on a glycoprotein of interest for further human-like processing in vivo (e.g., more than 30 mole %). The $Man_5GlcNAc_2$ intermediate may be used as a substrate for further N-glycan modification to produce $GlcNAcMan_5GlcNAc_2$ (FIG. 1B; see above). Accordingly, the combinatorial DNA library of the present invention may be used to produce enzymes that subsequently produce $GlcNAcMan_5GlcNAc_2$, or other desired complex N-glycans, in a useful quantity.

A further aspect of the fusion constructs produced using the combinatorial DNA library of the present invention is that they enable sufficient and often near complete intracellular N-glycan trimming activity in the engineered host cell. Preferred fusion constructs produced by the combinatorial DNA library of the invention encode a glycosylation enzyme, e.g., a mannosidase, which is effectively localized to an intracellular host cell compartment and thereby exhibits very little and preferably no extracellular activity. The preferred fusion constructs of the present invention that encode a mannosidase enzyme are shown to localize where the N-glycans are modified, namely, the ER and the Golgi. The fusion enzymes of the present invention are targeted to such particular organelles in the secretory pathway where they localize and act upon N-glycans such as $Man_8GlcNAc_2$ to produce $Man_5GlcNAc_2$ on a glycoprotein of interest.

Figure 33:
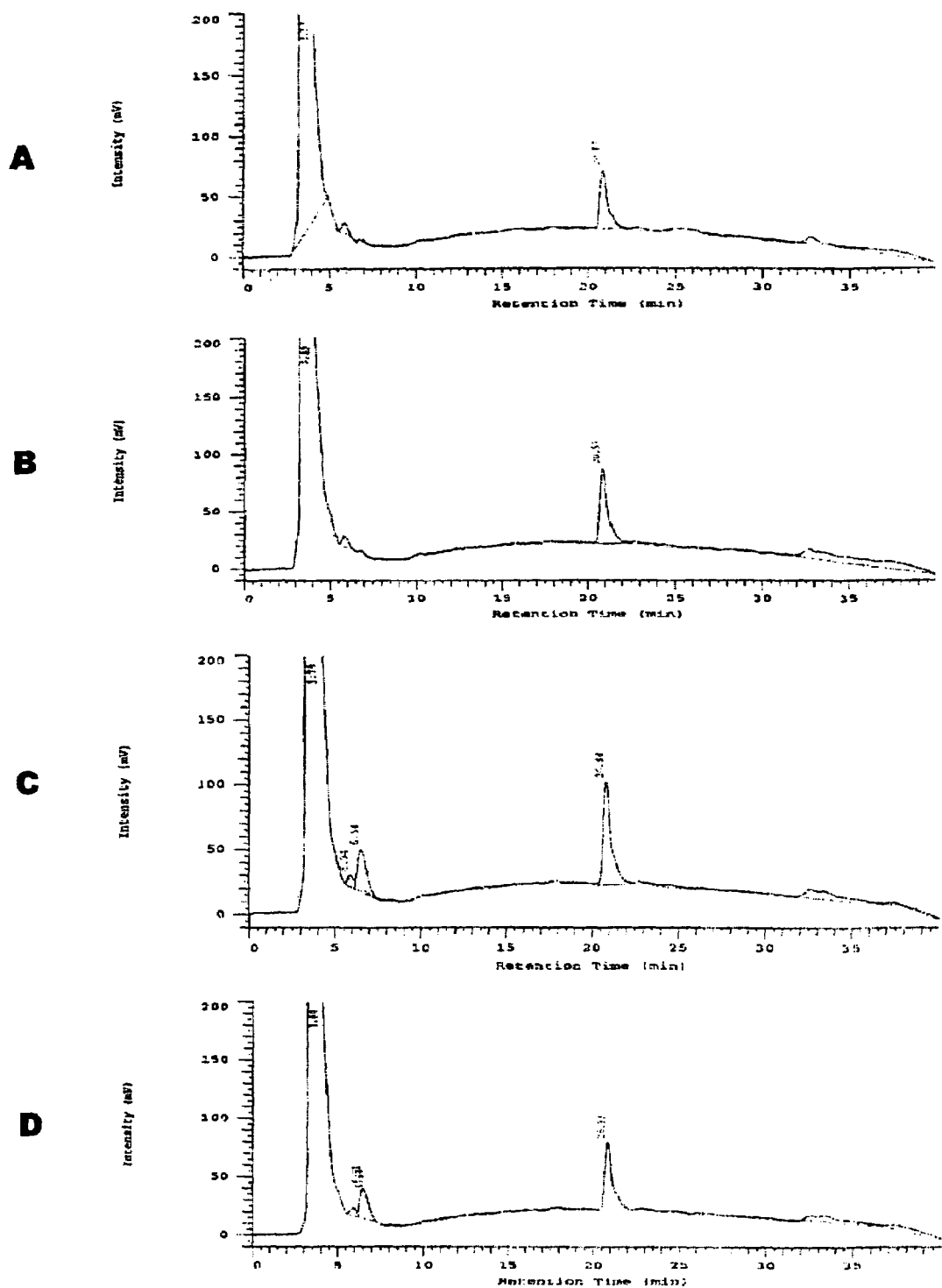
FIG. 33 shows a high performance liquid chromatogram, which demonstrates a lack of extracellular GnTIII activity (pVA53) in the supernatant. The N-glycan $GlcNAcMan_5GlcNAc_2$ purified from K3 expressed in PBP-3 strain was added to: BMMY (A); 1 mM UDP-GlcNAc (Sigma Chemical Co., St. Louis, Mo.)) in BMMY (B); the supernatant of YSH-44 transformed with pVA53 [YSH-57] (C); and the supernatant of YSH-57+1 mM UDP-GlcNAc (D).
Figure 34:
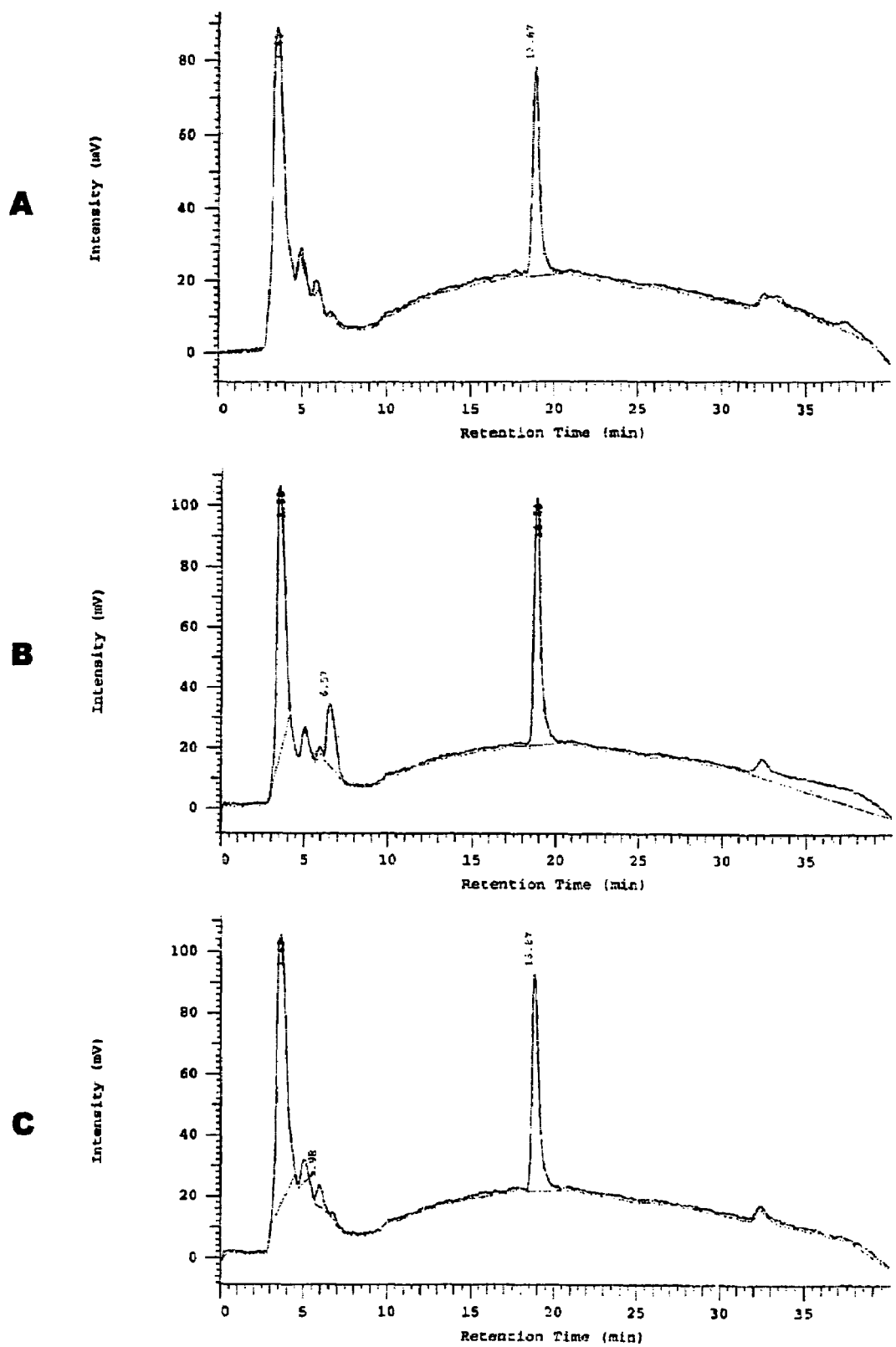
FIG. 34 shows a high performance liquid chromatogram, which demonstrates a lack of extracellular GnTIII activity (pVA53) in the supernatant. The N-glycan $GlcNAc_2Man_3GlcNAc_2$ purified from K3 expressed in YSH-44 strain was added to: BMMY (A); 1 mM UDP-GlcNAc (Sigma Chemical Co., St. Louis, Mo.)) in BMMY (B); and the supernatant of YSH-44 transformed with pVA53 [YSH-57] (C).

GnTIII fusion constructs generated from a combinatorial DNA library to produce bisected glycans were assayed to determine any extracellular activity: An example of a GnTIII fusion constructs exhibiting in vivo alteration of host cell glycosylation is designated pVA53. After transforming *P. pastoris* YSH-1 with the fusion construct pVA53, the supernatant was tested to detect any ex vivo GnTIII activity. FIG. 33 shows no apparent change in the standard substrate $GlcNAcMan_5GlcNAc_2$ under conditions that would reveal extracellular GnTIII activity in the medium (Example 22). Similarly, FIG. 34 shows no detectable extracellular GnTIII activity in the medium in *P. pastoris* YSH-57 reacting with the substrate $GlcNAc_2Man_3GlcNAc_2$ (Example 23).

Enzymes produced by the combinatorial DNA library of the present invention can modify N-glycans on a glycoprotein of interest as shown for K3 or IFN-β proteins expressed in *P. pastoris*, as shown in FIGS. 5, 6, and 25-34 (see also Examples 2, 4, and 18-23). It is, however, appreciated that other types of glycoproteins, without limitation, including erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II, and α-feto proteins may be glycosylated in this way.

Constructing a Combinatorial DNA Library of Fusion Constructs:

A combinatorial DNA library of fusion constructs features one or more cellular targeting signal peptides ("targeting peptides") generally derived from N-terminal domains of native proteins (e.g., by making C-terminal deletions). Some targeting peptides, however, are derived from the C-terminus of native proteins (e.g. SEC12). Membrane-bound proteins of the ER or the Golgi are preferably used as a source for targeting peptide sequences. These proteins have sequences encoding a cytosolic tail (ct), a transmembrane domain (tmd) and a stem region (sr) which are varied in length. These regions are recognizable by protein sequence alignments and comparisons with known homologs and/or other localized proteins (e.g., comparing hydrophobicity plots).

The targeting peptides are indicated herein as short (s), medium (m) and long (l) relative to the parts of a type II membrane. The targeting peptide sequence indicated as short (s) corresponds to the transmembrane domain (tmd) of the membrane-bound protein. The targeting peptide sequence indicated as long (l) corresponds to the length of the transmembrane domain (tmd) and the stem region (sr). The targeting peptide sequence indicated as medium (m) corresponds to the transmembrane domain (tmd) and approximately half the length of the stem region (sr). The catalytic domain regions are indicated herein by the number of nucleotide deletion with respect to its wild-type glycosylation enzyme.

Sub-Libraries

In some cases a combinatorial nucleic acid library of the invention may be assembled directly from existing or wild-type genes. In a preferred embodiment, the DNA library is assembled from the fusion of two or more sub-libraries. By the in-frame ligation of the sub-libraries, it is possible to create a large number of novel genetic constructs encoding useful targeted protein domains such as those which have glycosylation activities.

Catalytic Domain Sub-Libraries Encoding Glycosylation Activities

One useful sub-library includes DNA sequences encoding enzymes such as glycosidases (e.g., mannosidases), glycosyltransferases (e.g., fucosyl-transferases, galactosyltransferases, glucosyltransferases), GlcNAc transferases and sialyltransferases. Catalytic domains may be selected from the host to be engineered, as well as from other related or unrelated organisms. Mammalian, plant, insect, reptile, algal or fungal enzymes are all useful and should be chosen to represent a broad spectrum of biochemical properties with respect to temperature and pH optima. In a preferred embodiment, genes are truncated to give fragments some of which encode the catalytic domains of the enzymes. By removing endogenous targeting sequences, the enzymes may then be redirected and expressed in other cellular loci.

The choice of such catalytic domains may be guided by the knowledge of the particular environment in which the catalytic domain is subsequently to be active. For example, if a particular glycosylation enzyme is to be active in the late Golgi, and all known enzymes of the host organism in the late Golgi have a certain pH optimum, or the late Golgi is known to have a particular pH, then a catalytic domain is chosen which exhibits adequate, and preferably maximum, activity at that pH, as discussed above.

Targeting Peptide Sequence Sub-Libraries

Another useful sub-library includes nucleic acid sequences encoding targeting signal peptides that result in localization of a protein to a particular location within the ER, Golgi, or trans Golgi network. These targeting peptides may be selected from the host organism to be engineered as well as from other related or unrelated organisms. Generally such sequences fall into three categories: (1) N-terminal sequences encoding a cytosolic tail (ct), a transmembrane domain (tmd) and part or all of a stem region (sr), which together or individually anchor proteins to the inner (lumenal) membrane of the Golgi; (2) retrieval signals which are generally found at the C-terminus such as the HDEL (SEQ ID NO:41) or KDEL (SEQ ID NO:42) tetrapeptide; and (3) membrane spanning regions from various proteins, e.g., nucleotide sugar transporters, which are known to localize in the Golgi.

In the first case, where the targeting peptide consists of various elements (ct, tmd and sr), the library is designed such that the ct, the tmd and various parts of the stem region are represented. Accordingly, a preferred embodiment of the sub-library of targeting peptide sequences includes ct, tmd, and/or sr sequences from membrane-bound proteins of the ER or Golgi. In some cases it may be desirable to provide the sub-library with varying lengths of sr sequence. This may be accomplished by PCR using primers that bind to the 5' end of the DNA encoding the cytosolic region and employing a series of opposing primers that bind to various parts of the stem region.

Still other useful sources of targeting peptide sequences include retrieval signal peptides, e.g. the tetrapeptides HDEL or KDEL, which are typically found at the C-terminus of proteins that are transported retrograde into the ER or Golgi. Still other sources of targeting peptide sequences include (a) type II membrane proteins, (b) the enzymes listed in Table 3, (c) membrane spanning nucleotide sugar transporters that are localized in the Golgi, and (d) sequences referenced in Table 5.

TABLE 5

Sources of useful compartmental targeting sequences

| Gene or Sequence | Organism | Function | Location of Gene Product |
|---|---|---|---|
| MNSI | A. nidulans | α-1,2-mannosidase | ER |
| MNSI | A. niger | α-1,2-mannosidase | ER |
| MNSI | S. cerevisiae | α-1,2-mannosidase | ER |
| GLSI | S. cerevisiae | glucosidase | ER |
| GLSI | A. niger | glucosidase | ER |
| GLSI | A. nidulans | glucosidase | ER |
| HDEL at C-terminus | Universal in fungi | retrieval signal | ER |
| SEC12 | S. cerevisiae | COPII vesicle protein | ER/Golgi |
| SEC12 | A. niger | COPII vesicle protein | ER/Golgi |
| OCH1 | S. cerevisiae | 1,6-mannosyltransferase | Golgi (cis) |
| OCH1 | P. pastoris | 1,6-mannosyltransferase | Golgi (cis) |
| MNN9 | S. cerevisiae | 1,6-mannosyltransferase complex | Golgi |
| MNN9 | A. niger | undetermined | Golgi |
| VAN1 | S. cerevisiae | undetermined | Golgi |
| VAN1 | A. niger | undetermined | Golgi |
| ANP1 | S. cerevisiae | undetermined | Golgi |

TABLE 5-continued

Sources of useful compartmental targeting sequences

| Gene or Sequence | Organism | Function | Location of Gene Product |
|---|---|---|---|
| HOC1 | S. cerevisiae | undetermined | Golgi |
| MNN10 | S. cerevisiae | undetermined | Golgi |
| MNN10 | A. niger | undetermined | Golgi |
| MNN11 | S. cerevisiae | undetermined | Golgi (cis) |
| MNN11 | A. niger | undetermined | Golgi (cis) |
| MNT1 | S. cerevisiae | 1,2-mannosyltransferase | Golgi (cis, medial) |
| KTR1 | P. pastoris | undetermined | Golgi (medial) |
| KRE2 | P. pastoris | undetermined | Golgi (medial) |
| KTR3 | P. pastoris | undetermined | Golgi (medial) |
| MNN2 | S. cerevisiae | 1,2-mannosyltransferase | Golgi (medial) |
| KTR1 | S. cerevisiae | undetermined | Golgi (medial) |
| KTR2 | S. cerevisiae | undetermined | Golgi (medial) |
| MNN1 | S. cerevisiae | 1,3-mannosyltransferase | Golgi (trans) |
| MNN6 | S. cerevisiae | Phosphomannosyltransferase | Golgi (trans) |
| 2,6 ST | H. sapiens | 2,6-sialyltransferase | trans Golgi network |
| UDP-Gal T | S. pombe | UDP-Gal transporter | Golgi |

In any case, it is highly preferred that targeting peptide sequences are selected which are appropriate for the particular enzymatic activity or activities to function optimally within the sequence of desired glycosylation reactions. For example, in developing a modified microorganism capable of terminal sialylation of nascent N-glycans, a process which occurs in the late Golgi in humans, it is desirable to utilize a sub-library of targeting peptide sequences derived from late Golgi proteins. Similarly, the trimming of Man$_8$GlcNAc$_2$ by an α-1,2-mannosidase to give Man$_5$GlcNAc$_2$ is an early step in complex N-glycan formation in humans (FIG. 1B). It is therefore desirable to have this reaction occur in the ER or early Golgi of an engineered host microorganism. A sub-library encoding ER and early Golgi retention signals is used.

A series of fusion protein constructs (i.e., a combinatorial DNA library) is then constructed by functionally linking one or a series of targeting peptide sequences to one or a series of sequences encoding catalytic domains. In a preferred embodiment, this is accomplished by the in-frame ligation of a sub-library comprising DNA encoding targeting peptide sequences (above) with a sub-library comprising DNA encoding glycosylation enzymes or catalytically active fragments thereof (see below).

The resulting library comprises synthetic genes encoding targeting peptide sequence-containing fusion proteins. In some cases it is desirable to provide a targeting peptide sequence at the N-terminus of a fusion protein, or in other cases at the C-terminus. In some cases, targeting peptide sequences may be inserted within the open reading frame of an enzyme, provided the protein structure of individual folded domains is not disrupted. Each type of fusion protein is constructed (in a step-wise directed or semi-random fashion) and optimal constructs may be selected upon transformation of host cells and characterization of glycosylation patterns in transformed cells using methods of the invention.

Figure 2:
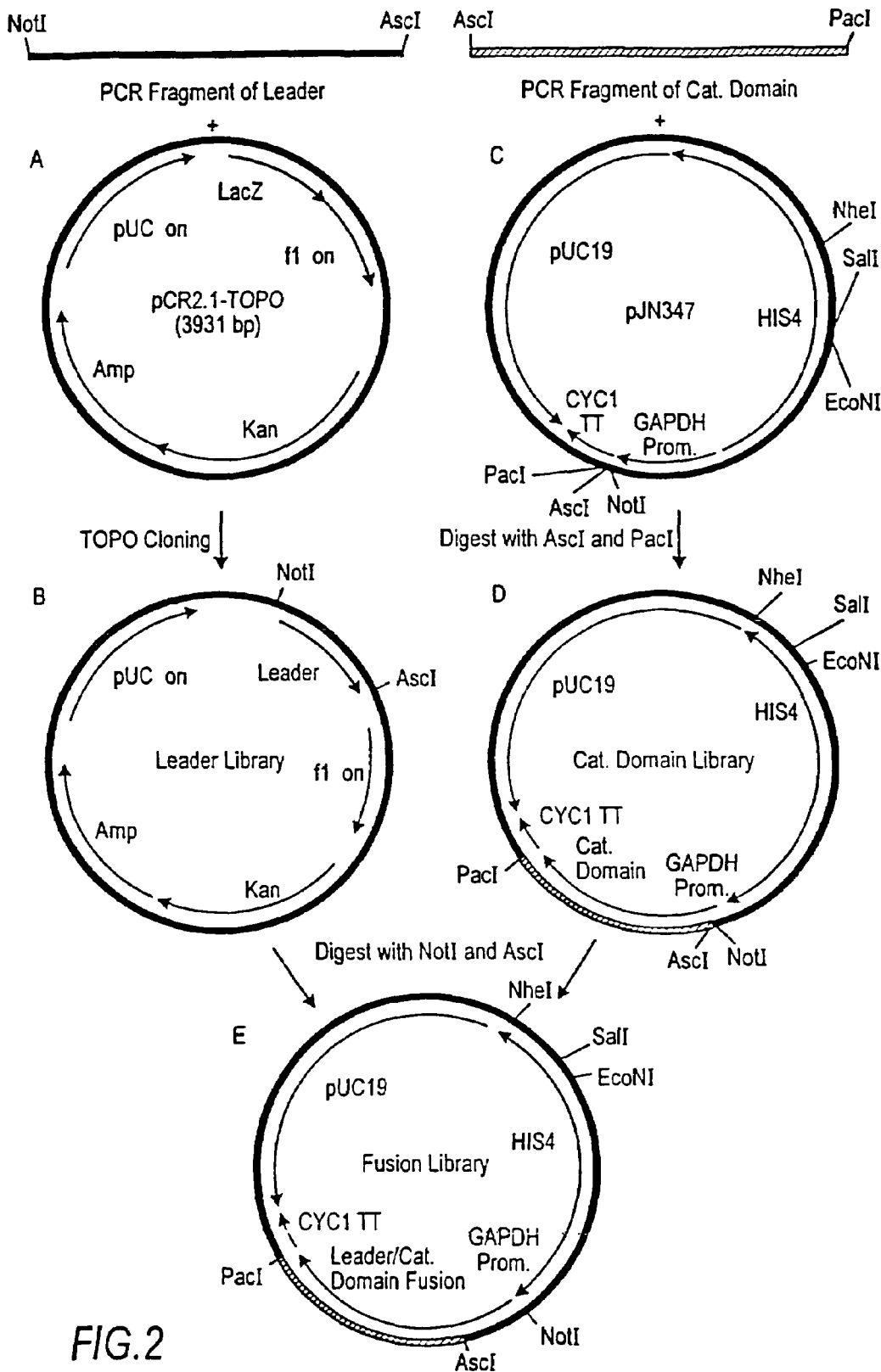
FIG. 2 depicts construction of a combinatorial DNA library of fusion constructs.

Alteration of Host Cell Glycosylation Using Fusion Constructs From Combinatorial Libraries:

The construction of a preferred combinatorial DNA library is illustrated schematically in FIG. 2 and described in Example 4. The fusion construct may be operably linked to a multitude of vectors, such as expression vectors well-known in the art. A wide variety of such fusion constructs were assembled using representative activities as shown in Table 6.

Combinations of targeting peptide/catalytic domains may be assembled for use in targeting mannosidase, glycosyltransferase and glycosidase activities in the ER, Golgi, and the trans Golgi network according to the invention. Surprisingly, the same catalytic domain may have no effect to a very profound effect on N-glycosylation patterns, depending on the type of targeting peptide used (see, e.g., Table 7, Example 4).

Mannosidase Fusion Constructs

Figure 6:
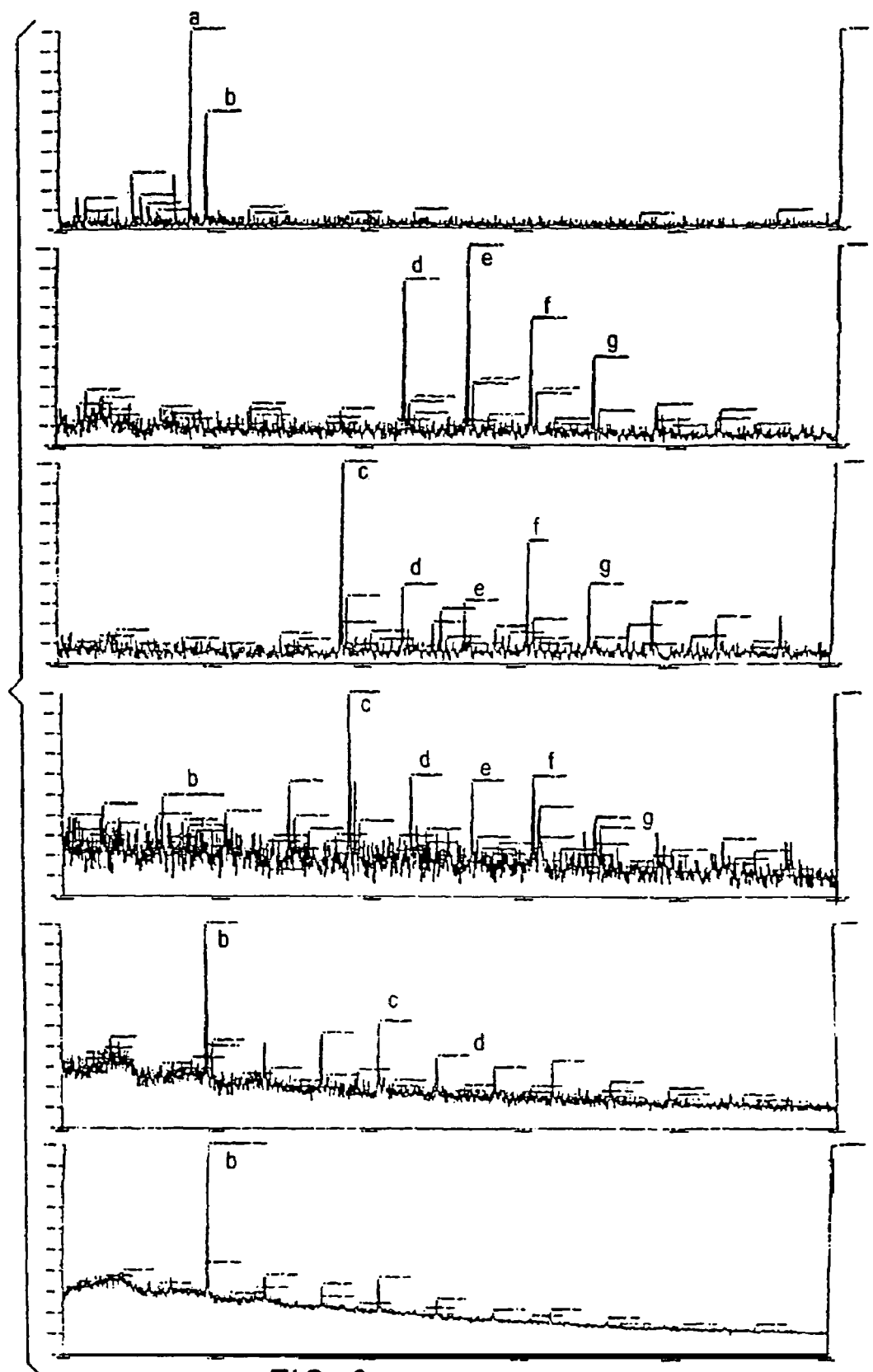
FIGS. 6A-6F show MALDI-TOF analysis demonstrating production of IFN-β glycoproteins having Man$_5$GlcNAc$_2$ as the predominant N-glycan structure in *P. pastoris*.
Figure 6A:
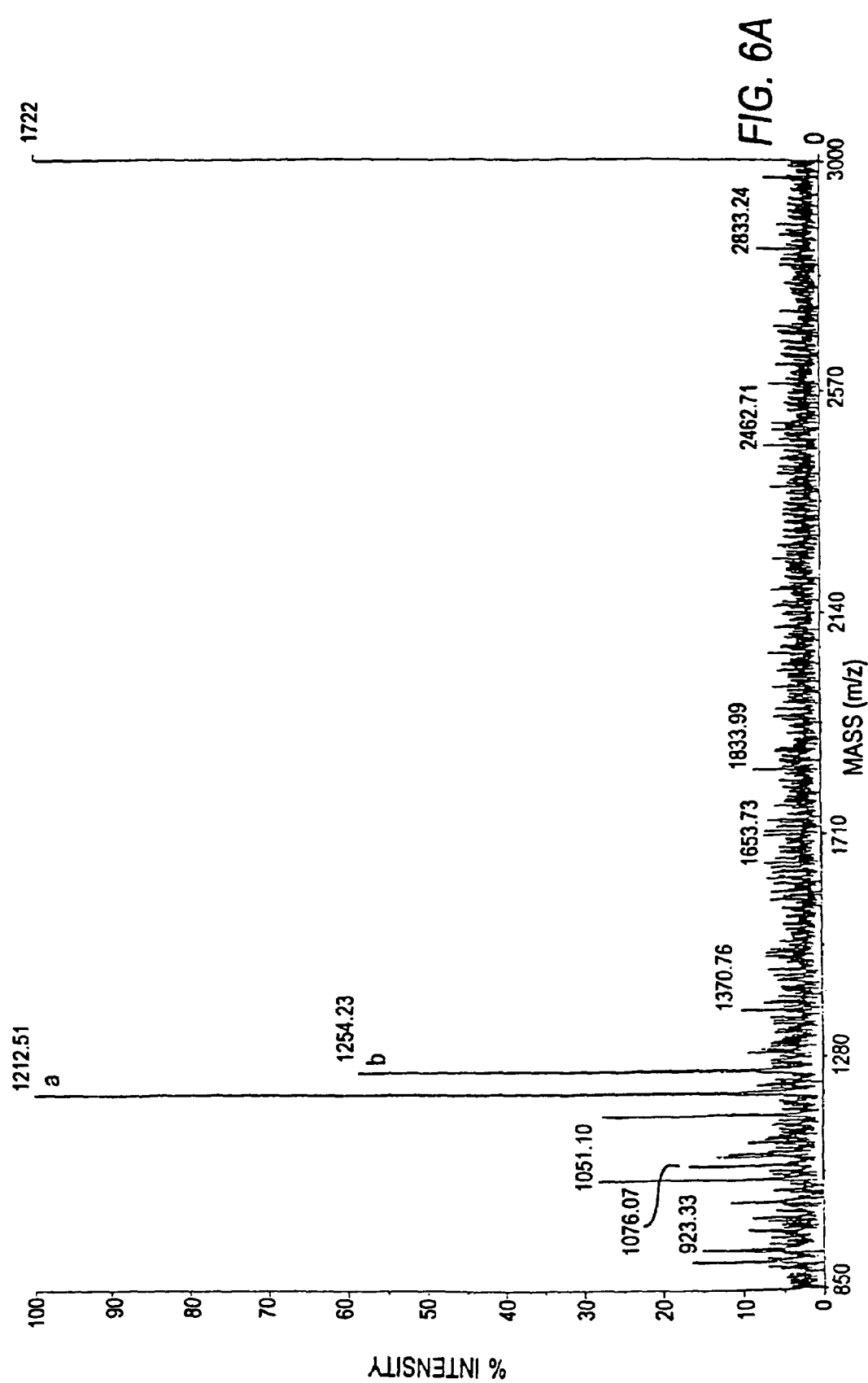
Figure 6B:
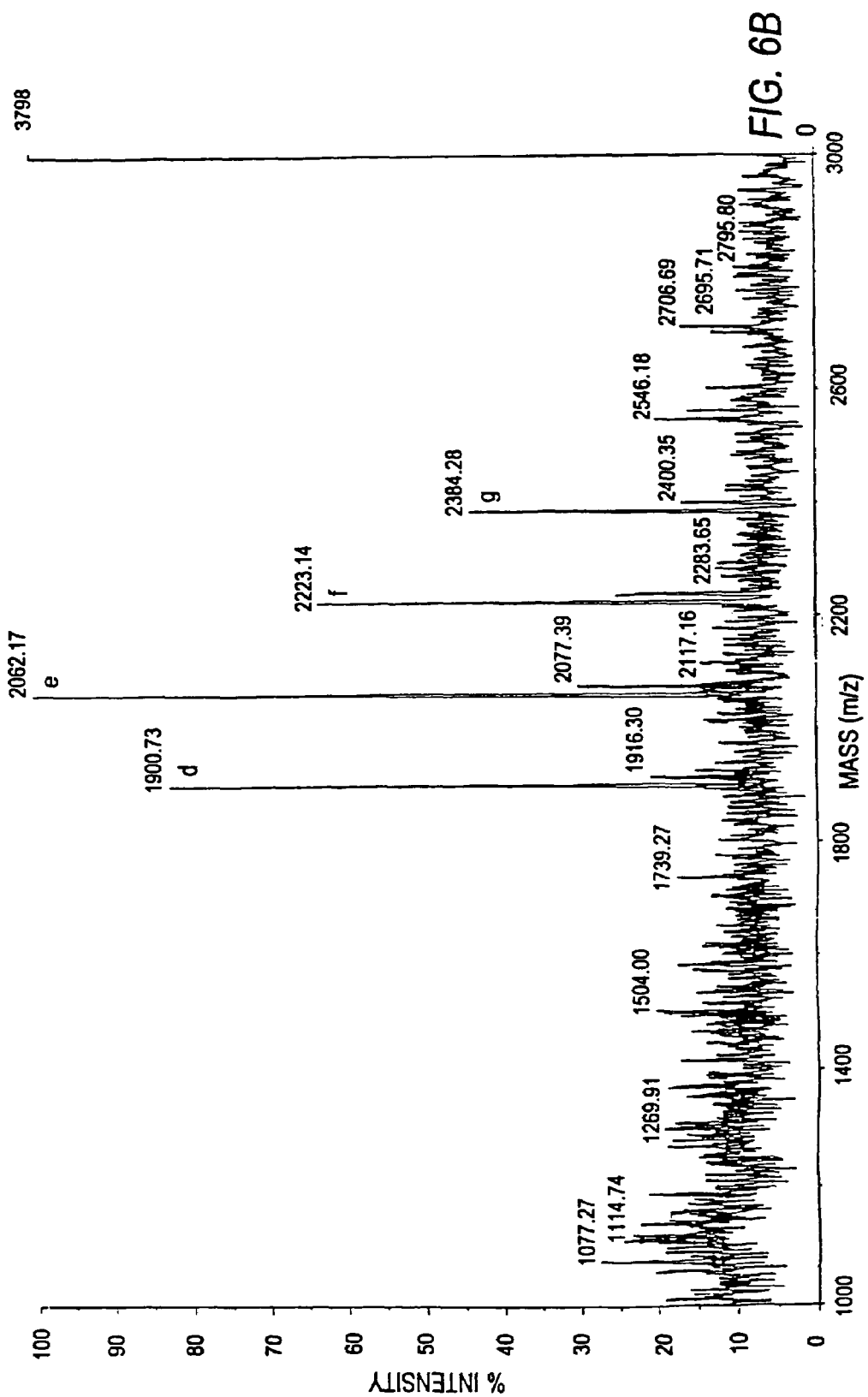
Figure 6C:
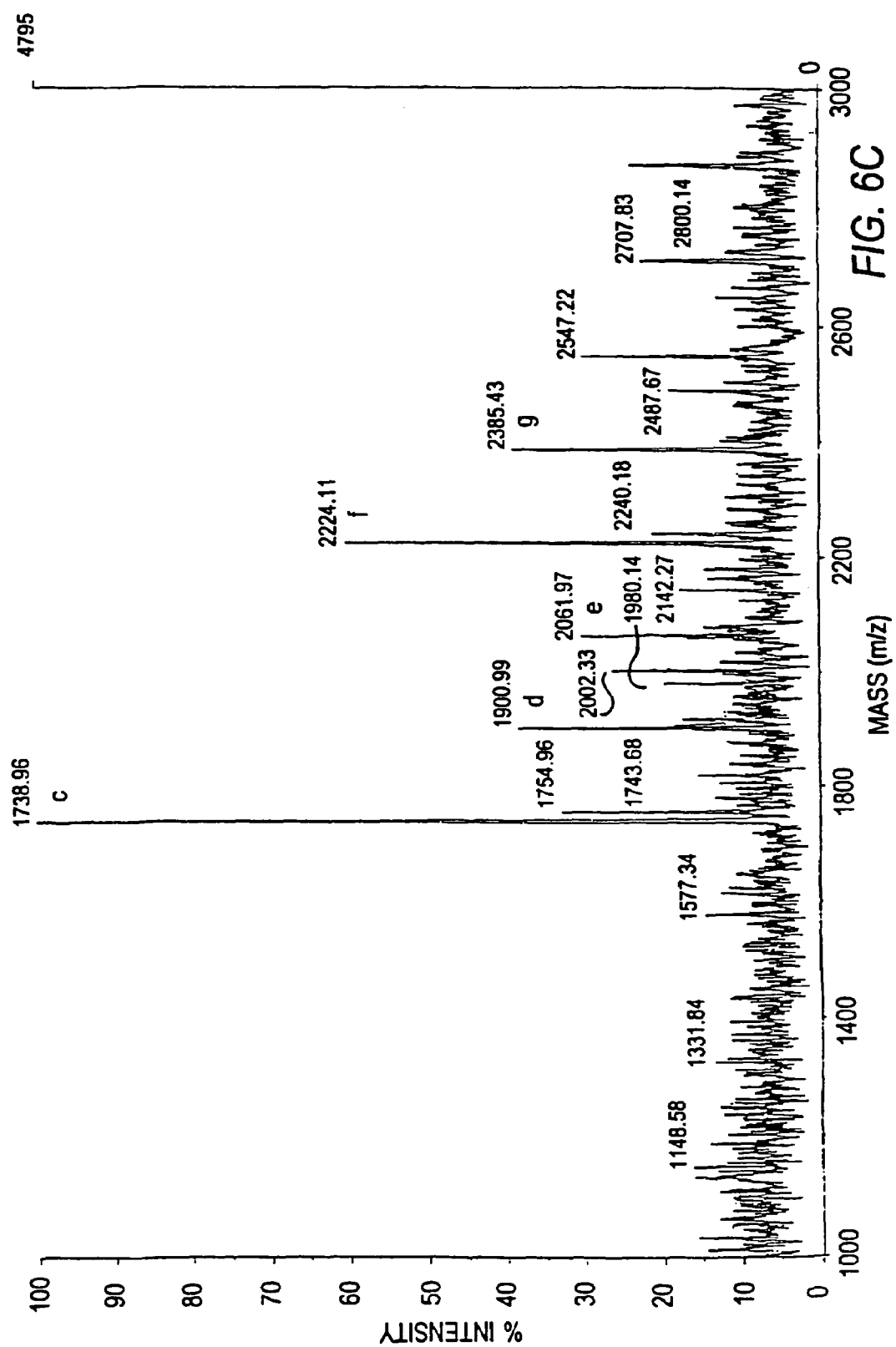
Figure 6D:
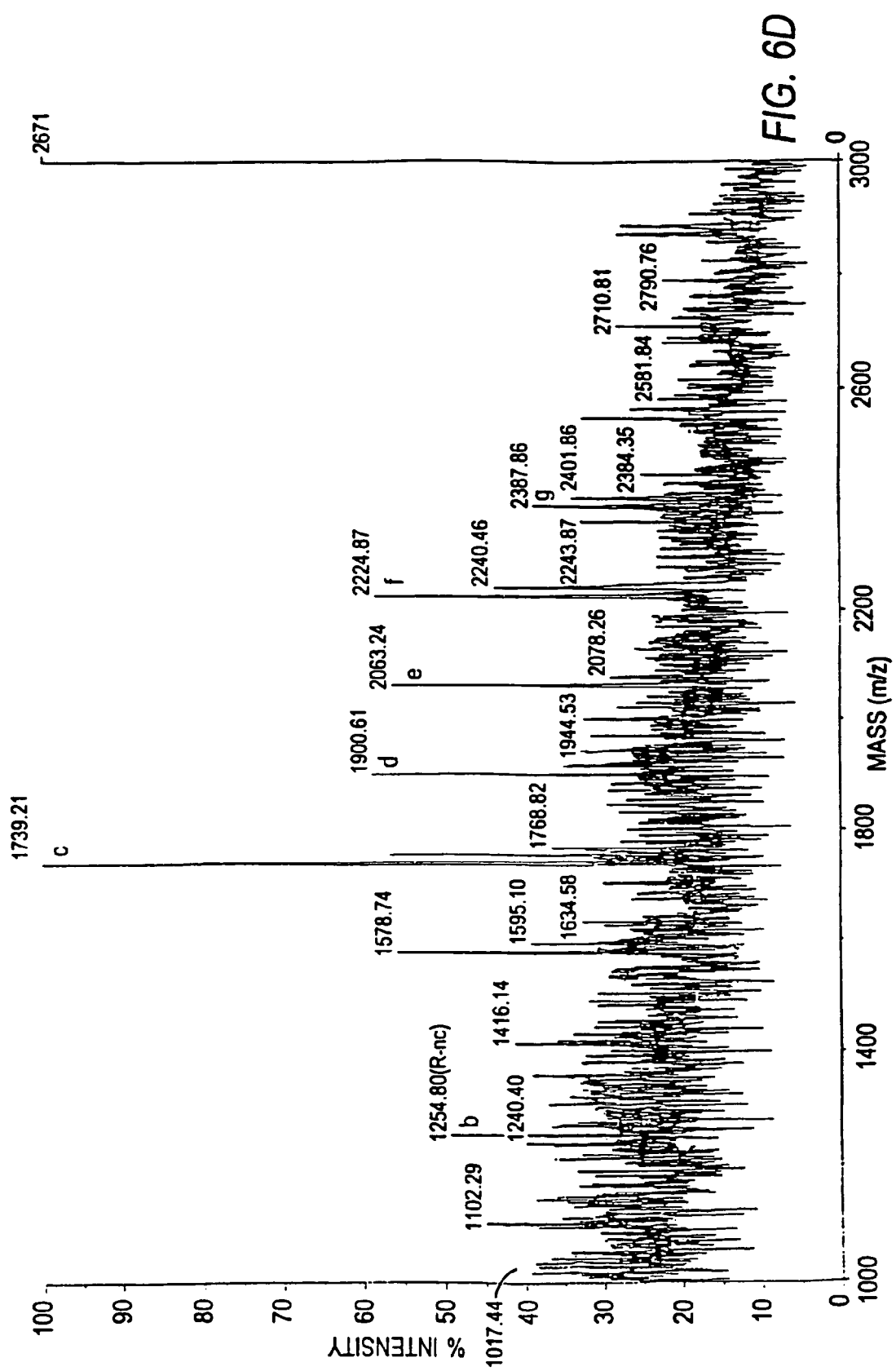
Figure 6E:
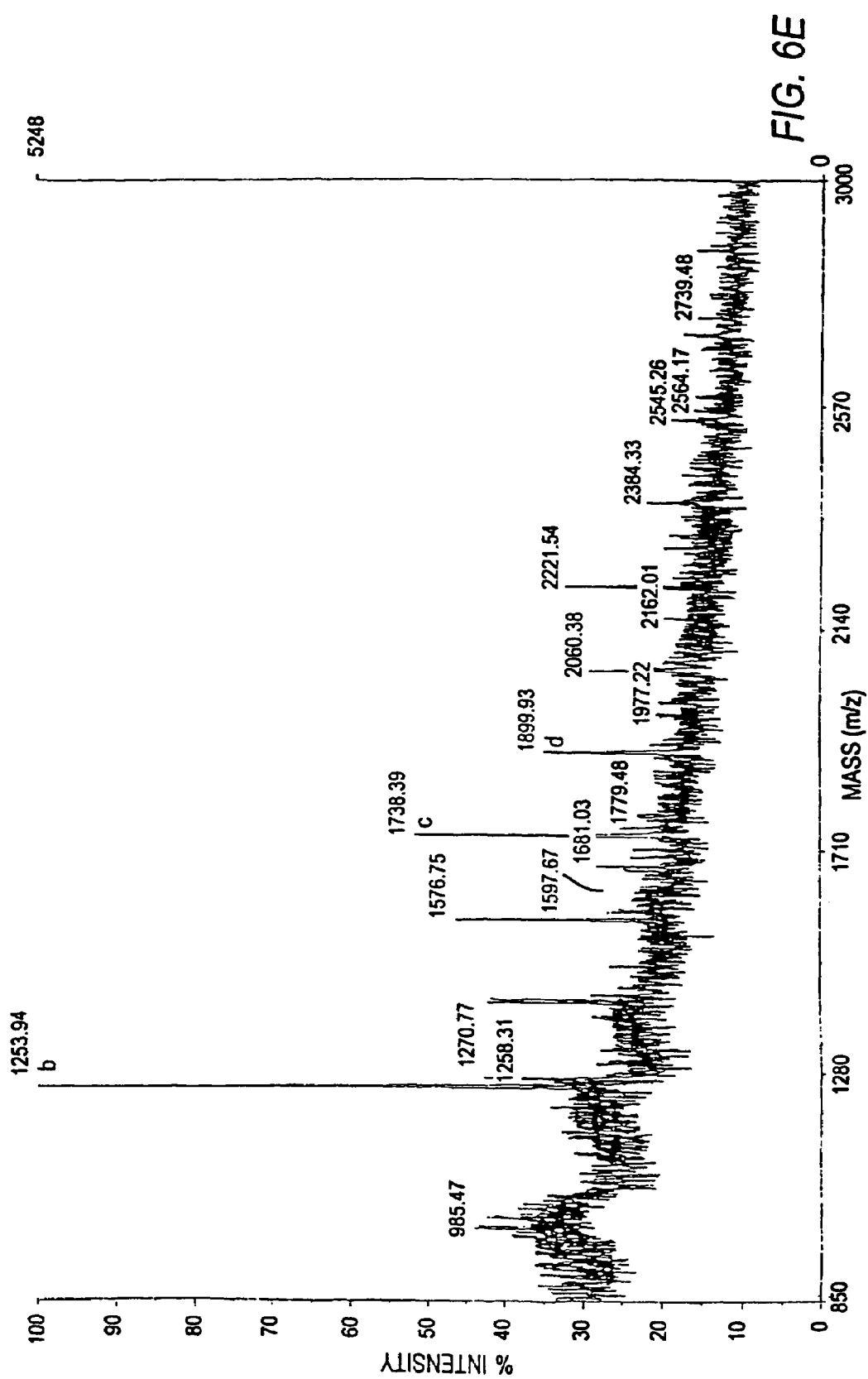
Figure 6F:
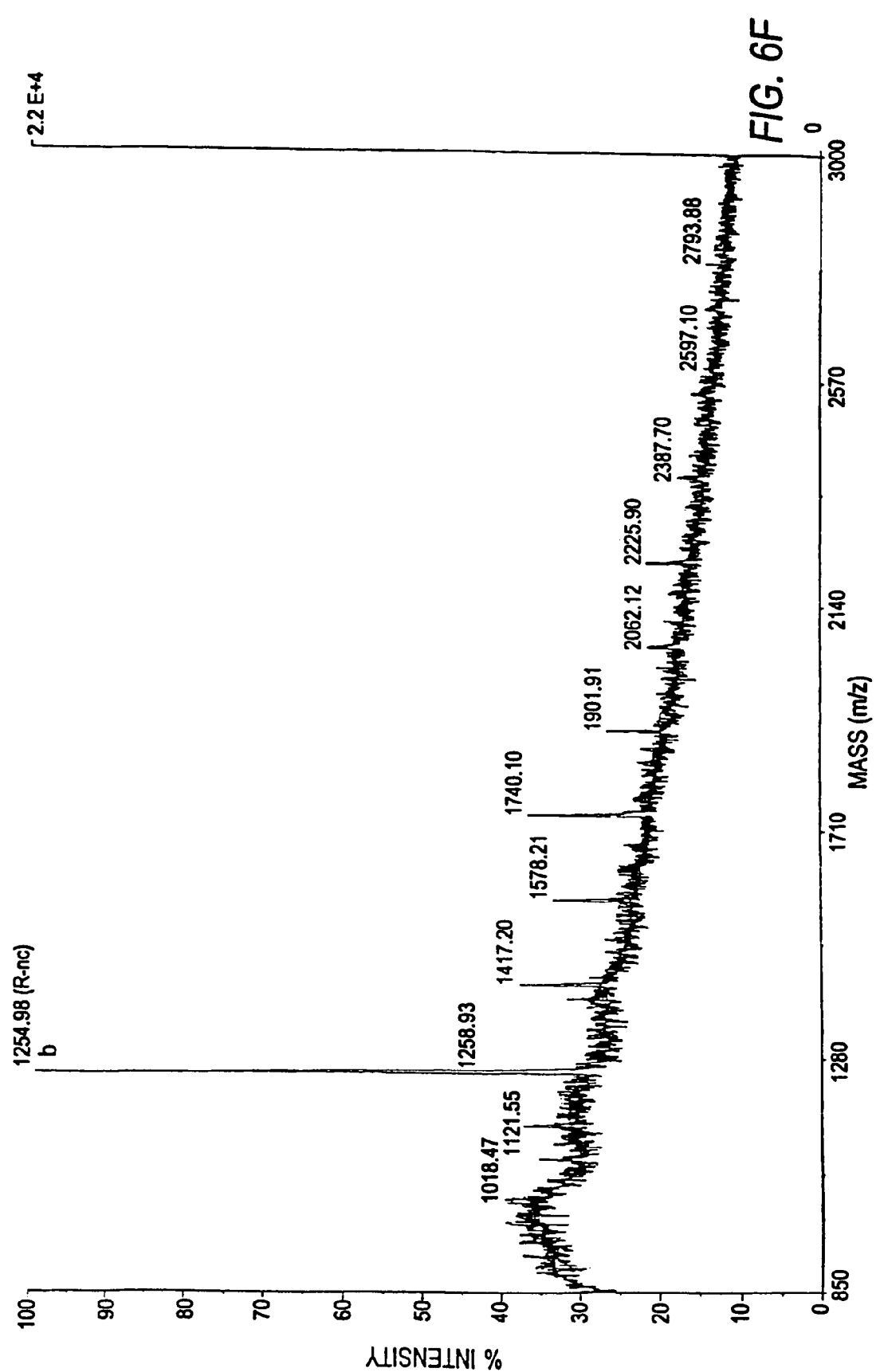
Figure 7:
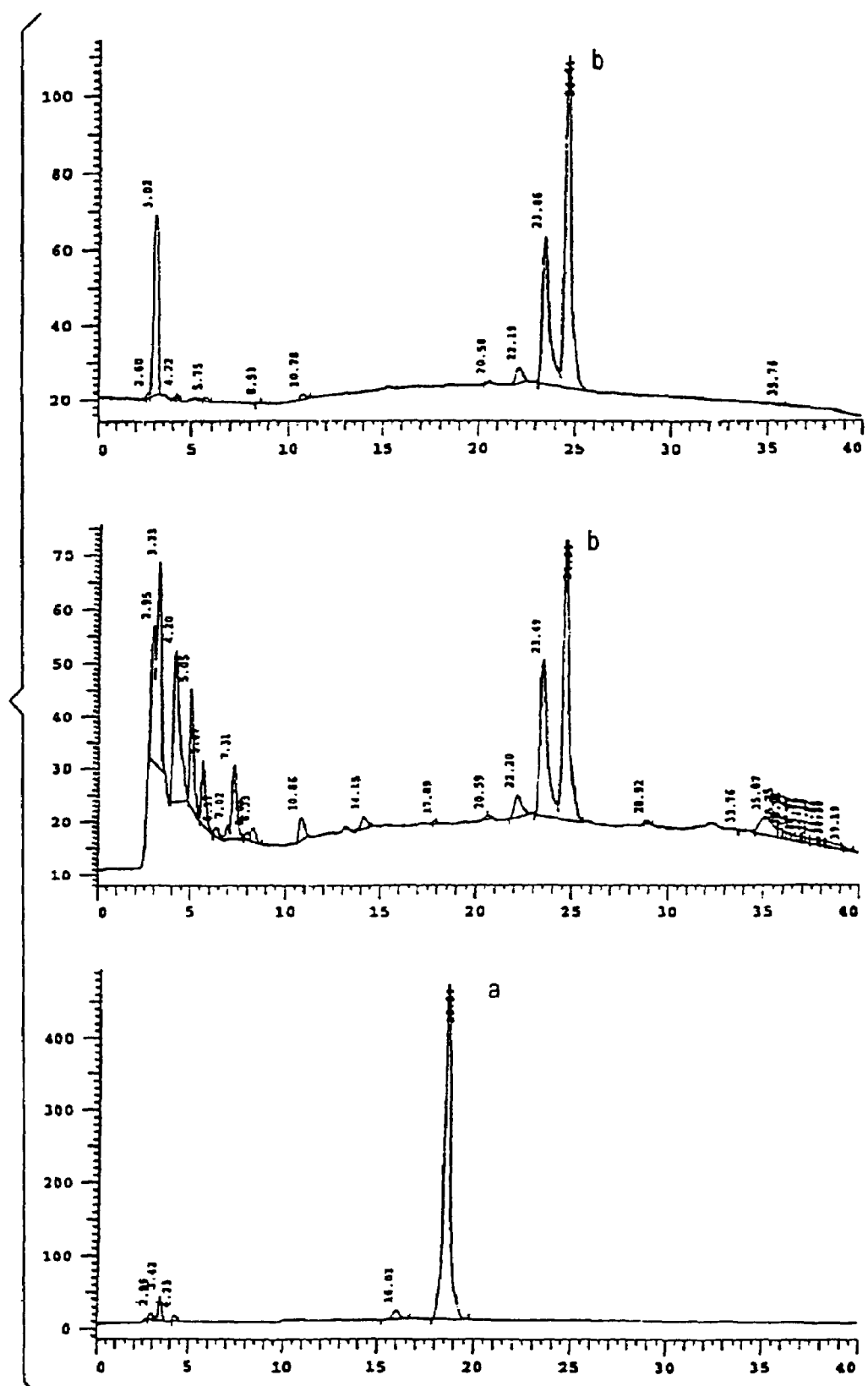
FIG. 7 shows a high performance liquid chromatogram for: (A) Man$_9$GlcNAc$_2$ standard labeled with 2-AB (negative control); (B) supernatant of medium *P. pastoris*, Δoch1 transformed with pFB8 mannosidase, which demonstrates a lack of extracellular mannosidase activity in the supernatant; and (C) Man$_9$GlcNAc$_2$ standard labeled with 2-AB after exposure to *T. reesei* mannosidase (positive control).
Figure 7A:
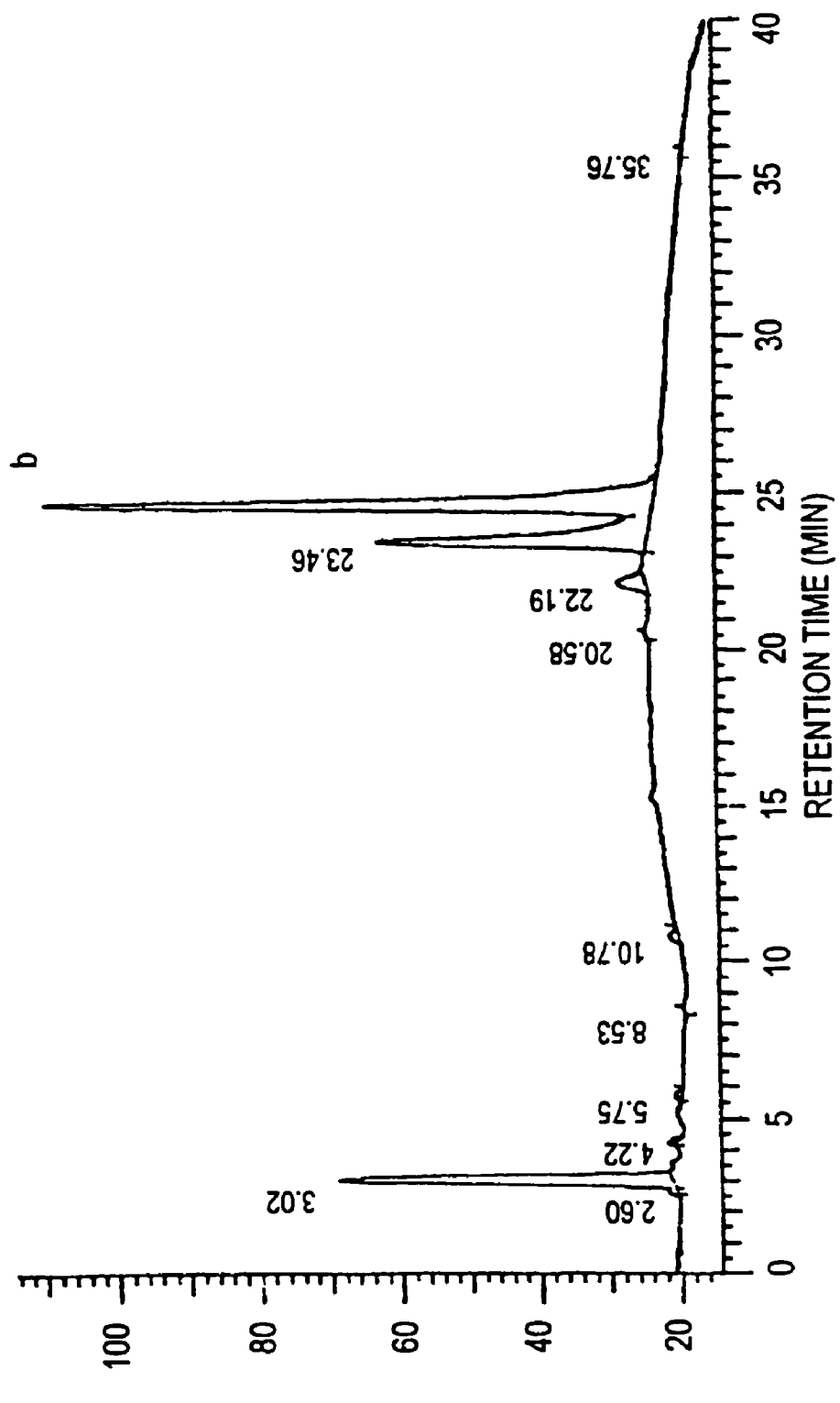
Figure 7B:
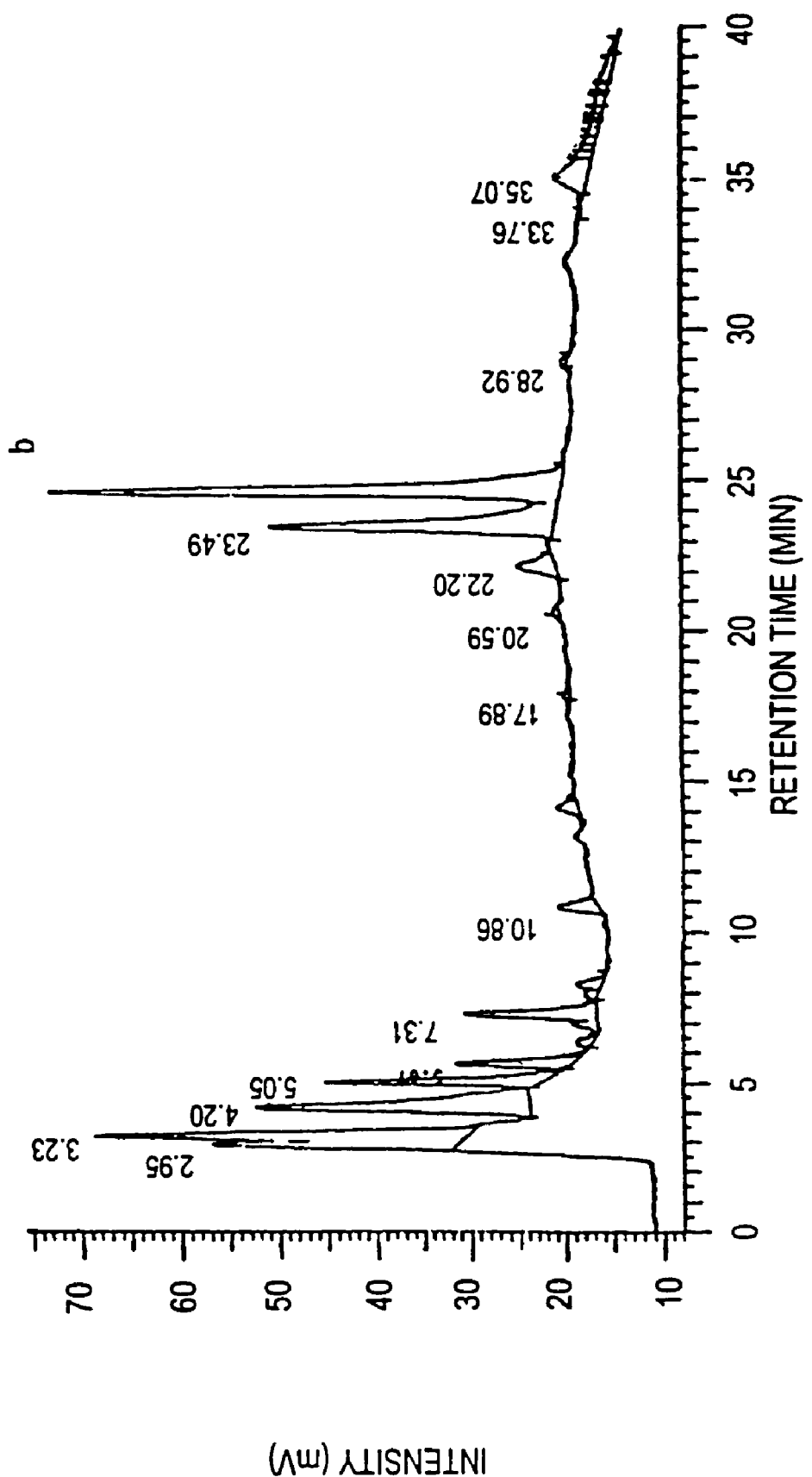

A representative example of a mannosidase fusion construct derived from a combinatorial DNA library of the invention is pFB8, which a truncated Saccharomyces SEC12(m) targeting peptide (988-1296 nucleotides of SEC12 from SwissProt P11655) ligated in-frame to a 187 N-terminal amino acid deletion of a mouse α-mannosidase IA (Genbank AN 6678787). The nomenclature used herein, thus, refers to the targeting peptide/catalytic domain region of a glycosylation enzyme as Saccharomyces SEC12(m)/mouse mannosidase IA Δ187. The encoded fusion protein localizes in the ER by means of the SEC12 targeting peptide sequence while retaining its mannosidase catalytic domain activity and is capable of producing in vivo N-glycans having a Man$_5$GlcNAc$_2$ structure (Example 4; FIGS. 6F and 7B).

Figure 8:
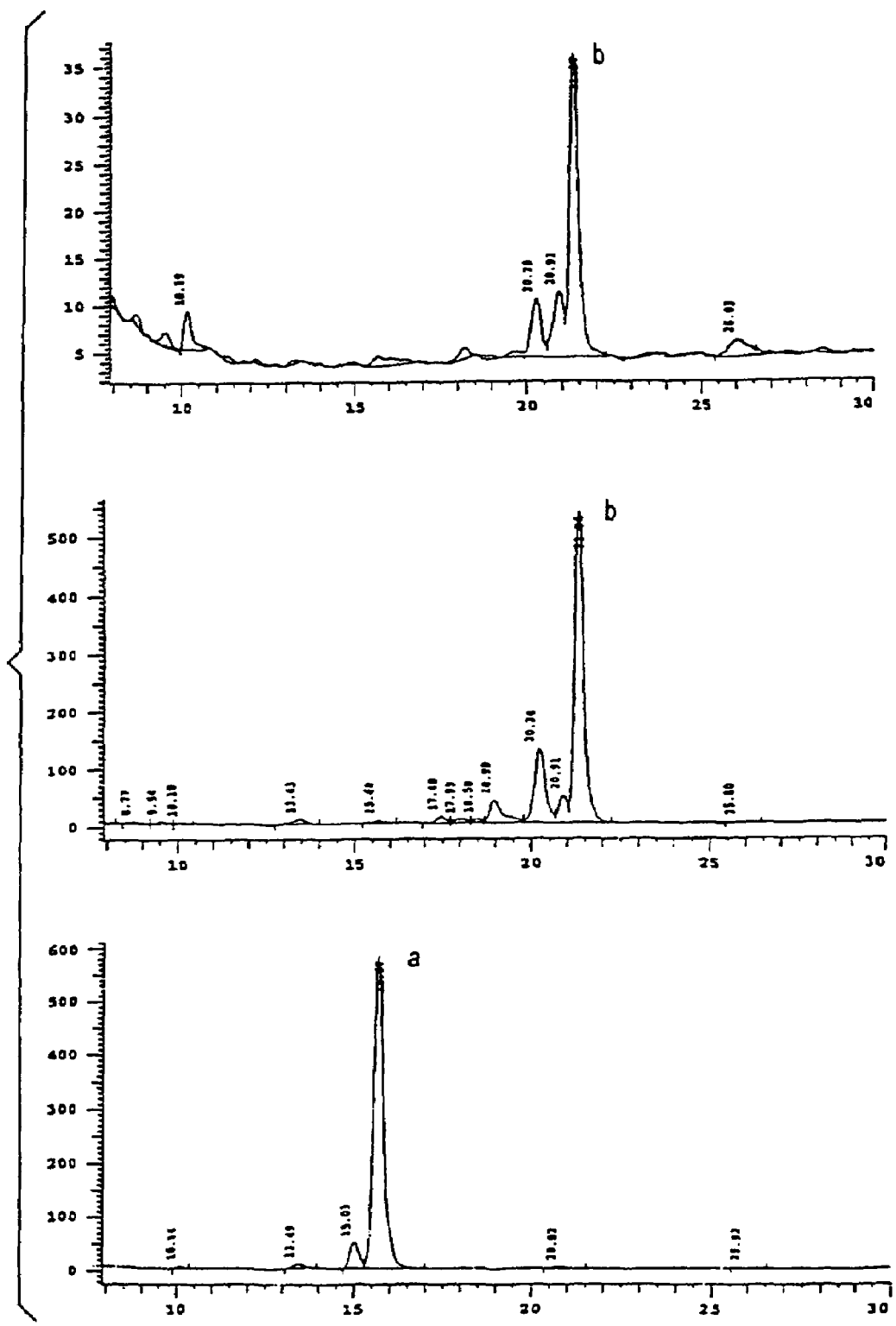
FIG. 8 shows a high performance liquid chromatogram for: (A) Man$_9$GlcNAc$_2$ standard labeled with 2-AB (negative control); (B) supernatant of medium *P. pastoris*, Δoch1 transformed with pGC5 mannosidase, which demonstrates a lack of extracellular mannosidase activity in the supernatant; and (C) Man$_9$GlcNAc$_2$ standard labeled with 2-AB after exposure to *T. reesei* mannosidase (positive control).
Figure 8A:
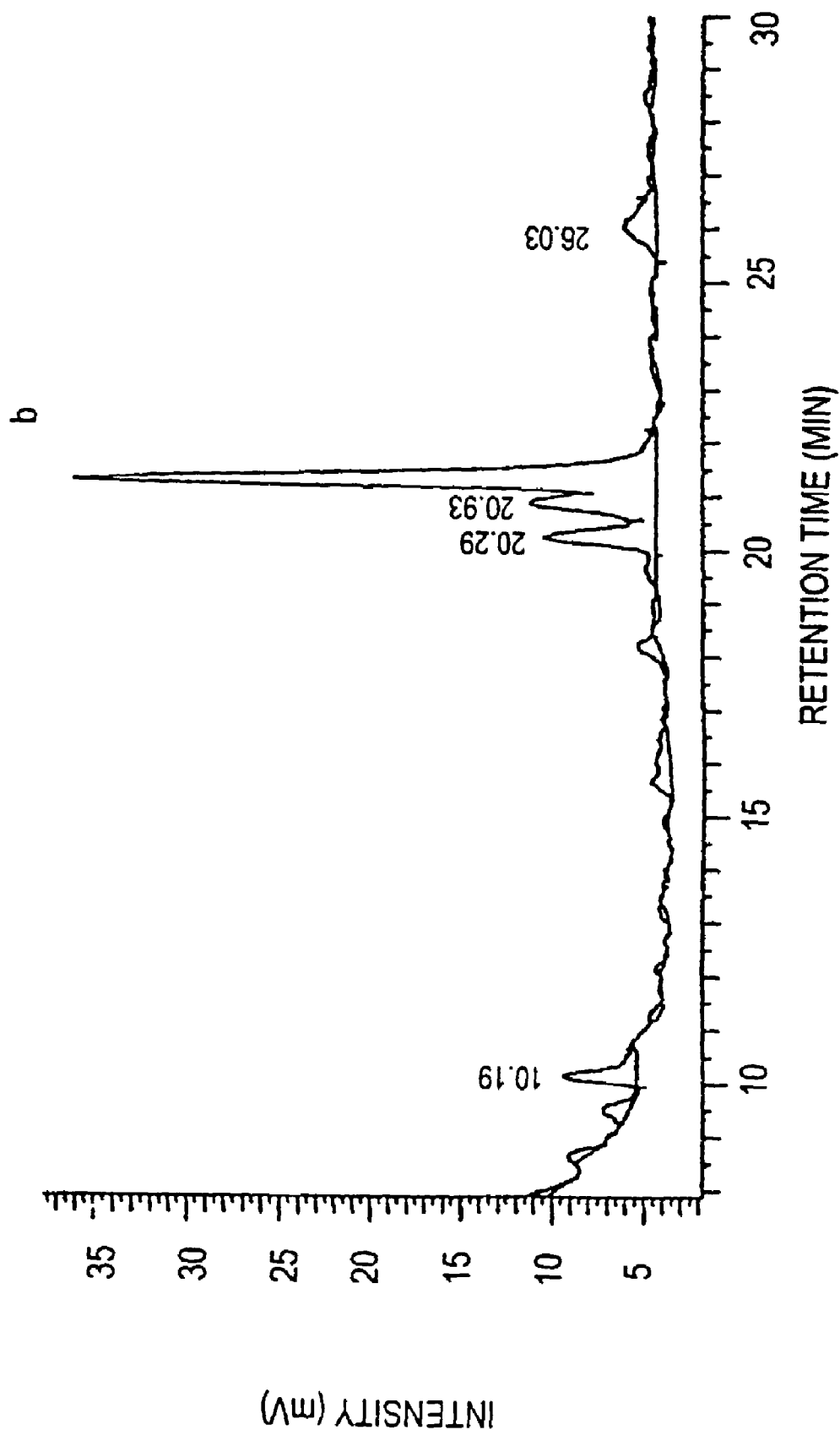
Figure 8B:
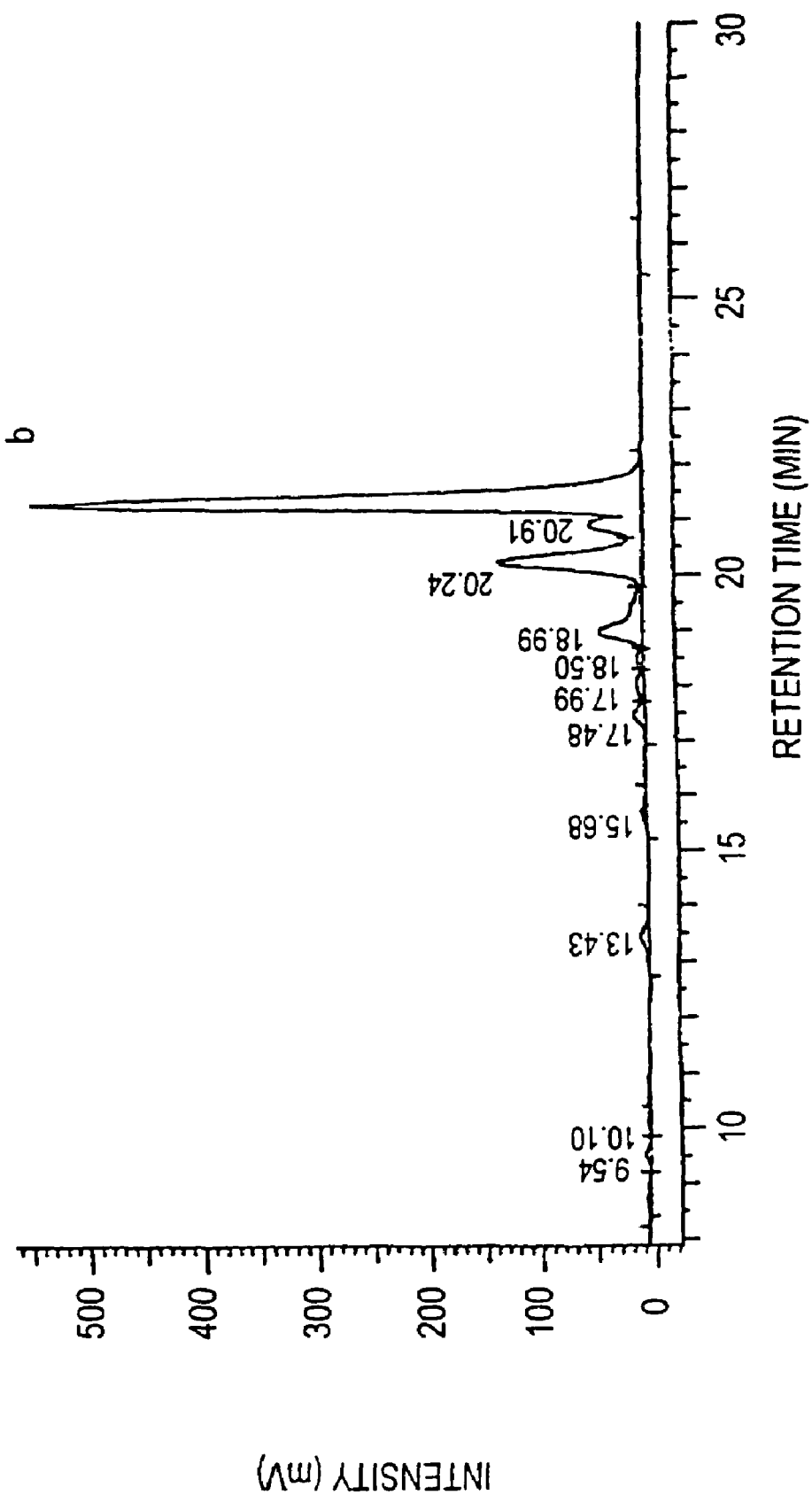

The fusion construct pGC5, Saccharomyces MNS1(m)/mouse mannosidase IB Δ99, is another example of a fusion construct having intracellular mannosidase trimming activity (Example 4; FIGS. 5D and 8B). Fusion construct pBC18-5 (Saccharomyces VAN1(s)/C. elegans mannosidase IB Δ80) is yet another example of an efficient fusion construct capable of producing N-glycans having a Man$_5$GlcNAc$_2$ structure in vivo. By creating a combinatorial DNA library of these and other such mannosidase fusion constructs according to the invention, a skilled artisan may distinguish and select those constructs having optimal intracellular trimming activity from those having relatively low or no activity. Methods using combinatorial DNA libraries of the invention are advantageous because only a select few mannosidase fusion constructs may produce a particularly desired N-glycan in vivo.

In addition, mannosidase trimming activity may be specific to a particular protein of interest. Thus, it is to be further understood that not all targeting peptide/mannosidase catalytic domain fusion constructs may function equally well to produce the proper glycosylation on a glycoprotein of interest. Accordingly, a protein of interest may be introduced into a host cell transfected with a combinatorial DNA library to identify one or more fusion constructs which express a mannosidase activity optimal for the protein of interest. One skilled in the art will be able to produce and select optimal fusion construct(s) using the combinatorial DNA library approach described herein.

It is apparent, moreover, that other such fusion constructs exhibiting localized active mannosidase catalytic domains (or more generally, domains of any enzyme) may be made using techniques such as those exemplified in Example 4 and described herein. It will be a matter of routine experimentation for one skilled in the art to make and use the combinatorial DNA library of the present invention to optimize, for example, Man$_5$GlcNAc$_2$ production from a library of fusion constructs in a particular expression vector introduced into a particular host cell.

Glycosyltransferase Fusion Constructs

Similarly, a glycosyltransferase combinatorial DNA library was made using the methods of the invention. A combinatorial DNA library of sequences derived from glycosyltransferase I (GnTI) activities were assembled with targeting peptides and screened for efficient production in a lower eukaryotic host cell of a GlcNAcMan$_5$GlcNAc$_2$ N-glycan structure on a marker glycoprotein. A fusion construct shown to produce GlcNAcMan$_5$GlcNAc$_2$ (pPB104), *Saccharomyces* MNN9(s)/human GnTI Δ38 was identified (Example 8). A wide variety of such GnTI fusion constructs were assembled (Example 8, Table 10). Other combinations of targeting peptide/GnTI catalytic domains can readily be assembled by making a combinatorial DNA library. It is also apparent to one skilled in the art that other such fusion constructs exhibiting glycosyltransferase activity may be made as demonstrated in Example 8. It will be a matter of routine experimentation for one skilled in the art to use the combinatorial DNA library method described herein to optimize GlcNAcMan$_5$GlcNAc$_2$ production using a selected fusion construct in a particular expression vector and host cell line.

As stated above for mannosidase fusion constructs, not all targeting peptide/GnTI catalytic domain fusion constructs will function equally well to produce the proper glycosylation on a glycoprotein of interest as described herein. However, one skilled in the art will be able to produce and select optimal fusion construct(s) using a DNA library approach as described herein. Example 8 illustrates a preferred embodiment of a combinatorial DNA library comprising targeting peptides and GnTI catalytic domain fusion constructs involved in producing glycoproteins with predominantly GlcNAcMan$_5$GlcNAc$_2$ structure.

Using Multiple Fusion Constructs to Alter Host Cell Glycosylation

Figure 10:
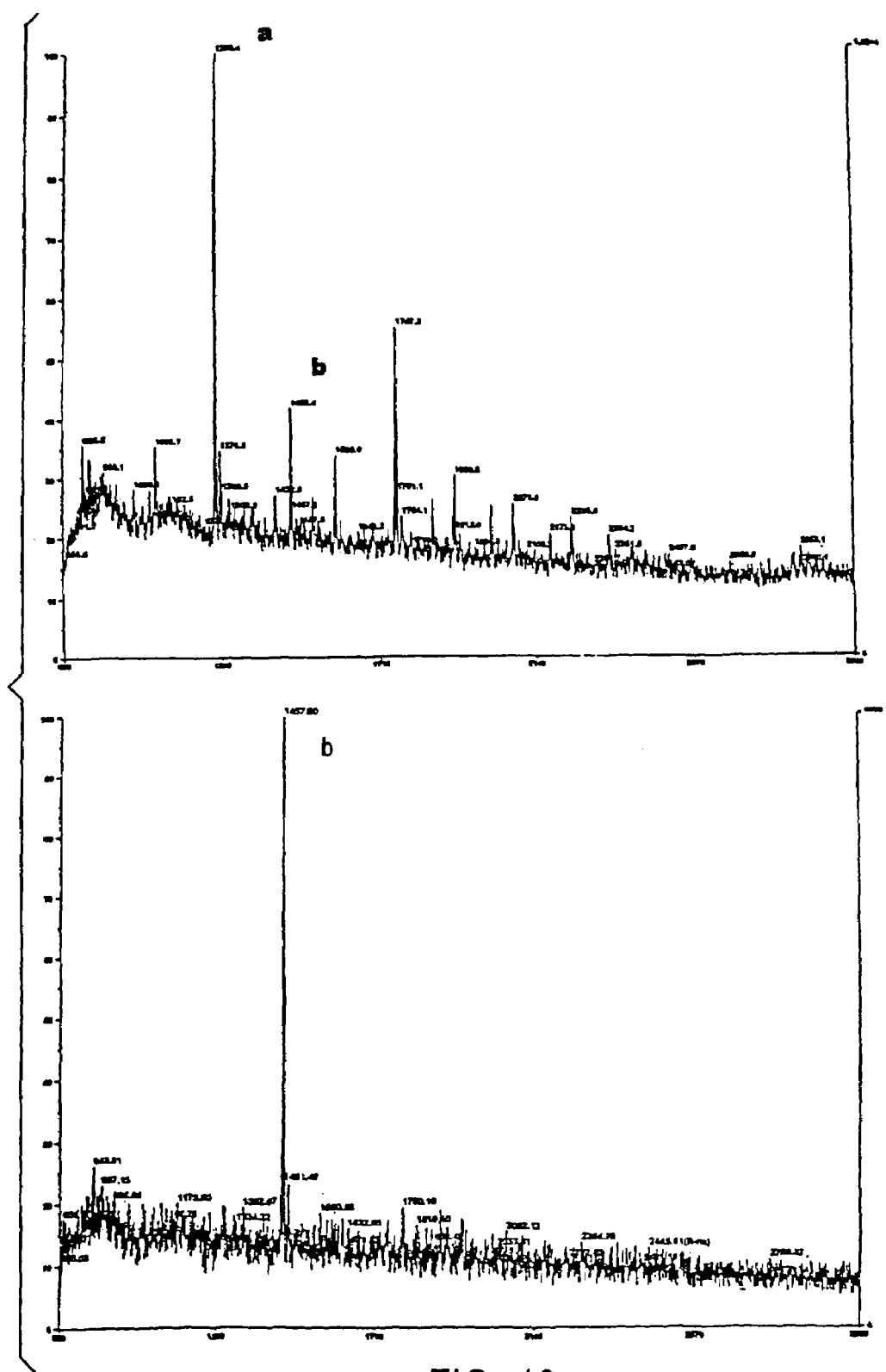
FIGS. 10A-10B demonstrate the activity of an UDP-GlcNAc transporter in the production of GlcNAcMan$_5$GlcNAc$_2$ in *P. pastoris*.
Figure 10A:
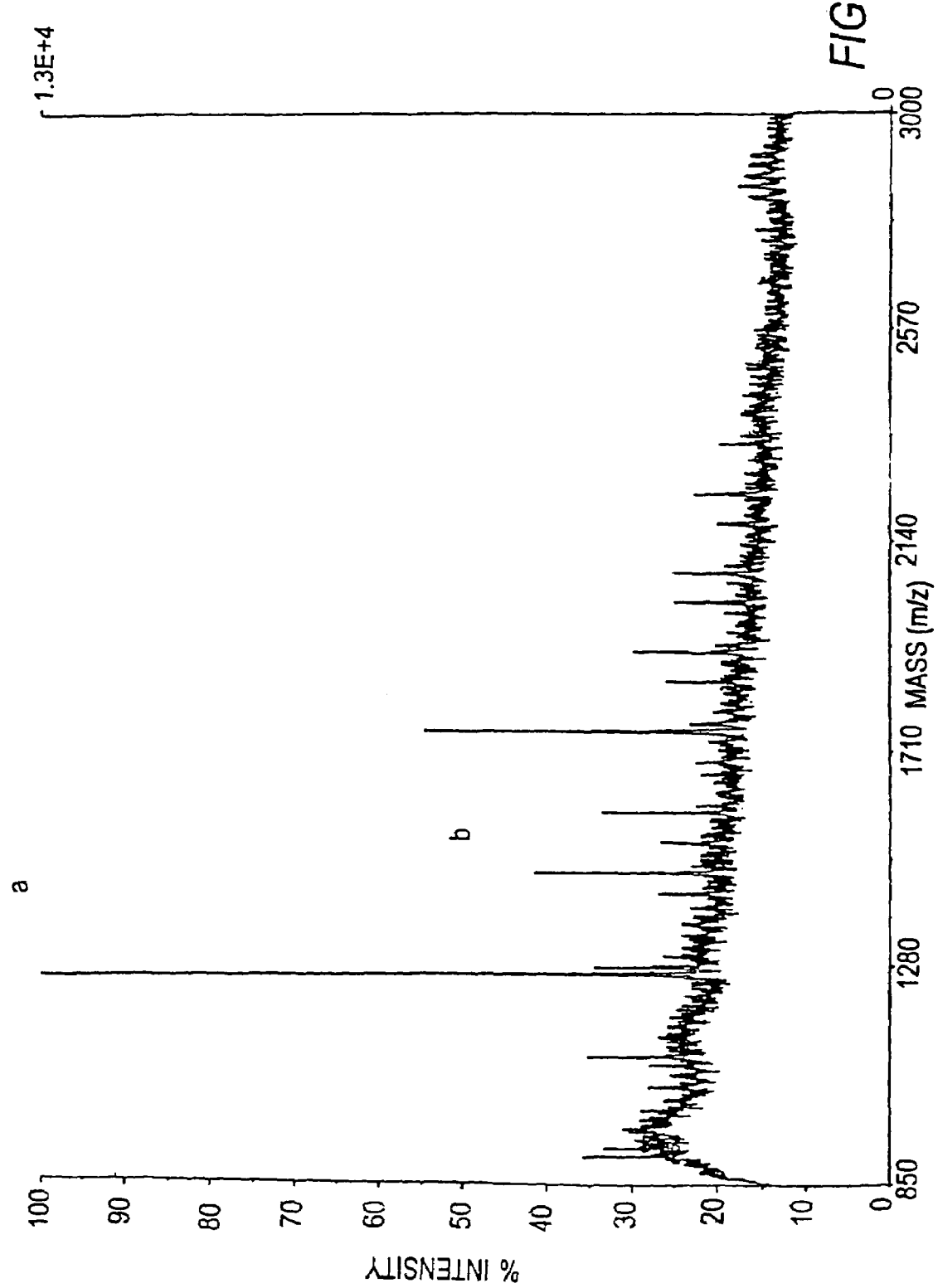
Figure 10B:
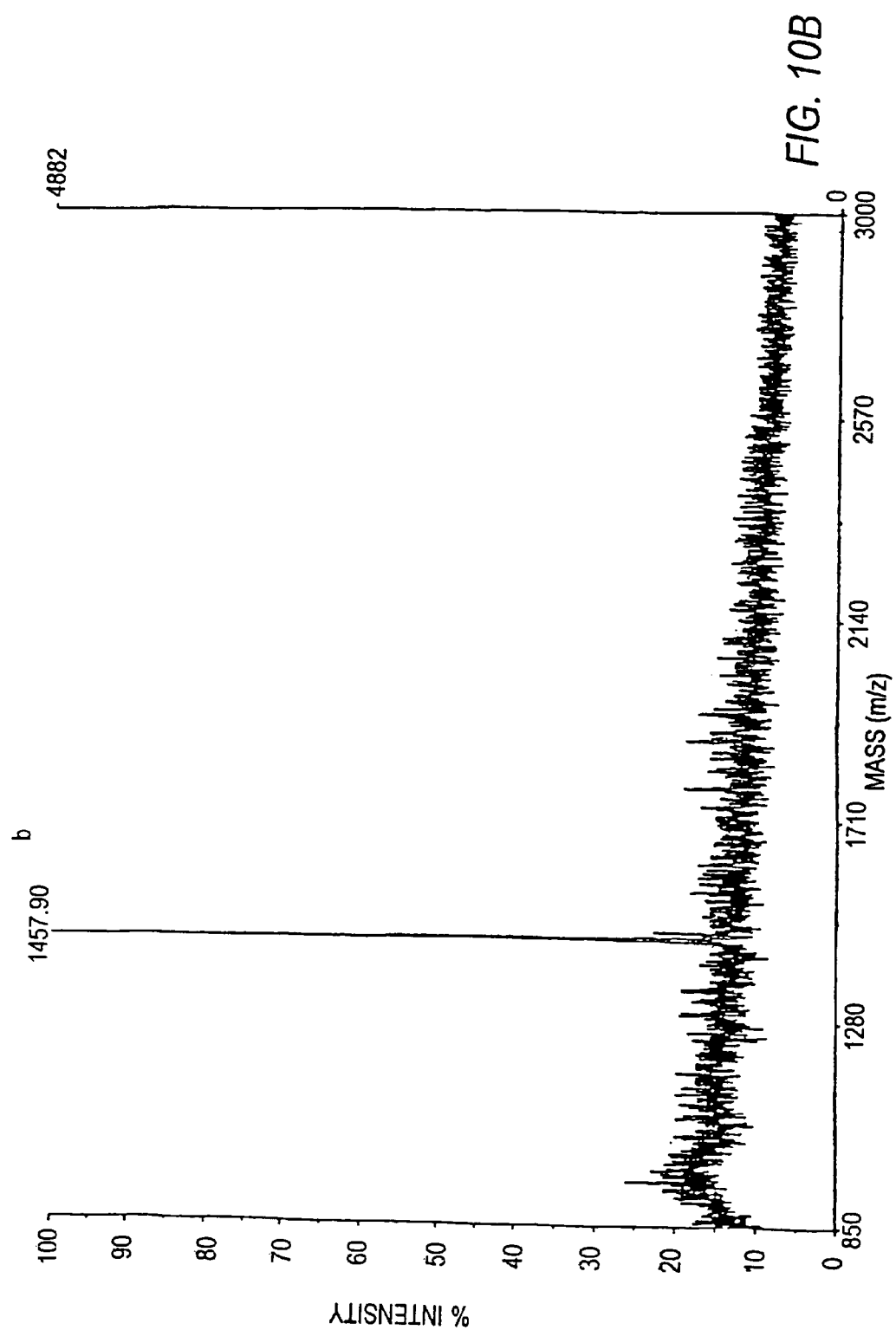

In another example of using the methods and libraries of the invention to alter host cell glycosylation, a *P. pastoris* strain with an OCH1 deletion that expresses a reporter protein (K3) was transformed with multiple fusion constructs isolated from combinatorial libraries of the invention to convert high mannose N-glycans to human-like N-glycans (Example 8). First, the mannosidase fusion construct pFB8 (*Saccharomyces* SEC12(m)/mouse mannosidase IA Δ187) was transformed into a *P. pastoris* strain lacking 1,6 initiating mannosyltransferases activity (i.e., och1 deletion; Example 1). Second, pPB103 comprising a *K. lactis* MNN2-2 gene (Genbank AN AF 106080) encoding an UDP-GlcNAc transporter was constructed to increase further production of GlcNAcMan$_5$GlcNAc$_2$. The addition of the UDP-GlcNAc transporter increased production of GlcNAcMan$_5$GlcNAc$_2$ significantly in the *P. pastoris* strain as illustrated in FIG. 10B. Third, pPB104 comprising *Saccharomyces* MNN9(s)/human GnTI Δ38 was introduced into the strain. This *P. pastoris* strain is referred to as "PBP-3." (See FIG. 36.)

It is understood by one skilled in the art that host cells such as the above-described yeast strains can be sequentially transformed and/or co-transformed with one or more expression vectors. It is also understood that the order of transformation is not particularly relevant in producing the glycoprotein of interest. The skilled artisan recognizes the routine modifications of the procedures disclosed herein may provide improved results in the production of the glycoprotein of interest.

The importance of using a particular targeting peptide sequence with a particular catalytic domain sequence becomes readily apparent from the experiments described herein. The combinatorial DNA library provides a tool for constructing enzyme fusions that are involved in modifying N-glycans on a glycoprotein of interest, which is especially useful in producing human-like glycoproteins. (Any enzyme fusion, however, may be selected using libraries and methods of the invention.) Desired transformants expressing appropriately targeted, active α-1,2-mannosidase produce K3 with N-glycans of the structure Man$_5$GlcNAc$_2$ as shown in FIGS. 5D and 5E. This confers a reduced molecular mass to the cleaved glycan compared to the K3 of the parent OCH1 deletion strain, as was detected by MALDI-TOF mass spectrometry in FIG. 5C.

Similarly, the same approach was used to produce another secreted glycoprotein: IFN-β comprising predominantly Man$_5$GlcNAc$_2$. The Man$_5$GlcNAc$_2$ was removed by PNGase digestion (Papac et al. (1998) *Glycobiology* 8:445-454) and subjected to MALDI-TOF as shown in FIGS. 6A-6F. A single prominent peak at 1254 (m/z) confirms Man$_5$GlcNA$_2$ production on IFN-β in FIG. 6E (pGC5) (*Saccharomyces* MNS1(m)/mouse mannosidase IB Δ99) and 6F (pFB8) (*Saccharomyces* SEC12(m)/mouse mannosidase IA Δ187). Furthermore, in the *P. pastoris* strain PBP-3 comprising pFB8 (*Saccharomyces* SEC12(m)/mouse mannosidase IA Δ187), pPB104 (*Saccharomyces* MNN9 (s)/human GnTI Δ38) and pPB103 (*K. lactis* MNN2-2 gene), the hybrid N-glycan GlcNAcMan$_5$GlcNAc$_2$ [b] was detected by MALDI-TOF (FIG. 10).

Figure 9:
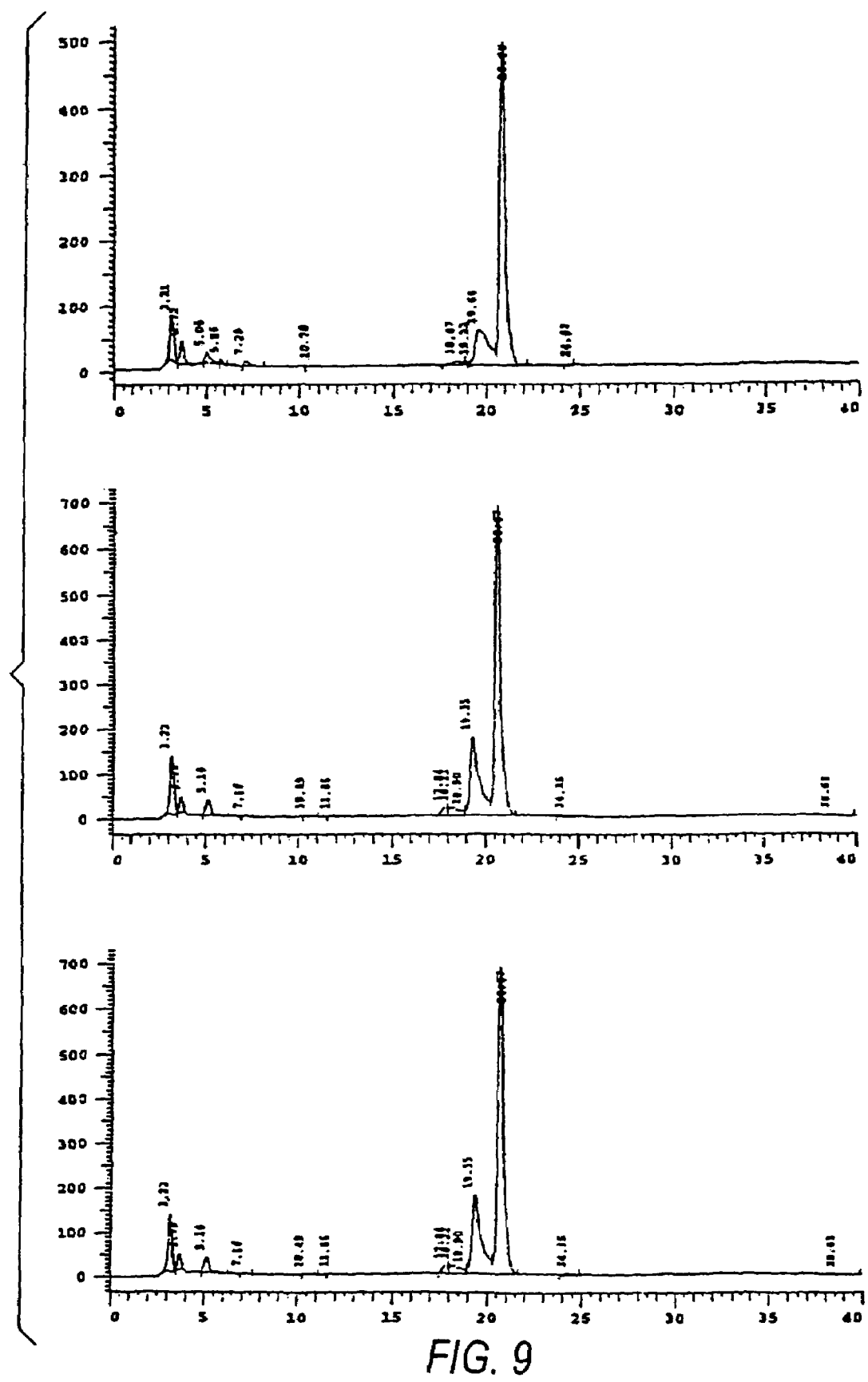
FIG. 9 shows a high performance liquid chromatogram for: (A) Man$_9$GlcNAc$_2$ standard labeled with 2-AB (negative control); (B) supernatant of medium *P. pastoris*, Δoch1 transformed with pBC18-5 mannosidase, which demonstrates lack of extracellular mannosidase activity in the supernatant; and (C) supernatant of medium *P. pastoris*, Δoch1 transformed with pDD28-3, which demonstrates activity in the supernatant (positive control).

After identifying transformants with a high degree of mannose trimming, additional experiments were performed to confirm that mannosidase (trimming) activity occurred in vivo and was not predominantly the result of extracellular activity in the growth medium (Example 6; FIGS. 7-9).

Although the present invention is exemplified using a *P. pastoris* host organism, it is understood by those skilled in the art that other eukaryotic host cells, including other species of yeast and fungal hosts, may be altered as described herein to produce human-like glycoproteins. The techniques described herein for identification and disruption of undesirable host cell glycosylation genes, e.g. OCH1, is understood to be applicable for these and/or other homologous or functionally related genes in other eukaryotic host cells such as other yeast and fungal strains. As described in Example 9, och1 mnn1 genes were deleted from *K. lactis* to engineer a host cell leading to N-glycans that are completely converted to Man$_5$GlcNAc$_2$ by 1,2-mannosidase (FIG. 12C).

The MNN1 gene was cloned from *K. lactis* as described in Example 9. Using gene-specific primers, a construct was made to delete the MNN1 gene from the genome of *K. lactis* (Example 9). Host cells depleted in och1 and mnn1 activities produce N-glycans having a Man$_9$GlcNAc$_2$ carbohydrate structure (see, e.g., FIG. 12B). Such host cells may be engineered further using, e.g., methods and libraries of the invention, to produce mammalian- or human-like glycoproteins.

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *K. lactis* MNN1 gene, and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided. In addition, also provided are vectors, including expression vectors, which comprise a nucleic acid molecule of the invention, as described further herein. Similarly host cells transformed with the nucleic acid molecules or vectors of the invention are provided.

Another aspect of the present invention thus relates to a non-human eukaryotic host strain expressing glycoproteins comprising modified N-glycans that resemble those made by human-cells. Performing the methods of the invention in species other than yeast and fungal cells is thus contemplated and encompassed by this invention. It is contemplated that a combinatorial nucleic acid library of the present invention may be used to select constructs that modify the glycosylation pathway in any eukaryotic host cell system. For example, the combinatorial libraries of the invention may also be used in plants, algae and insects, and in other eukaryotic host cells, including mammalian and human cells, to localize proteins, including glycosylation enzymes or catalytic domains thereof, in a desired location along a host cell secretory pathway. Preferably, glycosylation enzymes or catalytic domains and the like are targeted to a subcellular location along the host cell secretory pathway where they are capable of functioning, and preferably, where they are designed or selected to function most efficiently.

Plant and insect cells may also be engineered to alter the glycosylation of expressed proteins using the combinatorial library and methods of the invention. Furthermore, glycosylation in mammalian cells, including human cells, may also be modified using the combinatorial library and methods of the invention. It may be possible, for example, to optimize a particular enzymatic activity or to otherwise modify the relative proportions of various N-glycans made in a mammalian host cell using the combinatorial library and methods of the invention.

Examples of modifications to glycosylation which can be affected using a method according to this embodiment of the invention are: (1) engineering a eukaryotic host cell to trim mannose residues from $Man_8GlcNAc_2$ to yield a $Man_5GlcNAc_2$ N-glycan; (2) engineering eukaryotic host cell to add an N-acetylglucosamine (GlcNAc) residue to $Man_5GlcNAc_2$ by action of GlcNAc transferase I; (3) engineering a eukaryotic host cell to functionally express an enzyme such as an N-acetylglucosaminyl Transferase (GnTI, GnTII, GnTIII, GnTIV, GnTV, GnTVI), mannosidase II, fucosyltransferase (FT), galactosyl tranferase (GalT) or a sialyltransferase (ST).

By repeating the method, increasingly complex glycosylation pathways can be engineered into a target host, such as a lower eukaryotic microorganism. In one preferred embodiment, the host organism is transformed two or more times with DNA libraries including sequences encoding glycosylation activities. Selection of desired phenotypes may be performed after each round of transformation or alternatively after several transformations have occurred. Complex glycosylation pathways can be rapidly engineered in this manner.

Sequential Glycosylation Reactions

In a preferred embodiment, such targeting peptide/catalytic domain libraries are designed to incorporate existing information on the sequential nature of glycosylation reactions in higher eukaryotes. Reactions known to occur early in the course of glycoprotein processing require the targeting of enzymes that catalyze such reactions to an early part of the Golgi or the ER. For example, the trimming of $Man_8GlcNAc_2$ to $Man_5GlcNAc_2$ by mannosidases is an early step in complex N-glycan formation (FIGS. 1B and 35A). Because protein processing is initiated in the ER and then proceeds through the early, medial and late Golgi, it is desirable to have this reaction occur in the ER or early Golgi. When designing a library for mannosidase I localization, for example, one thus attempts to match ER and early Golgi targeting signals with the catalytic domain of mannosidase I.

Generating Additional Sequence Diversity

The method of this embodiment is most effective when a nucleic acid, e.g., a DNA library transformed into the host contains a large diversity of sequences, thereby increasing the probability that at least one transformant will exhibit the desired phenotype. Single amino acid mutations, for example, may drastically alter the activity of glycoprotein processing enzymes (Romero et al. (2000) *J. Biol. Chem.* 275(15):11071-4). Accordingly, prior to transformation, a DNA library or a constituent sub-library may be subjected to one or more techniques to generate additional sequence diversity. For example, one or more rounds of gene shuffling, error prone PCR, in vitro mutagenesis or other methods for generating sequence diversity, may be performed to obtain a larger diversity of sequences within the pool of fusion constructs.

Expression Control Sequences

In addition to the open reading frame sequences described above, it is generally preferable to provide each library construct with expression control sequences, such as promoters, transcription terminators, enhancers, ribosome binding sites, and other functional sequences as may be necessary to ensure effective transcription and translation of the fusion proteins upon transformation of fusion constructs into the host organism.

Suitable vector components, e.g., selectable markers, expression control sequences (e.g., promoter, enhancers, terminators and the like) and, optionally, sequences required for autonomous replication in a host cell, are selected as a function of which particular host cell is chosen. Selection criteria for suitable vector components for use in a particular mammalian or a lower eukaryotic host cell are routine. Preferred lower eukaryotic host cells of the invention include *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp. *Fusarium gramineum, Fusarium venenatum* and *Neurospora crassa*. Where the host is *Pichia pastoris*, suitable promoters include, for example, the AOX1, AOX2, GAPDH and P40 promoters.

Selectable Markers

It is also preferable to provide each construct with at least one selectable marker, such as a gene to impart drug resistance or to complement a host metabolic lesion. The presence of the marker is useful in the subsequent selection of transformants; for example, in yeast the URA3, HIS4, SUC2, G418, BLA, or SH BLE genes may be used. A multitude of selectable markers are known and available for use in yeast, fungi, plant, insect, mammalian and other eukaryotic host cells.

Transformation

The nucleic acid library is then transformed into the host organism. In yeast, any convenient method of DNA transfer may be used, such as electroporation, the lithium chloride method, or the spheroplast method. In filamentous fungi and plant cells, conventional methods include particle bombardment, electroporation and agrobacterium mediated transformation. To produce a stable strain suitable for high-density culture (e.g., fermentation in yeast), it is desirable to integrate the DNA library constructs into the host chromosome. In a preferred embodiment, integration occurs via homologous recombination, using techniques well-known in the art. For example, DNA library elements are provided with flanking sequences homologous to sequences of the host organism. In this manner, integration occurs at a defined site in the host genome, without disruption of desirable or essential genes.

In an especially preferred embodiment, library DNA is integrated into the site of an undesired gene in a host chromosome, effecting the disruption or deletion of the gene. For example, integration into the sites of the OCH1, MNN1, or MNN4 genes allows the expression of the desired library DNA while preventing the expression of enzymes involved in yeast hypermannosylation of glycoproteins. In other embodiments, library DNA may be introduced into the host via a nucleic acid molecule, plasmid, vector (e.g., viral or retroviral vector), chromosome, and may be introduced as an autonomous nucleic acid molecule or by homologous or random integration into the host genome. In any case, it is generally desirable to include with each library DNA construct at least one selectable marker gene to allow ready selection of host organisms that have been stably transformed. Recyclable marker genes such as ura3, which can be selected for or against, are especially suitable.

Screening and Selection Processes

After transformation of the host strain with the DNA library, transformants displaying a desired glycosylation phenotype are selected. Selection may be performed in a single step or by a series of phenotypic enrichment and/or depletion steps using any of a variety of assays or detection methods. Phenotypic characterization may be carried out manually or using automated high-throughput screening equipment. Commonly, a host microorganism displays protein N-glycans on the cell surface, where various glycoproteins are localized.

One may screen for those cells that have the highest concentration of terminal GlcNAc on the cell surface, for example, or for those cells which secrete the protein with the highest terminal GlcNAc content. Such a screen may be based on a visual method, like a staining procedure, the ability to bind specific terminal GlcNAc binding antibodies or lectins conjugated to a marker (such lectins are available from E.Y. Laboratories Inc., San Mateo, Calif.), the reduced ability of specific lectins to bind to terminal mannose residues, the ability to incorporate a radioactively labeled sugar in vitro, altered binding to dyes or charged surfaces, or may be accomplished by using a Fluorescence Assisted Cell Sorting (FACS) device in conjunction with a fluorophore labeled lectin or antibody (Guillen et al. (1998) *Proc. Natl. Acad. Sci. USA* 95(14):7888-7892).

Accordingly, intact cells may be screened for a desired glycosylation phenotype by exposing the cells to a lectin or antibody that binds specifically to the desired N-glycan. A wide variety of oligosaccharide-specific lectins are available commercially (e.g., from EY Laboratories, San Mateo, Calif.). Alternatively, antibodies to specific human or animal N-glycans are available commercially or may be produced using standard techniques. An appropriate lectin or antibody may be conjugated to a reporter molecule, such as a chromophore, fluorophore, radioisotope, or an enzyme having a chromogenic substrate (Guillen et al., 1998. *Proc. Natl. Acad. Sci. USA* 95(14): 7888-7892).

Screening may then be performed using analytical methods such as spectrophotometry, fluorimetry, fluorescence activated cell sorting, or scintillation counting. In other cases, it may be necessary to analyze isolated glycoproteins or N-glycans from transformed cells. Protein isolation may be carried out by techniques known in the art. In a preferred embodiment, a reporter protein is secreted into the medium and purified by affinity chromatography (e.g. Ni-affinity or glutathione-S-transferase affinity chromatography). In cases where an isolated N-glycan is preferred, an enzyme such as endo-β-N-acetylglucosaminidase (Genzyme Co., Boston, Mass.; New England Biolabs, Beverly, Mass.) may be used to cleave the N-glycans from glycoproteins. Isolated proteins or N-glycans may then be analyzed by liquid chromatography (e.g., HPLC), mass spectroscopy, or other suitable means. U.S. Pat. No. 5,595,900 teaches several methods by which cells with desired extracellular carbohydrate structures may be identified. In a preferred embodiment, MALDI-TOF mass spectrometry is used to analyze the cleaved N-glycans.

Prior to selection of a desired transformant, it may be desirable to deplete the transformed population of cells having undesired phenotypes. For example, when the method is used to engineer a functional mannosidase activity into cells, the desired transformants will have lower levels of mannose in cellular glycoprotein. Exposing the transformed population to a lethal radioisotope of mannose in the medium depletes the population of transformants having the undesired phenotype, i.e., high levels of incorporated mannose (Huffaker and Robbins (1983) *Proc Natl Acad Sci USA*. 80(24): 7466-70). Alternatively, a cytotoxic lectin or antibody, directed against an undesirable N-glycan, may be used to deplete a transformed population of undesired phenotypes (e.g., Stanley and Siminovitch (1977) *Somatic Cell Genet* 3(4):391-405). U.S. Pat. No. 5,595,900 teaches several methods by which cells with a desired extracellular carbohydrate structures may be identified. Repeatedly carrying out this strategy allows for the sequential engineering of more and more complex glycans in lower eukaryotes.

To detect host cells having on their surface a high degree of the human-like N-glycan intermediate GlcNAcMan$_3$GlcNAc$_2$, for example, one may select for transformants that allow for the most efficient transfer of GlcNAc by GlcNAc Transferase from UDP-GlcNAc in an in vitro cell assay. This screen may be carried out by growing cells harboring the transformed library under selective pressure on an agar plate and transferring individual colonies into a 96-well microtiter plate. After growing the cells, the cells are centrifuged, the cells resuspended in buffer, and after addition of UDP-GlcNAc and GnTII, the release of UDP is determined either by HPLC or an enzyme linked assay for UDP. Alternatively, one may use radioactively labeled UDP-GlcNAc and GnTII, wash the cells and then look for the release of radioactive GlcNAc by N-actylglucosaminidase. All this may be carried manually or automated through the use of high throughput screening equipment. Transformants that release more UDP, in the first assay, or more radioactively labeled GlcNAc in the second assay, are expected to have a higher degree of GlcNAcMan$_3$GlcNAc$_2$ on their surface and thus constitute the desired phenotype. Similar assays may be adapted to look at the N-glycans on secreted proteins as well.

Alternatively, one may use any other suitable screen such as a lectin binding assay that is able to reveal altered glycosylation patterns on the surface of transformed cells. In this case the reduced binding of lectins specific to terminal mannoses may be a suitable selection tool. *Galantus nivalis* lectin binds specifically to terminal α-1,3 mannose, which is expected to be reduced if sufficient mannosidase II activity is present in the Golgi. One may also enrich for desired transformants by carrying out a chromatographic separation step that allows for the removal of cells containing a high terminal mannose content. This separation step would be carried out with a lectin column that specifically binds cells with a high terminal mannose content (e.g., *Galantus nivalis* lectin bound to agarose, Sigma, St. Louis, Mo.) over those that have a low terminal mannose content.

In addition, one may directly create such fusion protein constructs, as additional information on the localization of active carbohydrate modifying enzymes in different lower eukaryotic hosts becomes available in the scientific literature. For example, it is known that human β1,4-GalTr can be fused to the membrane domain of MNT, a mannosyltransferase from *S. cerevisiae*, and localized to the Golgi apparatus while retaining its catalytic activity (Schwientek et al. (1995) *J. Biol. Chem.* 270(10):5483-9). If *S. cerevisiae* or a related organism is the host to be engineered one may directly incorporate such findings into the overall strategy to obtain complex N-glycans from such a host. Several such gene fragments in *P. pastoris* have been identified that are related to glycosyltransferases in *S. cerevisiae* and thus could be used for that purpose.

Integration Sites

As one ultimate goal of this genetic engineering effort is a robust protein production strain that is able to perform well in an industrial fermentation process, the integration of multiple genes into the host (e.g., fungal) chromosome preferably involves careful planning. The engineered strain may likely have to be transformed with a range of different genes, and these genes will have to be transformed in a stable fashion to ensure that the desired activity is maintained throughout the fermentation process. As described herein, any combination of various desired enzyme activities may be engineered into the fungal protein expression host, e.g., sialyltransferases, mannosidases, fucosyltransferases, galactosyltransferases, glucosyltransferases, GlcNAc transferases, ER and Golgi specific transporters (e.g. syn and antiport transporters for UDP-galactose and other precursors), other enzymes involved in the processing of oligosaccharides, and enzymes involved in the synthesis of activated oligosaccharide precursors such as UDP-galactose, CMP-N-acetylneuraminic acid. Examples of preferred methods for modifying glycosylation in a lower eukaryotic host cell, such as *Pichia pastoris*, are shown in Table 6.

TABLE 6

Some preferred embodiments for modifying glycosylation in a lower eukaroytic microorganism

| Desired Structure | Suitable Catalytic Activities | Suitable Sources of Localization Sequences | Suitable Gene Deletions | Suitable Transporters and/or Phosphatases |
|---|---|---|---|---|
| $Man_5GlcNAc_2$ | α-1,2-mannosidase (murine, human, *Bacillus* sp., *A. nidulans*) | Mns1 (N-terminus, *S. cerevisiae*) Och1 (N-terminus, *S. cerevisiae*, *P. pastoris*) Ktr1 Mnn9 Mnt1 (*S. cerevisiae*) KDEL, HDEL (C-terminus) | OCH1 MNN4 MNN6 | none |
| $GlcNAcMan_5GlcNAc_2$ | GlcNAc Transferase I, (human, murine, rat etc.) | Och1 (N-terminus, *S. cerevisiae*, *P. pastoris*) KTR1 (N-terminus) Mnn1 (N-terminus, *S. cerevisiae*) Mnt1 (N-terminus, *S. cerevisiae*) GDPase (N-terminus, *S. cerevisiae*) | OCH1 MNN4 MNN6 | UDP-GlcNAc transporter (human, murine, *K. lactis*) UDPase (human) |
| $GlcNAcMan_3GlcNAc_2$ | mannosidase II | Ktr1 Mnn1 (N-terminus, *S. cerevisiae*) Mnt1(N-terminus, *S. cerevisiae*) Kre2/Mnt1 (*S. cerevisiae*) Kre2 (*P. pastoris*) Ktr1 (*S. cerevisiae*) Ktr1 (*P. pastoris*) Mnn1 (*S. cerevisiae*) | OCH1 MNN4 MNN6 | UDP-GlcNAc transporter (human, murine, *K. lactis*) UDPase (human) |
| $GlcNAc_{(2-4)}$-$Man_3GlcNAc_2$ | GlcNAc Transferase II, III, IV, V (human, murine) | Mnn1 (N-terminus, *S. cerevisiae*) Mnt1 (N-terminus, *S. cerevisiae*) Kre2/Mnt1 (*S. cerevisiae*) Kre2 (*P. pastoris*) Ktr1 (*S. cerevisiae*) Ktr1 (*P. pastoris*) Mnn1 (*S. cerevisiae*) | OCH1 MNN4 MNN6 | UDP-GlcNAc transporter (human, murine, *K. lactis*) UDPase (human) |
| $Gal_{(1-4)}GlcNAc_{(2-4)}$-$Man_3GlcNAc_2$ | β-1,4-Galactosyl transferase (human) | Mnn1 (N-terminus, *S. cerevisiae*) Mnt1(N-terminus, *S. cerevisiae*) Kre2/Mnt1 (*S. cerevisiae*) Kre2 (*P. pastoris*) Ktr1 (*S. cerevisiae*) Ktr1 (*P. pastoris*) Mnn1 (*S. cerevisiae*) | OCH1 MNN4 MNN6 | UDP-Galactose transporter (human, *S. pombe*) |
| $NANA_{(1-4)}$-$Gal_{(1-4)}GlcNAc_{(2-4)}$-$Man_3GlcNAc_2$ | α-2,6-Sialyltransferase (human) α-2,3-Sialyltransferase | KTR1 MNN1 (N-terminus, *S. cerevisiae*) MNT1 (N-terminus, *S. cerevisiae*) Kre2/Mnt1 (*S. cerevisiae*) Kre2 (*P. pastoris*) | OCH1 MNN4 MNN6 | CMP-Sialic acid transporter (human) |

TABLE 6-continued

Some preferred embodiments for modifying glycosylation in a lower eukaroytic microorganism

| Desired Structure | Suitable Catalytic Activities | Suitable Sources of Localization Sequences | Suitable Gene Deletions | Suitable Transporters and/or Phosphatases |
|---|---|---|---|---|
| | | Ktr1 (*S. cerevisiae*) Ktr1 (*P. pastoris*) MNN1 (*S. cerevisiae*) | | |

As any strategy to engineer the formation of complex N-glycans into a host cell such as a lower eukaryote involves both the elimination as well as the addition of particular glycosyltransferase activities, a comprehensive scheme will attempt to coordinate both requirements. Genes that encode enzymes that are undesirable serve as potential integration sites for genes that are desirable. For example, 1,6 mannosyltransferase activity is a hallmark of glycosylation in many known lower eukaryotes. The gene encoding alpha-1,6 mannosyltransferase (OCH1) has been cloned from *S. cerevisiae* and mutations in the gene give rise to a viable phenotype with reduced mannosylation. The gene locus encoding alpha-1,6 mannosyltransferase activity therefore is a prime target for the integration of genes encoding glycosyltransferase activity. In a similar manner, one can choose a range of other chromosomal integration sites that, based on a gene disruption event in that locus, are expected to: (1) improve the cells ability to glycosylate in a more human-like fashion, (2) improve the cells ability to secrete proteins, (3) reduce proteolysis of foreign proteins and (4) improve other characteristics of the process that facilitate purification or the fermentation process itself.

Target Glycoproteins

The methods described herein are useful for producing glycoproteins, especially glycoproteins used therapeutically in humans. Glycoproteins having specific glycoforms may be especially useful, for example, in the targeting of therapeutic proteins. For example, mannose-6-phosphate has been shown to direct proteins to the lysosome, which may be essential for the proper function of several enzymes related to lysosomal storage disorders such as Gaucher's, Hunter's, Hurler's, Scheie's, Fabry's and Tay-Sachs disease, to mention just a few. Likewise, the addition of one or more sialic acid residues to a glycan side chain may increase the lifetime of a therapeutic glycoprotein in vivo after administration. Accordingly, host cells (e.g., lower eukaryotic or mammalian) may be genetically engineered to increase the extent of terminal sialic acid in glycoproteins expressed in the cells. Alternatively, sialic acid may be conjugated to the protein of interest in vitro prior to administration using a sialic acid transferase and an appropriate substrate. Changes in growth medium composition may be employed in addition to the expression of enzyme activities involved in human-like glycosylation to produce glycoproteins more closely resembling human forms (Weikert et al. (1999) *Nature Biotechnology* 17, 1116-1121; Werner et al. (1998) *Arzneimittelforschung* 48(8):870-880; Andersen and Goochee (1994) *Cur. Opin. Biotechnol.* 5:546-549; Yang and Butler (2000) *Biotechnol.Bioengin.* 68(4):370-380). Specific glycan modifications to monoclonal antibodies (e.g. the addition of a bisecting GlcNAc) have been shown to improve antibody dependent cell cytotoxicity (Umana et al. (1999) *Nat. Biotechnol.* 17(2):176-80), which may be desirable for the production of antibodies or other therapeutic proteins.

Therapeutic proteins are typically administered by injection, orally, pulmonary, or other means. Examples of suitable target glycoproteins which may be produced according to the invention include, without limitation: erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, interleukins, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, Dnase II, and α-feto proteins.

Expression of GnT-III to Boost Antibody Functionality

The addition of N-acetylglucosamine residues to the GlcNAcMan$_3$GlcNAc$_2$ structure by N-acetylglucosaminyltransferases II and III yields a so-called bisected N-glycan GlcNAc$_3$Man$_3$GlcNAc$_2$ (FIG. 15). This structure has been implicated in greater antibody-dependent cellular cytotoxicity (ADCC) (Umana et al. (1999) *Nat. Biotechnol.* 17(2):176-80). Re-engineering glycoforms of immunoglobulins expressed by mammalian cells is a tedious and cumbersome task. Especially in the case of GnTIII, where over-expression of this enzyme has been implicated in growth inhibition, methods involving regulated (inducible) gene expression had to be employed to produce immunoglobulins with bisected N-glycans (Umana et al. (1999) *Biotechnol Bioeng.* 65(5): 542-9; Umana et al. (1999) *Nat. Biotechnol.* 17(2):176-80); Umana et al. WO 03/011878; U.S. Pat. No. 6,602,684.

Accordingly, in another embodiment, the invention provides systems and methods for producing human-like N-glycans having bisecting N-acetylglucosamine (GlcNAc) on a trimannose or pentamannose core structure. In a preferred embodiment, the invention provides a system and method for producing immunoglobulins having bisected N-glycans. The systems and methods described herein will not suffer from previous problems, e.g., cytotoxicity associated with overexpression of GnTIII or ADCC, as the host cells of the invention are engineered and selected to be viable and preferably robust cells which produce N-glycans having substantially modified human-type glycoforms such as GlcNAc$_2$Man$_3$GlcNAc$_2$. Thus, addition of a bisecting N-acetylglucosamine in a host cell of the invention will have a negligible effect on the growth-phenotype or viability of those host cells.

In addition, work by others has shown that there is no linear correlation between GnTIII expression levels and the degree of ADCC. Umana et al. (1999) *Nature Biotechnol.* 17:176-80. Thus, finding the optimal expression level in mammalian cells and maintaining it throughout an FDA approved fermentation process seems to be a challenge. However, in cells of the invention, such as fungal cells, finding a promoter of appropriate strength to establish a robust, reliable and optimal GnTIII expression level is a comparatively easy task for one of skill in the art.

A host cell such as a yeast strain capable of producing glycoproteins with bisecting N-glycans is engineered according to the invention, by introducing into the host cell a GnTIII activity (Example 12). Preferably, the host cell is transformed with a nucleic acid that encodes GnTIII (see, e.g., FIG. 24) or a domain thereof having enzymatic activity, optionally fused to a heterologous cell signal targeting peptide (e.g., using the libraries and associated methods of the invention.) Host cells engineered to express GnTIII will produce higher antibody titers than mammalian cells are capable of. They will also produce antibodies with higher potency with respect to ADCC.

Antibodies produced by mammalian cell lines transfected with GnTIII have been shown to be as effective as antibodies produced by non-transfected cell-lines, but at a 10-20 fold lower concentration (Davies et al. (2001) *Biotechnol. Bioeng.* 74(4):288-94). An increase of productivity of the production vehicle of the invention over mammalian systems by a factor of twenty, and a ten-fold increase of potency will result in a net-productivity improvement of two hundred. The invention thus provides a system and method for producing high titers of an antibody having high potency (e.g., up to several orders of magnitude more potent than what can currently be produced). The system and method is safe and provides high potency antibodies at low cost in short periods of time. Host cells engineered to express GnTIII according to the invention produce immunoglobulins having bisected N-glycans at rates of at least 50 mg/liter/day to at least 500 mg/liter/day. In addition, each immunoglobulin (Ig) molecule (comprising bisecting GlcNAcs) is more potent than the same Ig molecule produced without bisecting GlcNAcs.

The following are examples which illustrate various aspects of the invention. These examples should not be construed as limiting: the examples are included for the purposes of illustration only.

Example 1

Cloning and Disruption of the OCH1 Gene in *P. pastoris*

Generation of an OCH1 Mutant of *P. pastoris*:

A 1215 bp ORF of the *P. pastoris* OCH1 gene encoding a putative α-1,6 mannosyltransferase was amplified from *P. pastoris* genomic DNA (strain X-33, Invitrogen, Carlsbad, Calif.) using the oligonucleotides 5'-ATGGCGAAGGCA-GATGGCAGT-3' (SEQ ID NO:3) and 5'-TTAGTCCTTC-CAACTTCCTTC-3' (SEQ ID NO:4) which were designed based on the *P. pastoris* OCH1 sequence (Japanese Patent Application Publication No. 8-336387). Subsequently, 2685 bp upstream and 1175 bp downstream of the ORF of the OCH1 gene were amplified from a *P. pastoris* genomic DNA library (Boehm, T. et al. (1999) *Yeast* 15(7):563-72) using the internal oligonucleotides 5'-ACTGCCATCTGCCTTCGC-CAT-3' (SEQ ID NO:47) in the OCH1 gene, and 5'-GTAATACGACTCACTATAGGGC-3' T7 (SEQ ID NO:48) and 5'-AATTAACCCTCACTAAAGGG-3' T3 (SEQ ID NO:49) oligonucleotides in the backbone of the library bearing plasmid lambda ZAP II (Stratagene, La Jolla, Calif.). The resulting 5075 bp fragment was cloned into the pCR2.1-TOPO vector (Invitrogen, Carlsbad, Calif.) and designated pBK9.

After assembling a gene knockout construct that substituted the OCH1 reading frame with a HIS4 resistance gene, *P. pastoris* was transformed and colonies were screened for temperature sensitivity at 37° C. OCH1 mutants of *S. cerevisiae* are temperature sensitive and are slow growers at elevated temperatures. One can thus identify functional homologs of OCH1 in *P. pastoris* by complementing an OCH1 mutant of *S. cerevisiae* with a *P. pastoris* DNA or cDNA library. About 20 temperature sensitive strains were further subjected to a colony PCR screen to identify colonies with a deleted och1 gene. Several och1 deletions were obtained.

The linearized pBK9.1, which has 2.1 kb upstream sequence and 1.5 kb downstream sequence of OCH1 gene cassette carrying *Pichia* HIS4 gene, was transformed into *P. pastoris* BK1 [GS115 (his4 Invitrogen Corp., San Diego, Calif.) carrying the human IFN-β gene in the AOX1 locus] to knock out the wild-type OCH1 gene. The initial screening of transformants was performed using histidine drop-out medium followed by replica plating to select the temperature sensitive colonies. Twenty out of two hundred histidine-positive colonies showed a temperature sensitive phenotype at 37° C. To exclude random integration of pBK9.1 into the *Pichia* genome, the 20 temperature-sensitive isolates were subjected to colony PCR using primers specific to the upstream sequence of the integration site and to HIS4 ORF. Two out of twenty colonies were och1 defective and further analyzed using a Southern blot and a Western blot indicating the functional och1 disruption by the och1 knock-out construct. Genomic DNA were digested using two separate restriction enzymes BglII and ClaI to confirm the och1 knock-out and to confirm integration at the open reading frame. The Western Blot showed och1 mutants lacking a discrete band produced in the GS 115 wild type at 46.2 kDa.

Example 2

Engineering of *P. pastoris* with α-1,2-Mannosidase to Produce $Man_5GlcNAc_2$-Containing IFN-β Precursors An α-1,2-mannosidase is required for the trimming of $Man_8GlcNAc_2$ to yield $Man_5GlcNAc_2$, an essential intermediate for complex N-glycan formation. While the production of a $Man_5GlcNAc_2$ precursor is essential, it is not necessarily sufficient for the production of hybrid and complex glycans because the specific isomer of $Man_5GlcNAc_2$ may or may not be a substrate for GnTI. An och1 mutant of *P. pastoris* is engineered to express secreted human interferon-β under the control of an aox promoter. A DNA library is constructed by the in-frame ligation of the catalytic domain of human mannosidase IB (an α-1,2-mannosidase) with a sub-library including sequences encoding early Golgi and ER localization peptides. The DNA library is then transformed into the host organism, resulting in a genetically mixed population wherein individual transformants each express interferon-β as well as a synthetic mannosidase gene from the library. Individual transformant colonies are cultured and the production of interferon is induced by addition of methanol. Under these conditions, over 90% of the secreted protein is glycosylated interferon-β.

Supernatants are purified to remove salts and low-molecular weight contaminants by $C_{18}$ silica reversed-phase chromatography. Desired transformants expressing appropriately targeted, active α-1,2-mannosidase produce interferon-β including N-glycans of the structure $Man_5GlcNAc_2$, which has a reduced molecular mass compared to the interferon-β of the parent strain. The purified interferon-β is analyzed by MALDI-TOF mass spectroscopy and colonies expressing the desired form of interferon-β are identified.

Example 3

Generation of an och1 Mutant Strain Expressing an α-1,2-Mannosidase, GnTI and GnTII for Production of a Human-Like Glycoprotein The 1215 bp open reading frame of the *P. pastoris* OCH1 gene as well as 2685 bp upstream and 1175 bp downstream was amplified by PCR (see also WO 02/00879), cloned into the pCR2.1-TOPO vector (Invitrogen) and designated pBK9. To create an och1 knockout strain containing multiple auxotrophic markers, 100 µg of pJN329, a plasmid containing an och1::URA3 mutant allele flanked with SfiI restriction sites was digested with SfiI and used to transform *P. pastoris* strain JC308 (Cereghino et al. (2001) *Gene* 263:159-169) by electroporation. Following incubation on defined medium lacking uracil for 10 days at room temperature, 1000 colonies were picked and re-streaked. URA$^+$ clones that were unable to grow at 37° C., but grew at room temperature, were subjected to colony PCR to test for the correct integration of the och1::URA3 mutant allele. One clone that exhibited the expected PCR pattern was designated YJN153. The Kringle 3 domain of human plasminogen (K3) was used as a model protein. A Neo$^R$ marked plasmid containing the K3 gene was transformed into strain YJN153 and a resulting strain, expressing K3, was named BK64-1.

Plasmid pPB103, containing the *Kluyveromyces lactis* MNN2-2 gene which encodes a Golgi UDP-N-acetylglucosamine transporter was constructed by cloning a blunt BglII-HindIII fragment from vector pDL02 (Abeijon et al. (1996) *Proc. Natl. Acad. Sci. U.S.A.* 93:5963-5968) into BglII and BamHI digested and blunt ended pBLADE-SX containing the *P. pastoris* ADE1 gene (Cereghino et al. (2001) *Gene* 263:159-169). This plasmid was linearized with EcoNI and transformed into strain BK64-1 by electroporation and one strain confirmed to contain the MNN2-2 by PCR analysis was named PBP1.

A library of mannosidase constructs was generated, comprising in-frame fusions of the leader domains of several type I or type II membrane proteins from *S. cerevisiae* and *P. pastoris* fused with the catalytic domains of several α-1,2-mannosidase genes from human, mouse, fly, worm and yeast sources (see, e.g., WO02/00879, incorporated herein by reference). This library was created in a *P. pastoris* HIS4 integration vector and screened by linearizing with SalI, transforming by electroporation into strain PBP1, and analyzing the glycans released from the K3 reporter protein. One active construct chosen was a chimera of the 988-1296 nucleotides (C-terminus) of the yeast SEC12 gene fused with a N-terminal deletion of the mouse α-1,2-mannosidase IA gene (FIG. 3), which was missing the 187 nucleotides. A *P. pastoris* strain expressing this construct was named PBP2.

A library of GnTI constructs was generated, comprising in-frame fusions of the same leader library with the catalytic domains of GnTI genes from human, worm, frog and fly sources (WO 02/00879). This library was created in a *P. pastoris* ARG4 integration vector and screened by linearizing with AatII, transforming by electroporation into strain PBP2, and analyzing the glycans released from K3. One active construct chosen was a chimera of the first 120 bp of the *S. cerevisiae* MNN9 gene fused to a deletion of the human GnTI gene, which was missing the first 154 bp. A *P. pastoris* strain expressing this construct was named PBP-3. (See also FIG. 36.)

A library of GnTII constructs was generated, which comprised in-frame fusions of the leader library with the catalytic domains of GnTII genes from human and rat sources (WO 02/00879). This library was created in a *P. pastoris* integration vector containing the NST$^R$ gene conferring resistance to the drug nourseothricin. The library plasmids were linearized with EcoRI, transformed into strain RDP27 by electroporation, and the resulting strains were screened by analysis of the released glycans from purified K3.

Materials for the Following Reactions

MOPS, sodium cacodylate, manganese chloride, UDP-galactose and CMP-N-acetylneuraminic acid were from Sigma. Trifluoroacetic acid (TFA) was from Sigma/Aldrich, Saint Louis, Mo. Recombinant rat α2,6-sialyltransferase from *Spodoptera frugiperda* and β1,4-galactosyltransferase from bovine milk were from Calbiochem (San Diego, Calif.). Protein N-glycosidase F, mannosidases, and oligosaccharides were from Glyko (San Rafael, Calif.). DEAE ToyoPearl resin was from TosoHaas. Metal chelating "HisBind" resin was from Novagen (Madison, Wis.). 96-well lysate-clearing plates were from Promega (Madison, Wis.). Protein-binding 96-well plates were from Millipore (Bedford, Mass.). Salts and buffering agents were from Sigma (St. Louis, Mo.). MALDI matrices were from Aldrich (Milwaukee, Wis.).

Protein Purification

Kringle 3 was purified using a 96-well format on a Beckman BioMek 2000 sample-handling robot (Beckman/Coulter Ranch Cucamonga, Calif.). Kringle 3 was purified from expression media using a C-terminal hexa-histidine tag. The robotic purification is an adaptation of the protocol provided by Novagen for their HisBind resin. Briefly, a 150 uL (µL) settled volume of resin is poured into the wells of a 96-well lysate-binding plate, washed with 3 volumes of water and charged with 5 volumes of 50 mM NiSO4 and washed with 3 volumes of binding buffer (5 mM imidazole, 0.5 M NaCl, 20 mM Tris-HCL pH7.9). The protein expression media is diluted 3:2, media/PBS (60 mM PO4, 16 mM KCl, 822 mM NaCl pH7.4) and loaded onto the columns. After draining, the columns are washed with 10 volumes of binding buffer and 6 volumes of wash buffer (30 mM imidazole, 0.5 M NaCl, 20 mM Tris-HCl pH7.9) and the protein is eluted with 6 volumes of elution buffer (1M imidazole, 0.5 M NaCl, 20 mM Tris-HCl pH7.9). The eluted glycoproteins are evaporated to dryness by lyophilyzation.

Release of N-Linked Glycans

The glycans are released and separated from the glycoproteins by a modification of a previously reported method (Papac, et al. A. J. S. (1998) *Glycobiology* 8, 445-454). The wells of a 96-well MultiScreen IP (Immobilon-P membrane) plate (Millipore) are wetted with 100 uL of methanol, washed with 3×150 uL of water and 50 uL of RCM buffer (8M urea, 360 mM Tris, 3.2 mM EDTA pH8.6), draining with gentle vacuum after each addition. The dried protein samples are dissolved in 30 uL of RCM buffer and transferred to the wells containing 10 uL of RCM buffer. The wells are drained and washed twice with RCM buffer. The proteins are reduced by addition of 60 uL of 0.1M DTT in RCM buffer for 1 hr at 37° C. The wells are washed three times with 300 uL of water and carboxymethylated by addition of 60 uL of 0.1M iodoacetic acid for 30 min in the dark at room temperature. The wells are again washed three times with water and the membranes blocked by the addition of 100 uL of 1% PVP 360 in water for 1 hr at room temperature. The wells are drained and washed three times with 300 uL of water and deglycosylated by the addition of 30 uL of 10 mM $NH_4HCO_3$ pH 8.3 containing one milliunit of N-glycanase (Glyko). After 16 hours at 37° C., the solution containing the glycans was removed by centrifugation and evaporated to dryness.

Matrix Assisted Laser Desorption Ionization Time of Flight Mass Spectrometry

Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybenzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than $5\times10^{-7}$ torr, and the low mass gate was 875 Da. Spectra were generated from the sum of 100-200 laser pulses and acquired with a 2 GHz digitizer. $Man_5GlcNAc_2$ oligosaccharide was used as an external molecular weight standard. All spectra were generated with the instrument in the positive ion mode. The estimated mass accuracy of the spectra was 0.5%.

Example 4

Engineering of *P. pastoris* to Produce $Man_5GlcNAc_2$ as the Predominant N-Glycan Structure Using a Combinatorial DNA Library An och1 mutant of *P. pastoris* (see Examples 1 and 3) was engineered to express and secrete proteins such as the kringle 3 domain of human plasminogen (K3) under the control of the inducible AOXI promoter. The Kringle 3 domain of human plasminogen (K3) was used as a model protein. A DNA fragment encoding the K3 was amplified using Pfu turbo polymerase (Strategene, La Jolla, Calif.) and cloned into EcoRI and XbaI sites of pPICZαA (Invitrogen, Carlsbad, Calif.), resulting in a C-terminal 6-His tag. In order to improve the N-linked glycosylation efficiency of K3 (Hayes et al. 1975 *J Arch. Biochem. Biophys.* 171, 651-655), $Pro_{46}$ was replaced with $Ser_{46}$ using site-directed mutagenesis. The resulting plasmid was designated pBK64. The correct sequence of the PCR construct was confirmed by DNA sequencing.

A combinatorial DNA library was constructed by the in-frame ligation of murine α-1,2-mannosidase IB (Genbank AN 6678787) and IA (Genbank AN 6754619) catalytic domains with a sub-library including sequences encoding Cop II vesicle, ER, and early Golgi localization peptides according to Table 6. The combined DNA library was used to generate individual fusion constructs, which were then transformed into the K3 expressing host organism, resulting in a genetically mixed population wherein individual transformants each express K3 as well as a localization signal/mannosidase fusion gene from the library. Individual transform ants were cultured and the production of K3 was induced by transfer to a methanol containing medium. Under these conditions, after 24 hours of induction, over 90% of the protein in the medium was K3. The K3 reporter protein was purified from the supernatant to remove salts and low-molecular weight contaminants by Ni-affinity chromatography. Following affinity purification, the protein was desalted by size exclusion chromatography on a Sephadex G10 resin (Sigma, St. Louis, Mo.) and either directly subjected to MALDI-TOF analysis described below or the N-glycans were removed by PNGase digestion as described below (Release of N-glycans) and subjected to MALDI-TOF analysis Miele et al. (1997) *Biotechnol. Appl. Biochem.* 25:151-157.

Figure 5:
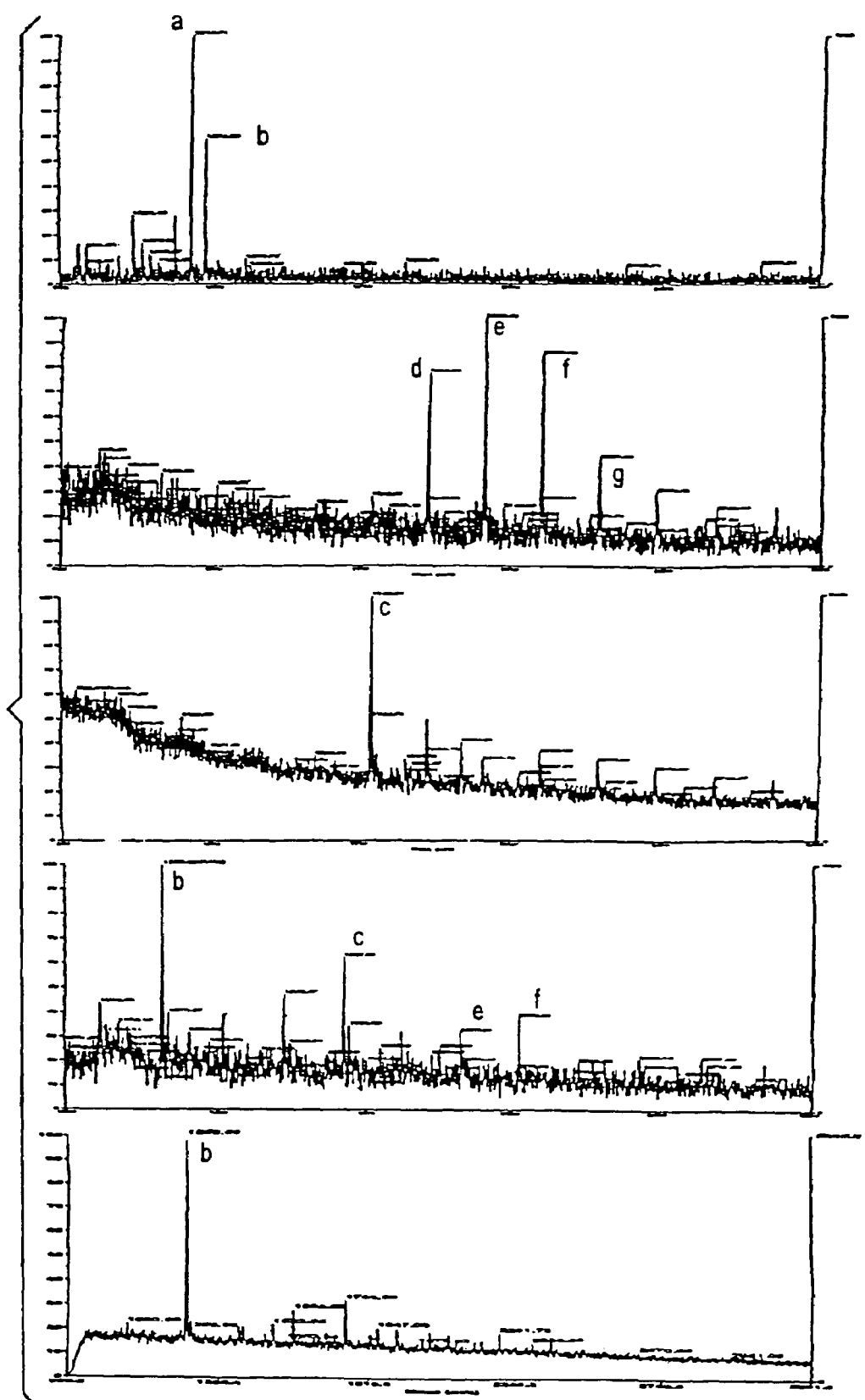
FIGS. 5A-5E show MALDI-TOF analysis demonstrating production of kringle 3 domain of human plasminogen (K3) glycoproteins having Man$_5$GlcNAc$_2$ as the predominant N-glycan structure in *P. pastoris*.
Figure 5A:
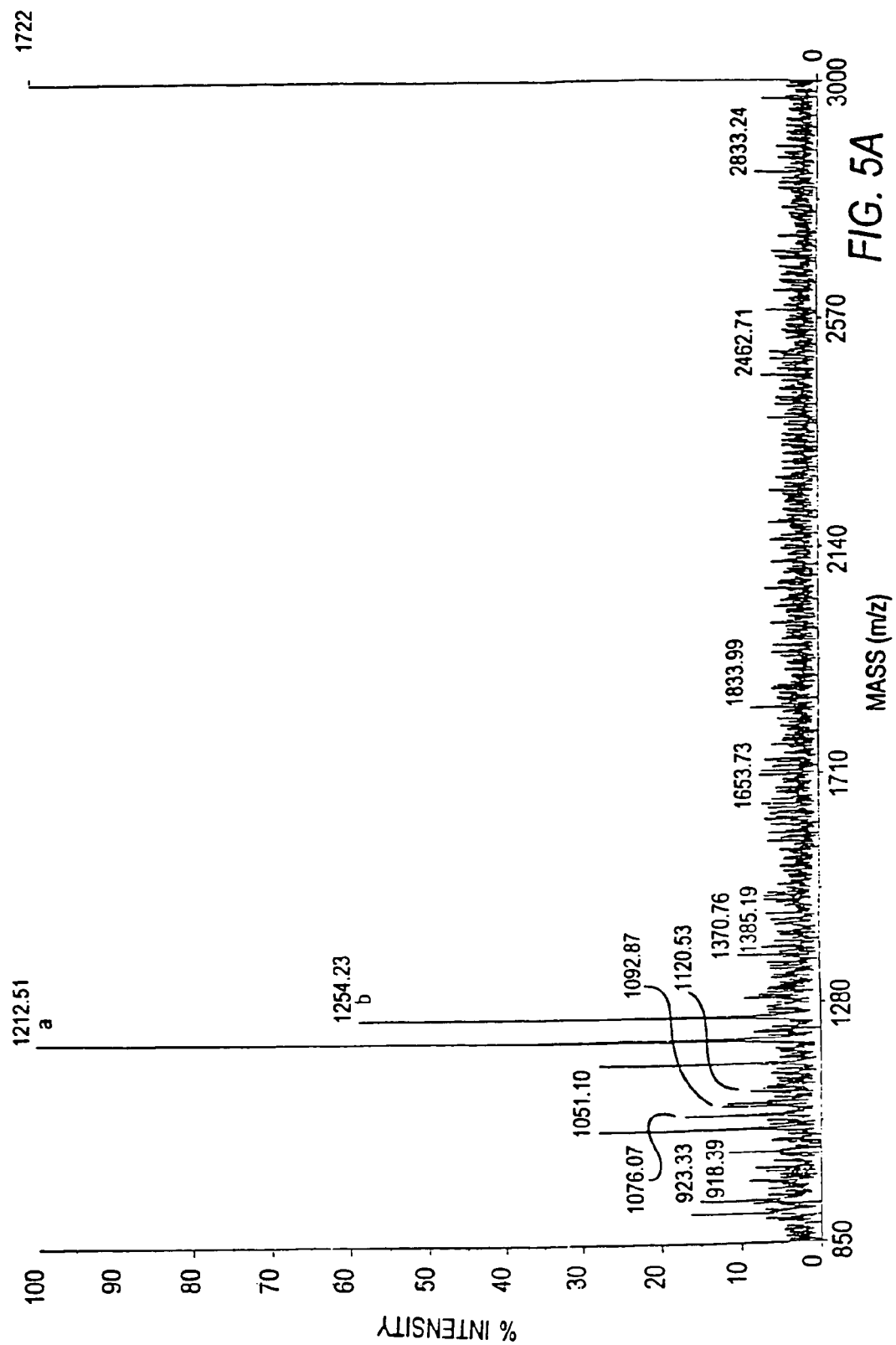
Figure 5B:
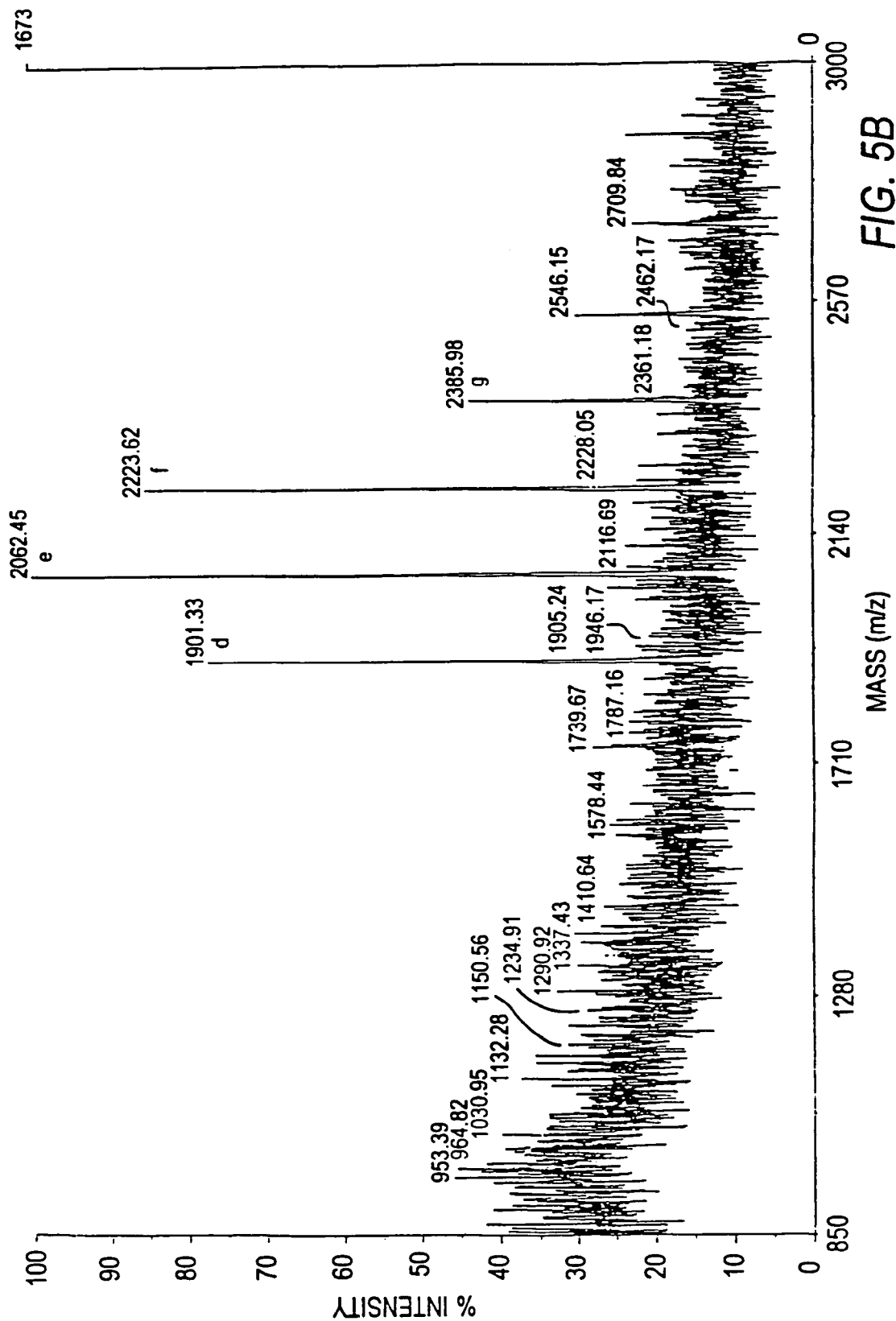
Figure 5C:
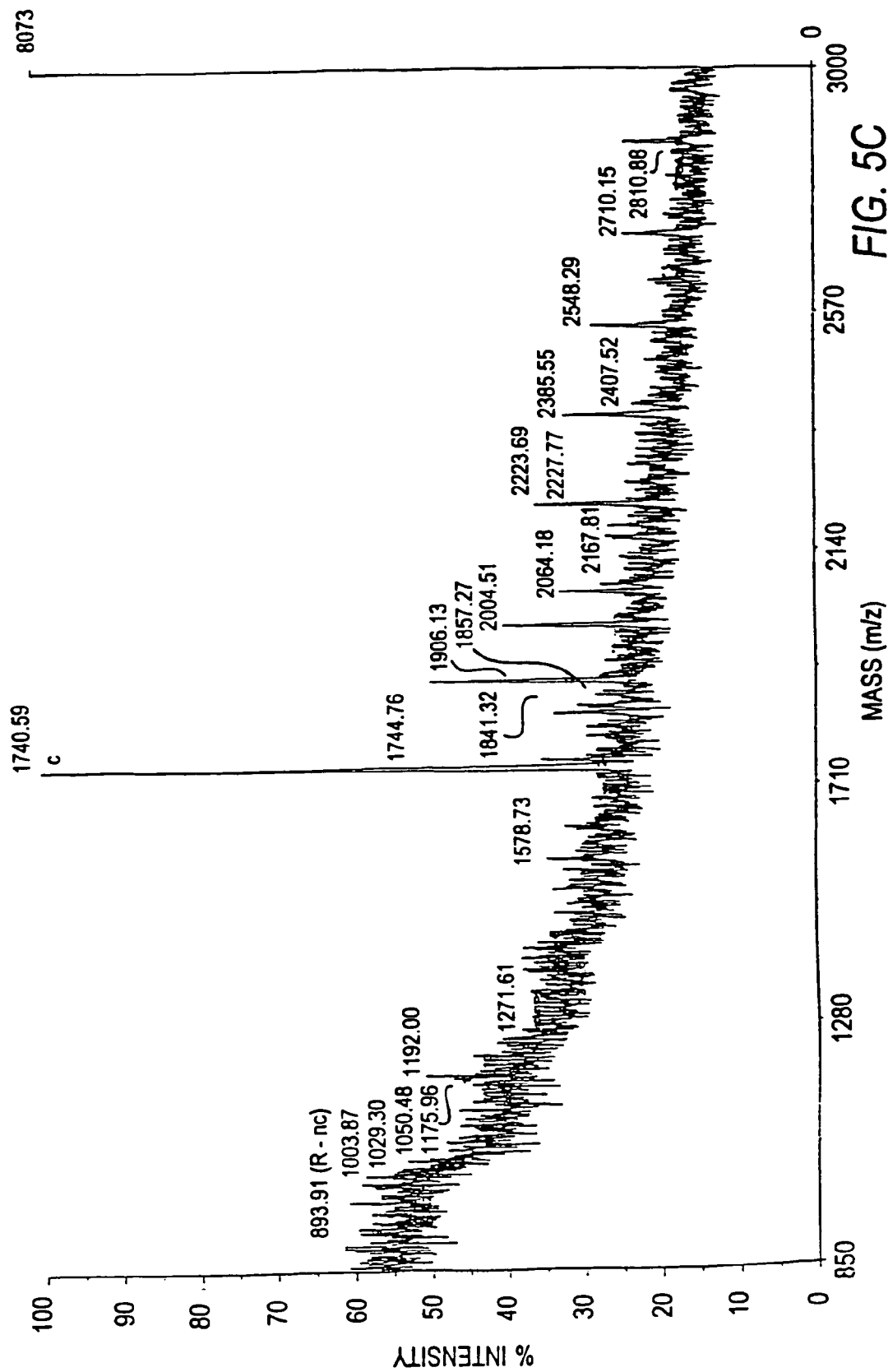
Figure 5E:
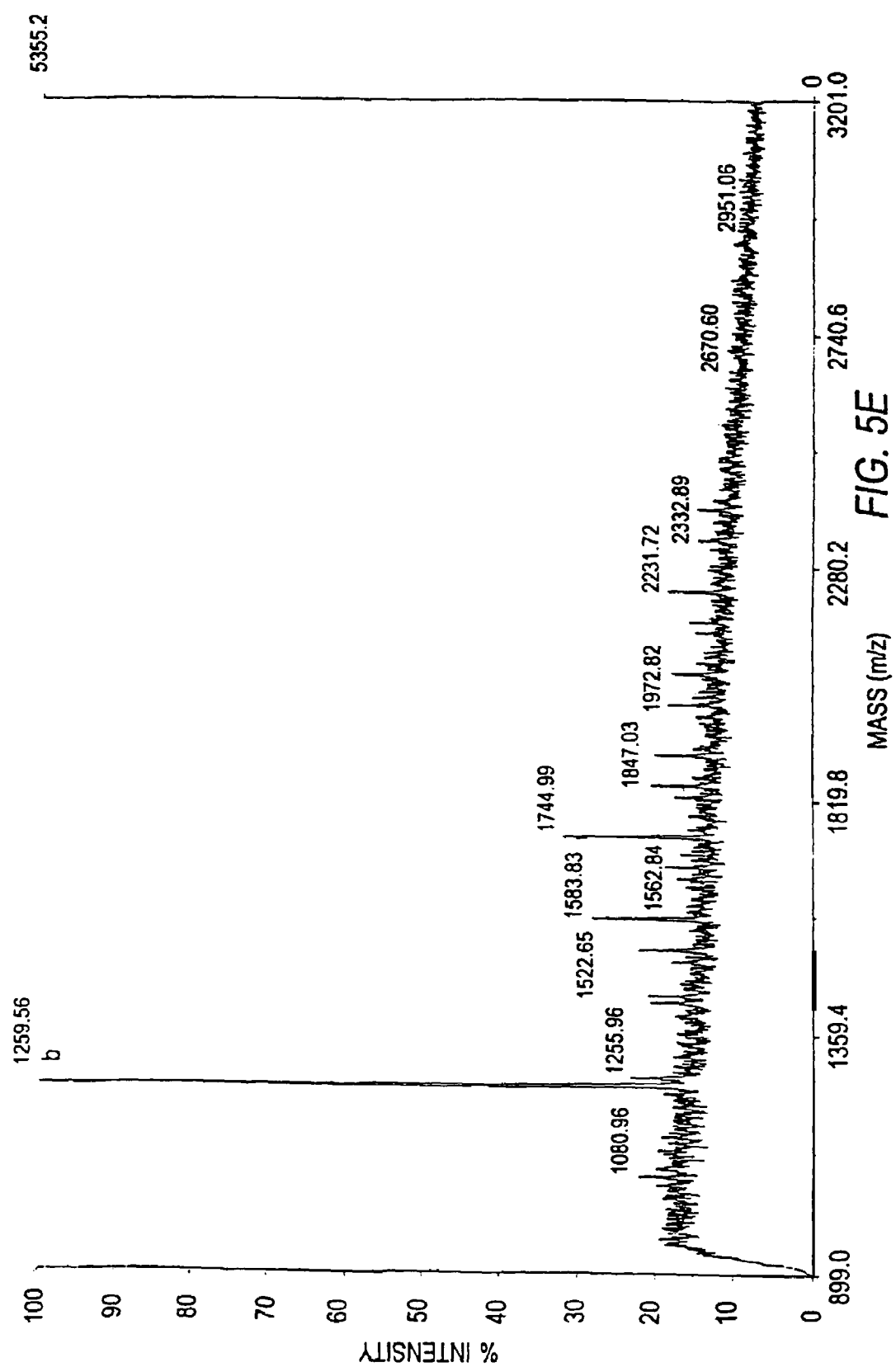

Following this approach, a diverse set of transformants were obtained; some showed no modification of the N-glycans compared to the och1 knockout strain; and others showed a high degree of mannose trimming (FIGS. 5D and 5E). Desired transformants expressing appropriately targeted, active α-1,2-mannosidase produced K3 with N-glycans of the structure $Man_5GlcNAc_2$. This confers a reduced molecular mass to the glycoprotein compared to the K3 of the parent och1 deletion strain, a difference which was readily detected by MALDI-TOF mass spectrometry (FIG. 5). Table 7 indicates the relative $Man_5GlcNAc_2$ production levels.

TABLE 7

A representative combinatorial DNA library of localization sequences/catalytic domains exhibiting relative levels of $Man_5GlcNAc_2$ production.

| | | Targeting peptide sequences | | | | |
|---|---|---|---|---|---|---|
| | | MNS1(s) | MNS1(m) | MNS1(I) | SEC12(s) | SEC12(m) |
| Catalytic Domians | Mouse mannosidase 1A Δ187 | FB4 ++ | FB5 + | FB6 − | FB7 ++ | FB8 ++++ |
| | Mouse mannosidase 1B Δ58 | GB4 ++ | GB5 + | GB6 + | GB7 ++ | GB8 + |
| | Mouse mannosidase 1B Δ99 | GC4 − | GC5 +++ | GC6 + | GC7 + | GC8 + |
| | Mouse mannosidase 1B Δ170 | GD4 − | GD5 − | GD6 − | GD7 + | GD8 + |

TABLE 8

Another combinatorial DNA library of localization sequences/catalytic domains exhibiting relative levels of Man$_5$GlcNAc$_2$ production.

| | | Targeting peptide sequences | | | | | |
|---|---|---|---|---|---|---|---|
| | | VAN1(s) | VAN1(m) | VANi(l) | MNN10(s) | MNN10(m) | MNN10(l) |
| Catalytic Domians | C. elegans mannosidase 1B Δ80 | BC18-5 +++++ | BC19 ++++ | BC20 +++ | BC27 +++++ | BC28 +++++ | BC29 +++ |
| | C. elegans mannosidase 1B Δ31 | BB18 +++++ | BB19 +++++ | BB20 ++++ | BB18 +++++ | BB19 +++++ | BB20 ++++ |

Targeting peptides were selected from MNS I (SwissProt P32906) in *S. cerevisiae* (long, medium and short) (see supra Nucleic Acid Libraries; Combinatorial DNA Library of Fusion Constructs) and SEC12 (SwissProt P11655) in *S. cerevisiae* (988-1140 nucleotides: short) and (988-1296: medium). Although majority of the targeting peptide sequences were N-terminal deletions, some targeting peptide sequences, such as SEC12 were C-terminal deletions. Catalytic domains used in this experiment were selected from mouse mannosidase 1A with a 187 amino acid N-terminal deletion; and mouse mannosidase 1B with a 58, 99 and 170 amino acid deletion. The number of (+)s, as used herein, indicates the relative levels of Man$_5$GlcNAc$_2$ production. The notation (−) indicates no apparent production of Man$_5$GlcNAc$_2$. The notation (+) indicates less than 10% production of Man$_5$GlcNAc$_2$ The notation (++) indicates about 10-20% production of Man$_5$GlcNAc$_2$. The notation with (+++) indicates about 20-40% production of Man$_5$GlcNAc$_2$. The notation with (++++) indicates about 50% production of Man$_5$GlcNAc$_2$. The notation with (+++++) indicates greater than 50% production of Man$_5$GlcNAC$_2$.

Table 9 shows relative amount of Man$_5$GlcNAc$_2$ on secreted K3. Six hundred and eight (608) different strains of *P. pastoris*, Δoch1 were generated by transforming them with a single construct of a combinatorial genetic library that was generated by fusing nineteen (19) α-1,2 mannosidase catalytic domains to thirty-two (32) fungal ER, and cis-Golgi leaders.

TABLE 9

| Amount of Man$_5$GlcNAc$_2$ on secreted K3 (% of total glycans) | Number of constructs (%) |
|---|---|
| N.D.* | 19 (3.1) |
| 0-10% | 341 (56.1) |
| 10-20% | 50 (8.2) |
| 20-40& | 75 (12.3) |
| 40-60% | 72 (11.8) |
| More than 60% | 51 (8.4)† |
| Total | 608 (100) |

*Several fusion constructs were not tested because the corresponding plasmids could not be propagated in *E. coli* prior to transformation into *P. pastoris*.
†Clones with the highest degree of Man$_5$GlcNAc$_2$ trimming (30/51) were further analyzed for mannosidase activity in the supernatant of the medium. The majority (28/30) displayed detectable mannosidase activity in the supernatant (e.g. FIG. 4B). Only two constructs displayed high Man$_5$GlcNAc$_2$ levels, while lacking mannosidase activity in the medium (e.g. FIG. 4C).

Table 7 shows two constructs pFB8 and pGC5, among others, displaying Man$_5$GlcNAc$_2$. Table 8 shows a more preferred construct, pBC18-5, a *S. cerevisiae* VAN1(s) targeting peptide sequence (from SwissProt 23642) ligated in-frame to a *C. elegans* mannosidase IB (Genbank AN CAA98114) 80 amino acid N-terminal deletion (*Saccharomyces* Van1(s)/*C. elegans* mannosidase IB Δ80). This fusion construct also produces a predominant Man$_5$GlcNAc$_2$ structure, as shown in FIG. 5E. This construct was shown to produce greater than 50% Man$_5$GlcNAc$_2$ (+++++).

Generation of a Combinatorial Localization/Mannosidase Library:

Generating a combinatorial DNA library of α-1,2-mannosidase catalytic domains fused to targeting peptides required the amplification of mannosidase domains with varying lengths of N-terminal deletions from a number of organisms. To approach this goal, the full length open reading frames (ORFs) of α-1,2-mannosidases were PCR amplified from either cDNA or genomic DNA obtained from the following sources: *Homo sapiens, Mus musculus, Drosophila melanogaster, Caenorhabditis elegans, Aspergillus nidulans* and *Penicillium citrinum*. In each case, DNA was incubated in the presence of oligonucleotide primers specific for the desired mannosidase sequence in addition to reagents required to perform the PCR reaction. For example, to amplify the ORF of the *M. musculus* α-1,2-mannosidase IA, the 5'-primer ATGCCCGTGGGGGGCCTGTTGC-CGCTCTTCAGTAGC (SEQ ID NO:52) and the 3'-primer TCATTTCTCTTTGCCATCAATTTCCT-TCTTCTGTTCACGG (SEQ ID NO:53) were incubated in the presence of Pfu DNA polymerase (Stratagene, La Jolla, Calif.) and amplified under the conditions recommended by Stratagene using the cycling parameters: 94° C. for 1 min (1 cycle); 94° C. for 30 sec, 68° C. for 30 sec, 72° C. for 3 min (30 cycles). Following amplification the DNA sequence encoding the ORF was incubated at 72° C. for 5 min with 1 U Taq DNA polymerase (Promega, Madison, Wis.) prior to ligation into pCR2.1-TOPO (Invitrogen, Carlsbad, Calif.) and transformed into TOP 10 chemically competent *E. coli*, as recommended by Invitrogen. The cloned PCR product was confirmed by ABI sequencing using primers specific for the mannosidase ORF.

To generate the desired N-terminal truncations of each mannosidase, the complete ORF of each mannosidase was used as the template in a subsequent round of PCR reactions wherein the annealing position of the 5'-primer was specific to the 5'-terminus of the desired truncation and the 3'-primer remained specific for the original 3'-terminus of the ORF. To facilitate subcloning of the truncated mannosidase fragment into the yeast expression vector, pJN347 (FIG. 2C) AscI and PacI restriction sites were engineered onto each truncation product, at the 5'- and 3'-termini respectively. The number and position of the N-terminal truncations generated for each mannosidase ORF depended on the position of the transmembrane (TM) region in relation to the catalytic domain (CD). For instance, if the stem region located between the TM and CD was less than 150 bp, then only one truncation for that protein was generated. If, however, the stem region was longer than 150 bp then either one or two more truncations were generated depending on the length of the stem region.

Figure 3:
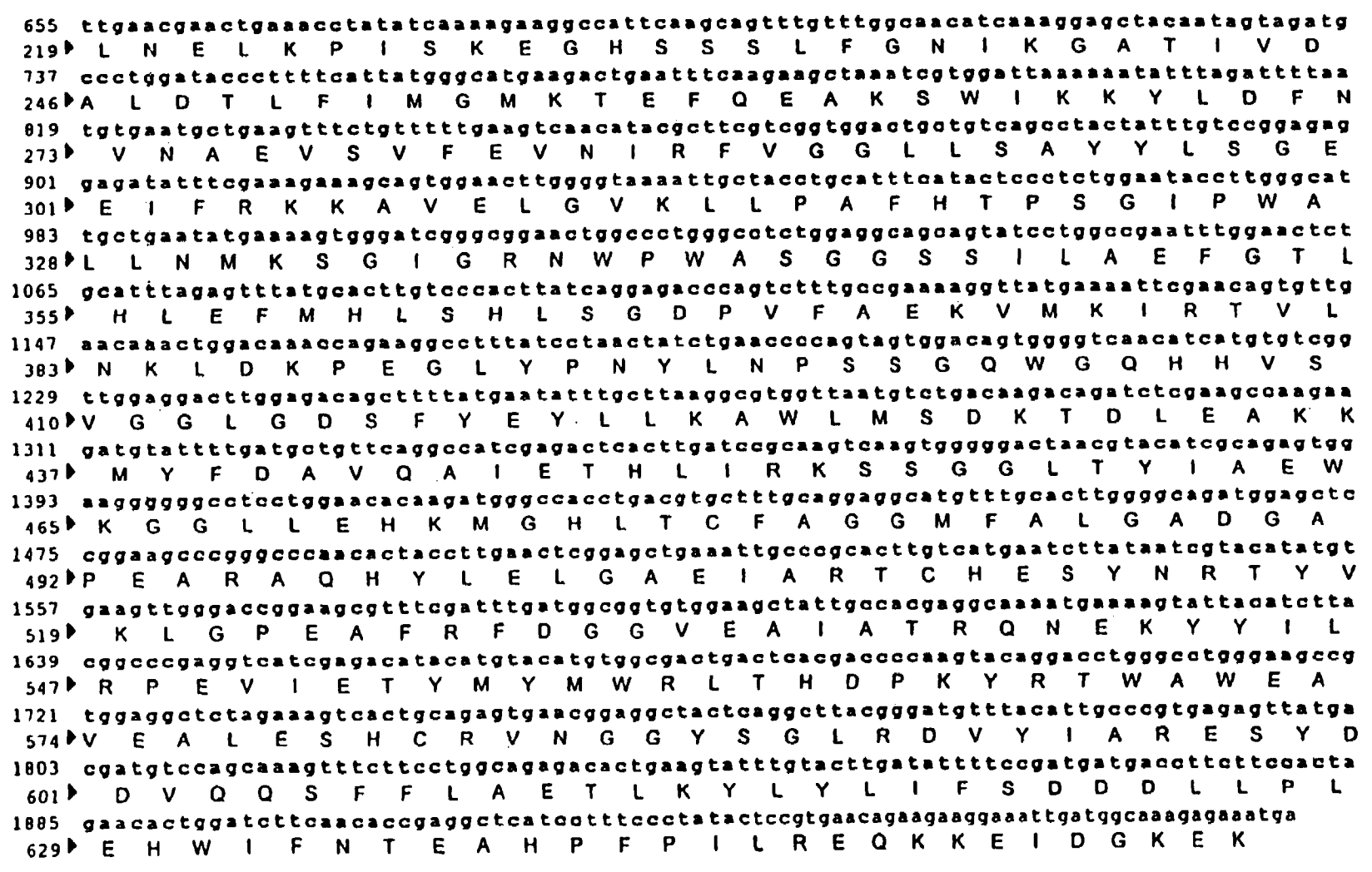

An example of how truncations for the *M. musculus* mannosidase IA (Genbank AN 6678787) were generated is described herein, with a similar approach being used for the other mannosidases. FIG. 3 illustrates the ORF of the *M. musculus* α-1,2-mannosidase IA with the predicted transmembrane and catalytic domains being highlighted in bold. Based on this structure, three 5'-primers were designed (annealing positions underlined in FIG. 3) to generate the Δ65-, Δ105- and Δ187-N-terminal deletions. Using the Δ65 N-terminal deletion as an example the 5'-primer used was 5'-GGCGCGCCGACTCCTCCAAGCTGCT-CAGCGGGGTCCTGTTCCAC-3' (SEQ ID NO:54) (with the AscI restriction site highlighted in bold) in conjunction with the 3'-primer 5'-CCTTAATTAATCATTTCTCTTTGC-CATCAATTTCCTTCTTCTGTTCACGG-3' (SEQ ID NO:55) (with the PacI restriction site highlighted in bold). Both of these primers were used to amplify a 1561 bp fragment under the conditions outlined above for amplifying the full length *M. musculus* mannosidase 1A ORF. Furthermore, like the product obtained for the full length ORF, the truncated product was also incubated with Taq DNA polymerase, ligated into pCR2.1-TOPO (Invitrogen, Carlsbad, Calif.), transformed into TOP10 and ABI sequenced. After having amplified and confirmed the sequence of the truncated mannosidase fragment, the resulting plasmid, pCR2.1-Δ65 mMannIA, was digested with AscI and PacI in New England Biolabs buffer #4 (Beverly, Mass.) for 16 h at 37° C. In parallel, the pJN347 (FIG. 2C) was digested with the same enzymes and incubated as described above. Post-digestion, both the pJN347 (FIG. 2C) back-bone and the truncated catalytic domain were gel extracted and ligated using the Quick Ligation Kit (New England Biolabs, Beverly, Mass.), as recommended by the manufacturers, and transformed into chemically competent DH5α cells (Invitrogen, Carlsbad, Calif.). Colony PCR was used to confirm the generation of the pJN347-mouse Mannosidase IAΔ65 construct.

Having generated a library of truncated α-1,2-mannosidase catalytic domains in the yeast expression vector pJN347 (FIG. 2C) the remaining step in generating the targeting peptide/catalytic domain library was to clone in-frame the targeting peptide sequences (FIG. 2). Both the pJN347-mannosidase constructs (FIG. 2D) and the pCR2.1TOPO-targeting peptide constructs (FIG. 2B) such as were incubated overnight at 37° C. in New England Biolabs buffer #4 in the presence of the restriction enzymes NotI and AscI. Following digestion, both the pJN347-mannosidase back-bone and the targeting peptide regions were gel-extracted and ligated using the Quick Ligation Kit (New England Biolabs, Beverly, Mass.), as recommended by the manufacturers, and transformed into chemically competent DH5α cells (Invitrogen, Carlsbad, Calif.). Subsequently, the pJN347-targeting peptide/mannosidase constructs were ABI sequenced to confirm that the generated fusions were in-frame. The estimated size of the final targeting peptide/alpha-1,2-mannosidase library contains over 1300 constructs generated by the approach described above. FIG. 2 illustrates construction of the combinatorial DNA library.

Figure 4A:
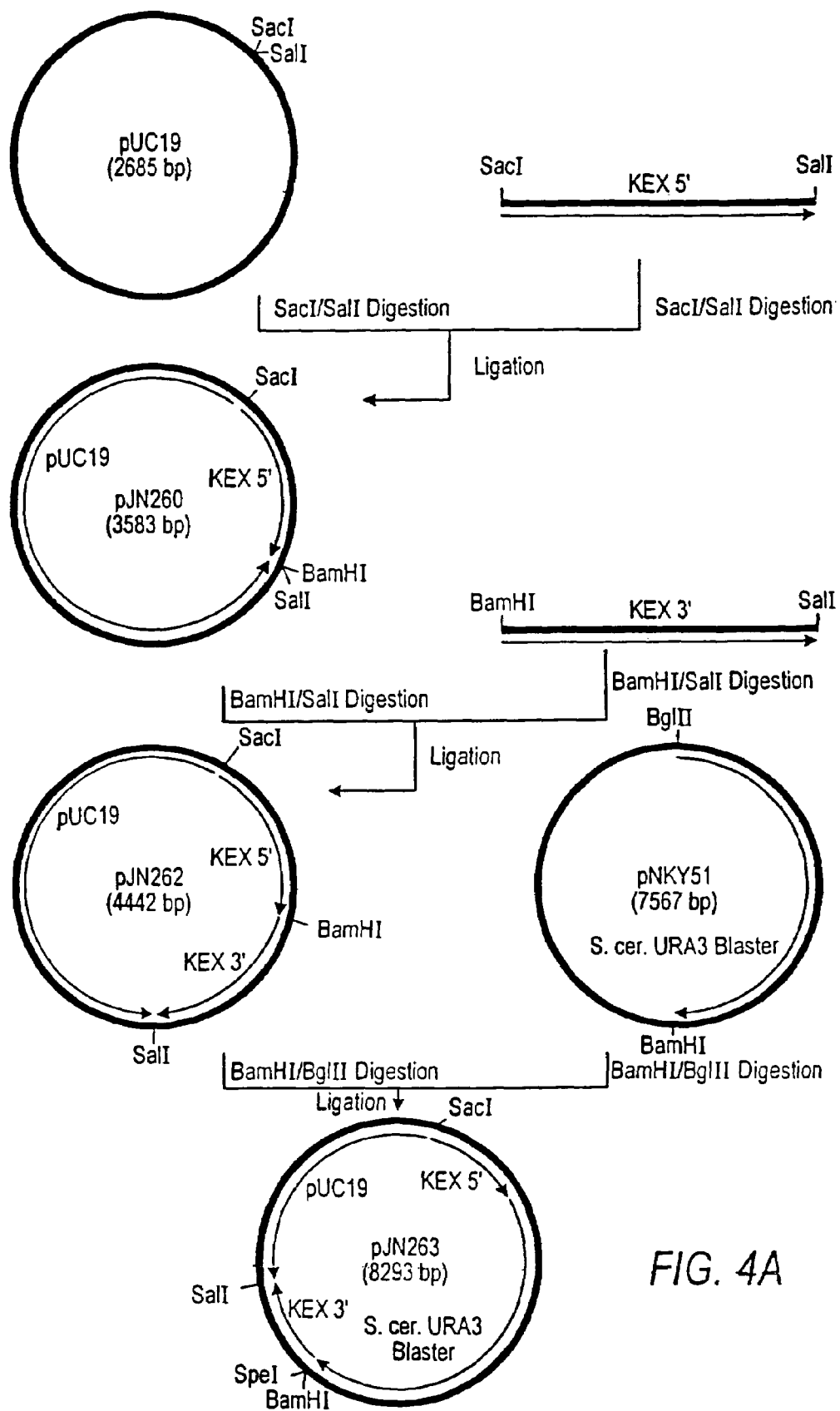
FIG. 4 illustrates engineering of vectors with multiple auxotrophic markers and genetic integration of target proteins in the *P. pastoris* OCH1 locus.
Figure 4B:
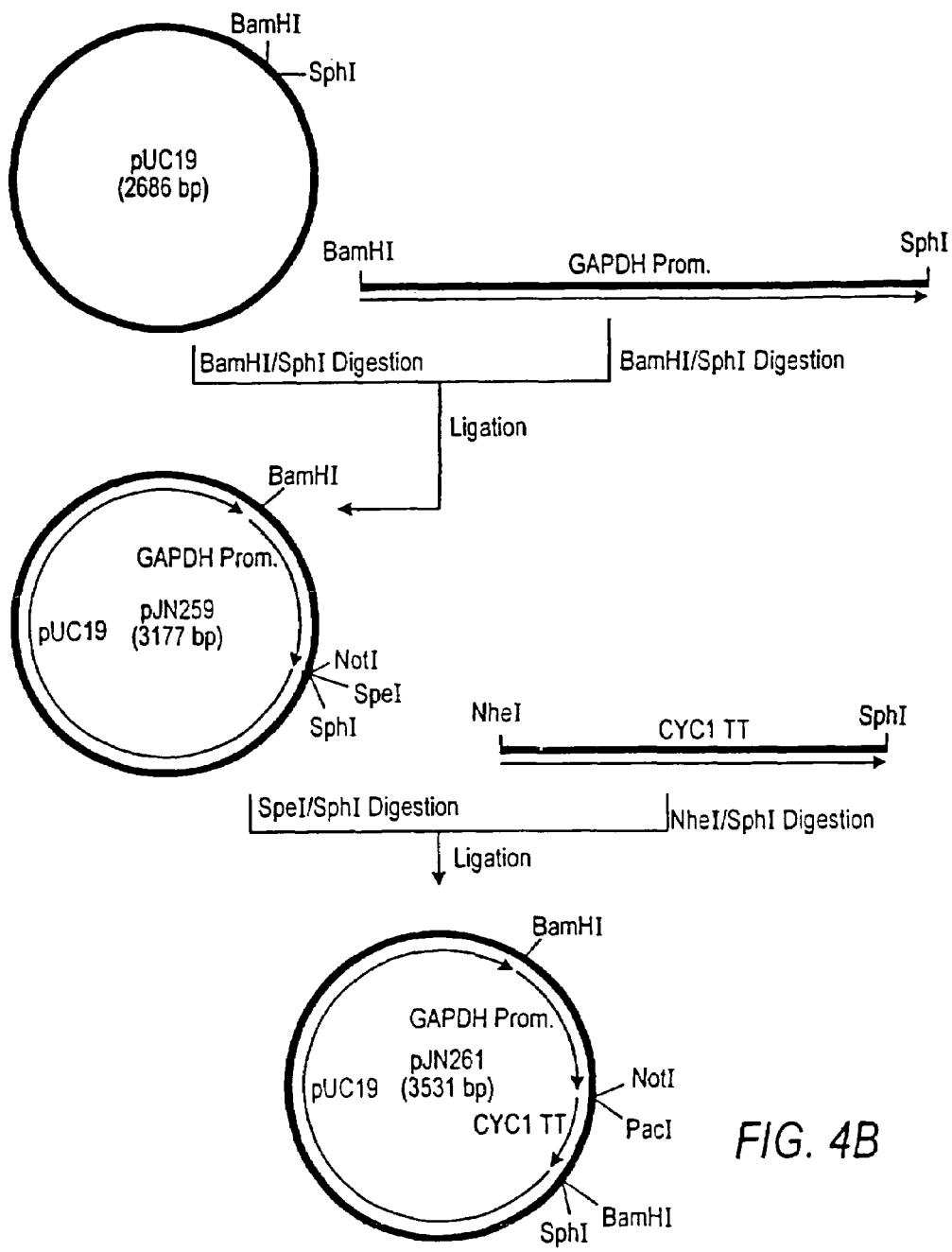

Engineering a *P. pastoris* OCH1 Knock-Out Strain with Multiple Auxotrophic Markers The first step in plasmid construction involved creating a set of universal plasmids containing DNA regions of the KEX1 gene of *P. pastoris* (Boehm et al. *Yeast* 1999 May; 15(7):563-72) as space holders for the 5' and 3' regions of the genes to be knocked out. The plasmids also contained the *S. cerevisiae* Ura-blaster (Alani et al. (1987) *Genetics* 116:541-545) as a space holder for the auxotrophic markers, and an expression cassette with a multiple cloning site for insertion of a foreign gene. A 0.9-kb fragment of the *P. pastoris* KEX1-5' region was amplified by PCR using primers GGCG<u>AGCTCGGCCTACCCGGCC</u>AAGGCTGAGATCA TTTGTCCAGCTTCAGA (SEQ ID NO:56) and GCCCAC<u>GTCGACGGATCCGTTTAAAC</u>ATCGATTGG AGAGGC TGACACCGCTACTA (SEQ ID NO:57) and *P. pastoris* genomic DNA as a template and cloned into the SacI, SalI sites of pUC19 (New England Biolabs, Beverly, Mass.). The resulting plasmid was cut with BamHI and SalI, and a 0.8-kb fragment of the KEX1-3' region that had been amplified using primers CG<u>GGATCCACTAGTATTTAAAT</u>CATATGTGCGAGT GTACAACTCTTCCCACATGG (SEQ ID NO:58) and GGACGC<u>GTCGACGGCCTACCCGGCC</u>GTACGAGGA ATTTCTCGGATGACTCTTTTC (SEQ ID NO:59) was cloned into the open sites creating pJN262. This plasmid was cut with BamHI and the 3.8-kb BamHI, BglII fragment of pNKY51 (Alani et al. (1987) *Genetics* 116:541-545) was inserted in both possible orientations resulting in plasmids pJN263 (FIG. 4A) and pJN284 (FIG. 4B).

An expression cassette was created with NotI and PacI as cloning sites. The GAPDH promoter of *P. pastoris* was amplified using primers CG<u>GGATCCCTCGAGAGATCT</u>TTTTTGTAGAAATG TCTTGGTGCCT (SEQ ID NO:60) and GGACAT<u>GCATGCACTAGTGCGGCCGCCACGTG</u>ATA GTTGTTCAATTGATTGAAATAGGGACAA (SEQ ID NO:61) and plasmid pGAPZ-A (Invitrogen) as template and cloned into the BamHI, SphI sites of pUC19 (New England Biolabs, Beverly, Mass.) (FIG. 4B). The resulting plasmid was cut with SpeI and SphI and the CYC1 transcriptional terminator region ("TT") that had been amplified using primers CCTT<u>GCTAGCTTAATTAACCGCGG</u>CACGTCCGACG GCGGCCCACGGGTCCCA (SEQ ID NO:62) and GGACAT<u>GCATGCGGATCCCTTAAGAGCCGGC</u>AG CTTGCAAATTAAAGCCTTCGAGCGTCCC (SEQ ID NO:63) and plasmid pPICZ-A (Invitrogen) as a template was cloned into the open sites creating pJN261 (FIG. 4B).

Figure 4C:
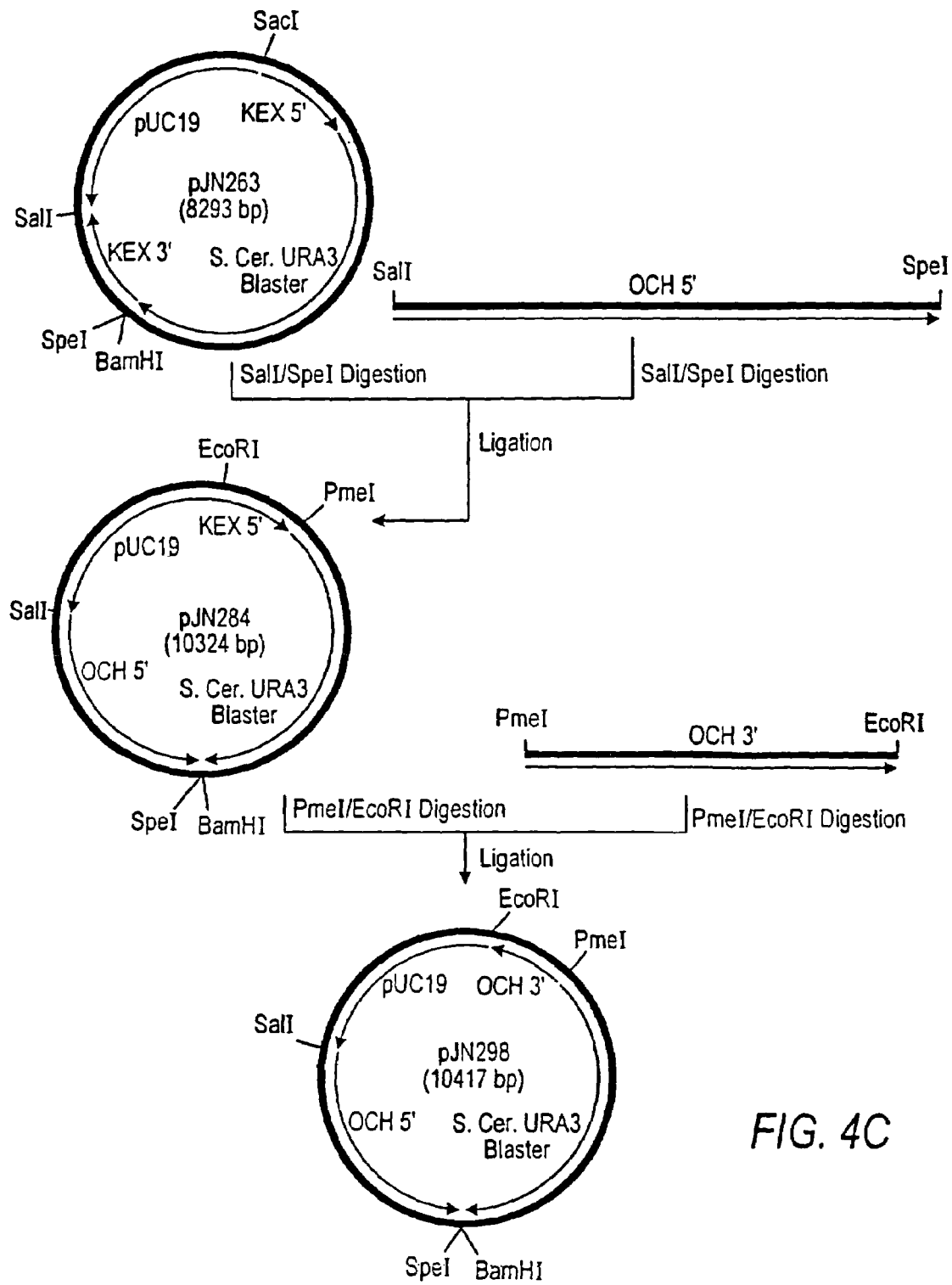
Figure 4D:
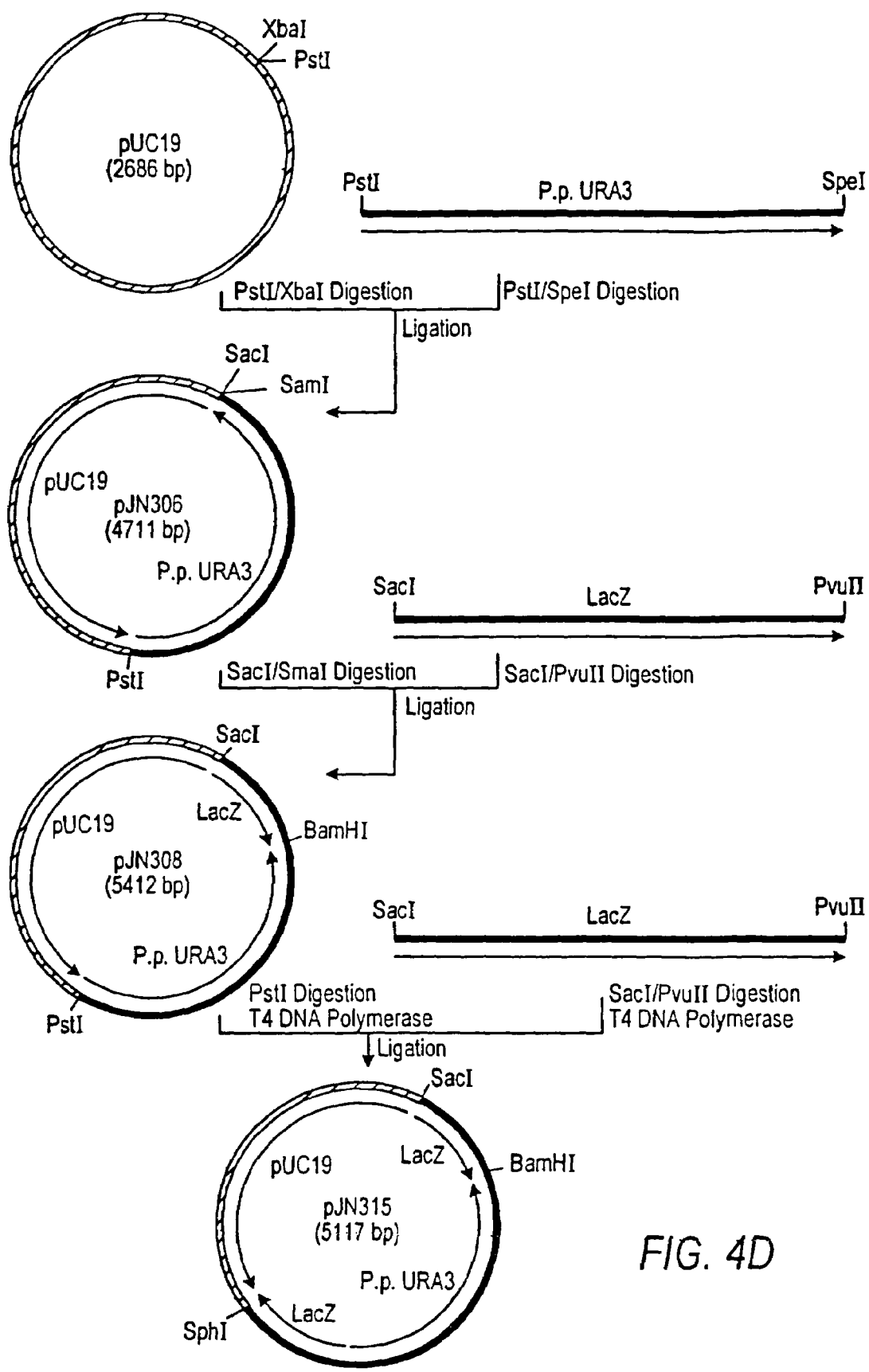
Figure 4E:
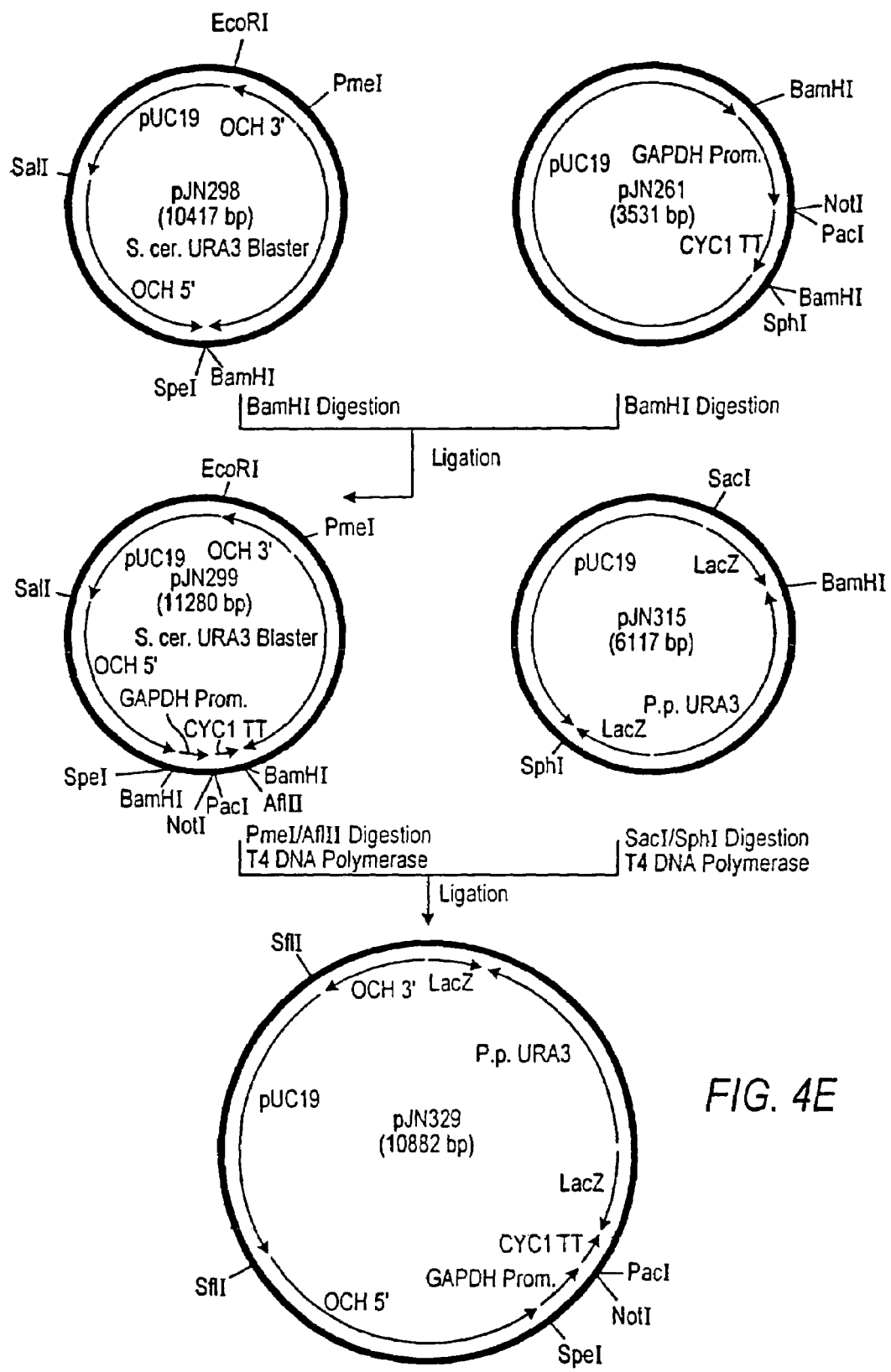

A knockout plasmid for the *P. pastoris* OCH1 gene was created by digesting pJN263 with SalI and SpeI and a 2.9-kb DNA fragment of the OCH1-5' region, which had been amplified using the primers GAACCAC<u>GTCGACGGCCATTGCGGCC</u>AAAACCTT TTTTCCTATTCAAACACAAGGCATTGC (SEQ ID NO:64) and CTCCAATACTAGTCGAAGATTATCTTCTACGGTGCC
TGGACTC (SEQ ID NO:65) and *P. pastoris* genomic DNA
as a template, was cloned into the open sites (FIG. 4C). The
resulting plasmid was cut with EcoRI and PmeI and a 1.0-kb
DNA fragment of the OCH1-3' region that had been generated using the primers TGGAAGGTTTAAACAAAGCTAGAGTAAAATAGATAT
AGCGAGATTAGAGAATG (SEQ ID NO:66) and AAGAATTCGGCTGGAAGGCCTTGTACCTTGATGT
AGTTCCCGTTTTCATC (SEQ ID NO:67) was inserted to
generate pJN298 (FIG. 4C). To allow for the possibility to
simultaneously use the plasmid to introduce a new gene, the
BamHI expression cassette of pJN261 (FIG. 4B) was cloned
into the unique BamHI site of pJN298 (FIG. 4C) to create
pJN299 (FIG. 4E).

The *P. pastoris* Ura3-blaster cassette was constructed using
a similar strategy as described in Lu et al. (1998) *Appl. Microbiol. Biotechnol.* 49:141-146. A 2.0-kb PstI, SpeI fragment of
*P. pastoris* URA3 was inserted into the PstI, XbaI sites of
pUC19 (New England Biolabs, Beverly, Mass.) to create
pJN306 (FIG. 4D). Then a 0.7-kb SacI, PvuII DNA fragment
of the lacZ open reading frame was cloned into the SacI, SmaI
sites to yield pJN308 (FIG. 4D). Following digestion of
pJN308 (FIG. 4D) with PstI, and treatment with T4 DNA
polymerase, the SacI-PvuII fragment from lacZ that had been
blunt-ended with T4 DNA polymerase was inserted generating pJN315 (FIG. 4D). The lacZ/URA3 cassette was released
by digestion with SacI and SphI, blunt ended with T4 DNA
polymerase and cloned into the backbone of pJN299 that had
been digested with PmeI and AflII and blunt ended with T4
DNA polymerase. The resulting plasmid was named pJN329
(FIG. 4E).

Figure 4F:
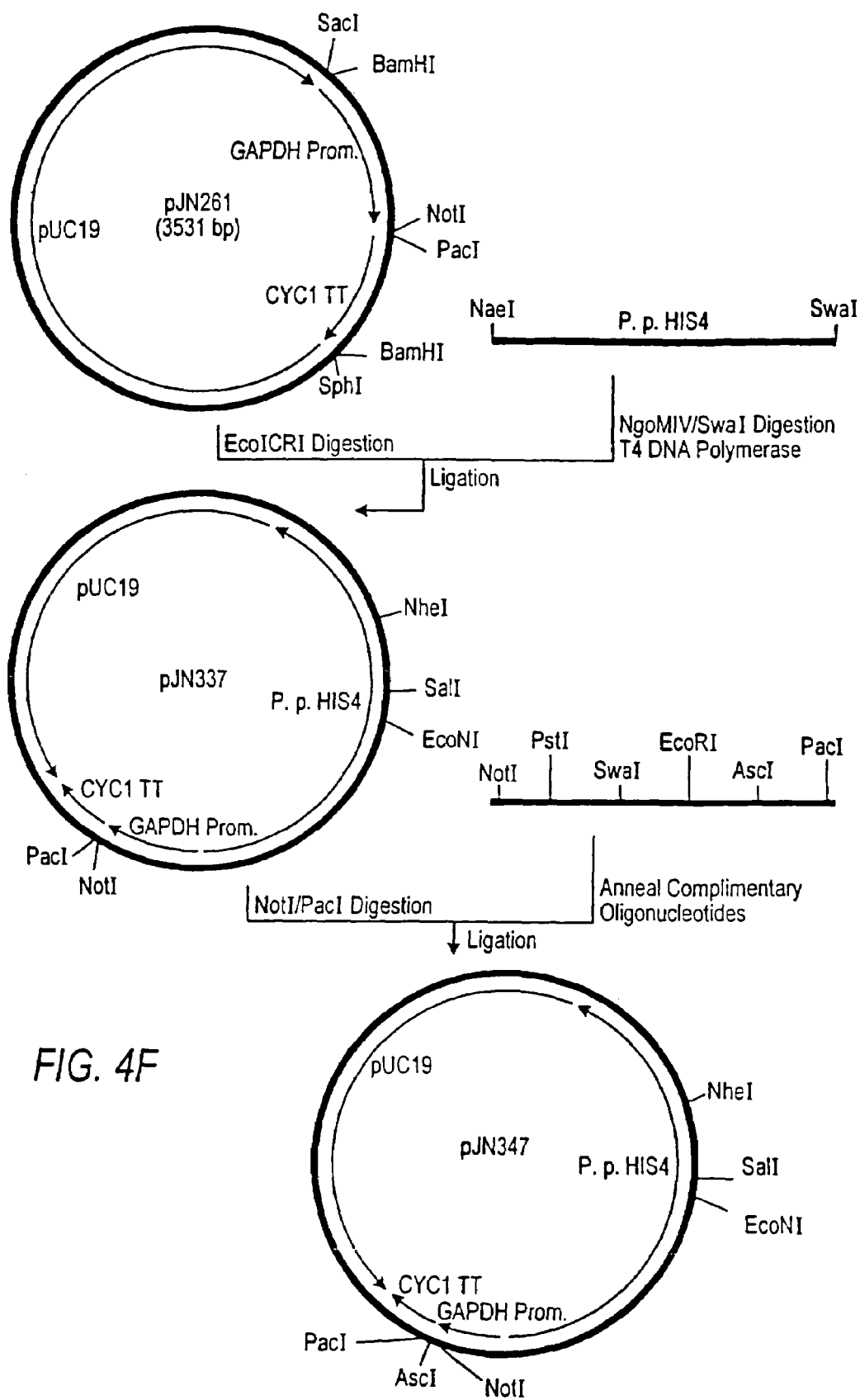

A HIS4 marked expression plasmid was created by cutting
pJN261 (FIG. 4F) with EcoICRI (FIG. 4F). A 2.7 kb fragment
of the *Pichia pastoris* HIS4 gene that had been amplified
using the primers GCCCAAGCCGGCCTTAAGGGATCTCCTGATGACT
GACTCACTGATAATAAAAATACGG (SEQ ID NO:68)
and GGGCGCGTATTTAAATACTAGTGGATCTATCGAATC
TAAATGTAAGTTAAAATCTCTAA (SEQ ID NO:69) cut
with NgoMIV and SwaI and then blunt-ended using T4 DNA
polymerase, was then ligated into the open site. This plasmid
was named pJN337 (FIG. 4F). To construct a plasmid with a
multiple cloning site suitable for fusion library construction,
pJN337 was cut with NotI and PacI and the two oligonucleotides GGCCGCCTGCAGATTTAAATGAATTC
GGCGCGCCTTAAT (SEQ ID NO:70) and
TAAGGCGCGCCGAATTCATTTAAATCTGCAGGGC
(SEQ ID NO:71) that had been annealed in vitro were ligated
into the open sites, creating pJN347 (FIG. 4F).

To create an och1 knockout strain containing multiple auxotrophic markers, 100 µg of pJN329 was digested with SfiI
and used to transform *P. pastoris* strain JC308 (Cereghino et
al. (2001) *Gene* 263:159-169) by electroporation. Following
transformation, the URA dropout plates were incubated at
room temperature for 10 days. One thousand (1000) colonies
were picked and restreaked. All 000 clones were then
streaked onto 2 sets of URA dropout plates. One set was
incubated at room temperature, whereas the second set was
incubated at 37° C. The clones that were unable to grow at 37°
C., but grew at room temperature, were subjected to colony
PCR to test for the correct OCH1 knockout. One clone that
showed the expected PCR signal (about 4.5 kb) was designated YJN153.

Example 5

Characterization of the Combinatorial DNA Library

Positive transformants screened by colony PCR confirming integration of the mannosidase construct into the *P. pastoris* genome were subsequently grown at room temperature
in 50 ml BMGY buffered methanol-complex medium consisting of 1% yeast extract, 2% peptone, 100 mM potassium
phosphate buffer, pH 6.0, 1.34% yeast nitrogen base, $4\times10^{-5}$% biotin, and 1% glycerol as a growth medium) until
$OD_{600nm}$ 2-6 at which point they were washed with 10 ml
BMMY (buffered methanol-complex medium consisting of
1% yeast extract, 2% peptone, 100 mM potassium phosphate
buffer, pH 6.0, 1.34% yeast nitrogen base, $4\times10^{-5}$% biotin,
and 1.5% methanol as a growth medium) media prior to
induction of the reporter protein for 24 hours at room temperature in 5 ml BMMY. Consequently, the reporter protein
was isolated and analyzed as described in Example 3 to characterize its glycan structure. Using the targeting peptides in
Table 6, mannosidase catalytic domains localized to either the
ER or the Golgi showed significant level of trimming of a
glycan predominantly containing $Man_8GlcNAc_2$ to a glycan
predominantly containing $Man_5GlcNAc_2$. This is evident
when the glycan structure of the reporter glycoprotein is
compared between that of *P. pastoris* och1 knock-out in
FIGS. 5C and 6C and the same strain transformed with *M. musculus* mannosidase constructs as shown in FIGS. 5D, 5E,
6D-6F. FIGS. 5 and 6 show expression of constructs generated from the combinatorial DNA library which show significant mannosidase activity in *P. pastoris*. Expression of pGC5
(*Saccharomyces* MNS1(m)/mouse mannosidase IB Δ99)
(FIGS. 5D and 6E) produced a protein which has approximately 30% of all glycans trimmed to $Man_5GlcNAc_2$, while
expression of pFB8 (*Saccharomyces* SEC12(m)/mouse mannosidase IA Δ187) (FIG. 6F) produced approximately 50%
$Man_5GlcNAc_2$ and expression of pBC18-5 (*Saccharomyces*
VAN1(s)/*C. elegans* mannosidase IB Δ80) (FIG. 5E) produced 70% $Man_5GlcNAc_2$.

Example 6

Trimming In Vivo by α-1,2-Mannosidase

To ensure that the novel engineered strains of Example 4 in
fact produced the desired $Man_5GlcNAc_2$ structure in vivo,
cell supernatants were tested for mannosidase activity (see
FIGS. 7-9). For each construct/host strain described below,
HPLC was performed at 30° C. with a 4.0 mm×250 mm
column of Altech (Avondale, Pa., USA) Econosil-$NH_2$ resin
(5 µm) at a flow rate of 1.0 ml/min for 40 min. In FIGS. 7 and
8, degradation of the standard $Man_9GlcNAc_2$ [b] was shown
to occur resulting in a peak which correlates to
$Man_8GlcNAc_2$. In FIG. 7, the $Man_9GlcNAc_2$ [b] standard
eluted at 24.61 min and $Man_5GlcNAc_2$ [a] eluted at 18.59
min. In FIG. 8, $Man_9GlcNAc_2$ eluted at 21.37 min and
$Man_5GlcNAc_2$ at 15.67 min. In FIG. 9, the standard
$Man_8GlcNAc_2$ [b] was shown to elute at 20.88 min.

Figure 7C:
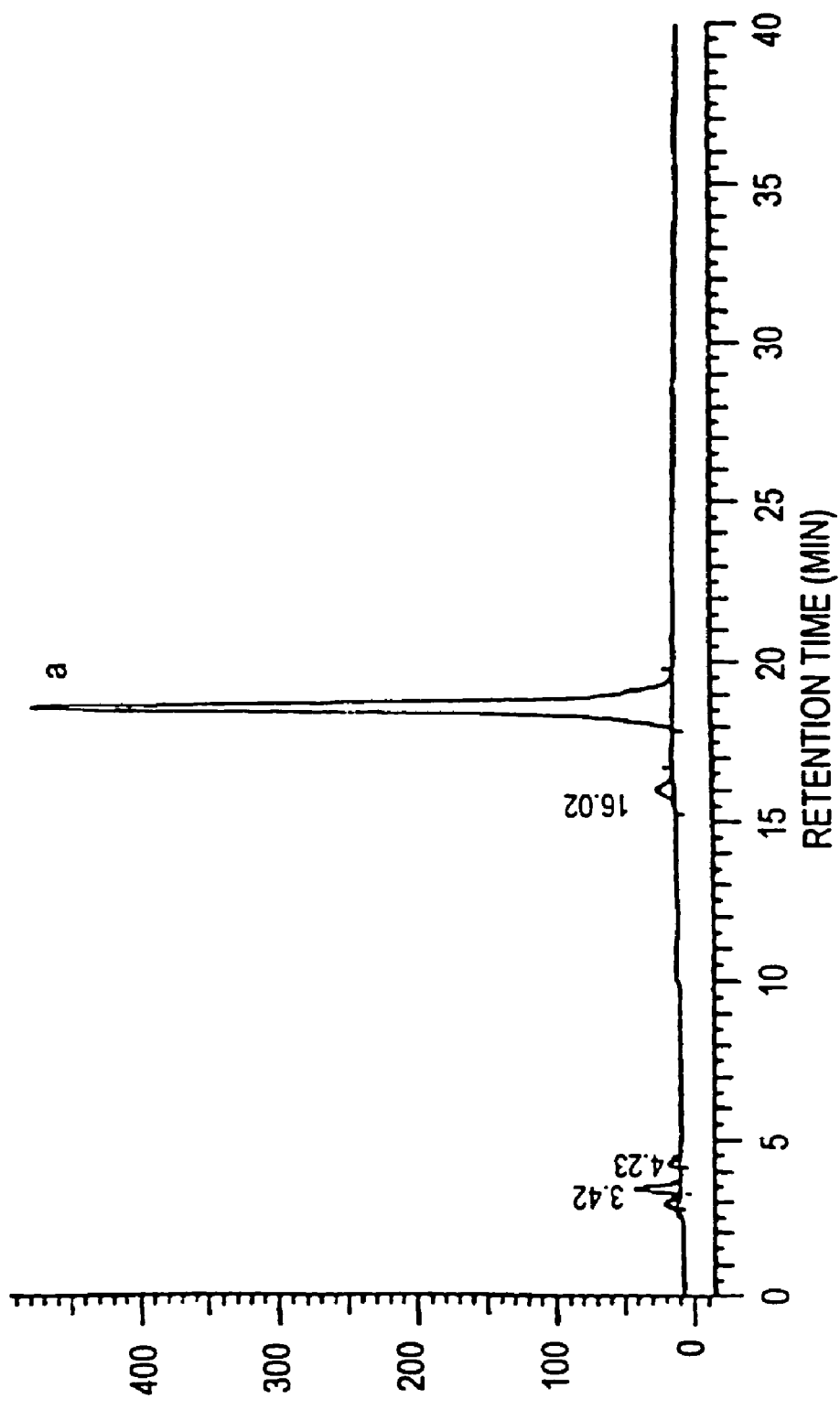

*P. pastoris* cells comprising plasmid pFB8 (*Saccharomyces* SEC12 (m)/mouse mannosidase IA Δ187) were grown at
30° C. in BMGY to an OD600 of about 10. Cells were
harvested by centrifugation and transferred to BMMY to
induce the production of K3 (kringle 3 from human plasminogen) under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient of 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 6F. The earlier removed aliquot of the supernatant was further tested for the presence of secreted mannosidase activity. A commercially available standard of 2-aminobenzamide-labeled N-linked-type oligomannose 9 (Man9-2-AB) (Glyko, Novato, Calif.) was added to: BMMY (FIG. 7A), the supernatant from the above aliquot (FIG. 7B), and BMMY containing 10 ng of 75 mU/mL of α-1,2-mannosidase from *Trichoderma reesei* (obtained from Contreras et al., WO 02/00856 A2) (FIG. 7C). After incubation for 24 hours at room temperature, samples were analyzed by amino silica HPLC to determine the extent of mannosidase trimming.

Figure 8C:
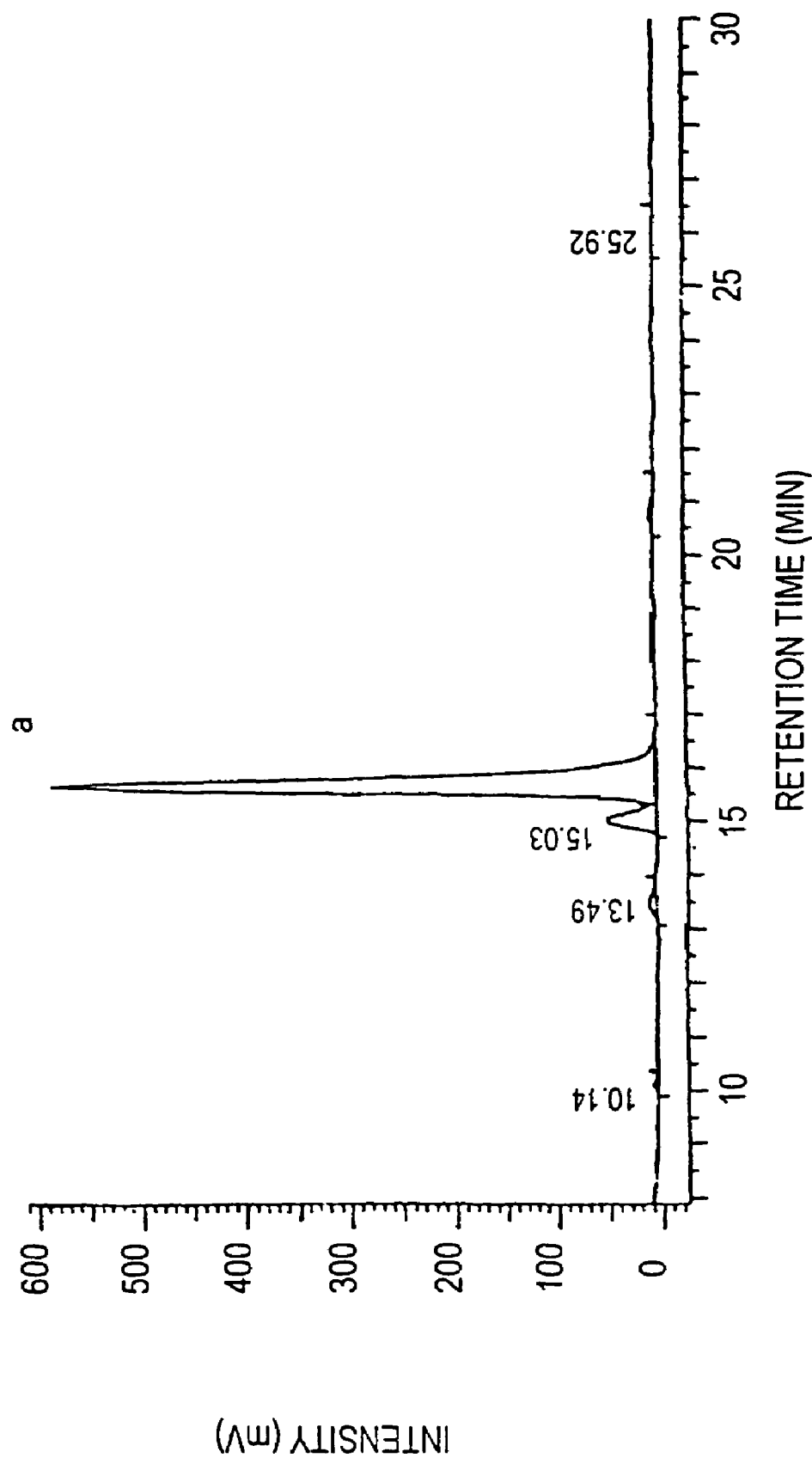

*P. pastoris* cells comprising plasmid pGC5 (*Saccharomyces* MNS1(m)/mouse mannosidase IB Δ99) were similarly grown and assayed. Cells were grown at room temperature in BMGY to an OD600 of about 10. Cells were harvested by centrifugation and transferred to BMMY to induce the production of K3 under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient of 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 5D. The earlier removed aliquot of the supernatant was further tested for the presence of secreted mannosidase activity as shown in FIG. 8B. A commercially available standard of Man9-2-AB (Glyko, Novato, Calif.) were added to: BMMY (FIG. 8A), supernatant from the above aliquot (FIG. 8B), and BMMY containing 10 ng of 75 mU/mL of α-1,2-mannosidase from *Trichoderma reesei* (obtained from Contreras et al., WO 02/00856 A2) (FIG. 8C). After incubation for 24 hours at room temperature, samples were analyzed by amino silica HPLC to determine the extent of mannosidase trimming.

Man9-2-AB was used as a substrate and it is evident that after 24 hours of incubation, mannosidase activity was virtually absent in the supernatant of the pFB8 (*Saccharomyces* SEC12(m)/mouse mannosidase IA Δ187) strain digest (FIG. 7B) and pGC5 (*Saccharomyces* MNS1(m)/mouse mannosidase IB Δ99) strain digest (FIG. 8B) whereas the positive control (purified α-1,2-mannosidase from *T. reesei* obtained from Contreras) leads to complete conversion of $Man_9GlcNAc_2$ to $Man_5GlcNAc_2$ under the same conditions, as shown in FIGS. 7C and 8C. This is conclusive data showing in vivo mannosidase trimming in *P. pastoris* pGC5 strain; and pFB8 strain, which is distinctly different from what has been reported to date (Contreras et al., WO 02/00856 A2).

Figure 9A:
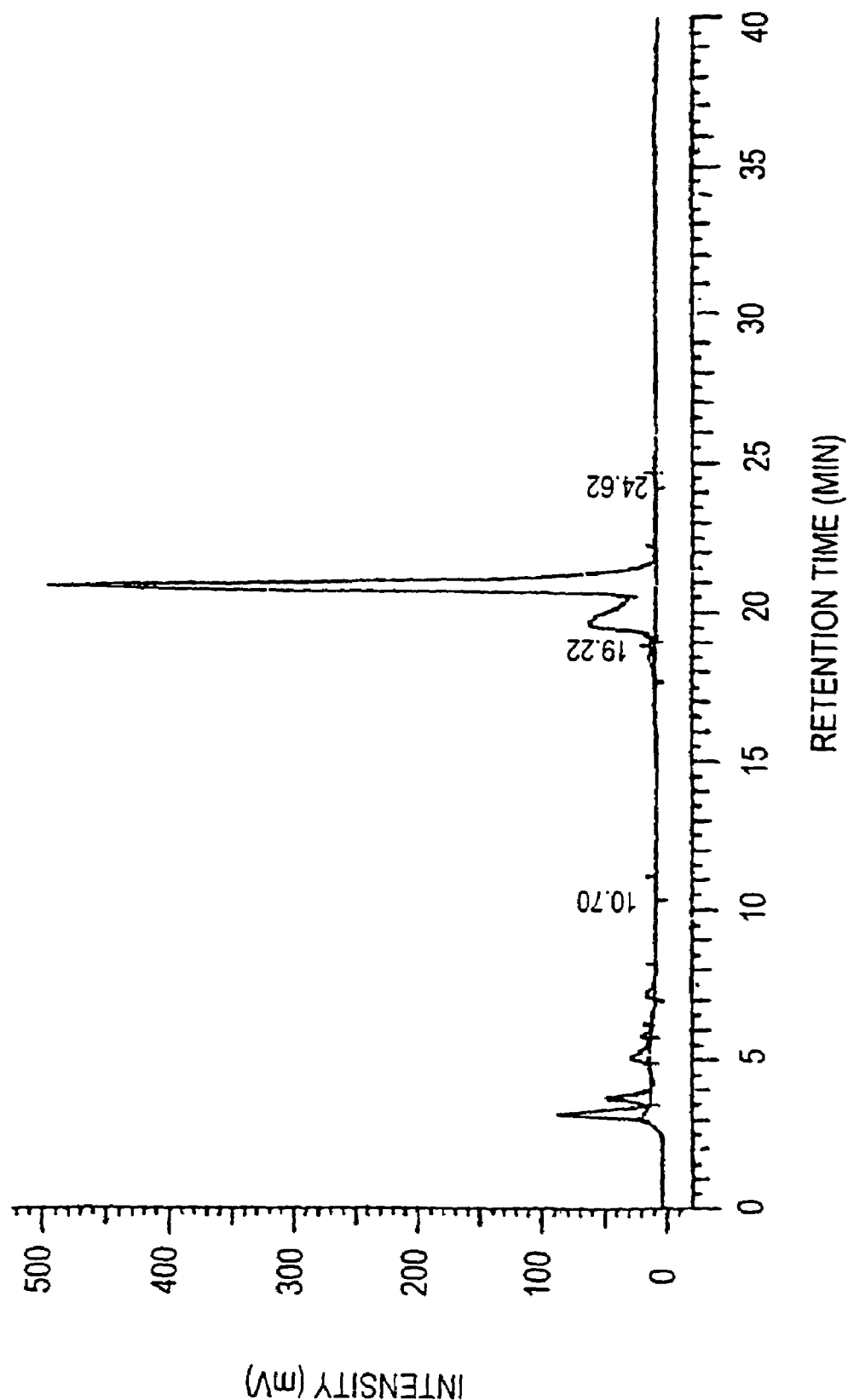
Figure 9B:
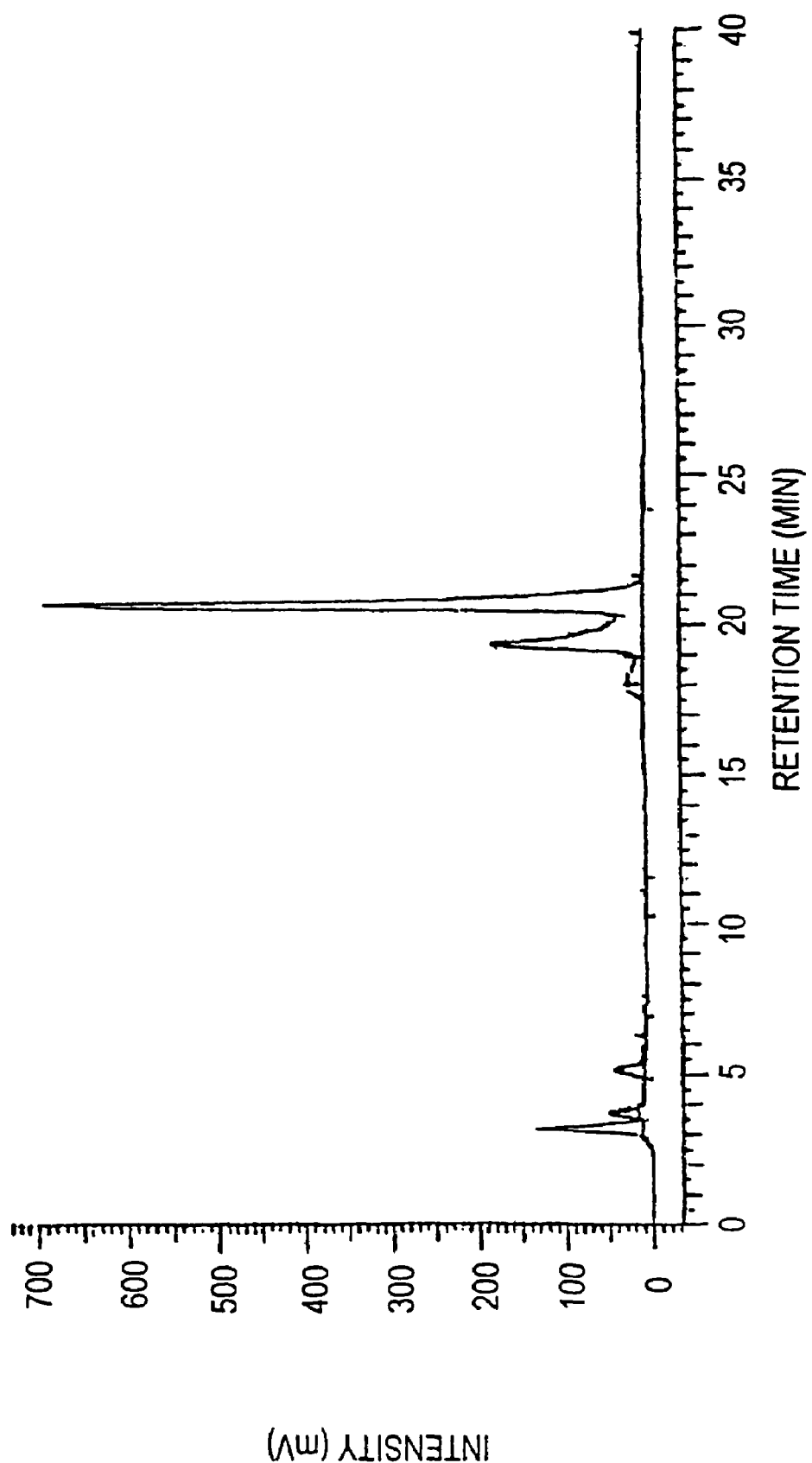
Figure 9C:
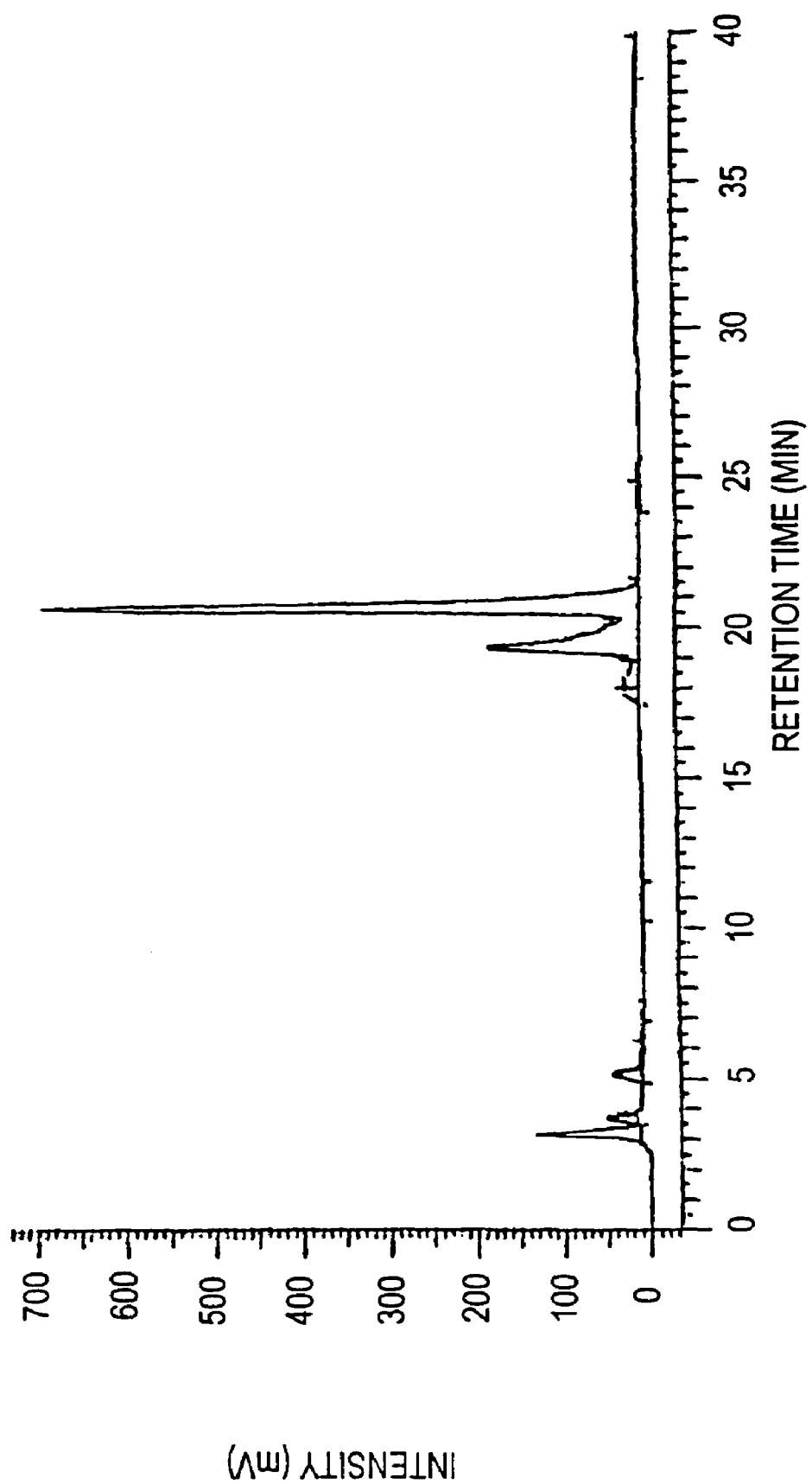

FIG. 9 further substantiates localization and activity of the mannosidase enzyme. *P. pastoris* comprising pBC18-5 (*Saccharomyces* VAN1(s)/*C. elegans* mannosidase IB Δ80) was grown at room temperature in BMGY to an OD600 of about 10. Cells were harvested by centrifugation and transferred to BMMY to induce the production of K3 under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 5E. The earlier removed aliquot of the supernatant was further tested for the presence of secreted mannosidase activity as shown in FIG. 9B. A commercially available standard of Man8-2-AB (Glyko, Novato, Calif.) was added to: BMMY (FIG. 9A), supernatant from the above aliquot pBC18-5 (*Saccharomyces* VAN1(s)/*C. elegans* mannosidase IB Δ80) (FIG. 9B), and BMMY containing media from a different fusion construct pDD28-3 (*Saccharomyces* MNN10(m) (from SwissProt 50108)/*H. sapiens* mannosidase IB Δ99) (FIG. 9C). After incubation for 24 hours at room temperature, samples were analyzed by amino silica HPLC to determine the extent of mannosidase trimming. FIG. 9B demonstrates intracellular mannosidase activity in comparison to a fusion construct pDD28-3 (*Saccharomyces* MNN10(m) *H. sapiens* mannosidase IB Δ99) exhibiting a negative result (FIG. 9C).

Example 7 pH Optimum Assay of Engineered α-1,2-Mannosidase

*P. pastoris* cells comprising plasmid pBB27-2 (*Saccharomyces* MNN10(s) (from SwissProt 50108)/*C. elegans* mannosidase IB Δ31) were grown at room temperature in BMGY to an OD600 of about 17. About 80 μL of these cells were inoculated into 600 μL BMGY and were grown overnight. Subsequently, cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant (pH 6.43). The supernatant was removed for mannosidase pH optimum assays. Fluorescence-labeled $Man_8GlcNAc_2$ (0.5 μg) was added to 20 μL of supernatant adjusted to various pH (FIG. 11) and incubated for 8 hours at room temperature. Following incubation the sample was analyzed by HPLC using an Econosil NH2 4.6×250 mm, 5 micron bead, amino-bound silica column (Altech, Avondale, Pa.). The flow rate was 1.0 ml/min for 40 min and the column was maintained to 30° C. After eluting isocratically (68% A:32% B) for 3 min, a linear solvent gradient (68% A:32% B to 40% A:60% B) was employed over 27 min to elute the glycans (18). Solvent A (acetonitrile) and solvent B (ammonium formate, 50 mM, pH 4.5. The column was equilibrated with solvent (68% A:32% B) for 20 min between runs.

Example 8

Engineering of *P. pastoris* to Produce N-Glycans with the Structure $GlcNAcMan_5GlcNAc_2$ GlcNAc Transferase I activity is required for the maturation of complex and hybrid N-glycans (U.S. Pat. No. 5,834, 251). $Man_5GlcNAc_2$ may only be trimmed by mannosidase II, a necessary step in the formation of human glycoforms, after the addition of N-acetylglucosamine to the terminal α-1,3 mannose residue of the trimannose stem by GlcNAc Transferase I (Schachter, 1991 Glycobiology 1(5):453-461). Accordingly, a combinatorial DNA library was prepared including DNA fragments encoding suitably targeted catalytic domains of GlcNAc Transferase I genes from *C. elegans* and *Homo sapiens*; and localization sequences from GLS, MNS, SEC, MNN9, VAN1, ANP1, HOC1, MNN10, MNN11, MNT1, KTR1, KTR2, MNN2, MNN5, YUR1, MNN1, and MNN6 from *S. cerevisiae* and *P. pastoris* putative α-1,2-mannosyltransferases based on the homology from *S. cerevisiae*: D2, D9 and J3, which are KTR homologs. Table 10 includes but does not limit targeting peptide sequences such as SEC and OCH1, from *P. pastoris* and *K. lactis* GnTI, (See Table 6 and Table 10)

TABLE 10

A representative combinatorial library of targeting peptide sequences/ catalytic domain for UDP-N-Acetylglucosaminyl Transferase I (GnTI)

| | | Targeting peptide | | | | |
|---|---|---|---|---|---|---|
| | | OCHI(s) | OCHI(m) | OCHI(l) | MNN9(s) | MNN9(m) |
| Catalytic Domain | Human, GnTI, Δ38 | PB105 | PB106 | PB107 | PB104 | N/A |
| | Human, GnTI, Δ86 | NB12 | NB13 | NB14 | NB15 | NB |
| | *C. elegans*, GnTI, Δ88 | OA12 | OA13 | OA14 | OA15 | OA16 |
| | *C. elegans*, GnTI, Δ35 | PA12 | PA13 | PA14 | PA15 | PA16 |
| | *C. elegans*, GnTI, Δ63 | PB12 | PB13 | PB14 | PB15 | PB16 |
| | *X. leavis*, GnTI, Δ33 | QA12 | QA13 | QA14 | QA15 | QA16 |
| | *X. leavis*, GnTI, Δ103 | QB12 | QB13 | QB14 | QB15 | QB16 |

Targeting peptide sequences were selected from OCH1 in *P. pastoris* (long, medium and short) (see Example 4) and MNN9 (SwissProt P39107) in *S. cerevisiae* (short and medium). Catalytic domains were selected from human GnTI with a 38 and 86 amino acid N-terminal deletion, *C. elegans* (gly-12) GnTI with a 35 and 63 amino acid deletion as well as *C. elegans* (gly-14) GnTI with a 88 amino acid N-terminal deletion and *X. leavis* GnTI with a 33 and 103 amino acid N-terminal deletion, respectively.

A portion of the gene encoding human N-acetylglucosaminyl Transferase I (MGATI, Accession# NM002406), lacking the first 154 bp, was amplified by PCR using oligonucleotides 5'-TGGCAGGCGCGCCTCAGTCAGCGCTCTCG-3' (SEQ ID NO:72) and 5'-AGGTTAATTA AGTGCTAATTC-CAGCTAGG-3' (SEQ ID NO:73) and vector pHG4.5 (ATCC# 79003) as template. The resulting PCR product was cloned into pCR2.1-TOPO and the correct sequence was confirmed. Following digestion with AscI and PacI the truncated GnTI was inserted into plasmid pJN346 to create pNA. After digestion of pJN271 with NotI and AscI, the 120 bp insert was ligated into pNA to generate an in-frame fusion of the MNN9 transmembrane domain with the GnTI, creating pNA 15.

The host organism is a strain of *P. pastoris* that is deficient in hypermannosylation (e.g. an och1 mutant), provides the substrate UDP-GlcNAc in the Golgi and/or ER (i.e., contains a functional UDP-GlcNAc transporter), and provides N-glycans of the structure Man$_5$GlcNAc$_2$ in the Golgi and/or ER (e.g. *P. pastoris* pFB8 (*Saccharomyces* SEC12(m)/mouse mannosidase IA Δ187) from above). First, *P. pastoris* pFB8 was transformed with pPB103 containing the *Kluyveromyces lactis* MNN2-2 gene (Genbank AN AF106080) (encoding UDP-GlcNAc transporter) cloned into BamHI and BglII site of pBLADE-SX plasmid (Cereghino et al. (2001) *Gene* 263: 159-169). Then the aforementioned combinatorial DNA library encoding a combination of exogenous or endogenous GnTI/localization genes was transformed and colonies were selected and analyzed for the presence of the GnTI construct by colony PCR. Our transformation and integration efficiency was generally above 80% and PCR screening can be omitted once robust transformation parameters have been established.

Protein Purification

K3 was purified from the medium by Ni-affinity chromatography utilizing a 96-well format on a Beckman BioMek 2000 laboratory robot. The robotic purification is an adaptation of the protocol provided by Novagen for their HisBind resin. Another screening method may be performed using a specific terminal GlcNAc binding antibody, or a lectin such as the GSII lectin from *Griffonia simplificolia*, which binds terminal GlcNAc (EY Laboratories, San Mateo, Calif.). These screens can be automated by using lectins or antibodies that have been modified with fluorescent labels such as FITC or analyzed by MALDI-TOF.

Secreted K3 can be purified by Ni-affinity chromatography, quantified and equal amounts of protein can be bound to a high protein binding 96-well plate. After blocking with BSA, plates can be probed with a GSII-FACS lectin and screened for maximum fluorescent response. A preferred method of detecting the above glycosylated proteins involves the screening by MALDI-TOF mass spectrometry following the affinity purification of secreted K3 from the supernatant of 96-well cultured transformants. Transformed colonies were picked and grown to an OD600 of 10 in a 2 ml, 96-well plate in BMGY at 30° C. Cells were harvested by centrifugation, washed in BMMY and resuspended in 250 ul of BMMY. Following 24 hours of induction, cells were removed by centrifugation, the supernatant was recovered and K3 was purified from the supernatant by Ni affinity chromatography. The N-glycans were released and analyzed by MALDI-TOF delayed extraction mass spectrometry as described herein.

In summary, the methods of the invention yield strains of *P. pastoris* that produce GlcNAcMan$_5$GlcNAc$_2$ in high yield, as shown in FIG. 10B. At least 60% of the N-glycans are GlcNAcMan$_5$GlcNAc$_2$. To date, no report exists that describes the formation of GlcNAcMan$_5$GlcNAc$_2$ on secreted soluble glycoproteins in any yeast. Results presented herein show that addition of the UDP-GlcNAc transporter along with GnTI activity produces a predominant GlcNAcMan$_5$GlcNAc$_2$ structure, which is confirmed by the peak at 1457 (m/z) (FIG. 10B).

Construction of Strain PBP-3:

The *P. pastoris* strain expressing K3, (Δoch1, arg-, ade-, his-) was transformed successively with the following vectors. First, pFB8 (*Saccharomyces* SEC12(m)/mouse mannosidase IA Δ187) was transformed in the *P. pastoris* strain by electroporation. Second, pPB103 containing *Kluyveromyces lactis* MNN2-2 gene (Genbank AN AF106080) (encoding UDP-GlcNAc transporter) cloned into pBLADE-SX plasmid (Cereghino et al. (2001) *Gene* 263:159-169) digested with BamHI and BglII enzymes was transformed in the *P. pastoris* strain. Third, pPB104 containing *Saccharomyces* MNN9(s)/human GnTI Δ38 encoding gene cloned as NotI-PacI fragment into pJN336 was transformed into the *P. pastoris* strain.

Example 9

Engineering *K. lactis* Cells to Produce N-Glycans with the Structure $Man_5GlcNAC_2$ Identification and Disruption of the *K. lactis* OCH1 Gene The OCH1 gene of the budding yeast *S. cerevisiae* encodes a 1,6-mannosyltransferase that is responsible for the first Golgi localized mannose addition to the $Man_8GlcNAc_2$ N-glycan structure on secreted proteins (Nakanishi-Shindo et al. (1993) *J. Biol. Chem.*; 268(35):26338-45). This mannose transfer is generally recognized as the key initial step in the fungal specific polymannosylation of N-glycan structures (Nakanishi-Shindo et al. (1993) *J. Biol. Chem.* 268(35): 26338-26345; Nakayama et al. (1992) *EMBO J.* 11(7):2511-19; Morin-Ganet et al (2000) *Traffic* 1(1):56-68). Deletion of this gene in *S. cerevisiae* results in a significantly shorter N-glycan structure that does not include this typical polymannosylation or a growth defect at elevated temperatures (Nakayama et al. (1992) *EMBO J.* 11 (7):2511-19).

The Och1p sequence from *S. cerevisiae* was aligned with known homologs from *Candida albicans* (Genbank accession # AAL49987), and *P. pastoris* along with the Hoc1 proteins of *S. cerevisiae* (Neiman et al (1997) *Genetics* 145 (3):637-45 and *K. lactis* (PENDANT EST database) which are related but distinct mannosyltransferases. Regions of high homology that were in common among Och1p homologs but distinct from the Hoc1p homologs were used to design pairs of degenerate primers that were directed against genomic DNA from the *K. lactis* strain MG1/2 (Bianchi et al (1987) *Current Genetics* 12:185-192). PCR amplification with primers RCD33 (CCAGAAGAATTCAATTYTGYCARTGG) (SEQ ID NO:74) and RCD34 (CAGTGAAAATACCTG-GNCCNGTCCA) (SEQ ID NO:75) resulted in a 302 bp product that was cloned and sequenced and the predicted translation was shown to have a high degree of homology to Och1 proteins (>55% to *S. cerevisiae* Och1p).

Figure 12A:
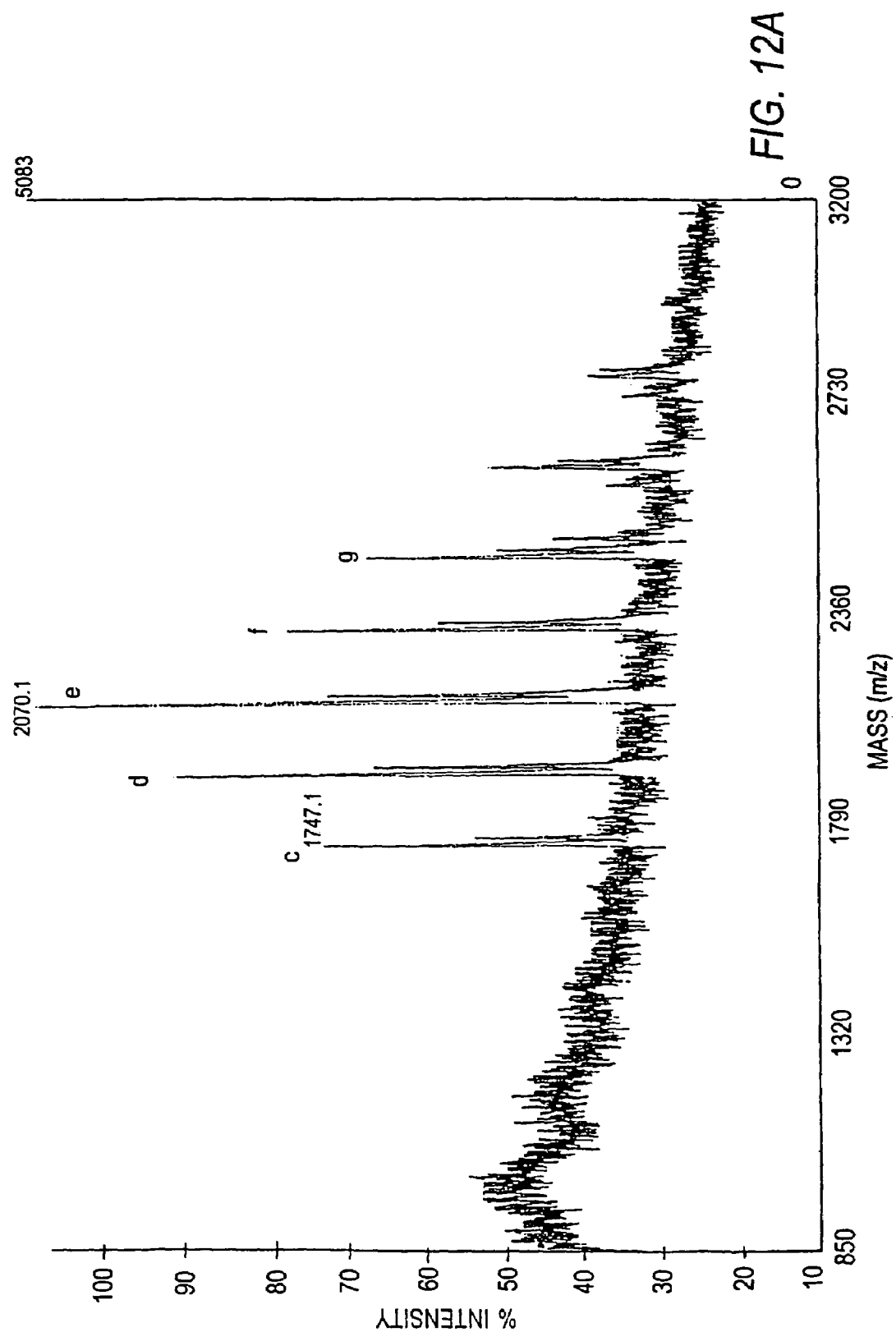

The 302 bp PCR product was used to probe a Southern blot of genomic DNA from *K. lactis* strain (MG1/2) with high stringency (Sambrook et al., *Molecular Cloning: A Laboratory Manual*, 2nd ed., Cold Spring Harbor Laboratory Press, Cold Spring Harbor, N.Y., 1989). Hybridization was observed in a pattern consistent with a single gene indicating that this 302 bp segment corresponds to a portion of the *K. lactis* genome and *K. lactis* (KlOCH1) contains a single copy of the gene. To clone the entire KlOCH1 gene, the Southern blot was used to map the genomic locus. Accordingly, a 5.2 kb BamHI/PstI fragment was cloned by digesting genomic DNA and ligating those fragments in the range of 5.2 kb into pUC 19 (New England Biolabs, Beverly, Mass.) to create a *K. lactis* subgenomic library. This subgenomic library was transformed into *E. coli* and several hundred clones were tested by colony PCR using RCD 33/34. The 5.2 kb clone containing the predicted KlOCH1 gene was sequenced and an open reading frame of 1362 bp encoding a predicted protein that is 46.5% identical to the *S. cerevisiae* OCH1 gene. The 5.2 kb sequence was used to make primers for construction of an och1::$KAN^R$ deletion allele using a PCR overlap method (Davidson et al. (2002) *Microbiol.* 148(Pt 8):2607-15). This deletion allele was transformed into two *K. lactis* strains and G418 resistant colonies selected. These colonies were screened by both PCR and for temperature sensitivity to obtain a strain deleted for the OCH1 ORF. The results of the experiment show strains which reveal a mutant PCR pattern, which were characterized by analysis of growth at various temperatures and N-glycan carbohydrate analysis of secreted and cell wall proteins following PNGase digestion. The och1 mutation conferred a temperature sensitivity which allowed strains to grow at 30° C. but not at 35° C. FIG. 12A shows a MALDI-TOF analysis of a wild type *K. lactis* strain producing N-glycans of $Man_8GlcNAc_2$ [c] and higher.

Identification, Cloning, and Disruption of the *K. lactis* MNN1 Gene

*S. cerevisiae* MNN1 is the structural gene for the Golgi α-1,3-mannosyltransferase. The product of MNN1 is a 762-amino acid type II membrane protein (Yip et al. (1994) *Proc Natl Acad Sci USA.* 91(7):2723-7). Both N-linked and O-linked oligosaccharides isolated from mnn1 mutants lack α-1,3-mannose linkages (Raschke et al. (1973) *J. Biol Chem.* 248(13):4660-66).

The Mnn1p sequence from *S. cerevisiae* was used to search the *K. lactis* translated genomic sequences (PEDANT). One 405 bp DNA sequence encoding a putative protein fragment of significant similarity to Mnn1p was identified. An internal segment of this sequence was subsequently PCR amplified with primers KMN1 (TGCCATCTTTTAGGTCCAGGC-CCGTTC) (SEQ ID NO:76) and KMN2 (GATCCCAC-GACGCATCGTATTTCTTTC), (SEQ ID NO:77) and used to probe a Southern blot of genomic DNA from *K. lactis* strain (MG 1/2). Based on the Southern hybridization data a 4.2 Kb BamHI-PstI fragment was cloned by generating a size-selected library as described herein. A single clone containing the *K. lactis* MNN1 gene was identified by whole colony PCR using primers KMN1 and KMN2 and sequenced. Within this clone a 2241 bp ORF was identified encoding a predicted protein that was 34% identical to the *S. cerevisiae* MNN1 gene. Primers were designed for construction of a mnn1:: $NAT^R$ deletion allele using the PCR overlap method (Davidson et al. (2002) *Microbiol.* 148(Pt 8):2607-15).

This disruption allele was transformed into a strain of *K. lactis* by electroporation and nourseothricin resistant transformants were selected and PCR amplified for homologous insertion of the disruption allele. Strains that reveal a mutant PCR pattern may be subjected to N-glycan carbohydrate analysis of a known reporter gene.

Figure 12B:
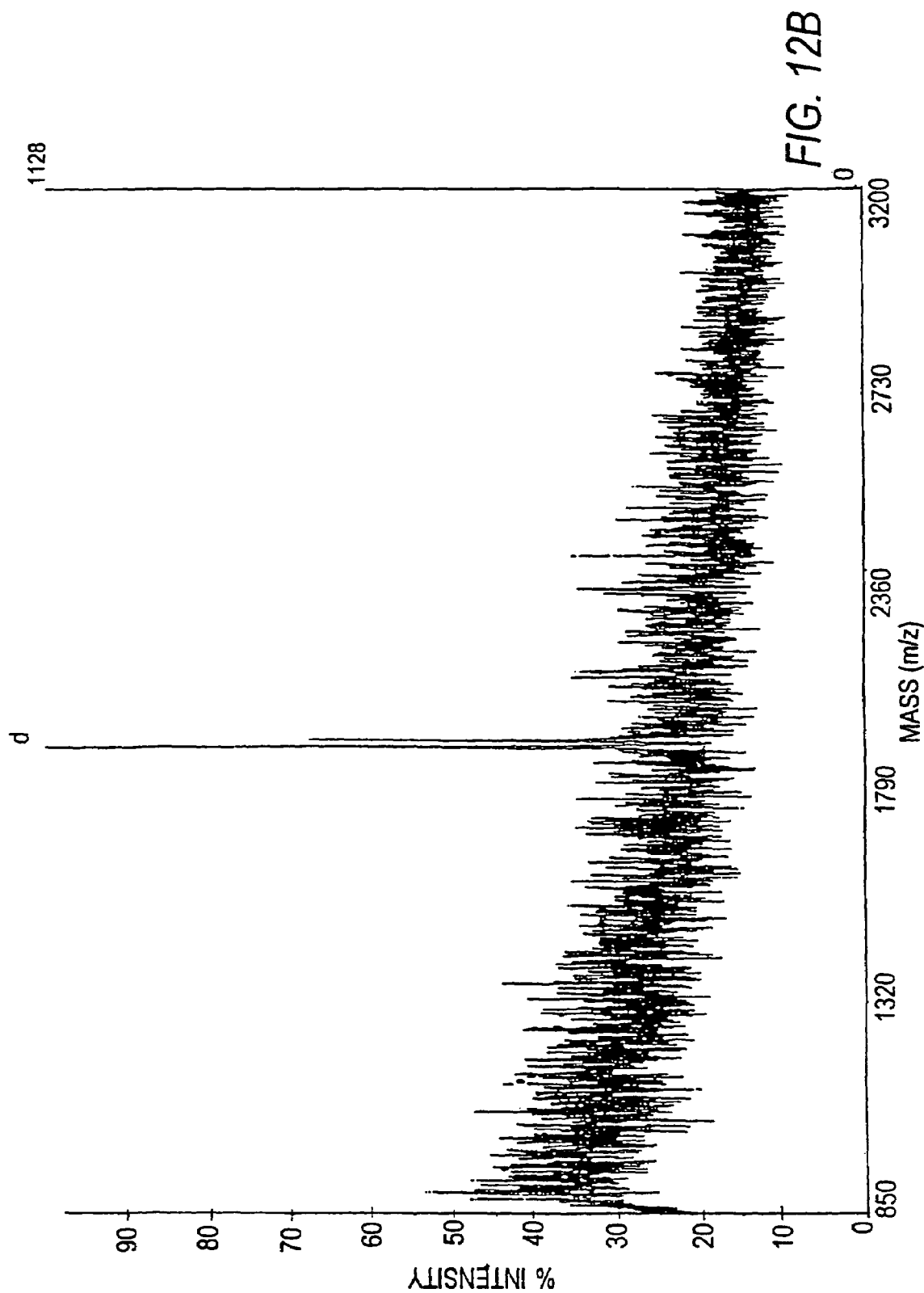

FIG. 12B depicts the N-glycans from the *K. lactis* och1 mnn1 deletion strain observed following PNGase digestion the MALDI-TOF as described herein. The predominant peak at 1908 (m/z) indicated as [d] is consistent with the mass of $Man_9GlcNAc_2$.

Additional methods and reagents which can be used in the methods for modifying the glycosylation are described in the literature, such as U.S. Pat. No. 5,955,422, U.S. Pat. No. 4,775,622, U.S. Pat. No. 6,017,743, U.S. Pat. No. 4,925,796, U.S. Pat. No. 5,766,910, U.S. Pat. No. 5,834,251, U.S. Pat. No. 5,910,570, U.S. Pat. No. 5,849,904, U.S. Pat. No. 5,955,347, U.S. Pat. No. 5,962,294, U.S. Pat. No. 5,135,854, U.S. Pat. No. 4,935,349, U.S. Pat. No. 5,707,828, and U.S. Pat. No. 5,047,335. Appropriate yeast expression systems can be obtained from sources such as the American Type Culture Collection, Rockville, Md. Vectors are commercially available from a variety of sources.

Example 10

Identification, Cloning and Deletion of the ALG3 Gene in P. pastoris and K. lactis Degenerate primers were generated based on an alignment of Alg3 protein sequences from *S. cerevisiae, H. sapiens*, and *D. melanogaster* and were used to amplify an 83 bp product from *P. pastoris* genomic DNA:

```
                                          (SEQ ID NO:78)
5'-GGTGTTTTGTTTTCTAGATCTTTGCAYTAYCARTT-3'
and (SEQ ID NO:79)
5'-AGAATTTGGTGGGTAAGAATTCCARCACCAYTCRTG-3'.
```

The resulting PCR product was cloned into the pCR2.1 vector (Invitrogen, Carlsbad, Calif.) and sequence analysis revealed homology to known ALG3/RHK1/NOT56 homologs (Genbank NC_001134.2, AF309689, NC_003424.1). Subsequently, 1929 bp upstream and 2738 bp downstream of the initial PCR product were amplified from a *P. pastoris* genomic DNA library (Boehm (1999) Yeast 15(7):563-72) using the internal oligonucleotides 5'-CCTAAGCTGGTAT-GCGTTCTCTTTGCCATATC-3' (SEQ ID NO:80) and 5'-GCGGCATAAACAATAATAGATGCTATAAAG-3' (SEQ ID NO:81) along with T3 (5'-AATTAACCCTCAC-TAAAGGG-3') (SEQ ID NO:49) and T7 (5'-GTAA TAC-GACTCACTATAGGGC-3') (SEQ ID NO:48) (Integrated DNA Technologies, Coralville, Iowa) in the backbone of the library bearing plasmid lambda ZAP II (Stratagene, La Jolla, Calif.). The resulting fragments were cloned into the pCR2.1-TOPO vector (Invitrogen) and sequenced. From this sequence, a 1395 bp ORF was identified that encodes a protein with 35% identity and 53% similarity to the *S. cerevisiae* ALG3 gene (using BLAST programs). The gene was named PpALG3.

The sequence of PpALG3 was used to create a set of primers to generate a deletion construct of the PpALG3 gene by PCR overlap (Davidson et al (2002) *Microbiol.* 148(Pt 8):2607-15). Primers below were used to amplify 1 kb regions 5' and 3' of the PpALG3 ORF and the KAN$^R$ gene, respectively:

```
RCD142 (5'-CCACATCATCCGTGCTACATATAG-3'),            (SEQ ID NO:82)

RCD144 (5'-ACGAGGCAAGCTAAACAGATCTCGAAGTATCGAGGGTTATCCAG-3'),  (SEQ ID NO:83)

RCD145 (5'-CCATCCAGTGTCGAAAACGAGCCAATGGTTCATGTCTATAAATC-3'),  (SEQ ID NO:84)

RCD147 (5'-AGCCTCAGCGCCAACAAGCGATGG-3'),           (SEQ ID NO:85)

RCD143 (5'-CTGGATAACCCTCGATACTTCGAGATCTGTTTAGCTTGCCTCGT-3'),  (SEQ ID NO:86)
and

RCD146 (5'-GATTTATAGACATGAACCATTGGCTCGTTTTCGACACTGGATGG-3').  (SEQ ID NO:87)
```

Subsequently, primers RCD142 and RCD147 were used to overlap the three resulting PCR products into a single 3.6 kb alg3::KAN$^R$ deletion allele.

Identification, Cloning and Deletion of the ALG3 Gene in *K. lactis*.

The ALG3p sequences from *S. cerevisiae, Drosophila melanogaster, Homo sapiens* etc were aligned with *K. lactis* sequences (PENDANT EST database). Regions of high homology that were in common homologs but distinct in exact sequence from the homologs were used to create pairs of degenerate primers that were directed against genomic DNA from the *K. lactis* strain MG1/2 (Bianchi et al, 1987). In the case of ALG3, PCR amplification with primers KAL-1 (5'-ATCCTTTACCGATGCTGTAT-3') (SEQ ID NO:88) and KAL-2 (5'-ATAACAGTATGTGTTACACGCGTGTAG-3') (SEQ ID NO:89) resulted in a product that was cloned and sequenced and the predicted translation was shown to have a high degree of homology to Alg3p proteins (>50% to *S. cerevisiae* Alg3p).

The PCR product was used to probe a Southern blot of genomic DNA from *K. lactis* strain (MG1/2) with high stringency (Sambrook et al., *Molecular Cloning: A Laboratory Manual*, 2nd ed., Cold Spring Harbor Laboratory Press, Cold Spring Harbor, N.Y., 1989). Hybridization was observed in a pattern consistent with a single gene. This Southern blot was used to map the genomic loci. Genomic fragments were cloned by digesting genomic DNA and ligating those fragments in the appropriate size-range into pUC19 to create a *K. lactis* subgenomic library. This subgenomic library was transformed into *E. coli* and several hundred clones were tested by colony PCR, using primers KAL-1 and KAL-2. The clones containing the predicted KlALG3 and KlALG61 genes were sequenced and open reading frames identified.

Primers for construction of an alg3::NAT$^R$ deletion allele, using a PCR overlap method (Davidson et al. (2002) *Microbiol.* 148(Pt 8):2607-15), were designed and the resulting deletion allele was transformed into two *K. lactis* strains and NAT-resistant colonies selected. These colonies were screened by PCR and transformants were obtained in which the ALG3 ORF was replaced with the och1::NAT$^R$ mutant allele.

Example 11

Figure 36:
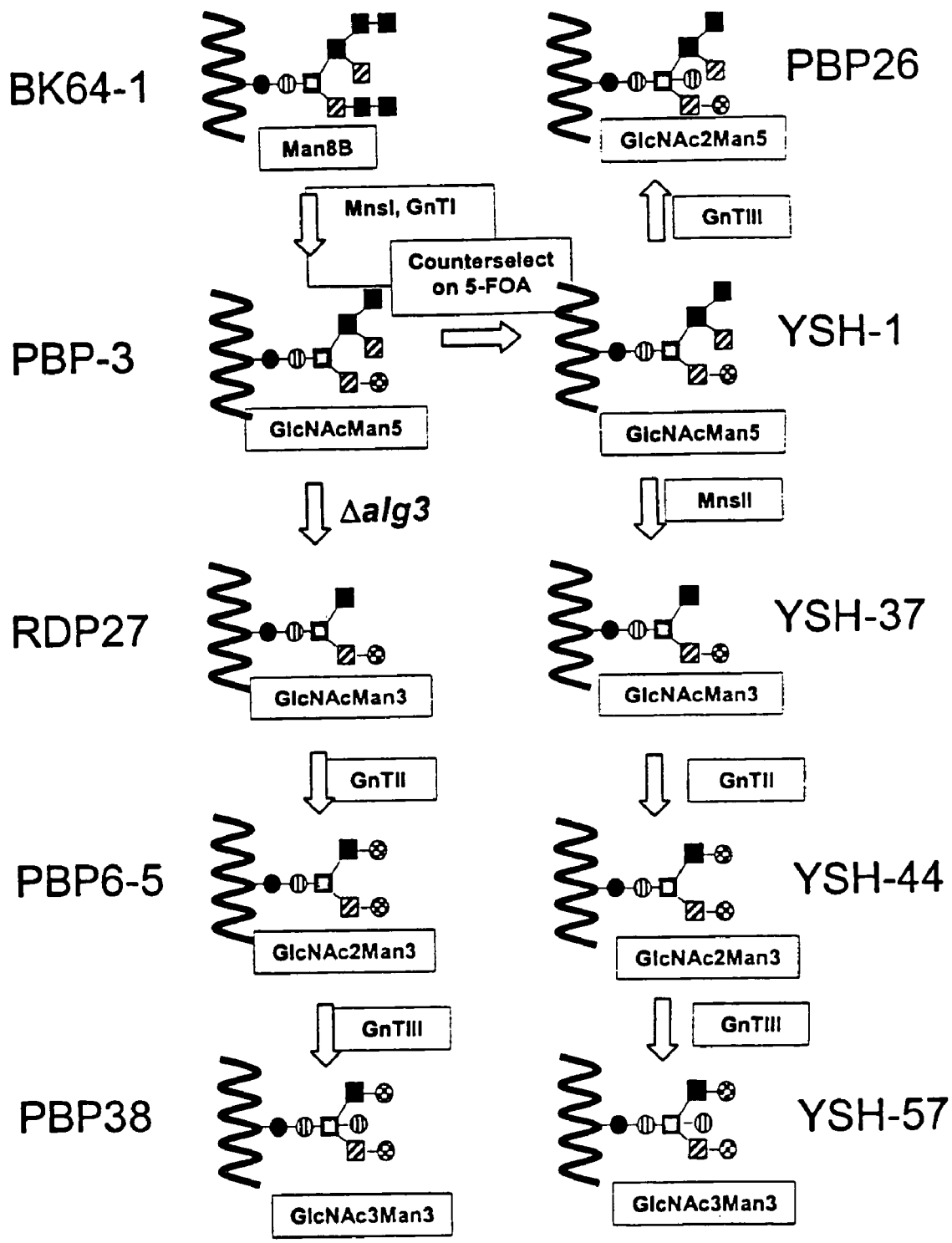
FIG. 36 is a schematic diagram showing the predominant secreted glycoform produced by each of the designated *P. pastoris* strains and the gene modification used to engineer each of the strains.

Generation of an alg3 och1 Mutant Strain Expressing an α-1,2-Mannosidase, GnT1 and GnTII for Production of a Human-Like Glycoprotein A *P. pastoris* alg3::KAN$^R$ deletion construct was generated as described in Example 10. Approximately 5 µg of the resulting PCR product was transformed into strain PBP-3 (see Example 3), and colonies were selected on YPD medium containing 200 µg/ml G418. One strain out of 20 screened by PCR was confirmed to contain the correct integration of the alg3::KAN$^R$ mutant allele and lack the wild-type allele. This strain was named RDP27 (FIG. 36).

A library of GnTII constructs was then generated, which was comprised of in-frame fusions of the leader library with the catalytic domains of GnTII genes from human and rat sources (WO 02/00879). This library was created in a *P. pastoris* integration vector containing the NST$^R$ gene conferring resistance to the drug nourseothricin. The library plasmids were linearized with EcoRI, transformed into strain RDP27 by electroporation, and the resulting strains were screened by analysis of the released glycans from purified K3. A *P. pastoris* strain expressing the rat GnTII fused in-frame to the *S. cerevisiae* MNN9(s) construct was named PBP6-5 (FIG. 36).

Generation of GnTII Expression Constructs

The construction of a GnTI expression vector (pNA15) containing a human GnTI gene fused with the N-terminal part of *S. cerevisiae* MNN9 gene is described in Choi et al. (2003) *Proc Natl Acad Sci U S A.* 100(9):5022-27. In a similar fashion, the rat GnTII gene was cloned. The rat GnTII gene (GenBank accession number U21662) was PCR amplified using Takara EX Taq™ polymerase (Panvera) from rat liver cDNA library (Clontech) with RAT1 (5'-TTCCTCACTG-CAGTCTTCTATAACT-3') (SEQ ID NO:90) and RAT2 (5'-TGGAGACCATGAGGTTCCGCATCTAC-3') (SEQ ID NO:91) primers. The PCR product was then cloned into pCR2.1-TOPO vector (Invitrogen) and sequenced. Using this vector as a template, the AscI-PacI fragment of GnTII, encoding amino-acids 88-443, was amplified with Pfu Turbo polymerase (Stratagene) and primers, RAT44 (5'-TT<u>GGCGCGCC</u>TCCCTAGTGTACCAGTTGA ACTTTG-3') (SEQ ID NO:92) and RAT11 (5'-GA<u>TTAATTAA</u>CTCACTGCAGTCTTCTATAA CT-3') (SEQ ID NO:93) respectively, introduced AscI and PacI restriction sites are underlined). Following confirmation by sequencing, the catalytic domain of rat GnTII was than cloned downstream of the PMA1 promoter as a AscI-PacI fragment in pBP124. In the final step, the gene fragment encoding the *S. cerevisiae* Mnn2 localization signal was cloned from pJN281 as a NotI-AscI fragment to generate an in-frame fusion with the catalytic domain of GnTII, to generate plasmid pTC53.

Example 12

Cloning and Expression of GnTIII to Produce Bisecting GlcNAcs which Boost Antibody Functionality The addition of an N-acetylglucosamine to the $GlcNAc_2Man_3GlcNAc_2$ structure by N-acetylglucosaminyltransferases III yields a so-called bisected N-glycan (see FIG. 15). This structure has been implicated in greater antibody-dependent cellular cytotoxicity (ADCC) (Umana et al. (1999) *Nat. Biotechnol.* 17(2):176-80).

A host cell such as a yeast strain capable of producing glycoproteins with bisected N-glycans is engineered according to the invention, by introducing into the host cell a GnTIII activity. Preferably, the host cell is transformed with a nucleic acid that encodes GnTIII (e.g., a mammalian such as the murine GnTIII shown in FIG. 24) or a domain thereof having enzymatic activity, optionally fused to a heterologous cell signal targeting peptide (e.g., using the libraries and associated methods of the invention.)

Figure 22:
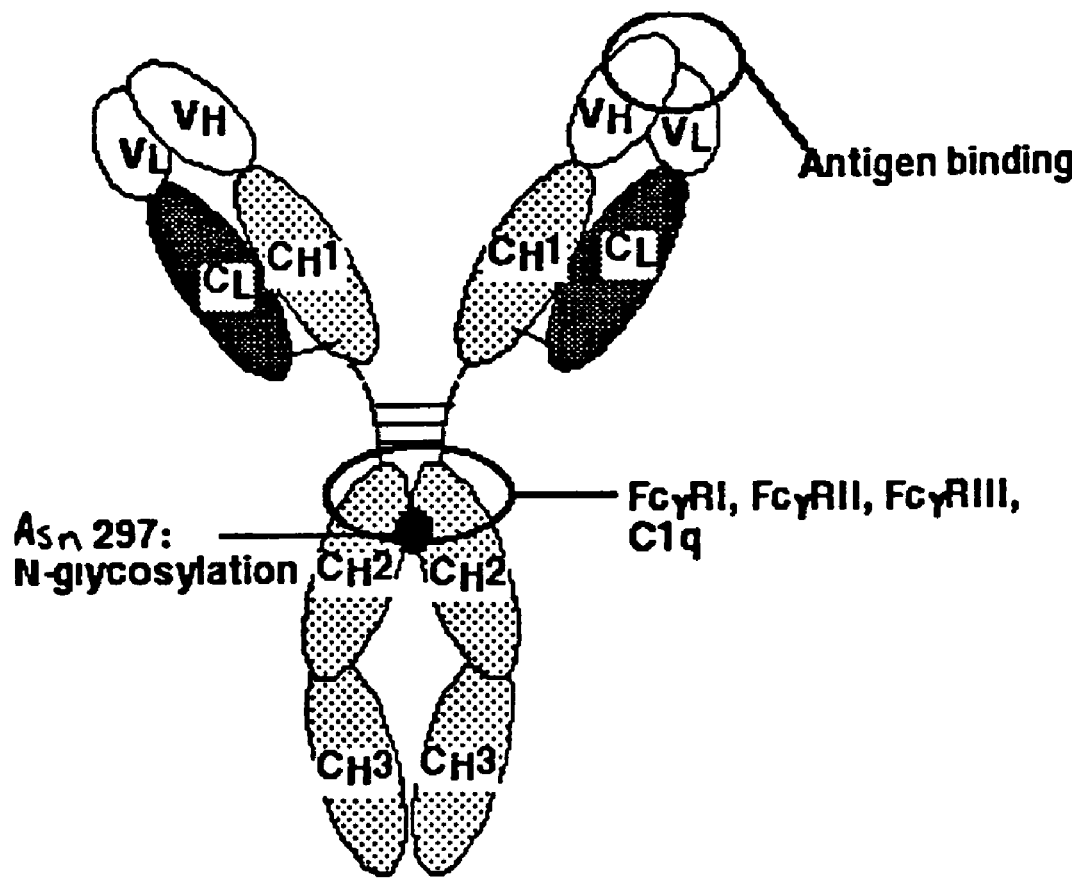
FIG. 22 shows a model of an IgG immunoglobulin. Heavy chain and light chain can be, based on similar secondary and tertiary structure, subdivided into domains. The two heavy chains (domains V$_H$, C$_H$1, C$_H$2 and C$_H$3) are linked through three disulfide bridges. The light chains (domains V$_L$ and C$_L$) are linked by another disulfide bridge to the C$_H$1 portion of the heavy chain and, together with the C$_H$1 and V$_H$ fragments, make up the Fab region. Antigens bind to the terminal portion of the Fab region. Effector-functions, such as Fc-gamma-Receptor binding have been localized to the C$_H$2 domain, just downstream of the hinge region and are influenced by N-glycosylation of asparagine 297 in the heavy chain.

IgGs consist of two heavy-chains ($V_H$, $C_H1$, $C_H2$ and $C_H3$ in FIG. 22), interconnected in the hinge region through three disulfide bridges, and two light chains ($V_L$, $C_L$ in FIG. 22). The light chains (domains $V_L$ and $C_L$) are linked by another disulfide bridge to the CH1 portion of the heavy chain and together with the $C_H1$ and $V_H$ fragment make up the so-called Fab region. Antigens bind to the terminal portion of the Fab region. The Fc region of IgGs consists of the $C_H3$, the $C_H2$ and the hinge region and is responsible for the exertion of so-called effector functions (see below).

The primary function of antibodies is binding to an antigen. However, unless binding to the antigen directly inactivates the antigen (such as in the case of bacterial toxins), mere binding is meaningless unless so-called effector-functions are triggered. Antibodies of the IgG subclass exert two major effector-functions: the activation of the complement system and induction of phagocytosis. The complement system consists of a complex group of serum proteins involved in controlling inflammatory events, in the activation of phagocytes and in the lytical destruction of cell membranes. Complement activation starts with binding of the C1 complex to the Fc portion of two IgGs in close proximity. C1 consists of one molecule, C1q, and two molecules, C1r and C1s. Phagocytosis is initiated through an interaction between the IgG's Fc fragment and Fc-gamma-receptors (FcγRI, II and III in FIG. 22). Fc receptors are primarily expressed on the surface of effector cells of the immune system, in particular macrophages, monocytes, myeloid cells and dendritic cells.

The $C_H2$ portion harbors a conserved N-glycosylation site at asparagine 297 (Asn297). The Asn297 N-glycans are highly heterogeneous and are known to affect Fc receptor binding and complement activation. Only a minority (i.e., about 15-20%) of IgGs bears a disialylated, and 3-10% have a monosialylated N-glycan (reviewed in Jefferis (2001) *Biopharm.* 14:19-26). Interestingly, the minimal N-glycan structure shown to be necessary for fully functional antibodies capable of complement activation and Fc receptor binding is a pentasacharide with terminal N-acetylglucosamine residues ($GlcNAc_2Man_3$) (reviewed in Jefferis, R., Glycosylation of human IgG Antibodies. BioPharm, 2001). Antibodies with less than a $GlcNAc_2Man_3$ N-glycan or no N-glycosylation at Asn297 might still be able to bind an antigen but most likely will not activate the crucial downstream events such as phagocytosis and complement activation. In addition, antibodies with fungal-type N-glycans attached to Asn297 will in all likelihood solicit an immune-response in a mammalian organism which will render that antibody useless as a therapeutic glycoprotein.

Cloning and Expression of GnTIII

The DNA fragment encoding part of the mouse GnTIII protein lacking the TM domain is PCR amplified from murine (or other mammalian) genomic DNA using forward (5'-TCCTGGCGCGCCTTCCCGAGAGAACTG-GCCTCCCTC-3') (SEQ ID NO:94) and reversed (5'-AATTAATTAACCCTAGCCCTCCGCTG-TATCCAACTTG-3') (SEQ ID NO:95) primers. Those primers include AscI and PacI restriction sites that may be used for cloning into the vector suitable for the fusion with leader library.

The nucleic acid (SEQ ID NO:45) and amino acid (SEQ ID NO:46) sequences of murine GnTIII are shown in FIG. 24.

Cloning of Immunoglobulin-Encoding Sequences

Protocols for the cloning of the variable regions of antibodies, including primer sequences, have been published previously. Sources of antibodies and encoding genes can be, among others, in vitro immunized human B cells (see, e.g., Borreback et al. (1988) *Proc. Natl. Acad. Sci. USA* 85:3995-3999), peripheral blood lymphocytes or single human B cells (see, e.g., Lagerkvist et al. (1995) *Biotechniques* 18:862-869; and Terness et al. (1997) *Hum. Immunol.* 56:17-27) and transgenic mice containing human immunoglobulin loci, allowing the creation of hybridoma cell-lines.

Using standard recombinant DNA techniques, antibody-encoding nucleic acid sequences can be cloned. Sources for the genetic information encoding immunoglobulins of interest are typically total RNA preparations from cells of interest, such as blood lymphocytes or hybridoma cell lines. For example, by employing a PCR based protocol with specific primers, variable regions can be cloned via reverse transcription initiated from a sequence-specific primer hybridizing to the IgG $C_H 1$ domain site and a second primer encoding amino acids 111-118 of the murine kappa constant region. The $V_H$ and $V_K$ encoding cDNAs can then be amplified as previously published (see, e.g., Graziano et al. (1995) *J Immunol.* 155 (10):4996-5002; Welschof et al. (1995) *J. Immunol. Methods* 179:203-214; and Orlandi et al. (1988) *Proc. Natl. Acad. Sci. USA* 86:3833). Cloning procedures for whole immunoglobulins (heavy and light chains) have also been published (see, e.g., Buckel et al. (1987) *Gene* 51:13-19; Recinos et al. (1994) *Gene* 149: 385-386; Recinos et al. (1995) *Gene* 158:311-12). Additional protocols for the cloning and generation of antibody fragment and antibody expression constructs have been described in *Antibody Engineering*, Kontermann and Dübel (2001), Eds., Springer Verlag: Berlin Heidelberg New York.

Figure 23:
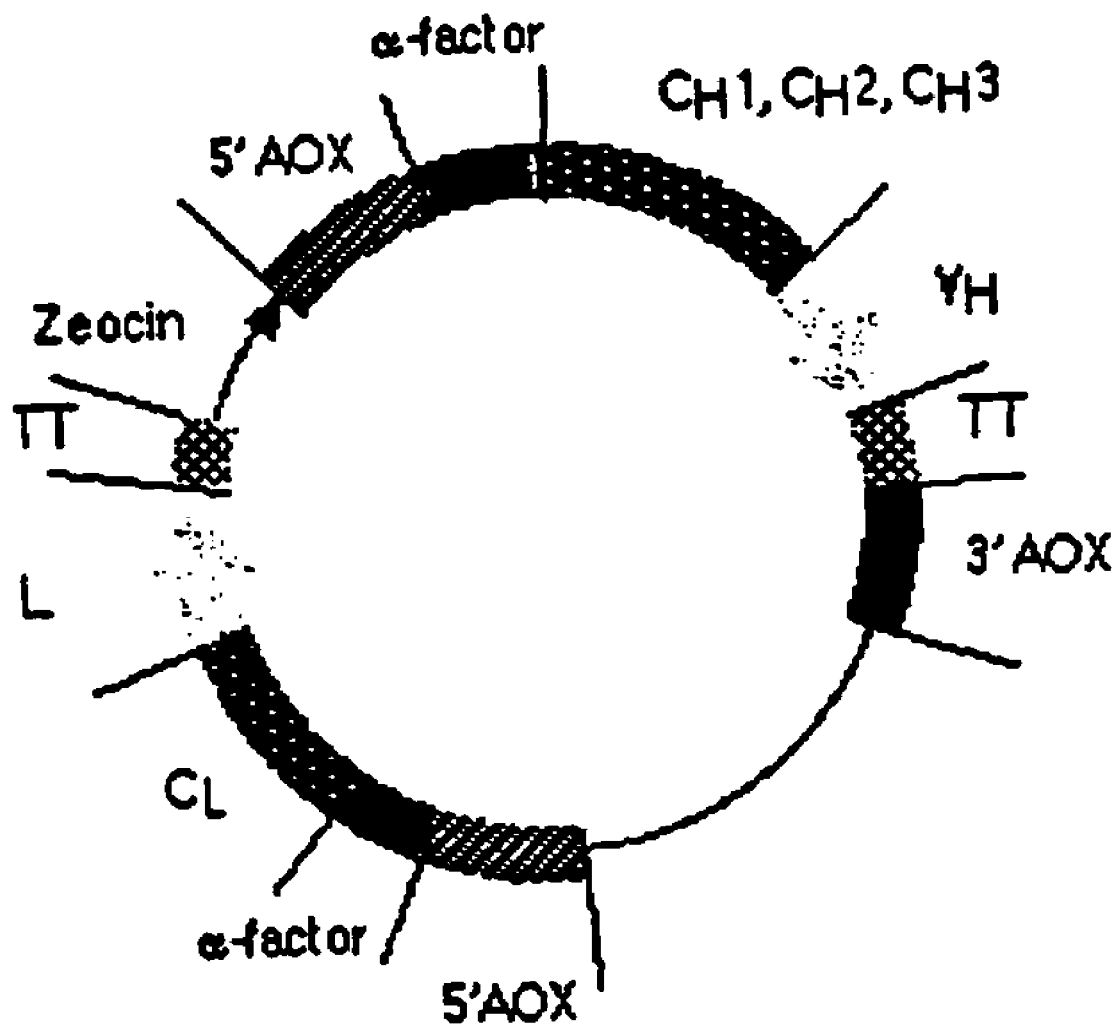
FIG. 23 is a schematic overview of a modular IgG1 expression vector.

Fungal expression plasmids encoding heavy and light chain of immunoglobulins have been described (see, e.g., Abdel-Salam et al. (2001) *Appl. Microbiol. Biotechnol.* 56:157-164; and Ogunjimi et al. (1999) *Biotechnology Letters* 21:561-567). One can thus generate expression plasmids harboring the constant regions of immunoglobulins. To facilitate the cloning of variable regions into these expression vectors, suitable restriction sites can be placed in close proximity to the termini of the variable regions. The constant regions can be constructed in such a way that the variable regions can be easily in-frame fused to them by a simple restriction-digest/ligation experiment. FIG. 23 shows a schematic overview of such an expression construct, designed in a very modular way, allowing easy exchange of promoters, transcriptional terminators, integration targeting domains and even selection markers.

As shown in FIG. 23, $V_L$ as well as $V_H$ domains of choice can be easily cloned in-frame with $C_L$ and the $C_H$ regions, respectively. Initial integration is targeted to the *P. pastoris* AOX locus (or homologous locus in another fungal cell) and the methanol-inducible AOX promoter will drive expression. Alternatively, any other desired constitutive or inducible promoter cassette may be used. Thus, if desired, the 5' AOX and 3' AOX regions as well as transcriptional terminator (TT) fragments can be easily replaced with different TT, promoter and integration targeting domains to optimize expression. Initially the alpha-factor secretion signal with the standard KEX protease site is employed to facilitate secretion of heavy and light chains. The properties of the expression vector may be further refined using standard techniques.

An Ig expression vector such as the one described above is introduced into a host cell of the invention that expresses GnTIII, preferably in the Golgi apparatus of the host cell. The Ig molecules expressed in such a host cell comprise N-glycans having bisecting GlcNAcs.

Example 13

Generation of Yeast Strain YSH-1 (Δoch1, α1,2-Mannosidase, GnTI)

The previously reported *P. pastoris* strain BK64 (Choi et al. (2003) *Proc Natl Acad Sci USA.* 100(9):5022-7), a triple auxotroph (ADE, ARG, HIS) possessing the OCH1 knockout and expressing the kringle 3 domain (K3) of human plasminogen, was used as the host strain. BK64 was transformed with the plasmid pPB103 linearized with the restriction enzyme EcoNI to introduce the *K. lactis* UDP-N-acetylglucosamine transporter into the host cell, thus creating the strain PBP-1. The mouse MnsI was introduced into this strain by transformation with the plasmid pFB8 linearized with the restriction enzyme EcoNI, generating strain PBP-2. K3 glycan analysis from proteins isolated from strain PBP-2 demonstrated that the primary glycoform present was $Man_5GlcNAc_2$.

PBP-2 was subsequently transformed with the human GnTI plasmid pNA15 linearized with the restriction enzyme AatII, generating the strain PBP-3. Analysis of the K3 glycoforms produced in strain PBP-3 demonstrated that the hybrid glycan $GlcNAcMan_5GlcNAc_2$ was the predominant structure. To recover the URA3 marker from PBP-3, this strain was grown in YPD prior to selection on minimal media containing 5-Fluoroorotic (5-FOA, BioVectra) and uracil (Boeke et al. (1984) *Mol. Gen. Genet.* 197:345-346). The recovered Ura-minus strain producing $GlcNAcMan_5GlcNAc_2$ glycoforms was designated YSH-1 (FIG. 36). The N-glycan profile from strain YSH-1 is shown in FIG. 25 (top) and displays a predominant peak at 1465 m/z corresponding to the mass of $GlcNAcMan_5GlcNAc_2$ [d].

Example 14

Generation of Yeast Strain YSH-37 (*P. pastoris* Expressing Mannosidase II)

YSH-1 (Example 13) was transformed with the *D. melanogaster* mannosidase IIΔ74/*S. cerevisiae* MNN2(s) plasmid (pKD53) linearized with the restriction enzyme ApaI, generating strain YSH-37 (FIG. 36). Analysis of the K3 glycan structures produced in strain YSH-37 (FIG. 25 (bottom)) demonstrated that the predominant glycoform at 1140 m/z corresponds to the mass of $GlcNAcMan_3GlcNAc_2$ [b] and other glycoforms $GlcNAcMan_4GlcNAc_2$ [c] at 1303 m/z and $GlcNAcMan_5GlcNAc_2$ [d] at 1465 m/z.

Example 15

Generation of Yeast Strain YSH-44

Strain YSH-37 (Example 14) was transformed with a plasmid encoding a rat GnTII/MNN2(s) leader, pTC53, linearized with the restriction enzyme EcoRI. The resulting strain, YSH-44 (FIG. 36), produced a K3 N-glycan having a single glycoform at 1356 m/z, corresponding to the mass of $GlcNAc_2Man_3GlcNAc_2$ [x], by positive mode MALDI-TOF mass spectrometry (FIG. 29).

Example 16

Construction of Plasmid pJN 348

The plasmid pBLURA-SX (from Jim Cregg) was digested with BamHI and BglII to release the AOX expression cassette. The BamHI fragment containing the GAPDH/CYC1 expression cassette from pJN261 (FIG. 4B) (Example 4) was then ligated into the pBLURA-SX backbone to create pJN338. The plasmid pJN338 was cut with NotI and PacI and the two oligonucleotides 5'-GGCCGCCTGCAGATTTAAATGAATTCG-GCGCGCCTTAAT-3' (SEQ ID NO:96) and 5'-TAAGGCGCGCC GAATTCATTTAAATCTGCAGG GC-3' (SEQ ID NO:97) that had been annealed in vitro, were ligated into the open sites, to create pJN348.

Example 17

Construction of an Integration Plasmid pRCD259

The PpURA3 containing GAPDH expression vector pJN348 was linearized with XhoI and blunted with T4 DNA polymerase and calf intestinal phosphatase (CIP) treated. The HYG resistance marker was digested from pAG32 with BglII and SacI and blunted, then ligated into pJN348 to create pRCD259 which can be used as a HYG expression vector that integrates at the PpURA3 locus.

Example 18

Generation of GnTIII Fusion Constructs

Fusion constructs between mammalian GnTIII and yeast targeting sequences were made using mouse Mgat3 gene (GenBank accession number L39373, Bhaumik et al., 1995). Three DNA fragments corresponding to N-terminal deletions Δ32, Δ86, and Δ212 of the mouse GnTIII gene were PCR amplified using Pfu Turbo polymerase (Stratagene) with forward

MG3-B (5'-TCCTGGCGCGCCTTCCCGAGAGAACTG-GCCTCCCTC-3') (SEQ ID NO:98),

MG3-C (5'-CCGAGGCGCGCCACAGAGGAACTGCAC-CGGGTG-3') (SEQ ID NO:99),

MG3-D (5'-ACCGAGGCGCGCCATCAACGCCATCAA-CATCAACCAC-3') (SEQ ID NO:100), and reverse MG3-A (5'-AATTAATTAACCCTAGCCCTCCGCTG-TATCCAACTTG-3') (SEQ ID NO:101) primers. The PCR products were then cloned into pJN 348 vector as AscI-PacI fragments and sequenced. The resulting vectors pVA (GnTIII Δ32), pVB (GnTIII Δ86), and pVC (GnTIII Δ212) were digested with NotI-AscI enzymes and used for the ligation with yeast leader library (leaders 20-67). These targeting peptides are fused to the catalytic domains selected from the mouse GnTIII with 32, 86, 212 amino acid N-terminal deletions. For example, the MNN2 targeting peptide from *S. cerevisiae* (long, medium and short) and GNT1 from *K. lactis* (short, and medium) (see Example 11) are shown in Table 11.

Example 19

Engineering of *P. pastoris* to Produce Bisected GlcNAc$_2$Man$_5$GlcNAc$_2$

The *P. pastoris* strain producing GlcNAcMan$_5$GlcNAc$_2$ (PBP-3) (see Example 8) was counterselected on 5-FOA, thereby selecting for loss of the URA3+ marker and a ura3− phenotype. This strain, designated YSH-1 (FIG. 36), was transformed with the library of N-acetylglucosaminyltransferase III (GnTIII) catalytic domains (vectors pVA, pVB, and pVC) and leaders. Transformants were grown at 30° C. in BMGY to an OD600 of about 10, harvested by centrifugation and transferred to BMMY to induce the production of K3 (kringle 3 from human plasminogen) under control of an AOX1 promoter. K3 was purified from the medium by Ni-affinity chromatography utilizing a 96-well format on a Beckman BioMek 2000 laboratory robot. The robotic purification is an adaptation of the protocol provided by Novagen for their HisBind resin (Example 3). The N-glycans were released by PNGase digestion (Example 3). The N-glycans were analyzed with a MALDI-TOF MS (Example 3). The GnTIII activities are shown in Table 11. The number of (+)s, as used herein, indicates the relative levels of bisected N-glycan production of % neutral glycans. Targeting peptide sequences were selected from selected from the group consisting of: *Saccharomyces* GLS1, *Saccharomyces* MNS1, *Saccharomyces* SEC12, *Pichia* SEC, *Pichia* OCH 1, *Saccharomyces* MNN9, *Saccharomyces* VAN 1, *Saccharomyces* ANP1, *Saccharomyces* HOC1, *Saccharomyces* MNN10, *Saccharomyces* MNN11, *Saccharomyces* MNT1, *Pichia* D2, *Pichia* D9, *Pichia* J3, *Saccharomyces* KTR1, *Saccharomyces* KTR2, *Kluyveromyces* GnTI, *Saccharomyces* MNN2, *Saccharomyces* MNN5, *Saccharomyces* YUR1, *Saccharomyces* MNN1, and *Saccharomyces* MNN6. The pVA53 transformants exhibiting the bisecting GlcNAc (e.g. GlcNAc$_2$Man$_5$GlcNAc$_2$) were designated PBP26 (FIG. 36).

Example 20

Engineering of *P. pastoris* YSH-44 to Produce Bisected GlcNAc$_3$Man$_3$GlcNAc$_2$ For the expression of GnTIII in the strain YSH-44 (FIG. 36), GnTIII constructs from vectors pVA53, pVB53, pVA54, and pVB54 were transferred as NotI-PacI fragments into pRCD259 to generate vectors pPB135, pPB137, pPB136, and pPB138. The vectors contain HYG resistance marker and

TABLE 11

A representative combinatorial library of targeting peptide sequences/catalytic domains exhibiting UDP-N-Acetylglucosaminyltransferase III (GnTIII) activity in *P. pastoris* YSH-1

|  |  | Targeting peptide | | | |
| --- | --- | --- | --- | --- | --- |
|  |  | S. cerevisiae MNN2(s) | S. cerevisiae MNN2(m) | S. cerevisiae MNN2(l) | K. lactis GNT1(m) |
| Catalytic Domian | Mouse GnTIII Δ32 | 50% (pVA53) | 30-40% (pVA54) | 20-30% (pVA55) | 0% (pVA51) |
|  | Mouse GnTIII Δ86 | 20-30% (pVB53) | 30-40% (pVB54) | 20-30% (pVB55) | 0% (pVB51) |
|  | Mouse GnTIII Δ212 | 0% (pVC53) | 0% (pVC54) | 0% (pVC55) | 0% (pVC51) |

*P. pastoris* URA3 gene as targeting sequence for genomic integration. Plasmids are linearized with SalI, transformed into strain YSH-44 by electroporation, selected on medium containing hygromycin and the resulting strains are screened by analysis of the released glycans from purified K3. Transformants were grown at 24° C. in BMGY to an OD600 of about 10, harvested by centrifugation and transferred to BMMY to induce the production of K3 (kringle 3 from human plasminogen) under control of an AOX1 promoter. K3 was purified from the medium by Ni-affinity chromatography utilizing a 96-well format on a Beckman BioMek 2000 laboratory robot (Example 3). The robotic purification is an adaptation of the protocol provided by Novagen for their HisBind resin (Example 3). The N-glycans were released by PNGase digestion. The N-glycans were analyzed with a MALDI-TOF MS (Example 3). The pPB135 transformants exhibiting the bisecting GlcNAc (e.g. $GlcNAc_2Man_5GlcNAc_2$) were designated YSH-57 (FIG. 36). Table 11 depicts the activity of the mouse GnTIII.

Example 21

Engineering of *P. pastoris* PBP6-5 to Produce Bisected $GlcNAc_3Man_3GlcNAc_2$

The *P. pastoris* PBP6-5 (Example 11) was transformed with the plasmid pPB135 (Table 11) encoding a mouse GnTIII catalytic domain (Δ32) ligated in frame to a targeting peptide derived from *S. cerevisiae* MNN2. Transformants were grown at 30° C. in BMGY to an OD600 of about 10, harvested by centrifugation and transferred to BMMY to induce the production of K3 (kringle 3 from human plasminogen) under control of an AOX1 promoter. K3 was purified from the medium by Ni-affinity chromatography utilizing a 96-well format on a Beckman BioMek 2000 laboratory robot. The robotic purification is an adaptation of the protocol provided by Novagen for their HisBind resin (Example 3). The N-glycans were released by PNGase digestion (Example 3). The N-glycans were analyzed with a MALDI-TOF MS (Example 3). Transformants exhibiting the bisecting GlcNAc (e.g. $GlcNAc_2Man_3GlcNAc_2$) were designated PBP-38 (FIG. 36). Table 11 depicts the activity of the mouse GnTIII.

Example 22

In Vitro GnTIII Activity Assay Using Substrate $GlcNAcMan_5GlcNAc_2$ in Engineered *P. pastoris* Strain YSH-57

To test any potential ex vivo GnTIII activity in the *P. pastoris* strain, YSH-57 cell culture supernatants were tested for GnTIII activity. *P. pastoris* YSH-57 cells were grown at 24° C. in BMGY to an OD600 of about 10. Cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant. An aliquot of the supernatant was removed for GnTIII assays and the remainder was used for the recovery of secreted soluble K3. K3 was purified from the medium by Ni-affinity chromatography utilizing a 96-well format on a Beckman BioMek 2000 laboratory robot. The robotic purification is an adaptation of the protocol provided by Novagen for their HisBind resin (Example 3). The N-glycans were released by PNGase digestion (Example 3). The earlier removed aliquot of the supernatant was further tested for the presence of secreted GnTIII activity. $GlcNAcMan_5GlcNAc_2$ purified from K3 expressed in PBP-3 strain was added to: BMMY (A) 1 mM UDP-GlcNAc (Sigma Chemical Co., St. Louis, Mo.)) in BMMY (B); the supernatant of YSH-44 transformed with pVA53 [YSH-57] (C); the supernatant of YSH-57+1 mM UDP-GlcNAc (D). After incubation for 8 hours at room temperature, samples were analyzed by amino silica HPLC to determine the extent of GnTIII activity.

Example 23

In Vitro GnTIII Activity Assay Using Substrate $GlcNAc_2Man_3GlcNAc_2$ in Engineered *P. pastoris* Strain YSH-57

To test any potential ex vivo GnTIII activity in the *P. pastoris* strain YSH-57 cell culture supernatants were tested for GnTIII activity. *P. pastoris* YSH-57 cells were grown at 24° C. in BMGY to an OD600 of about 10. Cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant. An aliquot of the supernatant was removed for GnTIII assays and the remainder was used for the recovery of secreted soluble K3. K3 was purified from the medium by Ni-affinity chromatography utilizing a 96-well format on a Beckman BioMek 2000 laboratory robot. The robotic purification is an adaptation of the protocol provided by Novagen for their HisBind resin (Example 3). The N-glycans were released by PNGase digestion (Example 3). The earlier removed aliquot of the supernatant was further tested for the presence of secreted GnTIII activity. $GlcNAc_2Man_3GlcNAc_2$ purified from K3 expressed in YSH-44 strain was added to: BMMY (A) 1 mM UDP-GlcNAc (Sigma Chemical Co., St. Louis, Mo.)) in BMMY (B); the supernatant of YSH-44 transformed with pVA53 [YSH-57] (C). After incubation for 8 hours at room temperature, samples were analyzed by amino silica HPLC to determine the extent of GnTIII activity.

---

We claim:

1. A yeast host cell that has been genetically engineered to be diminished or depleted in the activity of an initiating α-1,6-mannosylatransferase and to comprise a nucleic acid sequence encoding an α-1,2-mannosidase, a nucleic acid sequence encoding a N-acetylglucosaminyltransferase I (GnT I), and a nucleic acid sequence encoding an N-acetylglucosaminyltransferase III (GnT III).

2. The yeast host cell of claim 1, wherein the GnT III has intracellular catalytic activity.

3. The yeast host cell of claim 1, further comprising a nucleic acid sequence encoding mannosidase II.

4. The yeast host cell of claim 1, wherein the GnT III produces a bisected glycan.

5. The yeast host cell of claim 1, wherein the initiating α-1,6-mannosylatransferase is OCH1.

6. The yeast host cell of claim 1, wherein the yeast is further diminished or depleted in the activity of Dol-P-Man: Man5GlcNAc2-PP-Dol mannosyltransferase.

7. The yeast host cell of claim 1, further comprising a nucleic acid sequence encoding a UDP N-acetylglucosaminyltransferase (GlcNAc) transporter.

8. The yeast host cell of claim 1, wherein the yeast is methylotrophic.

9. A yeast host cell that has been genetically engineered to be diminished or depleted in the activity of an initiating α-1,6-mannosylatransferase and to comprise a nucleic acid sequence encoding an α-1,2-mannosidase, a nucleic acid sequence encoding an N-acetylglucosaminyltransferase I (GnT I), a nucleic acid sequence encoding an N-acetylglucosaminyltransferase II (GnT II), and a nucleic acid sequence encoding an N-acetylglucosaminyltransferase III (GnT III).

10. The yeast host cell of claim 9, wherein the GnT II and the GnT III have intracellular catalytic activity.

11. The yeast host cell of claim 9, further comprising a nucleic acid sequence encoding mannosidase II.

12. The yeast host cell of claim 9, wherein the GnT III produces a bisected glycan.

13. The host cell of claim 9, wherein the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., and *Candida albicans*.

14. The yeast host cell of claim 9, wherein the initiating α-1,6-mannosylatransferase is OCH1.

15. The yeast host cell of claim 9, wherein the yeast is further diminished or depleted in the activity of Dol-P-Man: Man5GlcNAc2-PP-Dol mannosyltransferase.

16. The yeast host cell of claim 9, further comprising a nucleic acid sequence encoding a UDP N-acetylglucosaminyltransferase (GlcNAc) transporter.

17. The yeast host cell of claim 9, wherein the yeast is methylotrophic.

18. A yeast host cell that has been genetically engineered to be diminished or depleted in the activity of an initiating α-1,6-mannosylatransferase and to comprise a nucleic acid sequence encoding an α-1,2-mannosidase, a nucleic acid sequence encoding a N-acetylglucosaminyltransferase I (GnT I), a nucleic acid sequence encoding an N-acetylglucosaminyltransferase III (GnT III), and a nucleic acid sequence encoding a mannosidase II.

19. The yeast host cell of claim 18, wherein the initiating α-1,6-mannosylatransferase is OCH1.

20. The yeast host cell of claim 18, wherein the yeast is further diminished or depleted in the activity of Dol-P-Man: Man5GlcNAc2-PP-Dol mannosyltransferase.

21. The yeast host cell of claim 18, further comprising a nucleic acid sequence encoding a UDP N-acetylglucosaminyltransferase (GlcNAc) transporter.

22. The yeast host cell of claim 18, wherein the yeast is methylotrophic.

\* \* \* \* \*